United States Patent
Fitzgerald et al.

(10) Patent No.: US 11,071,726 B2
(45) Date of Patent: Jul. 27, 2021

(54) TREATING GASTRIC CANCER USING COMBINATION THERAPIES COMPRISING LIPOSOMAL IRINOTECAN, OXALIPLATIN, 5-FLUOROURACIL (AND LEUCOVORIN)

(71) Applicant: Ipsen Biopharm Ltd., Wrexham (GB)

(72) Inventors: Jonathan Basil Fitzgerald, Arlington, MA (US); Ashish Kalra, Belmont, MA (US); Shannon Leonard, S. Hamilton, MA (US); Stephan Braun, Paris (FR); Bin Zhang, Belmont, MA (US)

(73) Assignee: Ipsen Biopharm Ltd.

( * ) Notice: Subject to any disclaimer, the term of this patent is extended or adjusted under 35 U.S.C. 154(b) by 0 days.

(21) Appl. No.: 16/346,436

(22) PCT Filed: Nov. 1, 2017

(86) PCT No.: PCT/GB2017/053293
§ 371 (c)(1),
(2) Date: Apr. 30, 2019

(87) PCT Pub. No.: WO2018/083470
PCT Pub. Date: May 11, 2018

(65) Prior Publication Data
US 2020/0030302 A1 Jan. 30, 2020

Related U.S. Application Data

(60) Provisional application No. 62/416,317, filed on Nov. 2, 2016.

(51) Int. Cl.
| | | |
|---|---|---|
| *A61K 31/437* | (2006.01) | |
| *A61P 35/00* | (2006.01) | |
| *A61K 33/243* | (2019.01) | |
| *A61K 9/00* | (2006.01) | |
| *A61K 9/127* | (2006.01) | |
| *A61K 31/513* | (2006.01) | |
| *A61K 31/519* | (2006.01) | |

(52) U.S. Cl.
CPC .......... *A61K 31/437* (2013.01); *A61K 9/0019* (2013.01); *A61K 9/127* (2013.01); *A61K 31/513* (2013.01); *A61K 31/519* (2013.01); *A61K 33/243* (2019.01); *A61P 35/00* (2018.01)

(58) Field of Classification Search
None
See application file for complete search history.

(56) References Cited

U.S. PATENT DOCUMENTS

| | | |
|---|---|---|
| 4,604,463 A | 8/1986 | Miyasaka et al. |
| 5,013,556 A | 5/1991 | Woodle et al. |
| 5,077,056 A | 12/1991 | Bally et al. |
| 5,192,549 A | 3/1993 | Barenolz et al. |
| 5,316,771 A | 5/1994 | Barenholz et al. |
| 5,538,954 A | 7/1996 | Koch et al. |
| 5,543,152 A | 8/1996 | Webb et al. |
| 5,593,622 A | 1/1997 | Yoshioka et al. |
| 5,676,971 A | 10/1997 | Yoshioka et al. |
| 5,783,568 A | 7/1998 | Schlessinger et al. |
| 5,785,987 A | 7/1998 | Hope et al. |
| 5,846,458 A | 12/1998 | Yoshioka et al. |
| 6,110,491 A | 8/2000 | Kirpotin |
| 6,210,707 B1 | 4/2001 | Papahadjopoulos et al. |
| 6,214,388 B1 | 4/2001 | Benz et al. |
| 6,241,999 B1 | 6/2001 | Ye et al. |
| 6,355,268 B1 | 3/2002 | Slater et al. |
| 6,403,569 B1 | 6/2002 | Achterrath |
| 6,465,008 B1 | 10/2002 | Slater et al. |
| 6,511,676 B1 | 1/2003 | Boulikas |
| 6,545,010 B2 | 4/2003 | Bissery |
| 6,720,001 B2 | 4/2004 | Chen et al. |
| 6,787,132 B1 | 9/2004 | Gabizon et al. |
| 6,794,370 B2 | 9/2004 | Achterrath |
| 7,022,336 B2 | 4/2006 | Papahadjopoulos et al. |
| 7,060,828 B2 | 6/2006 | Madden et al. |
| 7,135,177 B2 | 11/2006 | Benz et al. |
| 7,219,016 B2 | 5/2007 | Rimm et al. |
| 7,244,448 B2 | 7/2007 | Madden et al. |
| 7,244,826 B1 | 7/2007 | Marks et al. |
| 7,507,407 B2 | 3/2009 | Benz |
| 7,829,113 B2 | 11/2010 | Okada et al. |
| 7,842,676 B2 | 11/2010 | Janoff et al. |
| 7,846,440 B2 | 12/2010 | Schoeberl et al. |

(Continued)

FOREIGN PATENT DOCUMENTS

| | | |
|---|---|---|
| CA | 2412790 A1 | 1/2002 |
| CN | 1829741 A | 9/2006 |

(Continued)

OTHER PUBLICATIONS

U.S. Appl. No. 16/302,050, filed Jan. 17, 2020 Non-Final Office Action, 17 pages.
U.S. Appl. No. 16/510,394, filed Mar. 6, 2020 Non-Final Office Action, 15 pages.
U.S. Appl. No. 16/567,902, filed Apr. 27, 2020 Non-Final Office Action, 20 pages.
Chiang N-J, et al., "A Phase I Dose-Escalation Study of PEP02 (Irinotecan Liposome Injection) in Combination with 5-Fluorouracil and Leucovorin in Advanced Solid Tumors," BMC Cancer. 16(1):907 (2016). doi: 10.1186/s12885-016-2933-6, pp. 1-8.
Chiesa MD, et al., "Sequential Chemotherapy with Dose-Dense Docetaxel, Cisplatin, Folinic Acid and 5-Fluorouracil (TCF-dd) Followed by Combination of Oxaliplatin, Folinic acid, 5-Fluorouracil and Irinotecan (COFFI) in Metastatic Gastric Cancer: Results of a Phase II Trial," Cancer Chemother Pharmacol. 67(1):41-8 (2011), epub 2010.

(Continued)

*Primary Examiner* — Brian J Davis
(74) *Attorney, Agent, or Firm* — McNeill Baur PLLC

(57) ABSTRACT

Combination therapy regimens including liposomal irinotecan, oxaliplatin and 5-fluorouracil are useful in the treatment of gastric cancer, including treatment of patients diagnosed with previously untreated gastric cancer. The combination therapy can include the administration of liposomal irinotecan, oxaliplatin, leucovorin and 5-fluorouracil once every two weeks.

21 Claims, 22 Drawing Sheets

(56) References Cited

U.S. PATENT DOCUMENTS

| | | | |
|---|---|---|---|
| 7,846,473 B2 * | 12/2010 | Yoshino | A61P 35/00 424/450 |
| 7,850,990 B2 | 12/2010 | Tardi et al. | |
| 7,871,620 B2 | 1/2011 | Benz et al. | |
| 7,892,554 B2 | 2/2011 | Marks et al. | |
| 8,067,432 B2 | 11/2011 | Anderson et al. | |
| 8,147,867 B2 | 4/2012 | Hong et al. | |
| 8,329,213 B2 | 12/2012 | Hong et al. | |
| 8,496,961 B2 | 7/2013 | Hong et al. | |
| 8,658,203 B2 | 2/2014 | Drummond et al. | |
| 8,703,181 B2 | 4/2014 | Hong et al. | |
| 8,992,970 B2 | 3/2015 | Hong et al. | |
| 9,339,497 B2 | 5/2016 | Bayever et al. | |
| 9,364,473 B2 | 6/2016 | Bayever et al. | |
| 9,452,162 B2 | 9/2016 | Bayever et al. | |
| 9,492,442 B2 | 11/2016 | Bayever et al. | |
| 9,511,155 B2 | 12/2016 | Drummond et al. | |
| 9,616,081 B2 | 4/2017 | Okabe | |
| 9,717,723 B2 | 8/2017 | Hong et al. | |
| 9,717,724 B2 | 8/2017 | Bayever et al. | |
| 9,724,303 B2 | 8/2017 | Hong et al. | |
| 9,730,891 B2 | 8/2017 | Hong et al. | |
| 9,737,528 B2 | 8/2017 | Drummond et al. | |
| 9,782,349 B2 | 10/2017 | Hong et al. | |
| 9,895,365 B2 | 2/2018 | Blanchette et al. | |
| 10,350,201 B2 | 7/2019 | Hong et al. | |
| 10,413,510 B2 | 9/2019 | Hong et al. | |
| 10,456,360 B2 | 10/2019 | Drummond et al. | |
| 10,478,428 B2 | 11/2019 | Blanchette et al. | |
| 10,722,508 B2 | 7/2020 | Hong et al. | |
| 10,980,795 B2 | 4/2021 | Bayever et al. | |
| 10,993,914 B2 | 5/2021 | Drummond et al. | |
| 2002/0035091 A1 | 3/2002 | Govindarajan et al. | |
| 2002/0102298 A1 | 8/2002 | Needham | |
| 2002/0146450 A1 | 10/2002 | Slater et al. | |
| 2002/0192275 A1 | 12/2002 | Zalipsky et al. | |
| 2003/0138481 A1 | 7/2003 | Zadi | |
| 2004/0002505 A1 | 1/2004 | Ozawa et al. | |
| 2004/0071768 A1 | 4/2004 | Sards et al. | |
| 2007/0110798 A1 | 5/2007 | Drummond et al. | |
| 2007/0219268 A1 | 9/2007 | Hausheer | |
| 2007/0265324 A1 | 11/2007 | Wernet et al. | |
| 2008/0108135 A1 | 5/2008 | Marks et al. | |
| 2009/0123419 A1 | 5/2009 | Sherman et al. | |
| 2009/0149397 A1 | 6/2009 | Ossovskaya et al. | |
| 2010/0056761 A1 | 3/2010 | Schoeberl et al. | |
| 2010/0068255 A1 | 3/2010 | Benz et al. | |
| 2011/0059076 A1 | 3/2011 | McDonagh et al. | |
| 2011/0104256 A1 | 5/2011 | Wang et al. | |
| 2011/0123523 A1 | 5/2011 | Schoeberl et al. | |
| 2012/0003160 A1 | 1/2012 | Wolf et al. | |
| 2012/0034295 A1 | 2/2012 | Spiegel et al. | |
| 2012/0045524 A1 | 2/2012 | Wernet et al. | |
| 2012/0269812 A1 | 10/2012 | Baum et al. | |
| 2012/0282325 A1 | 11/2012 | Tong et al. | |
| 2013/0209481 A1 | 8/2013 | Zhou | |
| 2013/0236459 A1 | 9/2013 | Baum et al. | |
| 2013/0274281 A1 | 10/2013 | Bradley | |
| 2014/0065204 A1 | 3/2014 | Hayes et al. | |
| 2014/0170075 A1 | 6/2014 | Drummond et al. | |
| 2015/0182460 A1 | 7/2015 | Hong et al. | |
| 2015/0182521 A1 | 7/2015 | Bayever et al. | |
| 2015/0328156 A1 | 11/2015 | Bayever et al. | |
| 2015/0374682 A1 | 12/2015 | Bayever et al. | |
| 2016/0030341 A1 | 2/2016 | Hong et al. | |
| 2016/0030342 A1 | 2/2016 | Hong et al. | |
| 2016/0058704 A1 | 3/2016 | Tardi et al. | |
| 2016/0074382 A1 | 3/2016 | Bayever et al. | |
| 2016/0206615 A1 | 7/2016 | Tangutoori et al. | |
| 2016/0303264 A1 | 10/2016 | Hendricks et al. | |
| 2016/0346272 A1 | 12/2016 | Bayever et al. | |
| 2017/0049767 A1 | 2/2017 | Blanchette et al. | |
| 2017/0049775 A1 | 2/2017 | Bayever et al. | |
| 2017/0202840 A1 | 7/2017 | Bayever et al. | |
| 2017/0333421 A1 | 11/2017 | Adiwijaya et al. | |

FOREIGN PATENT DOCUMENTS

| | | |
|---|---|---|
| CN | 101878229 A | 11/2010 |
| CN | 1980637 B | 2/2014 |
| WO | 1997028156 A1 | 8/1997 |
| WO | 2000023052 A1 | 4/2000 |
| WO | 2003013536 A2 | 2/2003 |
| WO | 2003030864 A1 | 4/2003 |
| WO | 2003101474 A1 | 12/2003 |
| WO | 2004017940 A3 | 4/2004 |
| WO | 2004093795 A3 | 11/2004 |
| WO | 2005000900 A1 | 1/2005 |
| WO | 2005107712 A1 | 11/2005 |
| WO | 2006110816 A2 | 10/2006 |
| WO | 2007076117 A2 | 7/2007 |
| WO | 2009040426 A1 | 4/2009 |
| WO | 2009126920 A3 | 3/2010 |
| WO | 2010125462 A2 | 11/2010 |
| WO | 2011066684 A1 | 6/2011 |
| WO | 2011153010 A1 | 12/2011 |
| WO | 2012012454 A1 | 1/2012 |
| WO | 2012031293 A1 | 3/2012 |
| WO | 2012078695 A2 | 6/2012 |
| WO | 2012079582 A1 | 6/2012 |
| WO | 2012146610 A1 | 11/2012 |
| WO | 2013006547 A2 | 1/2013 |
| WO | 2013138371 A1 | 9/2013 |
| WO | 2013158803 A1 | 10/2013 |
| WO | 2013188586 A1 | 12/2013 |
| WO | 2014113167 A1 | 7/2014 |
| WO | 2014157444 A1 | 10/2014 |
| WO | 2016094402 A1 | 6/2016 |
| WO | 2016168451 A1 | 10/2016 |
| WO | 2017031442 A1 | 2/2017 |
| WO | 2017031445 A1 | 2/2017 |
| WO | 2017034957 A1 | 3/2017 |
| WO | 2017066726 A1 | 4/2017 |
| WO | 2017172678 A1 | 10/2017 |
| WO | 2017199093 A1 | 11/2017 |
| WO | 2018083470 A1 | 5/2018 |

OTHER PUBLICATIONS

Hsueh C-T, et al., "Nanovectors for Anti-Cancer Drug Delivery in the Treatment of Advanced Pancreatic Adenocarcinoma," World J Gastroenterol. 22(31):7080-90 (2016).

Ko A, "Nanomedicine Developments in the Treatment of Metastatic Pancreatic Cancer: Focus on Nanoliposomal Irinotecan," Int J Nanomedicine. 11:1225-35 (2016).

PCT/GB2017/053293: PCT International Preliminary Report on Patentability dated May 7, 2019, 7 pages.

PCT/GB2017/053293: PCT International Search Report and Written Opinion dated Feb. 2, 2018, 12 pages.

Peinert S, et al., "Safety and Efficacy of Weekly 5-Fluorouracil/Folinic Acid/Oxaliplatin/Irinotecan in the First-Line Treatment of Gastrointestinal Cancer," Ther Adv Med Oncol. 2(3):161-74 (2010).

Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013).

Melis M, et al., "Can We Downstage Regionally Advanced Pancreatic Cancer to Resectable: a Phase I/II Study of Induction Oxaliplatin and 5FU Chemo-Radiation," 52nd Annual Meeting for Society for Surgery of the Alimentary Tract, May 6-10, 2011, http://meetings.ssat.com/abstracts/11ddw/P57.cgi, Abstract P57, 1 printed page.

Merrimack Pharmaceuticals, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releases/news-release-details/merrimack-announces-inclusion-onivyder-irinotecan-liposome, 2 printed pages.

Oettle H, et al., "Second-Line Oxaliplatin, Folinic Acid, and Fluorouracil Versus Folinic Acid and Fluorouracil Alone for Gemcitabine-

(56) References Cited

OTHER PUBLICATIONS

Refractory Pancreatic Cancer: Outcomes From the CONKO-003 Trial," J Clin Oncol. 32(23):2423-9 (2014).
Oh S, et al., "Pilot Study of Irinotecan/Oxaliplatin (IROX) Combination Chemotherapy for Patients with Gemcitabine-and 5-Fluorouracil-Refractory Pancreatic Cancer," Invest New Drugs. 28(3):343-9 (2010), Epub May 15, 2009.
Ohkawa S, et al., "Randomised Phase II Trial of S-1 Plus Oxaliplatin vs S-1 in Patients with Gemcitabine-Refractory Pancreatic Cancer," Br J Cancer. 112(9):1428-34 (2015).
Okusaka T, et al., "Phase II Study of FOLFIRINOX for Chemotherapy-Naïve Japanese Patients with Metastatic Pancreatic Cancer," Cancer Sci. 105(10):1321-6 (2014).
Onivyde [MM-398] package insert, revision Oct. 22, 2015, retrieved from http://www.accessdata.fda.gov/drugsatfda_docs/label/2015/207793lbl.pdf, 18 pages.
Oxaliplatin package insert, revision Nov. 2013, retrieved from https://www.accessdata.fda.gov/drugsatfda_docs/label/2013/022160s009lbl.pdf, 43 pages.
Peddi P, et al., "Multi-Institutional Experience with FOLFIRINOX in Pancreatic Adenocarcinoma," Journal of the Pancreas (JOP). 13(5):497-501 (2012), online access, 11 printed pages.
Petrioli R, et al., "Gemcitabine, Oxaliplatin, and Capecitabine (GEMOXEL) Compared with Gemcitabine Alone in Metastatic Pancreatic Cancer: A Randomized Phase II Study," Cancer Chemother Pharmacol. 75(4):683-90 (2015).
Qin B, et al., "In-vitro Schedule-Dependent Interaction Between Oxaliplatin and 5-Fluorouracil in Human Gastric Cancer Cell Lines," Anti-Cancer Drugs. 17(4):445-53 (2006).
Rombouts S, et al., "FOLFIRINOX in Locally Advanced and Metastatic Pancreatic Cancer: A Single Centre Cohort Study," J Cancer. 7(13):1861-6 (2016).
Shimada S, et al., "Irinotecan Plus Low-Dose Cisplatin for α-Fetoprotein-Producing Gastric Carcinoma with Multiple Liver Metastases: Report of Two Cases," Surg Today. 32(12):1075-80 (2002).
Slatter J, et al., "Pharmacokinetics, Metabolism, and Excretion of Irinotecan (CPT-11) Following I.V. Infusion of [14C]CPT-11 in Cancer Patients," Drug Metab Dispos. 28(4):423-33 (2000).
Stein S, et al., "Final Analysis of a Phase II Study of Modified FOLFIRINOX in Locally Advanced and Metastatic Pancreatic Cancer," Br J Cancer 114(7):737-43 (2016).
Tanaka R, et al., "Synergistic Interaction Between Oxaliplatin and SN-38 in Human Gastric Cancer Cell Lines In Vitro," Oncol Rep. 14(3):683-8 (2005).
Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
Van Cutsem E, et al., "A Phase Ib Dose-Escalation Study of Erlotinib, Capecitabine and Oxaliplatin in Metastatic Colorectal Cancer Patients," Ann Oncol. 19(2):332-9 (2008), Epub Nov. 6, 2007.
Wainberg Z, et al., "A phase 1/2, open-label, dose-expansion study of liposomal irinotecan (nal-IRI) plus 5-fluorouracil/leucovorin (5-FU/LV) and oxaliplatin (OX) in patients with previously untreated metastatic pancreatic cancer (mPAC)." Presentation presented at the ESMO 21st World Congress on Gastrointestinal Cancer, Barcelona, Spain, Jul. 3-6, 2019, 13 pages.
Wainberg Z, et al., Abstract SO-005: "A Phase 1/2, Open-Label, Dose-Expansion Study of Liposomal Irinotecan (NaI-IRI) Plus 5-Fluorouracil/Leucovorin (5-FU/LV) and Oxaliplatin (OX) in Patients with Previously Untreated Metastatic Pancreatic Cancer," Ann Oncol. 30(Suppl 4): doi:10.1093/annonc/mdz157 | iv123 (Jul. 2019), 1 page.
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).

Ychou, M, et al., "An Open Phase I Study Assessing the Feasibility of the Triple Combination: Oxaliplatin Plus Irinotecan Plus Leucovorin/5-Fluorouracil Every 2 Weeks in Patients With Advanced Solid Tumors," Ann Oncol. 14(3):481-9 (2003).
Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
Alberts S, et al. "Gemcitabine and Oxaliptatin for Metastatic Pancreatic Adenocarcinoma: A North Central Cancer Treatment Group Phase II Study," Ann Oncol. 14(4):580-5 (2003).
Alcindor T, et al., "Oxaliplatin: A Review in the Era of Molecularly Targeted Therapy," Curr Oncol. 18(1):18-25 (2011).
Amodeo S, et al., "Can we downstage locally advanced pancreatic cancer to resectable? A phase I/II study of induction oxaliplatin and 5-FU chemoradiation," J Gastrointest Oncol. 9(5):922-35 (2018).
Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).
Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.
Cantore M, et al., "Combined Irinotecan and Oxaliplatin in Patients with Advanced Pre-Treated Pancreatic Cancer," Oncology 67(2):93-7 (2004).
Chiesa M, et al., "A Pilot Phase II Study of Chemotherapy with Oxaliplatin, Folinic Acid, 5-Fluorouracil and Irinotecan in Metastatic Gastric Cancer," Tumori. 93(3):244-7 (2007).
Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 8 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT00940758: Jul. 16, 2009 update, "Pharrnacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Feb. 3, 2010 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Mar. 1, 2012 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01359007: May 23, 2011 update, "A Phase II Study Evaluating the Rate of R0 Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.

(56) References Cited

OTHER PUBLICATIONS

Clinical Trials Identifier NCT01359007: May 28, 2015 update, "A Phase II Study Evaluating the Rate of R0 Resection (Microscopically Negative Margins) After Induction Therapy With 5-Fluorouracil, Leucovorin, Oxaliplatln, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01446458: Oct. 4, 2011 update, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.
Clinical Trials Identifier NCT01523457: Jan. 31, 2012 update, "Phase II Study of Modified FOLFIRINOX in Advanced Pancreatic Cancer." Retrieved from ClinicalTrials.gov archive, 4 printed pages.
Clinical Trials Identifier NCT01643499: Jul. 17, 2012 update, "A Genotype-guided Dosing Study of mFOLFIRINOX in Previously Untreated Patients with Advanced Gastrointestinal Malignancies." Retrieved from ClinicalTrials.gov archive, 5 printed pages.
Clinical Trials Identifier NCT01688336: Sep. 18, 2012 update, "Phase II Single Arm Clinical Trial of FOLFIRINOX for Unresectable Locally Advanced and Borderline Resectable Pancreatic Cancer." Retrieved from ClinicalTrials.gov archive, 5 printed pages.
Clinical Trials Identifier NCT01771146: Jan. 17, 2013 update, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.
Clinical Trials Identifier NCT01926197: Aug. 19, 2013 update, "A Randomized Phase III Study Evaluating Modified FOLFIRINOX (mFFX) With or Without Stereotactic Body Radiotherapy (SBRT) in the Treatment of Locally Advanced Pancreatic Cancer." Retrieved from ClinicalTrials.gov archive, 3 printed pages.
Clinical Trials Identifier NCT01992705: Nov. 22, 2013 update, "Neoadjuvant FOLFIRINOX and Stereotactic Body Radiotherapy (SBRT) Followed by Definitive Surgery for Patients with Borderline Resectable Adenocarcinoma: A Single-Arm Pilot Study." Retrieved from ClinicalTrials.gov archive, 5 printed pages.
Clinical Trials Identifier NCT02028806: Jan. 6, 2014 update, "Phase II Trial to Investigate the Efficacy and Safety of mFOLFIRINOX in Patients with Metastatic Pancreatic Cancer in China." Retrieved from ClinicalTrials.gov archive, 4 printed pages.
Clinical Trials Identifier NCT02047474: Jan. 27, 2014 update, "Phase II Study of Peri-Operative Modified Folfirinox in Localized Pancreatic Cancer." Retrieved from ClinicalTrials.gov archive, 5 printed pages.
Clinical Trials Identifier NCT02109341: Apr. 8, 2014 update, "Phase I/II Study to Evaluate Nab-paclitaxel in Substitution of CPT11 or Oxaliplatin in FOLFIRINOX Schedule as First Line Treatment on Metastatic Pancreatic Cancer." Retrieved from ClinicalTrials.gov archive, 5 printed pages.
Clinical Trials Identifier NCT02143219: May 20, 2014 update, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma." Retrieved from ClinicalTrials.gov archive, 5 printed pages.
Clinical Trials Identifier NCT02148549: May 27, 2014 update, "The Pilot Study of Neoadjuvant Chemotherapy of FIRINOX for Patients With Borderline Resectable Pancreatic Cancer" Retrieved from ClinicalTrials.gov archive, 4 printed pages.
Clinical Trials Identifier NCT02896803: Sep. 11, 2016 update, "A Phase II Trial of Bolus Fluorouracil and Oxaliplatin (mFLOX) as First-line Regimen for Patients With Unresectable or Metastatic Pancreatic Cancer Not Eligible for Infusional Fluorouracil, Irinotecan and Oxaliplatin." Retrieved from ClinicalTrials.gov archive, 4 printed pages.

Clinical Trials Identifier NCT02896907: Sep. 11, 2016 update, "A Pilot Study of Intravenous Ascorbic Acid and Folfirinox in the Treatment of Advanced Pancreatic Cancer." Retrieved from ClinicalTrials.gov archive, 4 printed pages.
Conroy T, et al., "FOLFIRINOX versus Gemcitabine for Metastatic Pancreatic Cancer," N Engl J Med. 364(19):1817-25 (2011).
Conroy T, et al., "Irinotecan Plus Oxaliplatin and Leucovorin-Modulated Fluorouracil in Advanced Pancreatic Cancer—A Groupe Tumeurs Digestives of the Fédération Nationale des Centres de Lutte Contre le Cancer Study," J Clin Oncol. 23(6):1228-36 (2005).
Dean A, et al., "A Phase 2, Open-Label Dose-Exploration Study of Liposomal Irinotecan (nal-IRI) Plus 5-Flurouracil/Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster handout at the Gastrointestinal Cancers Symposium ASCO 2016, 2 pages.
Delord J, et al., "Population Pharmacokinetics of Oxaliplatin," Cancer Chemother Pharmacol. 51(2):127-31 (2003), Epub Dec. 4, 2002.
Ducreux M, et al., "Randomized Phase II Study Evaluating Oxaliplatin Alone, Oxaliplatin Combined with Infusional 5-FU, and Infusional 5-FU Alone in Advanced Pancreatic Carcinoma Patients," Ann Oncol. 15(3): 467-73 (2004).
ELOXATIN package insert, revision Dec. 28, 2011, retrieved from https://www.accessdata.fda.gov/drugsatfda_docs/label/2011/021492s012lbl.pdf, 51 pages.
Extra J, et al., "Phase I Study of Oxaliplatin in Patients with Advanced Cancer," Cancer Chemother Pharmacol. 25 (4):299-303 (1990).
Fischel J, et al., "Ternary Combination of Irinotecan, Fluorouracil-Folinic Acid and Oxaliplatin: Results on Human Colon Cancer Cell Lines," Br J Cancer 84(4):579-85 (2001).
Gaddy D, "Preclinical Anti-tumor Activity of Nanoliposomal Irinotecan (Nal-IRI, MM-398) + 5-FU + Oxaliplatin in Pancreatic Cancer." Abstract presented at AACR 2016, 1 page.
Gaddy D, et al., "Preclinical Anti-tumor Activity of Nanoliposomal Irinotecan (nal-IRI, MM-398) + 5-FU + Oxaliplatin in Pancreatic Cancer." Poster presented at AACR 2016, 5 pages.
Guichard S, et al., "Combination of Oxaliplatin and Irinotecan on Human Colon Cancer Cell Lines: Activity In Vitro and In Vivo," Anticancer Drugs. 12(9):741-51 (2001).
Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).
Lee M, et al., "5-Fluorouracil/Leucovorin Combined wtih Irinotecan and Oxaliplatin (FOLFIRINOX) as Second-Line Chemotherapy in Patients with Advanced Pancreatic Cancer Who Have Progressed on Gemcitabine-Based Therapy," Chemotherapy. 59(4):273-9 (2013).
Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer. 93(2):190-4 (2005).
Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23 (15):3509-16 (2005).
Mahaseth H, et al., "Modified FOLFIRINOX Regimen With Improved Safety and Maintained Efficacy in Pancreatic Adenocarcinoma," Pancreas. 42(8):1311-5 (2013).
Mathé G, et al., "A Phase I Trial of Trans-1-diamino-cyclohexane Oxalate-platinum (I-OHP)," Biomed Pharmacother, 40(10):372-376 (1986).

(56) References Cited

OTHER PUBLICATIONS

Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).
Maxwell F, et al., "CA 19-9 levels in patients with metastatic pancreatic adenocarcinoma receiving first-line therapy with liposomal irinotecan plus 5-fluorouracil/leucovorin and oxaliplatin (NAPOX)," Poster presented at the American Association for Cancer Research (AACR) Special Conference on Pancreatic Cancer: Advances in Science and Clinical Care, Sep. 6-9, 2019, Boston, MA, 7 pages.
U.S. Appl. No. 11/121,294, filed May 2, 2005, U.S. Pat. No. 8,147,867, Issued.
U.S. Appl. No. 11/601,451, filed Nov. 17, 2006, U.S. Pat. No. 8,658,203, Issued.
U.S. Appl. No. 13/416,204, filed Mar. 9, 2012, U.S. Pat. No. 8,329,213, Issued.
U.S. Appl. No. 13/654,373, filed Oct. 17, 2012, U.S. Pat. No. 8,703,181, Issued.
U.S. Appl. No. 14/151,632, filed Jan. 9, 2014, Abandoned.
U.S. Appl. No. 14/175,365, filed Feb. 7, 2014, U.S. Pat. No. 8,992,970, Issued.
U.S. Appl. No. 14/632,422, filed Feb. 26, 2015, U.S. Pat. No. 9,717,723, Issued.
U.S. Appl. No. 14/879,302, filed Oct. 9, 2015, U.S. Pat. No. 9,730,891, Issued.
U.S. Appl. No. 14/879,358, filed Oct. 9, 2015, Abandoned.
U.S. Appl. No. 14/964,239, filed Dec. 9, 2015, Abandoned.
U.S. Appl. No. 14/965,140, filed Dec. 10, 2015, U.S. Pat. No. 9,724,303, Issued.
U.S. Appl. No. 14/966,458, filed Dec. 11, 2015, U.S. Pat. No. 9,782,349, Issued.
U.S. Appl. No. 14/979,666, filed Dec. 28, 2015, Abandoned.
U.S. Appl. No. 15/227,561, filed Aug. 3, 2016, Abandoned.
U.S. Appl. No. 15/227,631, filed Aug. 3, 2016, Abandoned.
U.S. Appl. No. 15/213,127, filed Jul. 18, 2016, Abandoned.
U.S. Appl. No. 15/296,536, filed Oct. 18, 2016, U.S. Pat. No. 9,737,528, Issued.
U.S. Appl. No. 15/363,761, filed Nov. 29, 2016, U.S. Pat. No. 10,413,510, Issued.
U.S. Appl. No. 15/363,923, filed Nov. 29, 2016, Abandoned.
U.S. Appl. No. 15/363,978, filed Nov. 29, 2016, U.S. Pat. No. 10,350,201, Issued.
U.S. Appl. No. 15/364,021, filed Nov. 29, 2016, Abandoned.
U.S. Appl. No. 15/664,976, filed Jul. 31, 2017, Published.
U.S. Appl. No. 15/896,389, filed Feb. 14, 2018, Published.
U.S. Appl. No. 15/896,436, filed Feb. 14, 2018, Abandoned.
U.S. Appl. No. 14/406,776, filed Dec. 10, 2014, U.S. Pat. No. 9,452,162, Issued.
U.S. Appl. No. 14/812,950, filed Jul. 29, 2015, U.S. Pat. No. 9,339,497, Issued.
U.S. Appl. No. 14/844,500, filed Sep. 3, 2015, U.S. Pat. No. 9,364,473, Issued.
U.S. Appl. No. 14/851,111, filed Sep. 11, 2015, U.S. Pat. No. 9,492,442, Issued.
U.S. Appl. No. 15/059,640, filed Mar. 3, 2016, Abandoned.
U.S. Appl. No. 15/241,128, filed Aug. 19, 2016, U.S. Pat. No. 9,717,724, Issued.
U.S. Appl. No. 15/341,377, filed Nov. 2, 2016, Abandoned.
U.S. Appl. No. 15/341,619, filed Nov. 2, 2016, Abandoned.
U.S. Appl. No. 15/652,513, filed Jul. 18, 2017, Abandoned.
U.S. Appl. No. 15/664,930, filed Jul. 31, 2017, Abandoned.
U.S. Appl. No. 16/012,351, filed Jun. 19, 2018, Published.
U.S. Appl. No. 16/012,372, filed Jun. 19, 2018, Published.
U.S. Appl. No. 14/964,571, filed Dec. 9, 2015, Abandoned.
U.S. Appl. No. 15/375,039, filed Dec. 9, 2016, Abandoned.
U.S. Appl. No. 15/928,649, filed Mar. 22, 2018, Abandoned.
U.S. Appl. No. 16/036,885, filed Jul. 16, 2018, Abandoned.
U.S. Appl. No. 16/805,304, filed Feb. 28, 2020, Pending.
U.S. Appl. No. 16/711,072, filed Dec. 11, 2019, Pending.
U.S. Appl. No. 15/337,274, filed Oct. 28, 2016, U.S. Pat. No. 9,895,365, Issued.
U.S. Appl. No. 15/852,551, filed Dec. 22, 2017, U.S. Pat. No. 10,478,428, Issued.
U.S. Appl. No. 16/586,609, filed Sep. 27, 2019, Pending.
U.S. Appl. No. 15/241,106, filed Aug. 19, 2016, Abandoned.
U.S. Appl. No. 15/809,815, filed Nov. 10, 2017, Published.
U.S. Appl. No. 15/403,441, filed Jan. 11, 2017, Abandoned.
U.S. Appl. No. 15/331,648, filed Oct. 21, 2016, Abandoned.
U.S. Appl. No. 15/331,393, filed Oct. 21, 2016, Abandoned.
U.S. Appl. No. 15/331,318, filed Oct. 21, 2016, Abandoned.
U.S. Appl. No. 15/645,645, filed Jul. 10, 2017, Abandoned.
U.S. Appl. No. 15/655,592, filed Jul. 20, 2017, Abandoned.
U.S. Appl. No. 15/661,868, filed Jul. 27, 2017, Abandoned.
U.S. Appl. No. 15/908,443, filed Feb. 28, 2018, Abandoned.
U.S. Appl. No. 15/768,352, filed Apr. 13, 2018, U.S. Pat. No. 10,456,360, Issued.
U.S. Appl. No. 15/967,633, filed May 1, 2018, Abandoned.
U.S. Appl. No. 15/967,638, filed May 1, 2018, Abandoned.
U.S. Appl. No. 15/501,394, filed Jul. 12, 2019, Published.
U.S. Appl. No. 15/567,902, filed Sep. 11, 2019, Published.
U.S. Appl. No. 15/598,633, filed May 18, 2017, Abandoned.
U.S. Appl. No. 15/948,571, filed Apr. 9, 2018, Abandoned.
U.S. Appl. No. 16/302,050, filed Nov. 15, 2018, Pending.
U.S. Appl. No. 15/346,436, filed Apr. 30, 2019, Pending.
U.S. Appl. No. 11/121,294, filed Aug. 17, 2009 Nonfinal Office Action, 33 pages.
U.S. Appl. No. 11/121,294, filed Mar. 12, 2010 Final Office Action, 15 pages.
U.S. Appl. No. 11/121,294, filed May 19, 2010 Advisory Action, 3 pages.
U.S. Appl. No. 11/121,294, filed Aug. 4, 2010 Nonfinal Office Action, 14 pages.
U.S. Appl. No. 11/121,294, filed Dec. 6, 2010 Final Office Action, 17 pages.
U.S. Appl. No. 11/121,294, filed Apr. 13, 2011 Nonfinal Office Action, 10 pages.
U.S. Appl. No. 11/121,294, filed Jul. 12, 2011 Examiner Interview Summary, 3 pages.
U.S. Appl. No. 11/121,294, filed Nov. 23, 2011 Final Office Action, 20 pages.
U.S. Appl. No. 11/601,451, filed Jan. 11, 2010 Nonfinal Office Action, 14 pages.
U.S. Appl. No. 11/601,451, filed Aug. 27, 2010 Final Office Action, 17 pages.
U.S. Appl. No. 11/601,451, filed Jul. 12, 2011 Examiner Interview Summary, 4 pages.
U.S. Appl. No. 13/416,204, filed May 8, 2012 Pre-Interview Communication, 4 pages.
U.S. Appl. No. 13/416,204, filed Jun. 29, 2012 Interview Summary and First Action Interview Office Action, 6 pages.
U.S. Appl. No. 13/654,373, filed Aug. 12, 2013 Nonfinal Office Action and Interview Summary, 10 pages.
U.S. Appl. No. 14/151,632, filed Apr. 18, 2016 Nonfinal Office Action, 9 pages.
U.S. Appl. No. 14/175,365, filed Jun. 26, 2014 Nonfinal Office Action, 20 pages.
U.S. Appl. No. 14/406,776, filed Feb. 26, 2016 Nonfinal Office Action, 9 pages.
U.S. Appl. No. 14/632,422, filed Jan. 10, 2017 Nonfinal Office Action, 18 pages.
U.S. Appl. No. 14/812,950, filed Oct. 2, 2015 Pre-Interview Communication, 3 pages.
U.S. Appl. No. 14/844,500, filed Dec. 16, 2015 Nonfinal Office Action, 25 pages.
U.S. Appl. No. 14/851,111, filed Feb. 25, 2016 Nonfinal Office Action, 13 pages.
U.S. Appl. No. 14/879,302, filed Aug. 15, 2016 Nonfinal Office Action, 30 pages.
U.S. Appl. No. 14/879,302, filed Dec. 15, 2016 Nonfinal Office Action, 14 pages.
U.S. Appl. No. 14/879,358, filed Dec. 28, 2015 Nonfinal Office Action, 20 pages.

(56) References Cited

OTHER PUBLICATIONS

U.S. Appl. No. 14/879,358, filed Jul. 12, 2016 Nonfinal Office Action, 14 pages.
U.S. Appl. No. 14/964,239, filed Nov. 4, 2016 Nonfinal Office Action, 21 pages.
U.S. Appl. No. 14/964,239, filed Apr. 26, 2017 Examiner Interview Summary, 2 pages.
U.S. Appl. No. 14/964,239, filed Jun. 21, 2017 Nonfinal Office Action, 16 pages.
U.S. Appl. No. 14/964,239, filed Dec. 11, 2017 Nonfinal Office Action, 15 pages.
U.S. Appl. No. 14/964,571, filed Feb. 13, 2017 Nonfinal Office Action, 8 pages.
U.S. Appl. No. 14/964,571, filed Nov. 1, 2017 Final Office Action, 14 pages.
U.S. Appl. No. 14/964,571, filed Sep. 25, 2018 Nonfinal Office Action, 12 pages.
U.S. Appl. No. 14/964,571, filed Jun. 12, 2019 Final Office Action, 15 pages.
U.S. Appl. No. 14/965,140, filed Mar. 10, 2016 Nonfinal Office Action, 24 pages.
U.S. Appl. No. 14/965,140, filed Jul. 13, 2016 Interview Summary and Nonfinal Office Action, 14 pages.
U.S. Appl. No. 14/965,140, filed Dec. 19, 2016 Nonfinal Office Action, 9 pages.
U.S. Appl. No. 14/966,458, filed Dec. 6, 2016 Nonfinal Office Action, 34 pages.
U.S. Appl. No. 14/966,458, filed Apr. 27, 2017 Examiner Interview Summary, 2 pages.
U.S. Appl. No. 14/979,666, filed Dec. 9, 2016 Nonfinal Office Action, 20 pages.
U.S. Appl. No. 15/059,640, filed Dec. 2, 2016 Nonfinal Office Action, 9 pages.
U.S. Appl. No. 15/227,561, filed Jul. 14, 2017 Nonfinal Office Action, 25 pages.
U.S. Appl. No. 15/227,561, filed Apr. 26, 2018 Nonfinal Office Action, 13 pages.
U.S. Appl. No. 15/227,561, filed Dec. 10, 2018 Final Office Action, 18 pages.
U.S. Appl. No. 15/227,631, filed Jul. 17, 2017 Nonfinal Office Action, 24 pages.
U.S. Appl. No. 15/227,631, filed Apr. 10, 2018 Nonfinal Office Action, 13 pages.
U.S. Appl. No. 15/227,631, filed Aug. 31, 2018 Nonfinal Office Action, 15 pages.
U.S. Appl. No. 15/227,631, filed Dec. 19, 2018 Final Office Action, 15 pages.
U.S. Appl. No. 15/241,106, filed Oct. 28, 2016 Pre-Interview Communication, 4 pages.
U.S. Appl. No. 15/241,106, filed Dec. 29, 2016 Nonfinal Office Action, 15 pages.
U.S. Appl. No. 15/241,106, filed Jul. 10, 2017 Final Office Action, 16 pages.
U.S. Appl. No. 15/241,128, filed Nov. 25, 2016 Nonfinal Office Action, 6 pages.
U.S. Appl. No. 15/296,536, filed Mar. 8, 2017 Nonfinal Office Action, 6 pages.
U.S. Appl. No. 15/331,393, filed Jan. 19, 2017 Pre-Interview Communication, 4 pages.
U.S. Appl. No. 15/331,393, filed Mar. 20, 2017: Examiner's Interview Summary and First Action Interview Office Action Summary, 5 pages.
U.S. Appl. No. 15/331,648, filed Jan. 19, 2017 Pre-Interview Communication, 4 pages.
U.S. Appl. No. 15/331,648, filed Mar. 17, 2017 Examiner's Interview Summary, 3 pages.
U.S. Appl. No. 15/337,274, filed Mar. 24, 2017 Nonfinal Office Action, 10 pages.
U.S. Appl. No. 15/341,377, filed Jan. 30, 2017 Nonfinal Office Action, 12 pages.
U.S. Appl. No. 15/341,377, filed Apr. 18, 2017 Final Office Action, 13 pages.
U.S. Appl. No. 15/341,619, filed Apr. 3, 2017 Pre-Interview Communication, 3 pages.
U.S. Appl. No. 15/363,761, filed Jan. 18, 2017 Nonfinal Office Action, 15 pages.
U.S. Appl. No. 15/363,761, filed Aug. 1, 2017 Final Office Action, 18 pages.
U.S. Appl. No. 15/363,761, filed Dec. 14, 2017 Examiner Interview Summary, 3 pages.
U.S. Appl. No. 15/363,923, filed Feb. 1, 2017 Nonfinal Office Action, 24 pages.
U.S. Appl. No. 15/363,923, filed Sep. 13, 2017 Final Office Action, 29 pages.
U.S. Appl. No. 15/363,978, filed Feb. 7, 2017 Nonfinal Office Action, 16 pages.
U.S. Appl. No. 15/363,978, filed Aug. 21, 2017 Final Office Action, 19 pages.
U.S. Appl. No. 15/363,978, filed Dec. 14, 2017 Examiner Interview Summary, 3 pages.
U.S. Appl. No. 15/364,021, filed Mar. 9, 2017 Nonfinal Office Action, 18 pages.
U.S. Appl. No. 15/364,021, filed Oct. 4, 2017 Final Office Action, 20 pages.
U.S. Appl. No. 15/375,039, filed Feb. 16, 2018 Nonfinal Office Action, 11 pages.
U.S. Appl. No. 15/403,441, filed Dec. 21, 2017 Nonfinal Office Action, 9 pages.
U.S. Appl. No. 15/645,645, filed Dec. 1, 2017 Nonfinal Office Action, 16 pages.
U.S. Appl. No. 15/652,513, filed Dec. 20, 2017 Nonfinal Office Action, 13 pages.
U.S. Appl. No. 15/661,868, filed Dec. 1, 2017 Nonfinal Office Action, 15 pages.
U.S. Appl. No. 15/664,930, filed Dec. 20, 2017 Nonfinal Office Action, 7 pages.
U.S. Appl. No. 15/664,976, filed Sep. 11, 2018 Nonfinal Office Action, 23 pages.
U.S. Appl. No. 15/664,976, filed May 21, 2019 Nonfinal Office Action, 11 pages.
U.S. Appl. No. 15/664,976, filed Nov. 4, 2019 Nonfinal Office Action, 9 pages.
U.S. Appl. No. 15/768,352, filed Feb. 14, 2019 Non-Final Office Action, 15 pages.
U.S. Appl. No. 15/768,352, filed Jun. 3, 2019 Examiner Interview Summary, 5 pages.
U.S. Appl. No. 15/768,352, filed Jun. 12, 2019 Notice of Allowance including Examiner's Reasons for Allowance and Examiner Interview Summary, 21 pages.
U.S. Appl. No. 15/768,352, filed Jul. 12, 2019 Examiner Interview Summary, 4 pages.
U.S. Appl. No. 15/768,352, filed Aug. 28, 2019 Notice of Allowance including Examiner's Reasons for Allowance and Examiner Interview Summary, 16 pages.
U.S. Appl. No. 15/809,815, filed Mar. 6, 2018 Nonfinal Office Action, 12 pages.
U.S. Appl. No. 15/809,815, filed Sep. 11, 2018 Final Office Action, 14 pages.
U.S. Appl. No. 15/809,815, filed Jul. 8, 2019 Non-Final Office Action, 13 pages.
U.S. Appl. No. 15/809,815, filed Feb. 27, 2020 Final Office Action, 16 pages.
U.S. Appl. No. 15/852,551, filed Jan. 11, 2019 Nonfinal Office Action, 5 pages.
U.S. Appl. No. 15/896,389, filed Jul. 18, 2019 Nonfinal Office Action, 24 pages.
U.S. Appl. No. 15/896,389, filed Jan. 31, 2020 Final Office Action, 28 pages.
U.S. Appl. No. 15/896,389, filed Mar. 26, 2020 Examiner Interview Summary and Applicant slides, 22 pages.
U.S. Appl. No. 15/896,389, filed Apr. 9, 2020 Advisory Action, 3 pages.

(56) References Cited

OTHER PUBLICATIONS

U.S. Appl. No. 15/896,436, filed Jul. 5, 2019 Nonfinal Office Action, 18 pages.
U.S. Appl. No. 15/967,638, filed Jan. 14, 2019 Nonfinal Office Action, 14 pages.
U.S. Appl. No. 16/012,351, filed Mar. 8, 2019 Non-Final Office Action, 13 pages.
U.S. Appl. No. 16/012,351, filed Jan. 7, 2020 Final Office Action, 9 pages.
U.S. Appl. No. 16/012,372, filed Mar. 8, 2019 Non-Final Office Action, 8 pages.
U.S. Appl. No. 16/012,372, filed Jan. 7, 2020 Final Office Action, 9 pages.
U.S. Appl. No. 16/036,885, filed Sep. 3, 2019 Non-Final Office Action, 15 pages.
Abraxane package insert, revision Dec. 23, 2011, retrieved from https://www.accessdatafda.gov/dugsatfda_docs/label/2011/021660s025s026s029lbl.pdf, 13 pages.
Abraxane package insert, revision Jul. 21, 2015, retrieved from https://www.accessdata.fda.gov/drugsalfda_docs/ label1/2015/021660s041lbl.pdf, 24 pages.
Adiwijaya B, et al., "Population Pharmacokinetics of Liposomal Irinotecan in Patients With Cancer," Clin Pharmacol Ther. 102(6):997-1005 (2017).
Ahmadi, et al., "Antibody-Targeted Delivery of Doxorubicin Entrapped in Sterically Stabilized Liposomes Can Eradicate Lung Cancer in Mice," Cancer Res. 53(7):1484-8 (1993).
Alagoz M, et al., "DNA Repair and Resistance to Topoisomerase I Inhibitors: Mechanisms, Biomarkers and Therapeutic Targets," Curr Med Chem. 19(23):3874-85 (2012).
Alfert M, et al., "A Selective Staining Method for the Basic Proteins of Cell Nuclei," Proc Natl Acad Sci USA. 39(10):991-9 (1953).
American Chemical Society (ACS), http://www.cancer.org/cancer/pancreaticcancer/detailedguide/pancreatic-cancer-what-is-pancreatic-cancer, retrieved Dec. 10, 2017, 7 printed pages.
American Chemical Society (ACS), http://www.cancer.org/cancer/pancreaticcancer/detailedguide/pancreatic-cancer-what-is-pancreatic-cancer, retrieved Dec. 1, 2016, 4 printed pages.
Anders C, et al., "Phase 1 Expansion Study of Irinotecan Liposome Injection (nal-IRI) in Patients with Metastatic Breast Cancer (mBC): Findings from the Cohort with Active Brain Metastasis (BM)." Presentation presented at the Society for Neuro-Oncology Inaugural Conference on Brain Metasteses, Aug. 16-17, 2019, New York, NY, 11 pages.
Anders C, et al., Abstract TRLS-06. "Phase 1 Expansion Study of Irinotecan Liposome Injection (nal-IRI) in Patients with Metastatic Breast Cancer (mBC): Findings from the Cohort with Active Brain Metastasis (BM)," Neuro-Oncology Advances. 1(Suppl 1):i9 doi.org/10.1093/noajnl/vdz014.039 (2019).
Ardizzoni a, et al., "Topotecan, A New Active Drug in the Second-Line Treatment of Small-Cell Lung Cancer: A Phase II Study in Patients with Refractory and Sensitive Disease," J Clin Oncol. 15(5):2090-6 (1997).
Author Unknown, "From Antinutrient to Phytonutrient: Phytic Acid Gains Respect." HighBeam Research, Environmental Nutrition, Apr. 1, 2004, 2 printed pages. URL: http://www.highbeam.com/doc/1G1-116341390.html/print (accessed Nov. 4, 2011).
Azrak R, et al., "Therapeutic Synergy Between Irinotecan and 5-Fluorouracil against Human Tumor Xenografts," Clin Cancer Res. 10(3):1121-9 (2004).
Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).
Bendell J, et al., "Treatment Patterns and Clinical Outcomes in Patients With Metastatic Colorectal Cancer Initially Treated with FOLFOX-Bevacizumab or FOLFIRI-Bevacizumab: Results From ARIES, a Bevacizumab Observational Cohort Study," Oncologist. 17(12):1486-95 (2012).
Bernards N, et al., "Liposomal Irinotecan Achieves Significant Survival and Tumor Burden Control in a Triple Negative Breast Cancer Model of Spontaneous Metastasis," Mol Pharm. 15(9):4132-8 (2018).
Bernards N, et al., "Liposomal Irinotecan Injection (nal-IRI) Achieves Significant Survival and Tumor Burden Control in a Triple Negative Breast Cancer Model of Spontaneous Metastasis," Poster presented at the World Molecular maging Congress Sep. 13-16, 2017, Philadelphia, Pennsylvania, 5 pages.
Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011).
Burris H, et al., "Phase II Trial of Oral Rubitecan in Previously Treated Pancreatic Cancer Patients," Oncologist. 10(3):183-90 (2005).
Butt R, et al., "Posffractionation for Enhanced Proteomic Analyses: Routine Electrophoretic Methods Increase the Resolution of Standard 2D-Page.," J Proteome Res. 4(3):982-91 (2005).
Camptosar package insert, revised May 16, 2002, 37 pages.
Camptosar package insert, revision Dec. 19, 2014, retrieved from https://www.accessdata.fda.gov/drugsatfda_docs/label/2014/020571s048lbl.pdf, initial U.S. approval 1996, 40 printed pages.
Camptosar package insert, revision May 14, 2010, retrieved from https://www.accessdata.fda.gov/drugsatfda_docs/label/2010/020571s0315032s0335036s037lbl.pdf, 37 pages.
Cassileth P, et al., "Antiemetic Efficacy of Dexamethasone Therapy in Patients Receiving Cancer Chemotherapy," Arch Intern Med. 143(7):1347-9 (1983).
Cereda S, et al., "XELIRI or FOLFIRI as Salvage Therapy in Advanced Pancreatic Cancer," Anticancer Res. 30(11):4785-90 (2010).
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Cancer Res.74(19 Suppl): Abstract 4626 (2014), 2 printed pages.
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Poster presented at AACR Annual Meeting Apr. 5-9, 2014, 6 pages.
Chan D, et al., "PEPO2 (Liposome Irinotecan) Effectively Inhibits Human Lung Squamous Cell Carcinoma and Small Cell Lung Cancers in Subcutaneous and Orthotopic Xenograft Tumor Models," J Thoracic Oncology. 6(6)(Suppl 2): 3420-1 (2011).
Chan D, et al., "PEPO2 (Liposome Irinotecan) Effectively Inhibits Human Squamous Cell Carcinoma and Small Cell Lung Cancers in Subcutaneous and Orthotopic Xenograft Tumor Models." Presentation at the 14th World Conference on Lung Cancer, 2011, 11 pages.
Chan D, et al., "PEPO2 (Liposome Irinotecan) Effectively Inhibits Human Squamous Cell Carcinoma and Small Cell Lung Cancers in Subcutaneous and Orthotopic Xenograft Tumor Models." Presentation at Santa Monica Lung Cancer Meeting, 2012, 9 pages.
Chang, T, et al., "Phase I Study of Nanoliposomal Irinotecan (PEP02) in Advanced Solid Tumor Patients," Cancer Chemother Pharmacol. 75(3):579-86 (2015).
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster presented at the Gastrointestinal Cancers Symposium of the ASCO meeting of Jan. 21-23, 2016, San Francisco, California, 16 pages.
Chen L, et al., "Effect of Baseline Carbohydrate Antigen 19-9 (CA19-9) Level on Overall Survival (OS) in NAPOLI-1 Trial: a Phase 3 Study of Mm-398 (nal-Iri), with or without 5-Fluorouracil and Leucovorin (5-FU/LV), versus 5-FU/LV in Metastatic Pancreatic Cancer (mPAC) Previously Treated with Gemcitabine-based Therapy." Poster handout at the Gastrointestinal Cancers Symposium of the ASCO meeting of Jan. 21-23, 2016, San Francisco, California, 2 pages.

(56) References Cited

OTHER PUBLICATIONS

Chen L, et al., "Expanded Analyses of NAPOLI-1: Phase 3 Study of MM-398 (nal-IRI), with or without 5-Fluorouracil and Leucovorin, versus 5-Fluorouracil and Leucovorin, in Metastatic Pancreatic Cancer (mPAC) Previously Treated with Gemcitabine-based Therapy." Presented Jan. 15, 2015, ASCO GI, 17 pages.

Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy." Poster presented at the ASCO meeting of May 29-Jun. 2, 2015, Chicago, Illinois, 1 page.

Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 6 printed pages.

Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.

Chen L, et al., "Phase I Study of Liposome Encapsulated Irinotecan (PEP02) in Advanced Solid Tumor Patients," Poster presented at the ASCO meeting of May 30-Jun. 3, 2008, Chicago, Illinois, 9 pages.

Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page.

Chen L, et al., "Safety Across Subgroups in NAPOLI-1: A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 10 pages.

Chen L, et al., Abstract PD-023. "Safety Across Subgroups in NAPOLI-1: A Phase 3 Study of nal-IRI (MM-398) ±-Fuorouracil and Leucovorin (5-FU/LV) Versus 5-FU/LV in Metastatic Pancreatic Cancer (mPAC) Previously Treated with Gemcitabine-Based Therapy." Annals of Oncology. 27(Suppl 2):ii102-ii117 (2016), 1 page.

Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.

Chibaudel B, et al., "PEPCOL: a GERCOR Randomized Phase II Study of Nanoliposomal Irinotecan PEPO2 (MM-398) or Irinotecan with Leucovorin/5-Fluorouracil as Second-Line Therapy in Metastatic Colorectal Cancer", Cancer Med. 5(4):676-83 (2016).

Chibaudel B, et al., "PEPCOL: A Randomized Non-Comparative Phase II Study to Evaluate the Efficacy and Safety of PEPO2 (MM-398) or Irinotecan in Combination with Leucovorin and 5-Fluorouracil as Second-Line Treatment for Patients with Unresectable Metastatic Colorectal Cancer. A GERCOR Study." Poster presented at ASCO 2015, 6 pages.

Chou T, et al., "Effect of Composition on the Stability of Liposomal Irinotecan Prepared by a pH Gradient Method," J Biosci Bioeng. 95(4):405-8 (2003).

Chuang V and M. Suno, "Levoleucovorin as Replacement for Leucovorin in Cancer Treatment," Ann Pharmacother. 46(10):1349-57 (2012).

Clarke J, et al., "A Phase 1 Trial of Intravenous Liposomal Irinotecan in Patients with Recurrent High-Grade Glioma," Cancer Chemother Pharmacol. 79(3):603-10 (2017).

Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.

Zhang Y, et al., "Poly(ADP-ribose) Polymerase and XPF-ERCC1 Participate in Distinct Pathways for the Repair of Topoisomerase I-Induced DNA Damage in Mammalian Cells," Nucleic Acids Res. 39(9):3607-20 (2011).

Zhao M, et al., "Clinical Observation of Irinotecan or Topotecan as Second-Line Chemotherapy on Treating 43 Patients with Small-Cell Lung Cancer," Chin Oncol. 21(2):156-8 (2011), text in Chinese with Tables 1-3 and Figure 1 in English.

Zheng J, et al., "[18F]FAZA-PET Detection of Hypoxia Changes following Anti-cancer Therapy." Poster presented at Annual World Molecular Imaging Congress, Sep. 18-21, 2013, 7 pages.

Zheng J, et al., "Longitudinal Tumor Hypoxia Imaging with [18F[FAZA-PET Provides Early Prediction of Nanoliposomal Irinotecan (nal-IRI) Treatment Activity," EJNMMI Res 5(1):57, 10 pp. (2015).

Zhou X, et al., "Clinical Analysis of Bevacizumab Plus FOLFIRI Regimen as Front-Line Therapy for Chinese Patients with Advanced Colorectal Cancer," J Cancer Ther. 2(4):470-4 (2011).

Znojek P, et al., "Preferential Potentiation of Topoisomerase I Poison Cytotoxicity by PARP Inhibition in S Phase," Br J Cancer. 111(7):1319-26 (2014).

Rahma O, et al., "Second-Line Treatment in Advanced Pancreatic Cancer: A Comprehensive Analysis of Published Clinical Trials," Ann Oncol. 24(8):1972-9 (2013), epub doi:10.1093/annonc/mdt166, May 12, 2013, pp. 1-8.

Ramanathan R, et al., "Correlation between Ferumoxytol Uptake in Tumor Lesions by MRI and Response to Nanoliposomal Irinotecan in Patients with Advanced Solid Tumors: A Pilot Study," Clin Cancer Res. 23(14):3638-48 (2017).

Ramanathan R, et al., "Lesion Characterization with Ferumoxytol MRI in Patients with Advanced Solid Tumors and Correlation with Treatment Response to MM-398, Nanoliposomal Irinotecan (nal-IRI)." Poster presented at EORTC-NCI-AACR International Conference on Molecular Targets and Cancer Therapeutics on Nov. 20, 2014, 7 pages.

Ramanathan R, et al., "Lesion Characterization with Ferumoxytol MRI in Patients with Advanced Solid Tumors and Correlation with Treatment Response to MM-398, Nanoliposomal Irinotecan (nal-IRI)," Abstract No. 261. Eur. J. Cancer, 50:87 (2014).

Ramanathan R, et al., "Pilot Study in Patients with Advanced Solid Tumors to Evaluate Feasibility of Ferumoxytol (FMX) As a Tumor Imaging Agent Prior to MM-398, a Nanoliposomal Irinotecan (nal-IRI)." Poster presented at AACR Annual Meeting 2014, San Diego, CA, 9 pages.

Raymond E, et al., "Multicentre Phase II Study and Pharmacokinetic Analysis of Irinotecan in Chemotherapy-Naive Patients with Glioblastoma," Ann Oncol. 14(4):603-14 (2003).

Reni M, et al., "Salvage Chemotherapy with Mitomycin, Docetaxel, and Irinotecan (MDI Regimen) in Metastatic Pancreatic Adenocarcinoma: A Phase I and II Trial," Cancer Invest. 22(5):688-96 (2004).

Rivory L, et al., "Pharmacokinetic Interrelationships of Irinotecan (CPT-11) and Its Three Major Plasma Metabolites in Patients Enrolled in Phase I/II Trials," Clin Cancer Res. 3(8):1261-6 (1997).

Rothenberg M, et al., "Phase I and Pharmacokinetic Trial of Weekly CPT-11," J Clin Oncol. 11(11):2194-204 (1993).

Sachdev J, et al., "A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398)." Poster presented at 38th Annual San Antonio Breast Cancer Symposium on Dec. 8, 2015, 10 pages.

Sachdev J, et al., "Characterization of Metastatic Breast Cancer Lesions with Ferumoxytol Mri and Clinical Response to MM-398, Nanoliposomal Irinotecan (nal-IRI), in 3 Subjects." Poster presented at San Antonio Breast Cancer Symposium 2014, 8 pages.

Sachdev J, et al., "Characterization of Metastatic Breast Cancer Lesions with Ferumoxytol MRI and Treatment Response to MM-398, Nanoliposomal Irinotecan (nal-IRI)," Cancer Res.75(9 Suppl): Abstract P5-01-06 (2015), 3 printed pages.

Sachdev J, et al., "Phase I Expansion Study of Irinotecan Liposome Injection (nal-IRI) in Patients with Metastatic Breast Cancer (mBC)."

(56) References Cited

OTHER PUBLICATIONS

Poster presented at the American Association for Cancer Research Annual Meeting 2019; Mar. 29-Apr. 3, 2019; Atlanta, GA, 9 printed pages.
Sachdev J, et al., Abstract CT048. "Phase I Expansion Study of Irinotecan Liposome Injection (nal-IRI) in Patients with Metastatic Breast Cancer (mBC)," Cancer Res. In Proceedings of the American Association for Cancer Research 4nnual Meeting 2019; Mar. 29-Apr. 3, 2019; Atlanta, GA. Cancer Res. 2019; 79(13 Suppl):Abstract nr CT048, 4 printed pages.
Sadzuka Y, et al. "Effect of Liposomalization on the Antitumor Activity, Side-Effects and Tissue Distribution of 2PT-11," Cancer Leff. 127(1-2): 99-106 (1998).
Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).
Saito R, et al., "Gadolinium-loaded Liposomes Allow for Real-Time Magnetic Resonance Imaging of Convection-Enhanced Delivery in the Primate Brain," Exp Neurol. 196(2):381-9 (2005).
Saito R, et al., "Tissue Affinity of the Infusate Affects the Distribution vol. During Convection-Enhanced Delivery into Rodent Brains: Implications for Local Drug Delivery," J Neurosci Methods. 154(1-2):225-32 (2006).
Saltz L, et al., "Irinotecan Plus Fluorouracil and Leucovorin for Metastatic Colorectal Cancer. Irinotecan Study Group," N Engl J Med. 343(13):905-14 (2000).
Siegel R, et al., "Cancer Statistics, 2015," CA Cancer J Clin. 65(1):5-29 (2015).
Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014).
Taïeb J., "FOLFIRI.3, A New Regimen Combining 5-Fluorouracil, Folinic Acid and Irinotecan, For Advanced Pancreatic Cancer: Results of an Association des Gastro-Enterologues Oncologues (Gastroenterologist Oncologist Association) Multicenter Phase II Study," Ann Oncol. 18(3):498-503 (2007), epub Dec 8, 2006.
Takahara N, et al., "Uridine Disphosphate Glucuronosyl Transferase 1 Family Polypeptide Al Gene (UGT1A1) Polymorphisms are Associated with Toxicity and Efficacy in Irinotecan Monotherapy for Refractory Pancreatic Cancer," Cancer Chemother Pharmacol. 71(1):85-92 (2013), Epub Sep. 29, 2012.
Tardi P. et al., "Drug Ratio-Dependent Antitumor Activity of Irinotecan and Cisplatin Combinations in Vitro and in Vivo," Mol Cancer Ther. 8(8):2266-75 (2009).
Tentori L, et al., "Influence of MLH1 on Colon Cancer Sensitivity to Poly(ADP-ribose) Polymerase Inhibitor Combined with Irinotecan," Int J Oncol. 43(1):210-8 (2013).
Tsai C, et al., "Nanovector-Based Therapies in Advanced Pancreatic Cancer," J Gastroint Oncol 2(3):185-94 (2011).
Tsubamoto H, et al., "Combination Chemotherapy with Itraconazole for Treating Metastatic Pancreatic Cancer in the Second-line or Additional Setting,". Anticancer Res. 35(7):4191-6 (2015).
U.S. Appl. No. 15/664,976; May 18, 2020 Final Office Action, 11 pages.
U.S. Appl. No. 15/896,389: Jun. 5, 2020 Notice of Allowance including Examiner's Reasons for Allowance and Examiner Interview Summary, 13 pages.
U.S. Appl. No. 16/012,372: Jul. 27, 2020 Non-Final Office Action, 8 pages.
U.S. Appl. No. 16/567,902: Aug. 10, 2020 Final Office Action, 21 pages.
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul, 20, 2006.
Ulrich-Pur H, et al., "Irinotecan Plus Raltitrexed vs Raltitrexed Alone in Patients with Gemcitabine-Pretreated Advanced Pancreatic Adenocarcinoma," Br J Cancer. 88(8):1180-4 (2003).
Ventura M, et al., "Ferumoxytol as an MR Imaging Surrogate Marker of Liposomal Drug Deposition and Longitudinal Efficacy in a Preclinical Model of Breast Cancer." Poster presented at World Molecular Imaging Congress, Sep. 13-16, 2017, Philadelphia, Pennsylvania, 6 pages.
Ventura M, et al., "Imaging-Based Assessment of the Treatment Efficacy of Nanoliposomal Irinotecan (nal-IRI) in a Triple Negative Breast Cancer Model of Spontaneous Metastasis." Poster presented at Annual World Molecular Imaging Congress, Sept 7-10, 2016, 8 pages.
Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).
Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.
Von Pawel J, et al., "Randomized Phase III Trial of Amrubicin Versus Topotecan as Second-Line Treatment for Patients with Small-Cell Lung Cancer," J Clin Oncol. 32(35):4012-9 and appendix (1 page) (2014).
Von Pawel J, et al., "Topotecan Versus Cyclophosphamide, Doxorubicin, and Vincristine for the Treatment of Recurrent Small-Cell Lung Cancer," J Clin Oncol. 17(2):658-67 (1999).
Wagener D, et al., "Phase II Trial of CPT-11 in Patients with Advanced Pancreatic Cancer: An EORTC Early Clinical Trials Group Study," Ann Oncol. 6(2):129-32 (1995).
Wählby C, et al., "Sequential Immunofluorescence Staining and Image Analysis for Detection of Large Numbers of Antigens in Individual Cell Nuclei," Cytometry. 47(1):32-41 (2002).
Wainberg Z, et aL, "First-line liposomal irinotecan + 5-fluorouracil/leucovorin + oxaliplatin in patients with pancreatic ductal adenocarcinoma: long-term follow-up results from a phase 1/2 study." Presentation presented at the ESMO World Congress on Gastrointestinal Cancer, Jul. 1-4, 2020, 13 pages.
Nainberg Z, et al., Abstract LBA-1. "First-line liposomal irinotecan + 5 fluorouracil/leucovorin + oxaliplatin in patients with pancreatic ductal adenocarcinoma: Long-term follow-up results from a phase 1/2 study," Ann Oncol. 31(Suppl 3): S241 doi.org/10.1016/j.annonc.2020.04.076 (2020).
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).
Waterhouse D, et al., "Lipid-Based Nanoformulation of Irinotecan: Dual Mechanism of Action Allows for Combination Chemo/Angiogenic Therapy," Nanomedicine 6(9):1645-54 (2011).
Wilson W, et al., "Targeting Hypoxia in Cancer Therapy," Nat Rev Cancer. 11(6):393-410 (2011).
Yeh B, et al., "Structural Basis for Activation of Fibroblast Growth Factor Signaling by Sucrose Octasulfate," Mol Cell Biol. 22(20):7184-92 (2002).
Yi S, et al, "Irinotecan Monotherapy As Second-Line Treatment in Advanced Pancreatic Cancer," Cancer Chemother Pharmacol. 63(6):1141-5 (2009), Epub Oct. 7, 2008.
Zander S, et al., "EZN-2208 (PEG-SN38) Overcomes ABCG2-Mediated Topotecan Resistance in BRCA1-Deficient Mouse Mammary Tumors," PLoS One. 7(9):345248 (2012), pp. 1-9.
Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).
Nentwich, F., "Doxorubicin Hydrochloride," In Intravenous Therapy: A Comprehensive Application of Intravenous Therapy and Medication Administration at p. 310. Published by Jones & Bartlett Learning, 1990.
Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).
Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective

(56) References Cited

OTHER PUBLICATIONS

Series of 70 Patients." J Clin Oncol. 29: 2011 (Suppl 4; Abstract 272). 2011 Gastrointestinal Cancers Symposium (2011), 2 printed pages.
NIH National Cancer Institute, "FDA Approves Irinotecan Liposome to Treat Pancreatic Cancer," Nov. 24, 2015 by NCI Staff, 2 printed pages.
No authors listed. "5HT3-receptor Antagonists as Antiemetics in Cancer," Drug Ther Bull. 43(8):57-62 (2005).
Noble C, et al., "Novel Nanoliposomal CPT-11 Infused by Convection-Enhanced Delivery in Intracranial Tumors: Pharmacology and Efficacy," Cancer Res. 66(5):2801-6 (2006).
Noble C, et al. "Pharmacokinetics, Tumor Accumulation and Antitumor Activity of Nanoliposomal Irinotecan Following Systemic Treatment of Intracranial Tumors," Nanomedicine. 9(14):2099-108 (2014).
O'Brien M, et al., "Phase III Trial Comparing Supportive Care Alone With Supportive Care With Oral Topotecan in Patients With Relapsed Small-Cell Lung Cancer," J Clin Oncol. 24(34):5441-7 (2006).
O'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).
Owonikoko T, et al., "A Systematic Analysis of Efficacy of Second-Line Chemotherapy in Sensitive and Refractory Small-Cell Lung Cancer," J Thorac Oncol. 7(5):866-72 (2012).
Pallis A, et al., "A Multicenter Randomized Phase II Study of the Irinotecan/Gemcitabine Doublet Versus Irinotecan Monotherapy in Previously Treated Patients with Extensive Stage Small-Cell Lung Cancer," Lung Cancer. 65(2)187-91 (2009), Epub Dec. 18, 2008.
Palomaki G, et al., "Can UGT1A1 Genotyping Reduce Morbidity and Mortality in Patients with Matatsic Colotectal Cancer Treated with Irinotecan?An Evidence-Based Review," Genet. Med. 11(1):21-34 (2009).
Park J, et al., "Anti-HER2 Immunoliposomes: Enhanced Efficacy Attributable to Targeted Delivery," Clin Cancer Res. 8(4):1172-81 (2002).
Patton W, "Detection Technologies in Proteme Analysis," J Chromatogr B. 771(1-2):3-31 (2002).
Pavillard V, et al., "Combination of Irinotecan (CPT11) and 5-Fluorouracil with an Analysis of Cellular Determinants of Drug Activity," Biochem Pharmacol. 56(10):1315-22 (1998).
Paz N, et al., "MM-398/PEP02, A Novel Liposomal Formulation of Irinotecan Demonstrates Stromal-Modifying Anti-Cancer Properties," Poster for abstract A63 presented at the AACR Special Conference on Pancreatic Cancer: Progress and Challenges; Jun. 18-21, 2012; Lake Tahoe, NV, 9 pages.
Paz N, et al., Abstract A63. "MM-398/PEP02, A Novel Liposomal Formulation of Irinotecan, Demonstrates Stromal-Modifying Anticancer Properties," In Proceedings of the AACR Special Conference on Pancreatic Cancer: Progress and Challenges; Jun. 18-21, 2012; Lake Tahoe, NV. Cancer Res. 2012;72(12 Suppl):Abstract nr A63, 3 printed pages.
Paz-Ares L, et aL, "Efficacy and Safety of Irinotecan Liposome Injection (nal-IRI) in Patients with Small Cell Lung cancer (SCLC)," Presentation presented at 2019 World Conference on Lung Cancer; Sep. 7-10, 2019; Barcelona, Spain; 9 pages.
Paz-Ares L, et aL, "Liposomal Irinotecan vs Topotecan in Patients with Small Cell Lung Cancer Who Have Progressed On/After Platinum-Based Therapy." Poster presented Sep. 23-26, 2018 at 19th World Conference on Lung Cancer meeting, 9 pages.
Paz-Ares L, et aL, "Resilient: Study of Irinotecan Liposome Injection (nal-IRI) in Patients with Small Cell Lung cancer—Preliminary Findings from Part 1 Dose-Defining Phase," Poster presented at ASCO in Chicago, IL May 31-Jun. 4, 2019, 6 pages.
Paz-Ares L, et aL, "Resilient: Study of Irinotecan Liposome Injection (nal-IRI) in Patients with Small Cell Lung Cancer—Preliminary Findings from Part 1 Dose-Defining Phase," Abstract No. 8562, J Clin Oncol. 37(15)(Suppl):8562 (2019), 3 pages.
Paz-Ares Rodriguez L, et al., Abstract OA03.03. "Initial Efficacy and Safety Results of Irinotecan Liposome Injection (Nal-IRI) in Patients With Small Cell Lung Cancer," 2019 World Conference on Lung Cancer Abstracts; Sep. 7-10, 2019; Barcelona, Spain; pp. 220-221.
PCT/IB2017/000681: PCT International Preliminary Report on Patentability dated Nov. 20, 2018, 6 pages.
PCT/IB2017/000681: PCT International Search Report and Written Opinion dated Aug. 25, 2017, 8 pages.
PCT/US2005/015349: PCT International Search Report and Written Opinion dated Aug. 18, 2005, 14 pages.
PCT/US2013/045495: PCT International Preliminary Report on Patentability dated Dec. 16, 2014, 8 pages.
PCT/US2013/045495: PCT International Search Report and Written Opinion dated Aug. 22, 2013, 11 pages.
PCT/US2013/046914: PCT International Preliminary Report on Patentability dated Dec. 23, 2014, 7 pages.
PCT/US2013/046914: PCT International Search Report dated Sep. 2, 2013, 3 pages.
PCT/US2013/075513: PCT International Preliminary Report on Patentability dated Jun. 16, 2015, 7 pages.
PCT/US2013/075513: PCT International Search Report dated Jun. 6, 2014, 2 pages.
PCT/US2014/062007: PCT International Preliminary Report on Patentability dated Apr. 26, 2016, 10 pages.
PCT/US2014/062007: PCT International Search Report dated Jan. 9, 2015, 3 pages.
PCT/US2015/064491: PCT International Preliminary Report on Patentability dated Jun. 13, 2017, 7 pages.
PCT/US2015/064491: PCT International Search Report dated Feb. 19, 2016, 4 pages.
PCT/US2016/027515: PCT International Preliminary Report on Patentability dated Oct. 17, 2017, 8 pages.
PCT/US2016/027515: PCT International Search Report dated Jun. 27, 2016, 4 pages.
PCT/US2016/047727: PCT International Preliminary Report on Patentability dated Feb. 27, 2018, 6 pages.
PCT/US2016/047727: PCT International Search Report and Written Opinion dated Nov. 16, 2016, 8 pages.
PCT/US2016/047814: PCT International Preliminary Report on Patentability dated Feb. 20, 2018, 6 pages.
PCT/US2016/047814: PCT International Search Report dated Nov. 17, 2016, 3 pages.
PCT/US2016/047827: PCT International Preliminary Report on Patentability dated Feb. 20, 2018, 6 pages.
PCT/US2016/047827: PCT International Search Report dated Nov. 17, 2016, 3 pages.
PCT/US2016/057247: PCT International Preliminary Report on Patentability dated Apr. 17, 2018, 8 pages.
PCT/US2016/057247: PCT International Search Report dated Dec. 23, 2016, 4 pages.
Pelzer U, et al., "A Randomized Trial in Patients With Gemcitabine Refractory Pancreatic Cancer. Final Results of the CONKO 003 Study," J Clin Oncol. 2008 ASCO Annual Meeting Proceedings. 26(155):4508 (2008), 2 printed pages.
Pelzer U, et al., "Second-Line Therapy in Refractory Pancreatic Cancer. Results of a Phase II Study," Onkologie. 32(3):99-102 (2009).
Pfizer Background Document on the UGT1A1 Polymorphisms and Irinotecan Toxicity: ACPS Nov. 3, 2004 Advisory Committee Meeting, 19 pages.
Pliarchopoulou K, et al., "Pancreatic Cancer: Current and Future Treatment Strategies," Cancer Treat Rev. 35(5):431-6 (2009).
Rahib L, et al., "Projecting Cancer Incidence and Deaths to 2030: The Unexpected Burden of Thyroid, Liver, and Pancreas Cancers in the United States," Cancer Res. 74(11):2913-21 (2014).
Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 6 printed pages.
Clinical Trials Identifier NCT00734682: Jan. 7, 2015 update, first posted Aug. 14, 2008, "A Phase I Trial of Nanoliposomal CPT-11

(56) References Cited

OTHER PUBLICATIONS (NL CPT-11) in Patients With Recurrent High-Grade Gliomas." Retrieved from ClinicalTrials.gov archive, 6 printed pages.
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Mar. 1, 2012 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Jan. 12, 2015 update, "A Phase II Study of PEP02 as a Second Line Therapy for Patients with Metastatic Pancreatic Cancer." Retrieved from ClinicalTrials.gov archive, 3 printed pages.
Clinical Trials Identifier NCT00813163: Apr. 6, 2017 update, first posted Dec. 22, 2008, "A Phase II Study of PEPO2 as a Second Line Therapy for Patients With Metastatic Pancreatic Cancer." Retrieved from ClinicalTrials.gov archive, 6 printed pages.
Clinical Trials Identifier NCT01375816: Jun. 16, 2011 update, "A Randomized Phase II Study of PEP02 or Irinotecan in Combination With Leucovorin and 5-Flourouracil in Second Line Therapy of Metastatic Colorectal Cancer" Retrieved from ClinicalTrials.gov archive, 5 printed pages.
Clinical Trials Identifier NCT01375816: Jun. 4, 2015 update, first posted Jun. 17, 2011, "A Randomized Phase II Study of PEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT01494506: Dec. 16, 2011 update, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages.
Clinical Trials Identifier NCT01494506: Aug. 9, 2012 update, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy." Retrieved from ClinicalTrials.gov archive, 3 printed pages.
Clinical Trials Identifier NCT01494506: Aug. 1, 2013 update, "A Randomized, Open Label Phase 3 Study of MM-398, With or Without S~Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 3 printed pages.
Clinical Trials Identifier NCT01494506: Jun. 16, 2016 update, "A Randomized, Open Label Phase 3 Study of MM-398, With or Without 5-Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 5 printed pages.
Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.
Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: May 6, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.
Clinical Trials Identifier NCT01770353: Jul. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.
Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors" Retrieved from ClinicalTrials.gov archive, 6 printed pages.
Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.
Clinical Trials Identifier NCT02551991: Sep. 30, 2019 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Retrieved from ClinicalTrials.gov archive, 5 printed pages.
Clinical Trials Identifier NCT02631733: Dec. 15, 2015 update, "A Phase I Study of a Combination of MM-398 and Veliparib in Solid Tumors." Retrieved from ClinicalTrials.gov archive, 6 printed pages.
Clinical Trials Identifier NCT02631733: Feb. 16, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jun. 20, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jun. 21, 2016 update, "A Phase I Study of a Combination of MM-398 and Veliparib in Stolid Tumors." Retrieved from ClinicalTrials.gov archive, 6 printed pages.
Clinical Trials Identifier NCT02631733: Jul. 6, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jul. 11, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jul. 19, 2016 update, "A Phase I Study of a Combination of MM-398 and Veliparib in Solid Tumors." Retrieved from ClinicalTrials.gov archive, 6 printed pages.
Clinical Trials Identifier NCT02631733: Aug. 7, 2016 update, "A Phase I Study of a Combination of MM-398 and Veliparib in Solid Tumors." Retrieved from ClinicalTrials.gov archive, 6 printed pages.
Clinical Trials Identifier NCT02631733: Sep. 21, 2016 update, "A Phase I Study of a Combination of MM-398 and Veliparib in Solid Tumors." Retrieved from ClinicalTrials.gov archive, 6 printed pages.
Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.
Clinical Trials Identifier NCT02884128: Aug. 25, 2016 update, "A Study of PEP02 in Combination With 5-fluorouracil (5-FU) and Leucovorin (LV) in Advanced Solid Tumors." Retrieved from ClinicalTrials.gov archive, 3 printed pages.
Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.
Clinical Trials Identifier NCT03088813: Sep. 30, 2019 update, first posted Mar. 23, 2017, "Study of Irinotecan Liposome Injection (ONIVYDE®) in Patients With Small Cell Lung Cancer." Retrieved from ClinicalTrials.gov archive, 8 printed pages.
Cortés J, et al., Abstract CT154. "Multicenter Open-Label, Phase II Trial, to Evaluate the Efficacy and Safety of Liposomal Irinotecan (nal-IRI) for Progressing Brain Metastases in Patients with HER2-Negative Breast Cancer (The Phenomenal Study)," In Proceedings

(56) References Cited

OTHER PUBLICATIONS of the American Association for Cancer Research Annual Meeting 2018; Apr. 14-18, 2018; Chicago, Illinois. Cancer Res. 2018;78(13 Suppl):Abstract nr CT154, 3 printed pages.

Davidson D, et al., "The PARP Inhibitor ABT-888 Synergizes Irinotecan Treatment of Colon Cancer Cell Lines," Invest New Drugs. 31(2);461-8 (2013) DOI: 10.1007/s10637-012-9886-7; Epub Oct. 9, 2012, 8 pages.

Dawidczyk C, et al., "State-of-the-art in Design Rules for Drug Delivery Platforms: Lessons Learned from FDA-Approved Nanomedicines," J Control Release. 187:133-44 (2014).

Dayyani F, et al., Abstract B14. "CA 19-9 levels in patients with metastatic pancreatic adenocarcinoma receiving first-line therapy with liposomal irinotecan plus 5-fluorouracil/leucovorin and oxaliplatin (NAPOX)," In Proceedings of the AACR Special Conference on Pancreatic Cancer Advances in Science and Clinical Care; Sep. 6-9, 2019; Boston, MA; Cancer Res. 2019; 79(24 Suppl): Abstract nr B14, 3 printed pages.

Dean A, et al., "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Poster presented at the 18th European Society of Medical Oncology World Congress on Gastrointestinal Cancer; Barcelona, Spain; Jun. 29-Jul. 2, 2016, 14 pages.

Dean A, et al., Abstract P-287. "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Annals of Oncology. 27(Suppl 2):ii1-i85 (2016), 1 page.

Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).

Dickinson P, et al., "Canine Spontaneous Glioma: A Translational Model System for Convection-Enhanced Delivery," Neuro Oncol. 12(9):928-40; Epub 10:1093/neuonc/noq046, 1-13 (2010).

Dósa E, et al., "Magnetic Resonance Imaging of Intracranial Tumors: Intra-Patient Comparison of Gadoteridol and erumoxytol," Neuro Oncol. 13(2):251-60 (2011) doi: 10.1093/neuonc/noq172. Epub 2010.

Douillard J, et al.,"Irinotecan Combined with Fluorouracil Compared with Fluorouracil Alone as First-line Treatment for Metastatic Colorectal Cancer: A Multicentre Randomised Trial," Lancet 355(9209):1041-7 (2000).

Doxil package insert, revision Apr. 16, 2015, retrieved from https://www.accessdata.fda.gov/drugsatfda_docs/label/2015/050718s048lbl.pdf, 28 pages.

Doxil package insert, revision Aug. 30, 2013, retrieved from https://www.accessdataida.gov/drugsatfda_docs/label/2013/050718s045lbl.pdf, 35 pages.

Doxil package insert, revision Jun. 10, 2008, retrieved from https://www.accessdata.fda.gov/drugsatfda_docs/label/2008/050718s033lbl.pdf, 34 pages.

Drummond D, et al., "Development of a Highly Active Nanoliposomal Irinotecan Using a Novel Intraliposomal Stabilization Strategy," Cancer Res. 66(6):3271-77 (2006).

Drummond D, et al., "Optimizing Liposomes for Delivery of Chemotherapeutic Agents to Solid Tumors," Pharmacol Rev. 51(4):691-743 (1999).

Eckardt J, et al., "Phase III Study of Oral Compared With Intravenous Topotecan As Second-Line Therapy in Small-Cell Lung Cancer," J Clin Oncol. 25(15):2086-92 (2007).

Eisenhauer E, et al., "New Response Evaluation Criteria in Solid Tumours: Revised RECIST Guideline (version 1.1)," Eur J Cancer. 45(2):228-47 (2009).

English translation of title and abstract for Hasegawa, Y, "Biomarker as Predictive Safety Testing in Oncology", Igaku No Ayumi (Journal of Clinical and Experimental Medicine), 224(13)1171-4 (2008) (original in Japanese).

EP2861210: Communication of Notices of Opposition (R. 79(1) EPC), dated Feb. 16, 2018, 1 page.

EP2861210: Notice of Opposition dated Feb. 5, 2018, 6 pp.

EP2861210: Opposition dated Feb. 5, 2018, Annex to Notice of Opposition, Facts and Arguments, 8 pages.

EP2861210: Opposition dated Feb. 5, 2018, D1 (Fusilev package insert, 2008, 7 pp.).

EP2861210: Opposition dated Feb. 5, 2018, D2 (Gebbia V, et al., "Irinotecan Plus Bolus/infusional 5-Fluorouracil and Leucovorin in Patients With Pretreated Advanced Pancreatic Carcinoma: a Multicenter Experience of the Gruppo Dncologico Italia Meridionale," Am J Clin Oncol. 33(5):461-64 (2010)).

EP2861210: Opposition dated Feb. 5, 2018, D3 (Zaniboni a, et al., "FOLFIRI as Second-Line Chemotherapy for Advanced Pancreatic Cancer: A GISCAD Multicenter Phase II Study," Cancer Chemother Pharmacol 69(6):1641-5 :2012)).

EP2861210: Opposition dated Feb. 5, 2018, D4 (Neuzillet C, et al., "FOLFIRI Regimen in Metastatic Pancreatic Adenocarcinoma Resistant to Gemcitabine and Platinum-Salts," World J Gastroenterol. 18(33):4533-41 (2012)).

EP2861210: Opposition dated Feb. 5, 2018, D5 (Yoo C, et al., "A Randomised Phase II Study of Modified FOLFIR1.3 vs Modified FOLFOX as Second-Line Therapy in Patients with Gemcitabine-Refractory Advanced Pancreatic Cancer," Br J Cancer. 101(10):1658-63 (2009)).

EP2861210: Opposition dated Feb. 5, 2018, D6 (Taleb J., "FOLFIRI. 3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec 8, 2006).

EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).

EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5):699-705 (2012)).

EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).

EP2861210: Opposition filed Feb. 5, 2018, D10 (CAMPTOSAR package insert, 2012, 39 pages).

EP2861210: Opposition filed Feb. 5, 2018, D11 (Hoskins J, et al., "UGT1A1*28 Genotype and Irinotecan-Induced Neutropenia: Dose Matters," J Natl Cancer Inst. 99(17):1290-95 (2007)).

EP2861210: Opposition dated Feb. 5, 2018, D12 (Tsai C, et al., "Nanovector-Based Therapies in Advanced Pancreatic Cancer," J Gastroint Oncol 2(3):185-94 (2011)).

EP2861210: Opposition dated Feb. 5, 2018, D13 (Ko A, et al., "A Multinational Phase II Study of Liposome Irinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).

EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus Fluorouracil and Leucovorin in Patients With Metastatic Pancreatic Cancer Who Have Failed Prior Gemcitabine-based Therapy," Retrieved from ClinicalTrials.gov archive, 1 printed page).

EP2861210: Response to EP Opposition Proceedings filed Aug. 24, 2018, 22 pages.

EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).

(56) References Cited

OTHER PUBLICATIONS

EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015)).
EP2861210: Response to EP Opposition Proceedings filed Aug. 24, 2018, D20 (MHRA Public Assessment Report for 5-Fluorouracil, 2006, 60 pages).
EP2861210: Summons to attend oral proceedings including preliminary opinion of the Opposition Division dated Jan. 30, 2019, 12 pages.
EP2861210: Opponent submission in opposition proceedings made following summons to attend oral proceedings, dated May 10, 2019, 20 pages.
EP2861210: Opponent submission in opposition proceedings made following summons to attend oral proceedings, dated May 10, 2019, D1b (Leucovorin calcium injection product label, Nov. 2011, 2 pages).
EP2861210: Opponent submission in opposition proceedings made following summons to attend oral proceedings, dated May 10, 2019, D22 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page).
EP2861210: Proprietor's Auxiliary Requests in Opposition Proceedings filed Jun. 28, 2019, including cover letter and clean and marked-up AR1, AR2, and AR3, 12 pages.
EP2861210: Minutes of the oral proceedings before the Opposition Division, dated Aug. 28, 2019, 9 pages.
EP2861210: Opposition Division's decision to revoke patent, dated Aug. 28, 2019, 27 pages.
EP2861210: Proprietor's statement of grounds of appeal to opposition decision dated Dec. 30, 2019, 35 pages.
EP2861210: Proprietor's Main and Auxiliary Requests MR, AR1, AR2, and AR3 with Proprietor's Statement of Grounds of Appeal in Opposition Proceedings filed Dec. 30, 2019, 4 pages.
EP2861210: Proprietor's statement of grounds of appeal to opposition decision dated Dec. 30, 2019, D23 (Declaration of Amy McKee M.D.) including D23A (Hoos W, et al., "Pancreatic Cancer Clinical Trials and Accrual in the United Sates." J Clin Oncol. 31(27):3432-8 (2013) and accompanying Appendix Table A1, Table A2, and Figure A1) and D23B (BIO Industry Analysis: Clinical Development Success Rates 2006-2015, Jul. 2016), 44 total pages.
EP2861210: Proprietor's statement of grounds of appeal to opposition decision dated Dec. 30, 2019, D24 (Declaration of Bruce Belanger, Ph.D.), 2 pages.
EP2861210: Reply to proprietor's grounds of appeal following opposition and cover letter, dated Jul. 27, 2020, 35 pages.
EP2861210: Reply to proprietor's grounds of appeal to opposition decision dated Jul. 27, 2020, D15c (EU clinical trial latabase for NAPOLI-1 study from Oct. 12, 2012, corresponds to D15b), 10 pages.
EP2861210: Reply to proprietor's grounds of appeal to opposition decision dated Jul. 27, 2020, D25 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).

EP2861210: Reply to proprietor's grounds of appeal to opposition decision dated Jul. 27, 2020, D26 (Drummond D, et al., "Development of a Highly Active Nanoliposomal Irinotecan Using a Novel Intraliposomal Stabilization Strategy," Cancer Res. 66(6):3271-77 (2006)).
EP2861210: Reply to proprietor's grounds of appeal to opposition decision dated Jul. 27, 2020, D27 (Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013)).
EP2861210: Reply to proprietor's grounds of appeal to opposition decision dated Jul. 27, 2020, D28 (Svenson S, "Clinical Translation of Nanomedicines," Current Opinion in Solid State and Materials Science. 16(6):287-294 (2012), article in press version, 7 pages).
EP2861210: Reply to proprietor's grounds of appeal to opposition decision dated Jul. 27, 2020, D29 (Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011)).
EP2861210: Reply to proprietor's grounds of appeal to opposition decision dated Jul. 27, 2020, D30 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 5 printed pages).
EP2861210: Reply to proprietor's grounds of appeal to opposition decision dated Jul. 27, 2020, D31 (Cunningham J, et al., "Randomized Phase II Study of PEP02, Irinotecan, or Docetaxel as a Second-Line Therapy in Gastric or Gastroesophageal Junction Adenocarcinoma," J Clin Oncol. 29(4_supp):Abstract 6 (2011), 5 printed pages).
EP2861210: Reply to proprietor's grounds of appeal to opposition decision dated Jul. 27, 2020, D32 (Gerber D, "Miscellaneous Agents—Cytotoxics and Hormonal Agents," J Thorac Oncol. 7(12 Suppl 5):S387-9 (2012)).
EP2861210: Reply to proprietor's grounds of appeal to opposition decision dated Jul. 27, 2020, D33 (Noble C, et al., "Novel Nanoliposomal CPT-11 Infused by Convection-Enhanced Delivery in Intracranial Tumors: Pharmacology and Efficacy," Cancer Res. 66(5):2801-6 (2006)).
EP2861210: Reply to proprietor's grounds of appeal to opposition decision dated Jul. 27, 2020, D34 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007)).
EP2861210: Reply to proprietor's grounds of appeal to opposition decision dated Jul. 27, 2020, D35 (Mullard A, "How Much Do Phase III Trials Cost?" Nat Rev Drug Discov. 17(111:777 (2018)).
EP2861210: Reply to proprietor's grounds of appeal to opposition decision dated Jul. 27, 2020, D36 (The Medicines for Human Use (Clinical Trials) Regulations, 2004, 86 pages).
FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages.
Fitzgerald J, et al., "Systems Pharmacology Identification of Tumour Nanoparticle Permeability as Predictor of Clinical Anti-Cancer Activity of MM-398, Nanoliposomal Irinotecan, nal-Iri." Poster presented at 15th International Conference on Systems Biology. Sep. 14-18, 2014, 10 pages.
Fleming D. "Importance of sequence in chemotherapy administration," retrieved from http://www.oncologynurseadvisor.com/advisor-forum/importance-of-sequence-in-chemotherapy-administration/article/378072/:2014).
Fuchs C, et al., "Phase III Comparison of Two Irinotecan Dosing Regimens in Second-Line Therapy of Metastatic Colorectal Cancer," J Clin Oncol. 21(5):807-14 (2003).
Gahramanov S, et al., "Pseudoprogression of Glioblastoma After Chemo- and Radiation Therapy: Diagnosis by Using Dynamic Susceptibility-Weighted Contrast-Enhanced Perfusion MR Imaging

(56) References Cited

OTHER PUBLICATIONS with Ferumoxytol versus Gadoteridol and Correlation with Survival," Radiology. 266(3):842-52 (2013). doi: 10.1148/radiol_12111472. Epub Nov. 30, 2012.

Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33 (5):461-64 (2010).

Gemzar package insert, revision Feb. 4, 2011, retrieved from https://www.accessdata.fda.gov/drugsatfda_docs/label/2011/020509s069lbl.pdf, 21 pages.

Gemzar package insert, revision May 8, 2014, retrieved from https://www.accessdata.fda.gov/drugsatfda_docs/label/2014/020509s077lbl.pdf, 18 pages.

Genther Williams S, et al., "Treatment with the PARP Inhibitor, Niraparib, Sensitizes Colorectal Cancer Cell Lines to Irinotecan Regardless of MSI/MSS Status," Cancer Cell Int. 15(1):14, doi: 10.1186/s12935-015-0162-8 (2015), pp. 1-11.

Gilbert D, et al., "Topoisomerase I Inhibition in Colorectal Cancer: Biomarkers and Therapeutic Targets," Br J Cancer. 106(1):18-24 (2012), doi: 10.1038/bjc.2011.498, Epub Nov. 22, 2011.

Globocan Cancer Facts Sheets: All Cancers 2012. Available from: http://globocan.iarc.fr/old/FactSheets/cancers/all-new.asp, accessed on Oct. 3, 2016, 9 printed pages.

Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).

Grant S, et aL, "Dose-Ranging Evaluation of the Substituted Benzamide Dazopride When Used as an Antiemetic in Patients Receiving Anticancer Chemotherapy," Cancer Chemother Pharmacol. 31(6):442-44 (1993).

Hanna N, et al., "Randomized Phase III Trial Comparing Irinotecan/Cisplatin with Etoposide/Cisplatin in Patients with Previously Untreated Extensive-Stage Disease Small-Cell Lung Cancer," J Clin Oncol. 24(13):2038-43 (2006).

Hare J, et al., "Treatment of Colorectal Cancer Using a Combination of Liposomal Irinotecan (Irinophore C(TM)) and 5-Fluorouracil," PLoS One. 8(4):e62349, doi: 10.1371/journal.pon.0062359, 12 pages (2013).

Hayashi H, et aL, "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.

Hayes M, et aL, "Assembly of Nucleic Acid-Lipid Nanoparticles from Aqueous-Organic Monophases," Biochim Biophys Acta. 1758(4):429-42 (2006).

Hong K, et al., "Anti-HER2 Immunoliposomes for Targeted Drug Delivery," Ann N Y Acad Sci. 886:293-6 (1999).

Honig A, et al., "Brain Metastases in Breast Cancer—an In Vitro Study to Evaluate New Systemic Chemotherapeutic Options," Anticancer Res. 25(3A):1531-7 (2005).

Hoskins J, et aL, "UGT1A1*28 Genotype and Irinotecan-Induced Neutropenia: Dose Matters," J Natl Cancer Inst. 99 (17):1290-95 (2007).

Huber R, et al., "Efficacy of a Toxicity-Adjusted Topotecan Therapy in Recurrent Small Cell Lung Cancer," Eur Respir J. 27(6):1183-9 (2006).

Hubner R, et aL, "Effects of nal-IRI (MM-398) ±-5-Fluorouracil on Quality of Life (QoL) in NAPOLI-1: A Phase 3 Study in Patients With Metastatic Pancreatic Ductal Adenocarcinoma (mPDAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 9 pages.

Hubner R, et aL, Abstract O-004. "Effects of nal-IRI (MM-398) ±-5-fluorouracil on Quality of Life (QoL) in Napoli-1: A Phase 3 Study in Patients with Metastatic Pancreatic Ductal Adenocarcinoma (mPDAC) Previously Treated with Gemcitabine." Annals of Oncology. 27(Suppl 2):ii118-ii128 (2016), 1 page.

Hycamtin (topotecan hydrochloride) for injection package insert, revision Feb. 28, 2014, retrieved from https://www.accessdata.fda.gov/drugsatfda_docs/label/2014/020671s020lbl.pdf, 23 pages.

Hycamtin (topotecan) for injection package insert, revision Jun. 2, 2015, retrieved from https://www.accessdata.fda.gov/drugsatfda_docs/label/2015/020671s021lbl.pdf, 21 pages.

Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).

Jacobs A, et al., "A Randomized Phase III Study of Rubitecan (ORA) vs. Best Choice (BC) in 409 Patients with Refractory Pancreatic Cancer Report from a North-American Multi-Center Study," J Clin Oncol., 2004 ASCO Annual Meeting Proceedings 22(145):4013 (2004).

Kalra A, et al., "Evaluating Determinants for Enhanced Activity of MM-398/PEP02; A Novel Nanotherapeutic Encapsulation of Irinotecan (CPT-11)." Poster for abstract 5696 presented at American Association for Cancer Research 103rd Annual Meeting 2012, Mar. 31-Apr. 4, 2012, Chicago, IL, 11 pages.

Kalra A, et al., "Preclinical Activity of Nanoliposomal Irinotecan Is Governed by Tumor Deposition and Intratumor Pro-Drug Conversion," Cancer Res. Author Manuscript Published OnlineFirst Oct. 1, 2014, 31 pages.

Kalra A, et al., "Preclinical Activity of Nanoliposomal Irinotecan Is Governed by Tumor Deposition and Intratumor Prodrug Conversion," Cancer Res. 74(23):7003-13 (2014).

Kalra A, et al., "Preclinical Activity of Nanoliposomal Irinolecan Is Governed by Tumor Deposition and Intratumor Prodrug Conversion," Cancer Res. 74(23):7003-13 (2014), published OnlineFirst, OF1-0F11, Oct. 1, 2014, 12 pages.

Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.

Kalra A, et al., "The Tumor Microenvironment Modulates the Delivery and Activation of Liposomal Encapsulated Irinotecan, MM-398," Poster for abstract 5622 presented at the 104th Annual Meeting of the American Association of Cancer Research, Apr. 6-10, 2013, Washington DC, 10 pages.

Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.

Kalra A, et al., Abstract 5622. "The Tumor Microenvironment Modulates the Delivery and Activation of Liposomal Encapsulated Irinotecan, MM-398." In Proceedings of the 104th Annual Meeting of the American Association of Cancer Research; Apr. 6-10, 2013. Cancer Res 2013;73(8 Suppl):Abstract nr 5622, doi:10.115811538-7445. AM2013-5622, 2 printed pages.

Kalra A, et al., Abstract 5696. "Evaluating Determinants for Enhanced Activity of MM-398/PEP02; A Novel Nanotherapeutic Encapsulation of Irinotecan (CPT-11)." In Proceedings of the 103rd Annual Meeting of the American Association for Cancer Research; Mar. 31-Apr. 4, 2012; Chicago, IL. Cancer Res 2012; 72(8 Suppl):Abstract nr 5696. doi:1538-7445.AM2012-5696, 3 printed pages.

Kalra A., "Magnetic Resonance Imaging (MRI) to Predict Tumor Drug Delivery and Response to Nanoliposomal Therapy." Presentation presented at Tumor Models Boston 2014, 32 pages.

Kambe M, et aL, "Phase I Study of Irinotecan by 24-h Intravenous Infusion in Combination with 5-Fluorouracil in Metastatic Colorectal Cancer," Int J Clin Oncol. 17(2):150-4 (2012).

Kang M, et al., "Activity of MM-398, Nanoliposomal Irinotecan (nal-IRI), in Ewing's Family Tumor Xenografts Is Associated with High Exposure of Tumor to Drug and High SLFN11 Expression," Clin Cancer Res. 21(5):1139-50 (2015).

Katsu T, et al., "Ion-Selective Electrode for Transmembrane pH Difference Measurements," Anal. Chem. 73(8):1849-54 (2001).

Kim J, et aL, "Efficient Prioritization of Potential Diagnostic Biomarkers Using a Systems Pharmacology Approach: Case Study of MM-398 (Irinotecan sucrosofate liposome injection)." Presenta-

(56) References Cited

OTHER PUBLICATIONS tion presented at the Pharmacokietics UK 2013 Meeting, Oct. 31, 2013, Harrogate, North Yorkshire, 34 pages.

Kim J, et aL, "Efficient Prioritization of Potential Diagnostic Biomarkers Using a Systems Pharmacology Approach: Case Study of MM-398, an Irinotecan Sucrosofate Liposome Injection)." Abstract for Pharmacokietics UK 2013 Meeting, Oct. 30 - Nov. 1, 2013, Harrogate, North Yorkshire, 2 pages.

Kim J, et aL, "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.

Kim J, et aL, "Systems Pharmacology Modeling Identifies Unique Parameters That Drive Tumor SN38 Levels for Liposomal Irinotecan (MM-398) Compared to Irinotecan." Poster presented at 14th International Conference on Systems Biology; Copenhagen, Denmark; Aug. 29-Sep. 4, 2013, 11 pages.

Kim J, et aL, "Systems Pharmacology Modeling Identifies Unique Parameters That Drive Tumor SN38 Levels for Liposomal Irinotecan (MM-398) Compared to Irinotecan." Abstract presented at 14th International Conference on Systems Biology; Copenhagen, Denmark; Aug. 29-Sep. 4, 2013, 1 page.

Kim J, et al., Abstract A6. "Sustained Intratumoral Activation of MM-398 Results in Superior Activity Over Irinotecan Demonstrated by Using a Systems Pharmacology Approach, " In: Proceedings of the AACR Special Conference on . . . , Chemical Systems Biology: Assembling and Interrogating Computational Models of the Cancer Cell by Chemical Perturbations; Jun. 27-30, 2012; Boston, MA. Cancer Res. 2012;72(13 Suppl):Abstract nr A6, 3 printed pages.

Kim J, et. al., "Systems Pharmacology Based Biomarker Potentially Predicts Clinical Anti-Cancer Activity of Mm-398, Nanoliposomal Irinotecan, nal-IRI." Poster presented at American Conference on Pharmacometrics, Oct., 12-15 2014, 10 pages.

Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).

Klinz S, et al., "Identifying Differential Mechanisms of Action for Mm-398/PEP02, a Novel Nanotherapeutic Encapsulation of Irinotecan." Poster presented at MCR, Nov. 12-16, 2011, 8 pages.

Klinz S, et al., "Identifying Differential Mechanisms of Action for MM-398/PEP02, a Novel Nanotherapeutic Encapsulation of Irinotecan," Mol Cancer Ther. 10(11 Suppl):Abstract C207. Molecular Targets and Therapeutics Meeting (2011), 2 printed pages.

Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACr Pancreatic meeting Orlando, FL, May 12-15, 2016, 10 pages.

Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenograft Model." Poster presented at AACR-NCI-EORTC International Conference on Molecular Targets and Cancer Therapeutics on Oct. 19, 2013, 7 pages.

Klinz S, et al.,"MM-302 a HER2-targeted Liposomal Doxorubicin, Shows Binding/Uptake and Efficacy in HER2 2+ Cells and Xenograft Models," Cancer Res. 71:Abstract 3637 (2011), 1 printed page.

Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).

Ko a, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.

Ko A, et al., "A Multinational Phase II Study of PEP02 (MM-398), Liposome Irinotecan, for Patients with Gemcitabine refractory Metastatic Pancreatic Cancer." Poster presented at the American Society of Clinical Oncology meeting, Jun. 3-Jun. 7, 2011, Chicago, Illinois, 9 pages.

Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).

Köhne C, et al., "Randomized Phase III Study of High-Dose Fluorouracil Given As a Weekly 24-Hour Infusion With or Without Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).

Korn R, "Advanced Imaging with Ferumoxytol MRI to Predict Drug Delivery." Presentation presented at Pancreatic Cancer 2014, Feb. 22, 2014, 23 pages.

Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting on Apr. 16-20, 2016, 5 pages.

Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).

Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).

Kummar S, et al. "Phase I Study of PARP Inhibitor ABT-888 in Combination with Topotecan in Adults with Refractory Solid Tumors and Lymphomas," Cancer Res. 71(17):5626-34 (2011), Epub Jul. 27, 2011.

Kandry R, et al., "Pharmacokinetic Study of Ferumoxytol: A New Iron Repalcement Therapy in Normal Subjects and Hemodialysis Patients," Am J Nephrol. 25(4):400-10 (2005).

Kee C, et al. "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).

Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast Cancer Symposium, Dec. 4-8, 2012, 2 printed pages.

Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.

Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.

Leonard S, et al., "Extended Topoisomerase 1 Inhibition Through Liposomal Irinotecan Results in Improved Efficacy over Topotecan and Irinotecan in Models of Small-Cell Lung Cancer," Anti-Cancer Drugs. 28(10):1086-96 (2017).

Leonard S, et al., "Irinotecan Liposome Injection has Greater Anti-Tumor Activity than Topotecan and Irinotecan in Mouse Models of Small Cell Lung Cancer," Poster presented at AACR 110th Annual World Congress 2017, Washington, DC, Apr. 1-5, 2017, 6 pages.

Leonard S, et al., "Preclinical Support for Evaluation of Irinotecan Liposome Injection (nal-IRI, MM-398) in Small Cell Lung Cancer," Abstracts from the IASLC 17th World Conference on Lung Cancer held Dec. 4-7, 2016, J Thoracic Oncology. 12(1)(Suppl):S699 (2016), 1 page.

Leonard S, et al., "Preclinical Support for Evaluation of Irinotecan Liposome Injection (nal-IRI, MM-398) in Small Cell Lung Cancer," Poster presented at 17th World Conference on Lung Cancer, Vienna, Austria, Dec 4-7, 2016, 5 pages.

(56) References Cited

OTHER PUBLICATIONS

Lorusso P, et al., "Abstract CT325: Combination of the PARP Inhibitor Veliparib (ABT888) with Irinotecan in Patients with Triple Negative Breast Cancer: Preliminary Activity and Signature of Response." Proceedings: AACR 106th Annual Meeting, Apr. 18-22, 2015, Philadelphia, PA (2015), 3 printed pages.

Lorusso P, et al., "Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors," Clin Cancer Res. 22(13):3227-37 (2016), Epub Feb. 3, 2016.

Lorusso P, et aL., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Supplement ASCO Meeting Library, Jun. 5, 2011, 1 page.

Lorusso P, et aL., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Journal of Clinical Oncology 29.15_suppl: Abstract 3000 (2011), 3 printed pages.

Lorusso P, et aL., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages.

Lynparzatm™ (olaparib) capsules package insert, ©AstraZeneca. 2014, Revised: Dec. 2014, 6 pages.

Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.

Maddison J, et al., "Sucralfate," In Small Animal Clinical Pharmacology at p. 474, published by W. B. Saunders (2002).

Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011).

Mamot C, et al., "Epidermal Growth Factor Receptor-Targeted Immunoliposomes Significantly Enhance the Efficacy of Multiple Anticancer Drugs In Vivo," Cancer Res. 65(24):11631-8 (2005).

Mamot C, et al., "Extensive Distribution of Liposomes in Rodent Brains and Brain Tumors Following Convection-Enhanced Delivery," J Neurooncol. 68(1):1-9 (2004).

Mans D, et aL., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).

Masuda N, et al., "CPT-11: a New Derivative of Camptothecin for the Treatment of Refractory or Relapsed Small-Cell Lung Cancer," J Clin Oncol. 10(8):1225-9 (1992).

Merrimack Pharmaceuticals, "Merrimack Pharmaceuticals Initiates Cross-Tumor Study to Investigate Potential Predictive Response Markers for a Developmental Nanotherapeutic Chemotherapy," Dec. 19, 2012. Retrieved from http://investors.merrimack.com/news-releases/news-release-details/merrimack-pharmaceuticals-initiates-cross-tumor-study, 2 printed pages.

Messerer C, et al., "Liposomal Irinotecan: Formulation Development and Therapeutic Assessment in Murine Xenograft Models of Colorectal Cancer," Clin Cancer Res. 10(19):6638-49 (2004).

Miles D, et al., "Combination Versus Sequential Single-Agent Therapy in Metastatic Breast Cancer," Oncologist. 7(suppl 6):13-19 (2002).

Miller M, et al. "Predicting Therapeutic Nanomedicine Efficacy Using a Companion Magnetic Resonance Imaging Vanoparticule," Sci Transl Med. 7:314ra183 (2015), pp. 1-12, Editor's Summary (1 page), and Supplementary Materials (24 pages).

Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).

Minami H, et al., "Irinotecan Pharmacokinetics/Pharmacodynamics and UGT1A Genetic Polymorphisms in Japanese: Roles of UGT1A1*6 and *28," Pharmacogenet Genomics. 17(7):497-504 (2007).

Mirtsching B, et al., "Irinotecan-induced Immune Thrombocytopenia," Am J Med Sci. 347(2):167-9 (2014).

Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.

Mohammad a, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.

Morgan R, et al., "Human Cell Line (COLO 357) of Metastatic Pancreatic Adenocarcinoma," Int J Cancer 25(5):591-8 (1980).

Mukhtar R, et al., "Elevated PCNA+ Tumor-Associated Macrophages in Breast Cancer are Associated with Early Recurrence and Non-Caucasian Ethnicity," Breast Cancer Res Treat. 130(2):635-44 (2011).

Mullany S, et al., "Effect of Adding the Topoisomerase I Poison 7-ethyl-10-hydroxy-camptothecin (Sn-38) to 5-Fluorouracil and Folinic Acid in HCT-8 Cells: Elevated dTTP Pools and Enhanced Cytotoxicity," Cancer Chemother Pharmacol. 42(5):391-9 (1998).

Münstedt K, et al., "Role of Dexamethasone Dosage in Combination with 5-HT3 Antagonists for Prophylaxis of Acute Chemotherapy-Induced Nausea and Vomiting," Br J Cancer. 79(3-4):637-9 (1999).

Murai J, et al., "Identification of Novel PARP Inhibitors Using a Cell-Based TDP1 Inhibitory Assay in a Quantitative High-Throughput Screening Platform," Author manuscript; Published in final edited form as: DNA Repair (AMST). 21:177-82 (2014), 13 pages.

Murai J, et al., "Rationale for Poly(ADP-ribose) Ploymerase (PARP) Inhibitors in Combination Therapy with Campothecins or Temozolomide Based on PARP Trapping versus Catalytic Inhibition," J Pharmacol Exp Ther. 349(3):408-16 (2014).

National Comprehensive Cancer Network Clinical Practice Guidelines in Oncology (NCCN Guidelines). "Pancreatic Adenocarcinoma." Version I.2016. Mar. 22, 2016 (PANC-9), 133 pages.

Bouché O, et al. "Randomized Multicenter Phase II Trial of a Biweekly Regimen of Fluorouracil and Leucovorin (LV5FU2), LV5FU2 Plus Cisplatin, or LV5FU2 Plus Irinotecan in Patients With Previously Untreated Metastatic Gastric Cancer: A Féderation Francophone De Cancérologie Digestive Group Study—FFCD 9803," J Clin Oncol. 22(21):4319-28 (2004).

Chiang, N-J, et al., "Development of Nanoliposomal Irinotecan (nal-IRI, MM-398, PEP02) in the Management of Metastatic Pancreatic Cancer," Expert Opin Pharmacother. 17(10):1413-20 (2016).

Koizumi W, at al., "Phase I/II Study of Bi-weekly Irinotecan plus Cisplatin in the Treatment of Advanced Gastric Cancer," Anticancer Res. 25(2B):1257-62 (2005).

Cerenzia W, et al., Abstract e16233. "Identifying Continuing Educational Needs Among Oncologists in Managing Patients With Pancreatic Cancer," J Clin Oncol. 36(15_Suppl):e16233 DOI: 10.1200/JCO.2018.36.15_suppl.e16233 (2018), 2 printed pages.

Chabot G, "Clinical Pharmacokinetics of Irinotecan," Clin. Pharmacokinet. 33(4):245-59 (1997).

Chan E, et al., "A Phase 1/2 Study Combining MM-151 + nal-IRI + 5-Fu + Leucovorin in RAS/RAF Wild-Type Metastatic Colorectal Cancer." Poster presented at the American Society of Clinical Oncology (ASCO) Annual Meeting, Chicago, Illinois, Jun. 3-7, 2016, 7 pages.

Chan E, et al., Abstract TP53633. "A Phase 1/2 Study Combining MM-151 + nal-IRI + 5-FU + Leucovorin in RAS-Wildtype Metastatic Colorectal Cancer (mCRC)," J Clin Oncol. 34(15_Suppl):TPS3633 10.1200/JCO.2016.34.15_suppl.TPS3633 (2016), 4 printed pages.

(56) References Cited

OTHER PUBLICATIONS

Chauhan V, et. al., "Normalization of Tumour Blood Vessels Improves the Delivery of Nanomedicines in a Size-Dependent Manner," Nat Nanotechnol. 7(6):383-8 (2012), author manuscript version, 15 pages.

Chen J, et al., "Improved Pharmacokinetics and Reduced Toxicity of Brucine After Encapsulation into Stealth Liposomes: Role of Phosphatidylcholine," Int J Nanomedicine. 7:3567-77 (2012).

Chen L-T, et al., "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy." Poster presented at the European Society for Medical Oncology (ESMO) World Congress on Gastrointestinal Cancer, Barcelona, Spain, Jun. 28-Jul. 1, 2017, 5 pages.

Chen L-T, et al., "CA19-9 Decrease and Overall Survival in the NAPOLI-1 Trial of Liposomal Irinotecan (nal-IRI) ± 5- Fluorouracil and Leucovorin (5-FU/LV) in Metastatic Pancreatic Ductal Adenocarcinoma Previously Treated With Gemcitabine-Based Therapy." Poster presented at the European Society for Medical Oncology Asia 2017 Congress, Singapore, Nov. 17-19, 2017, 8 pages.

Chen L-T, et al., "Early Dose Reduction/Delay and the Efficacy of Liposomal Irinotecan With Fluorouracil and Leucovorin in Metastatic Pancreatic Ductal Adenocarcinoma (mPDAC): A Post Hoc Analysis of NAPOLI-1,"Pancreatology. 21(1):192-9 (2021). Epub 2020.

Chen L-T, et al., "Efficacy and Safety of Liposomal Irinotecan (nal-IRI) + 5-Fluorouracil and Leucovorin in Patients With Metastatic Pancreatic Ductal Adenocarcinoma Who Previously Received Gemcitabine-Based Therapy: Post Hoc Analysis of the Napoli-1 Trial." Poster presented at the American Society of Clinical Oncology Gastrointestinal Cancers Symposium (ASCO GI), San Francisco, CA, Jan. 19-21, 2017, 9 pages.

Chen L-T, et al., "Final Results of NAPOLI-1: A Phase 3 Study of nal-IRI (MM-398) ± 5-Fluorouracil and Leucovorin (5-FU/LV) vs 5-FU/LV in Metastatic Pancreatic Ductal Adenocarcinoma (mPDAC) Previously Treated With Gemcitabine-Based Therapy." Poster presented at the European Society for Medical Oncology (ESMO) Annual congress, Copenhagen, Denmark, Oct. 7-11, 2016, 8 pages.

Chen L-T, et al., "Impact of Dose Reduction or Dose Delay on the Efficacy of Liposomal Irinotecan (nal-IRI)+5-Fluorouracil/ Leucovorin (5-FU/LV): Survival Analysis From NAPOLI-1." Poster presented at the European Society for Medical Oncology (ESMO) Annual Congress, Munich, Germany, Oct. 19-23, 2018, 9 pages.

Chen L-T, et al., "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)." Poster presented at the European Society for Medical Oncology (ESMO) Annual Congress, Munich, Germany, Oct. 19-23, 2018, 9 pages.

Chen L-T, et al., Abstract 221PD. "Efficacy and Safety of Nanoliposomal Irinotecan (nal-IRI, MM-398, PEP02, BAX-2398) in Patients With Metastatic Pancreatic Cancer in Asia: A Subgroup Analysis of the Phase 3 NAPOLI-1 Study," Ann Oncol. 27(Supp_9):ix69-ix70 doi:10.1093/annonc/mdw582 (2016).

Chen L-T, et al., Abstract 227P. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Suppl_10):x66-x67 doi: 1093/annonc/mdx660 (2017).

Chen L-T, et al., Abstract 303. "Efficacy and Safety of Liposomal Irinotecan (nal-IRI) + 5-Fluorouracil and Leucovorin (5-FU/LV) in Patients (pts) With Metastatic Pancreatic Ductal Adenocarcinoma (mPDAC) Who Previously Received Gemcitabine (Gem)-Based Therapy: Post Hoc Analysis of the NAPOLI-1 Trial," J Clin Oncol. 35(4_Suppl):303 DOI: 10.1200/JCO.2017.35.4_suppl.303 (2017), 2 printed pages.

Chen L-T, et al., Abstract 3707. "Final Results of NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.

Chen L-T, et al., Abstract 734P. "Impact of Dose Reduction or Dose Delay on the Efficacy of Liposomal Irinotecan (nal-IRI)+5-Fluorouracil/ Leucovorin (5-FU/LV): Survival Analysis From NAPOLI-1," Ann Oncol. 29(Suppl_8):viii250-viii251 doi:10.1093/annonc/mdy282 (2018).

Chen L-T, et al., Abstract 749P. "The Prognostic Value of the Modified Glasgow Prognostic Score (mGPS) in ?Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)," Ann Oncol_29(Suppl_8):viii255-viii256 doi:10.1093/annonc/mdy282 (2018).

Chen L-T, et al., Abstract PD-017. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Supp_3):6-7 doi:10.1093/annonc/mdx263 (2017).

Chin V, eL al., "Chemotherapy and Radiotherapy for Advanced Pancreatic Cancer (Review)," Cochrane Database Syst Rev. 3(3):CD011044 doi: 10.1002/14651858.CD011044.pub2 (2018), 143 pages.

Choi C, et al., "Effects of 5-Fluorouracil and Leucovorin in the Treatment of Pancreatic-Biliary Tract Adenocarcinomas," Am J Clin Oncol. CCT 23(4): 425-8 (2000), 7 printed pages.

Chu C-J, et al., "Efficiency of Cytoplasmic Delivery by pH-Sensitive Liposomes to Cells in Culture," Pharm Res. 7(8):824-34 (1990).

Clarke J, et al., "A Phase I Trial of Intravenous Liposomal Irinotecan in Patients With Recurrent High-Grade Gliomas." Poster presented at the American Society of Clinical Oncology (ASCO) Annual Conference, Chicago, IL, May 29-Jun. 2, 2015, 7 pages.

Clarke J, et al., Abstract 2029. "A Phase I Trial of Intravenous Liposomal Irinotecan in Patients With Recurrent High-Grade Gliomas," J Clin Oncol. 33(15_Suppl):2029 DOI: 10.1200/jco.2015.33.15_suppl_2029 (2015), 2 printed pages.

Clinical Trials Identifier NCT00426127: Dec. 29, 2017 update, first posted Jan. 24, 2007, "Docetaxel and Liposomal Doxorubicin Chemotherapy With Enoxaparin in Patients With Advanced Pancreatic Cancer," Retrieved from ClinicalTrials.gov archive, 8 printed pages.

ClinicalTrials.gov search results for Onivyde, retrieved from clinicaltrials.gov website on Jan. 27, 2021, 27 pages.

Cockrum P, et al., "Impact of Dose Reductions on Clinical Outcomes Among Patients With Metastatic Pancreatic cancer Treated With Liposomal Irinotecan in Oncology Clinics in the US." Poster presented at the American Society of Clinical Oncology Gastrointestinal Cancers Symposium (ASCO GI), San Francisco, CA, Jan. 23-25, 2020, 8 pages.

Cockrum P, et al., Abstract 665. "Impact of Dose Reductions on Clinical Outcomes Among Patients (pts) With Metastatic Pancreatic Cancer (mPC) Treated With Liposomal Irinotecan (nal-IRI) in Oncology Clinics in the United States," J Clin Oncol. 38(4_Suppl):665 DOI: 10.1200/JCO.2020.38.4_suppl.665 (2020), 2 printed pages.

Cockrum P, et al., Abstract e16739. "National Comprehensive Cancer Network (NCCN) Category I/FDA-Approved Metastatic Pancreatic Adenocarcinoma (mPDAC) Treatments in Commercially Insured Patients: an Analysis of Inpatient (IP) and Emergency Room (ER) Admissions," J Clin Oncol. 38(15_Suppl):e16739 DOI: 101200/JCO.2020.38.15_suppl.e16739 (2020), 2 printed pages.

Cockrum P, et al., Abstract PCN134. "An Examination of Quality Metrics: Inpatient and Emergency Department Burden of Commercially Insured Treated Metastatic Pancreatic Cancer (mPC) Patients in the United States (US)," Value in Health. 23(Suppl 1):546 (2020).

Cockrum P, et al., Abstract PCN167. "An Integrated Delivery Network Focus on Cost Drivers in Chemotherapy: The Economic Burden of Neutropenia and Inpatient Admissions Among Commercially Insured Metastatic Pancreatic Cancer Patients (mPC)," Value in Health. 23(Suppl 1):S52 (2020).

(56) References Cited

OTHER PUBLICATIONS

Colbern G, et al., "Encapsulation of the Topoisomerase I Inhibitor GL147211C in Pegylated (STEALTH) Liposomes: Pharmacokinetics and Antitumor Activity in HT29 Colon Tumor Xenografts," Clin Cancer Res. 4(12):3077-82 (1998).
Colucci G, et. al., "Randomized Phase III Trial of Gemcitabine Plus Cisplatin Compared With Single-Agent Gemcitabine as First-Line Treatment of Patients With Advanced Pancreatic Cancer: The GIP-1 Study," J Clin Oncol. 28(10)1645-51 (2010).
Comella P, et. al., "Irinotecan Plus Leucovorin-Modulated 5-Fluorouracil I.V. Bolus Every Other Week May Be a Suitable Therapeutic Option Also for Elderly Patients With Metastatic Colorectal Carcinoma," Br J Cancer. 89(6):992-6 (2003).
Custodio a, et. al., "Second-Line Therapy for Advanced Pancreatic Cancer: A Review of the Literature and Future Directions," Cancer Treat Rev. 35(8):676-84 (2009).
Daleke D, et al., "Endocytosis of Liposomes by Macrophages: Binding, Acidification and Leakage of Liposomes Monitored by a New Fluorescence Assay," Biochim Biophys Acta. 1024(2):352-66 (1990).
DaunoXome (daunorubicin citrate liposome injection) package insert, rev. Dec. 2011, 11 pages.
De Jong F, et al., "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma Previously Treated With Gemcitabine," Poster presented at the Australian Gastro-Intestinal Trials Group, 18th Annual Scientific Meeting, Melbourne, Australia, Sep. 14-16, 2016, 10 pages.
De Jong F, et al., Abstract. "Effects of nal-IRI (MM-398; A Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma (mPDAC) Previously Treated With Gemcitabine," Australian Gastro-Intestinal Trials Group, 18th Annual Scientific Meeting, Melbourne, Australia, Sep. 14-16, 2016, 2 pages.
Dean a, et al., Abstract. "Expanded Analyses of Napoli-1: Phase 3 Study of Mm-398 (nal-Iri), With or Without 5- 7luorouracil and Leucovorin (5-Fu/Lv), Versus 5-Fu/Lv, in Metastatic Pancreatic Cancer (mPAC) Previously Treated Nith Gemcitabine-Based Therapy," 18th Annual Scientific Meeting of the Australasian Gastro-Intestinal Trials Group :Agitg), Melbourne, Australia, Sep. 14-16, 2016, 2 pp.
Dean a, et al., Abstract. "Liposomal Irinotecan (nal-Iri, Mm-398)-Containing Regimens Versus nab-Paclitaxel Plus 3emcitabine as First-Line Therapy in Patients With Metastatic Pancreatic Adenocarcinoma (mPAC): a Randomized, open-Label Phase 2 Study," 18th Annual Scientific Meeting of the Australasian Gastro-Intestinal Trials Group :Agitg), Melbourne, Australia, Sep. 14-16, 2016, 2 pp.
Derksen J, et. al., "Interaction of Immunoglobulin-Coupled Liposomes with Rat Liver Macrophages in Vitro," Exp Cell Res. 168(1):105-15 (1987).
Dewhirst M, et al., "Microvascular Studies on the Origins of Perfusion-Limited Hypoxia," Br J Cancer Suppl. 27: 3247-51 (1996).
Dicko A, et al., "Intra and Inter-Molecular Interactions Dictate the Aggregation State of Irinotecan Co-Encapsulated with Floxuridine Inside Liposomes," Pharm Res. 25(7)1702-13 (2008).
Dieguez G, et al., "Real-World Rates of Hematologic Laboratory Abnormalities and Associated Cost Among Metastatic Pancreatic Cancer Therapeutic Regimens," Poster presented at the American Society of Clinical Oncology Gastrointestinal Cancers Symposium (ASCO GI), San Francisco, CA, Jan. 23-25, 2020, 6 pages.
Dieguez G, et al., Abstract 670. "Real-World Rates of Hematology Lab Abnormalities and Associated Cost Among Metastatic Pancreatic Cancer (mPC) Therapeutic Regimens," J Clin Oncol. 38(4_Suppl):670 DOI: 10.1200/JCO.2020.38.4_suppl.670 (2020), 2 printed pages.
Doris J, et al., Abstract CT12. "The Cost of Adverse Events for FDA-Approved/Nccn Category 1 Treatments for Medicare Fee-For-Service (FFS) Patients With Metastatic Pancreatic Cancer: Focus on Liposomal Irinotecan-Based Regimens," Hematology Oncology Pharmacy Association (HOPA) Annual Conference, Mar. 11-14, 2020, available at eventscribe.com/2020/posters/HOPAahead/SplitViewer.asp?PID=Njg0NzA2NjU1NjE, (2020), 2 pages.
Dos Santos N, et al., "Improved Retention of Idarubicin After Intravenous Injection Obtained for Cholesterol-Free Liposomes," Biochim Biophys Acta. 1561(2):188-201 (2002).
Drummond D, et al., "Clinical Development of Histone Deacetylase Inhibitors as Anticancer Agents," Annu Rev Pharmacol Toxicol. 45:495-528 and C1-C2 (2005).
Kim G, et al., Abstract e16740. "Real-World Use of Liposomal Irinotecan-Based Regimens Among Patients (pts) With Metastatic Pancreatic Adenocarcinoma (mPDAC) in the United States (U.S.)," J Clin Oncol. 38(15_Suppl):e16740 DOI: 10.1200/JCO.2020.38.15_suppl.e16740 (2020), 2 printed pages.
Kim H, et. al., "Phase II Study of Palliative S-1 in Combination With Cisplatin as Second-Line Chemotherapy for Gemcitabine-Refractory Pancreatic Cancer Patients," Oncol Lett. 3(6):1314-8 (2012).
Kim Y, et. al., "Phase II Study of 5-Fluorouracil and Paclitaxel in Patients With Gemcitabine-Refractory Pancreatic Cancer," Cancer Chemother Pharmacol. 63(3):529-33 (2009). Epub 2008.
Kindler H, et. al., "Arsenic Trioxide in Patients With Adenocarcinoma of the Pancreas Refractory to Gemcitabine: A Phase II Trial of the University of Chicago Phase II Consortium," Am J Clin Oncol. 31(6):553-6 (2008).
Kindler H, et. al., "Gemcitabine Plus Bevacizumab Compared With Gemcitabine Plus Placebo in Patients With Advanced Pancreatic Cancer: Phase III Trial of the Cancer and Leukemia Group B (CALGB 80303)," J Clin Oncol. 28(22):3617-22 (2010).
Kipps E, et. al., "Liposomal Irinotecan in Gemcitabine-Refractory Metastatic Pancreatic Cancer: Efficacy, Safety and Pace in Therapy," Ther Adv Med Oncol. 9(3):159-70 (2017).
Kirpotin D, et al., "Building and Characterizing Antibody-Targeted Lipidic Nanotherapeutics," Methods Enzymol. 502:139-66 (2012).
Kirpotin D, et al., "Targeting of Liposomes to Solid Tumors: The Case of Sterically Stabilized Anti-HER2 Immunoliposomes," J Liposome Res. 7:391-417 (1997).
Kirpotin D, et al., Chapter 4.7, "Targeting of Sterically Stabilized Liposomes to Cancers Overexpressing HER2/neu Proto-Oncogene," In Medical Applications of Liposomes, Lasic D and Papahadjopoulos D, eds., pp325-345 (1998).
Klapdor R and Fenner C, "Irinotecan(Campto R): Efficacy as Third/Forth Line Therapy in Advanced Pancreatic Cancer," Anticancer Res. 20(6D): 5209-12 (2000).
Klapdor R, et. al., "Reflections on Treatment Strategies for Palliative Chemotherapy of Pancreatic Cancer," Anticancer Res. 27(4A): 1789-94 (2007).
Kline C, et. al., "Preliminary Observations Indicate Variable Patterns of Plasma 5-Fluorouracil (5-FU) Levels During Dose Optimization of Infusional 5-FU in Colorectal Cancer Patients," Cancer Biol Ther. 12(7):557-68 (2011).
Klinz S, et al., Abstract e16205. "DNA Damage With Liposomal Irinotecan (nal-IRI) in Pancreatic Cancer Xenografts: Multimodal Analysis of Deposition Characteristics," J Clin Oncol. 36(15_Suppl):e16205 Doi: 10.1200/JCO.2018.36.15_suppl.e16205 (2018), 2 printed pages.
Ko A, et. al., "A Phase II Study of Bevacizumab Plus Erlotinib for Gemcitabine-Refractory Metastatic Pancreatic Cancer," Cancer Chemother Pharmacol. 66(6):1051-7 (2010).
Koeller J, et al., Abstract e16751. "Trends in Real-World Clinical Outcomes Among Patients (pts) With Metastatic Pancreatic Adenocarcinoma (mPDAC) Treated With Liposomal Irinotecan Based Regimens in the United States (US)," J Clin Oncol. 38(15_Suppl):e16751 DOI: 10.1200/JCO.2020.38.15_suppl.e16751 (2020), 2 printed pages.
Krauss W, et al., "Emerging Antibody-Based HER2 (ErbB2/neu) Therapeutics," Breast Dis. 11:113-24 (2000).
Kraut E, et. al., Abstract 2017. "Final Results of a Phase I Study of Liposome Encapsulated SN-38 (LE-SN38): Safety, Pharmacogenomics, Pharmacokinetics, and Tumor Response," J Clin Oncol. 23(16_Suppl):2017 (2005), 3 printed pages.

(56) References Cited

OTHER PUBLICATIONS

Kulke M, et. al', "A Phase II Trial of Irinotecan and Cisplatin in Patients with Metastatic Neuroendocrine Tumors," Dig Dis Sci. 51(6):1033-8 (2006).

Kulke M, et. al., "Capecitabine Plus Erlotinib in Gemcitabine-Refractory Advanced Pancreatic Cancer," J Clin Oncol. 25(30):4787-92 (2007).

Kulke M, et. al., "Randomized Phase II Study of Gemcitabine Administered at a Fixed Dose Rate or in Combination With Cisplatin, Docetaxel, or Irinotecan in Patients With Metastatic Pancreatic Cancer: CALGB 89904," J Clin Oncol. 27(33):5506-12 (2009).

Lakatos G, et al., "Prognostic Value of Baseline Biliary Stents on Outcomes in Patients With Metastatic Pancreatic Ductal Adenocarcinoma (mPDAC) in the Napoli-1 Trial." Poster presented at the European Society for Medical Oncology 20th World Congress on Gastrointestinal Cancer, Barcelona, Spain, Jun. 20-23, 2018, 10 pages.

Lakatos G, et al., Abstract P-151. "Prognostic Value of Baseline Biliary Stents on Outcomes in Patients With Metastatic Pancreatic Ductal Adenocarcinoma (mPDAC) in the NAPOLI-1 Trial," Ann Oncol. 29(Suppl_5):v42 doi:10.1093/annonc/mdy151 (2018).

Lamichfiane N, et. al., "Liposomes: Clinical Applications and Potential for Image-Guided Drug Delivery," Molecules. 23(2)288 doi: 10.3390/molecules2302028 (2018), 17 pages.

Larsen A, et al., "Influence of Liposomal Irinotecan (nal-IRI) and Non-Liposomal Irinotecan, Alone and in Combination, on Tumor Growth and Angiogenesis in Colorectal Cancer (CRC) Models." Poster presented at the American Society of Clinical Oncology Gastrointestinal Cancers Symposium (ASCO GI), San Francisco, CA, Jan. 18-20, 2018, 9 pages.

Larsen A, et al., Abstract 771. "Influence of Liposomal Irinotecan (nal-IRI) and Non-Liposomal Irinotecan, Alone and in Combination, on Tumor Growth and Angiogenesis in Colorectal Cancer (CRC) Models," J Clin Oncol. 36(4_Suppl):711 DOI: 10.1200/JCO.2018.36.4_suppl.711 (2018), 2 printed pages.

Latimer H, et al., Abstract C5. "Utilization of Hospital Inpatient Services Among Patients With Metastatic Pancreatic Cancer With Commercial and Medicare Insurance Treated With FDA-Approved/NCCN Category 1 Regimens," J Manag Care Spec Pharm. 26(10-a):S20 (2020).

Le A, et.al., "Conceptual Framework for Cutting the Pancreatic Cancer Fuel Supply," Clin Cancer Res. 18(16):4285-90 (2012).

Lecovorin Calcium package insert, Teva, revised Oct. 2009, 6 pages.

Lee H, et al., "(64)Cu-Mm-302 Positron Emission Tomography Quantifies Variability of Enhanced Permeability and Retention of Nanoparticles in Relation to Treatment Response in Patients with Metastatic Breast Cancer," Clin Cancer Res. 23(15):4190-4202 (2017).

Lee H, et al. "A Gradient-Loadable (64)Cu-Chelator for Quantifying Tumor Deposition Kinetics of Nanoliposomal Therapeutics by Positron Emission Tomography," Nanomedicine. 11(1):155-65 (2015). Epub 2014.

Lee K, et al., Abstract P-153. "Decreased Appetite (DA) at Baseline Impacts Prognosis in the NAPOLI-1 Phase 3 Study in Metastatic Pancreatic Ductal Adenocarcinoma (mPDAC)," Ann Oncol. 29(Suppl_5):v42-v43 doi:10.1093/annonc/mdy151 (2018).

Lee K-H, et al., "Decreased Appetite (DA) at Baseline Impacts Prognosis in the NAPOLI-1 Phase 3 Study in Metastatic Pancreatic Ductal Adenocarcinoma (mPDAC)." Poster presented at the European Society for Medical Oncology 20th World Congress on Gastrointestinal Cancer, Barcelona, Spain, Jun. 20-23, 2018, 9 pages.

Leonard S, et al., "Deposition Characteristics and Resulting DNA Damage Patterns of Liposomal Irinotecan (nal-IRI) in Pancreatic Cancer Xenografts." Poster presented at the American Society of Clinical Oncology Gastrointestinal Cancers Symposium (ASCO GI), San Francisco, CA, Jan. 18-20, 2018, 9 pages.

Leonard S, et al., Abstract 335. "Deposition Characteristics and Resulting DNA Damage Patterns of Liposomal Irinotecan (nal-IRI) in Pancreatic Cancer Xenografts," J Clin Oncol. 36(4_Suppl):335 DOI: 10.1200/JCO.2018.36.4_suppl.335 (2018), 2 printed pages.

Li J and Saif M, "Any Progress in the Management of Advanced Pancreatic Cancer? Highlights from the 45th ASCO 4nnual Meeting." JOP. J Pancreas (Online) 10(4):361-5 (2009).

Li J et al.' "Any Second-Line Therapy for Advanced Pancreatic Cancer? Highlights from the 2010 ASCO Gastrointestinal Cancers Symposium." JOP. J Pancreas (Online). 11(2):151-3 (2010).

Liu B, et al. "Mapping Tumor Epitope Space by Direct Selection of Single-Chain Fv Antibody Libraries on Prostate Cancer Cells," Cancer Res. 64(2):704-10 (2004).

Liu B., et al. "Recombinant Full-Length Human IgG1s Targeting Hormone-Refractory Prostate Cancer," J Mol Med (Berl). 85(10):1113-23 (2007).

Liu J-J, et al.' "Simple and Efficient Liposomal Encapsulation of Topotecan by Ammonium Sulfate Gradient: Stability, Pharmacokinetic and Therapeutic Evaluation," Anticancer Drugs. 13(7):709-17 (2002).

Löhr J, et. al., "Cationic Liposomal Paclitaxel Plus Gemcitabine or Gemcitabine Alone in Patients With Advanced Pancreatic Cancer: a Randomized Controlled Phase II Trial," Ann Oncology. 23(5):1214-22 (2012). Epub 2011.

Lundberg B, et al., "Conjugation of Apolipoprotein B with Liposomes and Targeting to Cells in Culture," Biochim Biophys Acta. 1149(2):305-12 (1993).

Ma W, et al., Abstract 2365. "Nanoliposomal Irinotecan (MM-398, nal-IRI) Population Pharmacokinetics (PK) and its Association With Efficacy and Safety in Patients With Solid Tumors Based on the Phase 3 Study NAPOLI-1 and Five Phase 1 and 2 Studies," Eur J Cancer. 51(3):S458 10.1016/S0959-8049(16)31281-3 (2015).

Ma W, et al., Abstract e13588. "Population Pharmacokinetics and Exposure-Safety Relationship of Nanoliposomal Irinotecan (MM-398, nal-IRI) in Patients With Solid Tumors," J Clin Oncol. 33(15_Suppl):e13588 DOI: 10.1200/co.2015.33.15_suppl.e13588 (2015), 2 printed pages.

Mabro M, et. al., "A Phase II Study of FOLFIRI-3 (Double Infusion of Irinotecan Combined With LV5FU) After FOLFOX in Advanced Colorectal Cancer Patients," Br J Cancer. 94(9):1287-92 (2006).

Mabro M, et. al., "Bimonthly Leucovorin, Infusion 5-Fluorouracil, Hydroxyurea, and Irinotecan (FOLFIRI-2) for Pretreated Metastatic Colorectal Cancer," Am J Clin Oncol. 26(3):254-8 (2003).

Macarulla Mercadé T, et al., "NAPOLI-1 Phase 3 Trial Outcomes by Prior Surgery, and Disease Stage, in Patients With Metastatic Pancreatic Ductal Adenocarcinoma (mPDAC)." Poster presented at the European Society for Medical Oncology Annual Congress, Munich, Germany, Oct. 19-23, 2018, 7 pages.

Macarulla Mercadé T, et al., "Prognostic Effect of Primary Tumour Location in the NAPOLI-1 Phase 3 Study in Metastatic Pancreatic Ductal Adenocarcinoma (mPDAC)." Poster presented at the European Society for Medical Oncology 19th World Congress on Gastrointestinal Cancer, Barcelona, Spain, Jun. 20-23, 2018, 10 pages.

Macarulla Mercadé T, et al., "Selected Subgroup Analyses of Liposomal Irinotecan in Patients With Metastatic Pancreatic Ductal Adenocarcinoma in the Global Napoli-1 Phase III Trial." Presentation presented at the European Society for Medical Oncology (Esmo) 20th World Congress on Gastrointestinal Cancer, Barcelona, Spain, Jun. 20-23, 2018, 16 pp.

Macarulla Mercadé T, et al., "Subgroup Analysis by Baseline Pain Intensity (BPI) and Baseline Analgesic Use (BAU) in NAPOLI-1, A phase 3 Study of Liposomal Irinotecan (nal IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.

Macarulla Mercadé T, et al., "Subgroup Analysis by Baseline Weight-Associated Parameters: A phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of clinical Oncology Gastrointestinal Cancers Symposium (ASCO GI), San Francisco, CA, Jan. 18-20, 2018, 7 pages.

(56) References Cited

OTHER PUBLICATIONS

Macarulla Mercadé T, et al., "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy." Poster presented at the European Society for Medical Oncology 20th World Congress on Gastrointestinal Cancer, Barcelona, Spain, Jun. 20-23, 2018, 10 pages.

Macarulla Mercadé T, et al., Abstract 379. "Subgroup Analysis by Baseline Pain Intensity (BPI) and Analgesic Use (BAU) in NAPOLI-1: A phase III Study of Liposomal Irinotecan (nal Iri)±5-Fluorouracil/ Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):379 DOI: 10.1200/JCO.2018.36.4_suppl.379 (2018), 4 printed pages.

Macarulla Mercadé T, et al., Abstract 410. "Subgroup Analysis by Baseline (BL) Weight-Associated Parameters: A phase III Study of Liposomal Irinotecan (nal-IRI)±5-Fluorouracil/Leucovorin (5-FU/LV) in Patients (pts) With Metastatic Pancreatic Ductal Adenocarcinoma (mPDAC) Previously Treated With Gemcitabine-Based (Gem) Therapy," J Clin Oncol. 36(4_Suppl):410 DOI: 10.1200/JCO.2018.36.4_suppl.410 (2018), 6 printed pages.

Macarulla Mercadé T, et al., Abstract 733P. "NAPOLI-1 Phase III Trial Outcomes by Prior Surgery, and Disease Stage, in Patients With Metastatic Pancreatic Ductal Adenocarcinoma (mPDAC)," Ann Oncol. 29(Supp_8)viii249-viii250 doi:10.1093/annonc/mdy282 (2018).

Macarulla Mercadé T, et al., Abstract O-004. "Selected Subgroup Analyses of Liposomal Irinotecan (nal-IRI) in Patients With Metastatic Pancreatic Ductal Adenocarcinoma (mPDAC) in the Global NAPOLI-1 Phase III Trial," Ann Oncol. 29(Suppl_5)v101 doi:10.1093/annonc/mdy149 (2018).

Macarulla Mercadé T, et al., Abstract P-150. "Prognostic Effect of Primary Tumour Location in the NAPOLI-1 Phase 3 Study in Metastatic Pancreatic Ductal Adenocarcinoma (mPDAC)," Ann Oncol. 29(Suppl_5)v41-v42 doi:10.1093/annonc/mdy151 (2018).

Macarulla Mercadé T, et al., Abstract P-152. "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy," Ann Oncol. 29(Suppl_5):v42 doi:10.1093/annonc/mdy151 (2018).

Macarulla T, et al., "Integrated Population Pharmacokinetic Modelling of Liposomal Irinotecan in Patients With Various Tumour Types, Including Untreated Metastatic Pancreatic Cancer (mPC)." Poster presented at the European Society for Medical Oncology (ESMO) Congress 2019, Barcelona, Spain, Sep. 27-Oct. 1, 2019, 6 pages.

Macarulla T, et al., "Subgroup Analysis by Prior Lines of Metastatic Therapy in NAPOLI-1, A Global, Randomized Phase 3 Study of Liposomal Irinotecan ± 5-Fluorouracil and Leucovorin, vs. 5-Fluorouracil and Leucovorin in Patients With Metastatic Pancreatic Ductal Adenocarcinoma Who Have Progressed Following Gemcitabine-Based Therapy." Poster presented at the American Society of Clinical Oncology (ASCO) Annual Conference, Chicago, IL, Jun. 2-6, 2017, 7 pages.

Macarulla T, et al., Abstract 4127. "Subgroup Analysis by Prior Lines of Metastatic Therapy (mtx) in NAPOLI-1: A Global, Randomized Phase 3 Study of Liposomal Irinotecan (nal-IRI) ± 5-Fluorouracil and Leucovorin (5-FU/LV), vs. 5-FU/LV in Patients (pts) With Metastatic Pancreatic Ductal Adenocarcinoma (mPDAC) Who Have Progressed Following Gemcitabine-Based Therapy," J Clin Oncol. 35(15_Suppl):4127 DOI: 10.1200/JCO.2017.35.15_suppl4127 (2017), 2 printed pages.

Macarulla T, et al., Abstract 691P. "Integrated Population Pharmacokinetic Modelling of Liposomal Irinotecan in Patients With Various Tumour Types, Including Untreated Metastatic Pancreatic Cancer (mPC)," Ann Oncol. 30(Suppl_5):v263 doi:10.1093/annonc/mdz247 (2019).

Mackenzie M, et. al., "A Phase I Study of OSI-211 and Cisplatin as Intravenous Infusions Given on Days 1, 2 and 3 Every 3 Weeks in Patients With Solid Cancers," Ann Oncol.15(4):665-70 (2004).

Malet-Martino M and Martino R, "Clinical Studies of Three Oral Prodrugs of 5-Fluorouracil (Capecitabine, UFT, S-1): A Review," Oncologist. 7(4):288-323 (2002).

Mamot C, et al. "Epidermal Growth Factor Receptor (EGFR)-Targeted Immunoliposomes Mediate Specific and Efficient Drug Delivery to EGFR- and EGFRvIII-Overexpressing Tumor Cells," Cancer Res. 63(12):3154-61 (2003).

Mamot C, et al., "Liposome-Based Approaches to Overcome Anticancer Drug Resistance," Drug Resist Updat. 6(5)271-9 (2003).

Mancini R and Modlin J, "Chemotherapy Administration Sequence: A Review of the Literature and Creation of a Sequencing Chart," J Hematol Oncol Pharm. 1(1):17-25 (2011).

Markham C, et al., "A Phase II Irinotecan-Cisplatin Combination in Advanced Pancreatic Cancer," Br J Cancer. 89(10):1860-4 (2003).

Martin L, et. al., "VEGF Remains an Interesting Target in Advanced Cancreas Cancer (APCA): Results of a Multi-Institutional Phase II Study of Bevacizumab, Gemcitabine, and Infusional 5-Fluorouracil in Patients With APCA," Ann Oncol. 23(11):2812-20 (2012).

Mathijssen R, et. al., "Clinical Pharmacokinetics and Metabolism of Irinotecan (CPT-11)," Clin Cancer Res. 7(8)2182-94 (2001).

Matrisian, et. al., "The Past, Present, and Future of Pancreatic Cancer Clinical Trials," American Society of Clinical Oncology Educational Book. 35:e205-15 (2016).

Matsusaka S, et. al., "Differential Effects of Two Fluorouracil Administration Regimens for Colorectal Cancer," Oncol Rep. 10(1):109-13 (2003).

Mayer L, et. al.,"Ratiometric Dosing of Anticancer Drug Combinations: Controlling Drug Ratios After Systemic Administration Regulates Therapeutic Activity in Tumor-Bearing Mice," Mol Cancer Ther. 5(7):1854-63 (2006).

McNamara M, et al., "Net-02: A Multi-Centre, Randomized, Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)." Poster presented at the 17th Annual European Neuroendocrine Tumor Society (ENETS) Conference for the Diagnosis and Treatment of Neuroendocrine Tumor Disease, Virtual Conference, Mar. 11-13, 2020, 4 pages.

McNamara M, et al., Abstract P04. "Net-02: A Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)," In Abstracts of the 17th Annual European Neuroendocrine Tumor Society (ENETS) Conference for the Diagnosis and Treatment of Neuroendocrine Tumor Disease, Virtual Conference, Mar. 11-13, 2020, p. 374.

Meerum Terwogt J, et. al., "Phase I and Pharmacokinetic Study of SPI-77, a Liposomal Encapsulated Dosage Form of Cisplatin," Cancer Chemother Pharmacol. 49(3):201-10 (2002).

Melisi D, et al., Abstract B04. "Effects of Nanoliposomal Irinotecan (nal-IRI; MM-398) ± 5-Fluorouracil and Leucavorin (5-FU/LV) on Quality of Life (QoL) in Patients (pts) With Metastatic Pancreatic Adenocarcinoma (mPAC) Previously Treated With Gemcitabine-Based Therapy: Results From the Phase 3 NAPOLI-1 Study," Ann Oncol. 27(Supp_4):iv18 doi:10.1093/annonc/mdw333.4 (2016).

Messerer C, et. al., "Liposomal Encapsulation of Irinotecan and Potential for the Use of Liposomal Drug in the Treatment of Liver Metastases Associated with Advanced Colorectal Cancer," MS Thesis, University of British Columbia, 2000, 90 pages.

Moore M, et. al., "Erlotinib Plus Gemcitabine Compared With Gemcitabine Alone in Patients With Advanced Pancreatic Cancer: A Phase III Trial of the National Cancer Institute of Canada Clinical Trials Group," J Clin Oncol. 25(15):1960-6 (2007).

Morise M, et al., "Low-dose Irinotecan as a Second-line Chemotherapy for Recurrent Small Cell Lung Cancer," Jpn J Clin Oncol. 44(9):846-51 (2014).

Muldoon L, et aL, "Comparing Service Utilization and Costs for Medicare FFS Patients With Metastatic Pancreatic Cancer by Chemotherapy Regimen and Line of Therapy." Poster presented at the

(56) References Cited

OTHER PUBLICATIONS

International Society for Pharmacoeconomics and Outcomes Research (ISPOR) Annual Meeting, New Orleans, LA, May 18-22, 2019, 6 pages.
Muldoon L, et al., Abstract e18357. "Treatment Patterns, Survival Rate, and Parts A and B Costs by Line of Therapy for FDA-Approved/NCCNCategory 1 Treatments for Patients With Metastatic Pancreatic Cancer," J Clin Oncol. 37(15_Suppl):e18357 DOI: 10.1200/JCO.2019.37.15_suppl.e18357 (2019), 2 printed pages.
Muldoon L, et aL, Abstract PCN302. "Comparing Service Utilization and Costs for Medicare FFS Patients With Metastatic Pancreatic Cancer by Chemotherapy Regimen and Line of Therapy," Value in Health. 22(Suppl 2):S113-S114 (2019).
Munzone E, "Adverse Side Effects Associated to Metronomic Chemotherapy," Presentation presented at Aiom Cancer Metronomic Therapy, Feb. 26, 2016, Milan, 32 pages.
Myocet liposomal, Summary of product characteristics and labelling and package leaflet, European Medicines Agency, available at ema.europa.eu/en/documents/product-information/myocet-liposomal-previously-myocet-epar-product-information_en.pdf, Date of first authorisation: Jul. 13, 2000, Date of latest renewal: Jul. 2, 2010, 37 pages.
Nakai Y, et. al., "Inhibition of Renin—Angiotensin System Affects Prognosis of Advanced Pancreatic Cancer Receiving Gemcitabine," Br J Cancer 103(11)1644-8 (2010).
Nakajima T, et. al., "Synergistic Antitumor Activity of the Novel SN-38-Incorporating Polymeric Micelles, NK012, combined With 5-Fluorouracil in a Mouse Model of Colorectal Cancer, As Compared With That of Irinotecan Plus 5-Fluorouracil," Int J Cancer. 122(9):2148-53 (2008).
Nardi M, et. al., Abstract 14520. "Metronomic Irinotecan and Standard FOLFIRI Regimen as First-Line Chemotherapy in Metastatic Colorectal Cancer (MCRC). Final Results of Phase II Study," J Clin Oncol. 25(18_suppl):14520 (2007), 1 printed page.
National Cancer Institute, "Irinotecan Hydrochloride Liposome,"Posted: Oct. 27, 2015, Updated:Mar. 28, 2019, available at cancergov/about-cancer/treatment/drugs/irinotecan-hydrochloride-liposome, 2 pages.
Neesse A, et al., "Stromal Biology and Therapy in Pancreatic Cancer," Gut. 60(6):861-8 (2011). Epub 2010.
Nelson R, "Lipsomal Irinotecan Boosts Survival in Pancreatic Cancer," Medscape, available at medscape.com/viewarhcle/838501, 2015, 2 printed pages.
Nieto J, et. al., "Metastatic Pancreatic Cancer 2008: Is the Glass Less Empty?," Oncologist. 13(5):562-76 (2008) and erratum found at Oncologist 13(6):738 (2008).
Noble C, et al, "Development of Ligand-Targeted Liposomes for Cancer Therapy," Expert Opin Ther Targets. 8(4):335-53 (2004).
Noordhuis P, et. al., "5-Fluorouracil Incorporation into RNA and DNA in Relation to Thymidylate Synthase Inhibition of Human Colorectal Cancers," Ann Oncol. 15(7):1025-32 (2004).
Oberstein P and Olive K, "Pancreatic Cancer: Why Is It So Hard to Treat?" Ther Adv Gastroenterol. 6(4):321-37(2013).
Oettle H and Lehmann T, "Gemcitabine-Resistant Pancreatic Cancer: A Second-Line Option," Lancet. 387(10018):507-8 (2016). Epub 2015.
Ogata Y, et. al., "Dosage Escalation Study of S-1 and Irinotecan in Metronomic Chemotherapy against Advanced Colorectal Cancer," Kurume Med J. 56(1-2):1-7 (2009).
Oncology News International, "Experts Debate Bolus vs Continuous Infusion 5-FU." Feb. 1, 2003, vol. 12, Issue 2, 3 printed pages.
O'Reilly E, et al., "Impact of Prior Irinotecan Exposure on Outcomes of Metastatic Pancreatic Cancer Patients." Poster presented at the American Society of Clinical Oncology Gastrointestinal Cancers Symposium (ASCO GI), San Francisco, CA, Jan. 23-25, 2020, 6 pages.
O'Reilly E, et al., "Real-World Patterns of Care Among Patients With Metastatic Pancreatic Cancer." Poster presented at the American Society of Clinical Oncology Gastrointestinal Cancers Symposium (ASCO GI), San Francisco, CA, Jan. 23-25, 2020, 6 pages.
O'Reilly E, et al., Abstract 666. "Real-World Patterns of Care Among Patients With Metastatic Pancreatic Cancer(mPC)," J Clin Oncol. 38(4_Suppl):666 DOI: 10.1200/JCO.2020.38.4_suppl_666 (2020), 2 printed pages.
Awasthi N, et al., "Antitumor Efficacy of a Liposomal Formulation of Irinotecan in Preclinical Gastric Cancer Models: Augmenting Its Response by Antiangiogenic Agents." Poster presented at the Annual Meeting of the American Association for Cancer Research 2020, Philadelphia, PA, Apr. 27-28, 2020 and Jun. 22-24, 2020, 6 pages.
Awasthi N, et al., Abstract 553. "Antitumor Efficacy of a Liposomal Formulation of Irinotecan in Preclinical Gastric Cancer Models: Augmenting Its Response by Antiangiogenic Agents," In Proceedings of the Annual Meeting of the American Association for Cancer Research 2020; Apr. 27-28, 2020 and Jun. 22-24, 2020. Cancer Res. 2020;80(16 Suppl):Abstract nr 553, DOI: 10.1158/1538-7445. AM2020-553, 2 printed pages.
Conroy T et al., Abstract 4010. "Randomized Phase III Trial Comparing FOLFIRINOX (F: 5FU/Leucovorin [LV], Irinotecan [I}, and Oxaliplatin [O]) Versus Gemcitibine (G) as First-Line Treatment for Metastatic Pancreatic Adenocarcinoma (MPA): Preplanned Interim Analysis Results of the PRODIGE 4/ACCORD 11 Trial" J Clin Oncol. 28(15_Suppl):4010 (2010), 3 printed pages.
Dean A, et al., "First-Line (1L) Liposomal Irinotecan + 5-Fluorouracil/ Leucovorin (5-FU/LV) + Oxaliplatin (OX) in Patients With Locally Advanced or Metastatic Pancreatic Ductal Adenocarcinoma: Exploratory Subgroup Analyses of Survival by Changes in CA 19-9 Levels." Poster presented at the European Society for Medical Oncology (ESMO) Virtual Congress 2020, Sep. 19-21, 2020, 7 pages.
Dean A, et al., "First-Line Liposomal Irinotecan + 5-Fluorouracil/ Leucovorin + Oxaliplatin in Patients With Pancreatic Ductal Adenocarcinoma: Results From a Phase 1/2 Study." Presentation presented at the Clinical Oncology Society of Australia (COSA): Virtual meeting, Nov. 11-13, 2020, 10 pages.
Dean a, et al., "NAPOLI-3: An Open-Label, Randomized, Phase III Study of First-Line Liposomal Irinotecan + 5-Fluorouracil/ Leucovorin + Oxaliplatin Versus nab-Paclitaxel + Gemcitabine in Patients With Metastatic Pancreatic Ductal Adenocarcinoma." Presentation presented at the Clinical Oncology Society of Australia (COSA): Virtual meeting, Nov. 11-13, 2020, 10 pages.
Dean A, et al., Abstract 1529P. "First-Line (10 Liposomal Irinotecan + 5-Fluorouracil/Leucovorin (5-FU/LV) + Oxaliplatin (OX) in Patients With Locally Advanced or Metastatic Pancreatic Ductal Adenocarcinoma (mPDAC): Exploratory Subgroup Analyses of Survival by Changes in CA 19-9 Levels," Ann Oncol. 31(Suppl_4):S881-S897 10.1016/annonc/annonc285 (2020), 3 printed pages.
Dean A, et al., Abstract 222. "First-Line Liposomal Irinotecan + 5-Fluorouracil/Leucovorin + Oxaliplatin in Patients With Pancreatic Ductal Adenocarcinoma: Results From a Phase 112 Study," Asia-Pac J Clin Oncol. 16(Suppl. 8):118-119 (2020).
Dean A, et al., Abstract 407. "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma," Asia-Pac J Clin Oncol. 16(Suppl. 8):202-3 (2020).
Dean A, et al., Abstract 4111. "A Phase 1/2, Open-Label Dose-Escalation Study of Liposomal Irinotecan (nal-IRI) Plus 5- Fluorouracil/ Leucovorin (5-FU/LV) and Oxaliplatin (OX) in Patients with Previously Untreated Metastatic Pancreatic Cancer (mPAC)," J Clin Oncol. 36(15_Suppl):4111 10.1200/JCO.2018.36.15_suppl.4111 (2018), 1 page.
Delord J, et. al., "A Phase I Clinical and Pharmacokinetic Study of Capecitabine (Xeloda®) and Irinotecan Combination Therapy (XELIRI) in Patients With Metastatic Gastrointestinal Tumours," Br J Cancer 92(5):820-6 (2005).
Fioravanti A, et. al., "Metronomic 5-Fluorouracil, Oxaliplatin and Irinotecan in Colorectal Cancer," Eur J Pharmacol. 619(1-3): 8-14 (2009).
Garufi C, et. al., "A Phase II Study of Irinotecan Plus Chronomodulated Oxaliplatin, 5-Fluorouracil and Folinic Acid in Advanced Colorectal Cancer Patients," Br J Cancer. 89(10):1870-5 (2003).
Gill S, et al., "Pancreox: A Randomized Phase III Study of Fluorouracil/ Leucovorin With or Without Oxaliplatin for Second-Line Advanced

(56) References Cited

OTHER PUBLICATIONS

Pancreatic Cancer in Patients Who Have Received Gemcitabine-Based Chemotherapy," J Clin Oncol. 34(32):3914-20 and Appendix (2016).
Goldberg R, et. al., "A Randomized Controlled Trial of Fluorouracil Plus Leucovorin, Irinotecan, and Oxaliplatin Combinations in Patients With Previously Untreated Metastatic Colorectal Cancer," J Clin Oncol. 22(1):23-30 (2004). Epub 2003.
Novarino A. et. al., "Oxaliplatin, 5-Fluorouracil, and Leucovorin as Second-Line Treatment for Advanced Pancreatic Cancer," Am J Clin Oncol. 32(1):44-8 (2009).
Olszewski A, et. al., "Phase I Study of Oxaliplatin in Combination with Gemcitabine, Irinotecan, and 5-Fluorouracil/Leucovorin(G-FLIE) in Patients with Metastatic Solid Tumors Including Adenocarcinoma of the Pancreas," J Gastrointest Cancer. 44(2):182-9 (2013).
Parekh H, et al., "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study)." Poster presented at the American Society of Clinical Oncology Gastrointestinal Cancers Symposium (ASCO GI), San Francisco, CA, Jan. 23-25, 2020, 3 pages.
Parekh H, et al., Abstract TPS790. "A Phase Ii, Open-Label Pilot Study Evaluating the Safety and Activity of Nal-Iri in Combination With 5 -FU and Oxaliplatin in Preoperative Treatment of Pancreatic Adenocarcinoma (NEO-Nal-IRI Study) (NCT03483038)," J Clin Oncol. 38(4_Suppl):TPS790 (2020), 2 printed pages.
Patel M, et.al., "Effects of Oxaliplatin and CPT-11 on Cytotoxicity and Nucleic Acid Incorporation of the Fluoropyrimidines," J Cancer Res Clin Oncol. 130(8):453-9 (2004).
Pelzer U, et al., "Best Supportive Care (BSC) Versus Oxaliplatin, Folinic Acid and 5-Fluorouracil (OFF) Plus BSC in Patients for Second-Line Advanced Pancreatic Cancer: A Phase III-Study from the German CONKO-Study Group," Eur J Cancer. 47(11):1676-81 (2011).
Poplin E, et. al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009).
Sancho A, et. al., Abstract 15625. "Oxaliplatin and Capecitabine After Gemcitabine Failure in Patients With Advanced Pancreatic, Biliary, and Gallbladder Adenocarcinoma (APBC)," J Clin Oncol. 26(15_suppl):15625 (2008), 5 printed pages.
Starling N, et. al., "A Dose Escalation Study of Gemcitabine Plus Oxaliplatin in Combination With Imatinib for Gemcitabine-Refractory Advanced Pancreatic Adenocarcinoma," Ann Oncol. 23(4):942-7 (2012). Epub 2011.
Stathopoulos G, et. al., "Liposomal Oxaliplatin in the Treatment of Advanced Cancer: A Phase I Study," Anticancer Res. 26(2B):1489-93 (2006).
Takahara N, et. al., "A Retrospective Study of S-1 and Oxaliplatin Combination Chemotherapy in Patients With Refractory Pancreatic Cancer," Cancer Chemother Pharmacol. 72(5):985-90 (2013).
Tsavaris N, et. al., "Second-Line Treatment With Oxaliplatin, Leucovorin and 5-Fluorouracil in Gemcitabine-Pretreated Advanced Pancreatic Cancer: A Phase II Study," Invest New Drugs. 23(4):369-75 (2005).
Wainberg Z, et al., "First-Line Liposomal Irinotecan + 5-Fluorouracil/Leucovorin + Oxaliplatin in Patients With Pancreatic Ductal Adenocarcinoma: Long-Term Follow-Up Results From a Phase 1/2 Study." Poster presented at the European Society for Medical Oncology (ESMO) World Congress on Gastrointestinal Cancer, virtual format, Jul. 1-4, 2020, 7 pages.
Wainberg Z, et al., "NAPOLI-3: An Open-Label, Randomized, Phase 3 Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma." Poster presented at the American Society of Clinical Oncology (ASCO) Annual Conference, virtual format, May 29-Jun. 2, 2020, 6 pages.
Wainberg Z, et al., Abstract TPS4661. "NAPOLI-3: An Open-Label, Randomized, Phase III Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma," J Clin Oncol. 38(15_Suppl):TPS4461 DOI: 10.1200/JCO.2020.38.15_suppl.TPS4661 (2020), 2 printed pages.
Xiong H, et. al., "Phase 2 Trial of Oxaliplatin Plus Capecitabine (XELOX) as Second-line Therapy for Patients With Advanced Pancreatic Cancer," Cancer. 113(8):2046-52 (2008).
Yang et al., "Oxaliplatin Long-Circulating Liposomes Improved Therapeutic Index of Colorectal Carcinoma," BMC Biotechnology. 11:21 doi: 10.1186/1472-6750-11-21 (2011), 8 pages.
Abra R, et. al., "The Next Generation of Liposome Delivery Systems: Recent Experience With Tumor-Targeted, Sterically-Stabilized Immunoliposomes and Active-Loading Gradients," J Liposome Res. 12(1-2):1-3 (2002).
Abrams T, et al., "Patterns of Chemotherapy Use in a U.S.-Based Cohort of Patients with Metastatic Pancreatic Cancer," Oncologist. 22(8):925-933 (2017).
Abushahin L, et al., "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan." Poster presented at the European Society for Medical Oncology Virtual Congress Sep. 19-21, 2020, 5 pages.
Abushahin L, et al., Abstract 1534P. "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan" Ann Oncol. 31(Suppl_4):S881-S897 10.1016/annonc/annonc285 (2020), 2 printed pages.
Abushahin L, et al., Abstract e16780. "Real-World Dosing, Management, and Clinical Outcomes of Patients (pts) With Metastatic Pancreatic Adenocarcinoma (mPDAC) Treated With Liposomal Irinotecan," J Clin Oncol. 38(15_Suppl):e16780 DOI: 10.1200/JCO.2020.38.15_suppl.e16780 (2020), 2 printed pages.
Ahn D, et al., "Real-World Dosing Patterns of Patients With Metastatic Pancreatic Cancer (mPC) Treated With Liposomal Irinotecan (nal-IRI) in US Oncology Clinics." Poster presented at the European Society for Medical Dncology (ESMO), Munich, Germany, Oct. 19-23, 2018, 8 pages.
Ahn D, et al., Abstract 735P. "Real-World Dosing Patterns of Patients (pts) With Metastatic Pancreatic Cancer (mPC) Treated With Liposomal Irinotecan (nal-IRI) in US Oncology Clinics," Ann Oncol. 29(Suppl_8):viii251 doi:10.1093/annonc/mdy282 (2018).
Alese O, et al., "A Phase I/II Study of Trifluridine/Tipiracil (TAS-102) in Combination With Nanoliposomal Irinotecan (NAL-IRI) in Advanced GI Cancers." Poster presented at Chan E, et al., "A Phase 112 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 1-5, 2018, 1 page.
Alese O, et al., Abstract TPS4155. "A Phase I/II Study of Trifluridine/Tipiracil (TAS-102) in Combination With Ganoliposomal Irinotecan (Nal-IRI) in Advanced GI Cancers," J Clin Oncol. 36(15_Suppl):TPS4155 DOI: 10.1200/JCO.2018.36.15_suppl.TPS4155 (2018), 5 printed pages.
Allegrini G, et. al., "A Pharmacokinetic and Pharmacodynamic Study on Metronomic Irinotecan in Metastatic Colorectal Cancer Patients," Br J Cancer. 98(8):1312-19 (2008).
Alves Da Silva A, et. al., "Standardization of the Infusion Sequence of Antineoplastic Drugs Used in the Treatment of Breast and Colorectal Cancers," Einstein (São Paulo). 16(2):eRW4074 doi: 10.1590/S1679-45082018RW4074 (2018), 9 pages.
Amzal B, et al., "Imputing Missing Values to Estimate Health-Related Quality of Life (HR-QoL) in Metastatic Pancreatic Cancer Treated With 5-Fluorouracil and Leucovorin, With and Without Liposomal Irinotecan (nal-IRI)." Poster presented at the International Society for Pharmacoeconomics and Outcomes Research (ISPOR) Annual Meeting, Boston, MA, May 20-24, 2017, 6 pages.
Amzal B, et al., Abstract PCN179. "Imputing Missing Values to Estimate Health-Related Quality of Life (HR-QoL) in Metastatic

(56) References Cited

OTHER PUBLICATIONS

Pancreatic Cancer (mpc) Treated With 5-Fluorouracil and Leucovorin, With and Without Liposomal Irinotecan (nal-IRI)," Value in Health. 20(5):A119 (2017).
Anders C, et al., Abstract e12003. "Pharmacokinetic (PK) Characterization of Irinotecan Liposome Injection in Patients (pts) With Metastatic Breast Cancer (mBC)," J Clin Oncol. 37(15_Suppl):e12003 DOI: 10.1200/JCO.2019.37.15_suppl.e12003 (2019), 2 printed pages.
Andre T, et. al., "Phase III Study Comparing a Semimonthly With a Monthly Regimen of Fluorouracil and Leucovorin As Adjuvant Treatment for Stage II and III Colon Cancer Patients: Final Results of GERCOR C96.1," Clin Oncol. 25(24):3732-8 (2007).
Aranda E, et. al., "Randomized Study of Weekly Irinotecan Plus High-Dose 5-Fluorouracil (FUIRI) Versus Biweekly Irinotecan Plus 5-Fluorouracil/Leucovorin (FOLFIRI) As First-Line Chemotherapy for Patients With Metastatic Colorectal Cancer: A Spanish Cooperative Group for the Treatmentof Digestive Tumors Study," Ann Oncol. 20(2):251-7 (2009).
Araneo M, et. al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," Cancer Invest. 21(4):489-96 (2003).
Atkins K, et al., "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)." Poster presented at the American Society of Clinical Oncology Gastrointestinal Cancers Symposium (ASCO GI), San Francisco, CA, Jan. 23-25, 2020, 1 page.
Atkins K, et al., Abstract TPS780. "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)," J Clin Oncol. 38(4_Suppl):TPS780 DOI: 10.1200/JCO.2020.38.4_suppl.TPS780 (2020), 2 printed pages.
Barbier S, et al., Abstract e16724. "Differentiation of Liposomal Irinotecan From Dose-Dense Non-Liposomal Irinotecan in Patient-Derived Pancreatic Cancer Xenograft Tumor Models," J Clin Oncol. 38(15_Suppl):e16724 DOI: 10.1200/JCO.2020.38.15_suppl.e16724 (2020), 5 printed pages.
Barenholz Y, "Development of Liposomal Drugs and Nano-Drugs: From Academic Research Via Incubators and Startups to FDA and EMA Approved Products. Part I: Science and Technology," Presentation presented at Barcelona NanoMed, Mar. 4-5 2014, 89 pages.
Barenholz Y, "Doxile®—The First FDA-Approved Nano-Drug: Lessons Learned," J Control Release. 160(2):117-34 (2012).
Barone C, et. al., "Schedule-Dependent Activity of 5-Fluorouracil and Irinotecan Combination in the Treatment of Human Colorectal Cancer: In Vitro Evidence and a Phase I Dose-Escalating Clinical Trial," Br J Cancer. 96(1):21-8 :2007). Epub 2006.
Barzi A, et al., Abstract e16229. "Real World Outcomes of Metastatic Pancreatic Cancer (mPC) Patients (pts) Treated With Liposomal Irinotecan (nal-IRI) in the US," J Clin Oncol. 36(15_Suppl):e16229 DOI: 10.1200/ JCO.2018.36.15_suppl.e16229 (2018), 2 printed pages.
Basu S, et. al., "Development and Validation of an UPLC-MS/MS Method for the Quantification of Irinotecan, SN 38 and SN-38 Glucuronide in Plasma, Urine, Feces, Liver and Kidney: Application to a Pharmacokinetic Study of Irinotecan in Rats," J Chromatogr B Analyt Technol Biomed Life Sci. 1015-1016: 34-41 (2016).
Batist G, et al., "Safety Pharmacokinetics, and Efficacy of CPX-1 Liposome Injection in Patients with Advanced Solid Tumors," Clin Cancer Res. 15(2):692-700 (2009).
Batist G, et al., Abstract 2014. "Phase 1 Study of CPX-1, A Fixed Ratio Formulation of Irinotecan (IRI) and Floxuridine (FLOX), in Patients With Advanced Solid Tumors," J Clin Oncol. 24(18_suppl):2014 (2006), 2 printed pages.
Batist G, et al., Abstract 2549. "Ratiometric Dosing of Irinotecan (IRI) and Floxuridine (FLOX) in a Phase I Trial: A New Approach for Enhancing the Activity of Combination Chemotherapy," J Clin Oncol. 25(18_suppl):2549 (2007), 5 printed pages.
Becker C, et al., "Multivariate Analysis of Health-Related Quality of Life (HR-QoL) in Metastatic Pancreatic Cancer Treated with 5-Fluorouracil and Leucovorin (5-FU/LV), With and Without Liposomal Irinotecan (nal-IRI)." Poster presented at the International Society for Pharmacoeconomics and Outcomes Research (ISPOR) Annual Meeting, Boston, MA, May 20-24, 2017, 7 pages.
Becker C, et al., Abstract PCN182. "Multivariate Analysis of Health-Related Quality of Life (HR-QoL) in Metastatic Pancreatic Cancer (mPC) Treated with 5- Fluorouracil and Leucovorin, With and Without Liposomal Irinotecan (nal-IRI)," Value in Health. 20(5):A120 (2017).
Becker C, et al., Abstract PCN58. "Budget Impact Analysis of Nanoliposomal Irinotecan for Treatment of Pancreatic Cancer Following Progression on Gemcitabine—A US Payer Perspective," Value in Health. 19(7):A718-A719 (2016).
Blanc J, et al., "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy." Poster presented at the European Society for Medical Oncology Asia 2017 Congress, Singapore, Nov. 17-19, 2017, 8 pages.
Blanc J, et al., Abstract 228P. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy," Ann Oncol. 28(Suppl_10):x67-x68 doi:10.1093/annonc/mdx660 (2017).
Blanc J, et al., Abstract PD-18. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated With Gemcitabine-Based Therapy," Ann Oncol. 28(Suppl_3):7 doi:10.1093/annonc/mdx263 (2017).
BlueCross Blue Shield of North Carolina Corporate Medical Policy, Bevacizumab in Advanced Adenocarcinoma of the Pancreas, File Name: bevacizumab_in_advanced_adenocarcinoma_of_the_pancreas, Origination: Mar. 2010, Last review: Feb. 2019, 5 pages.
Boeck S and Heinemann V, "Second-Line Therapy in Gemcitabine-Pretreated Patients With Advanced Pancreatic Cancer," J Clin Oncol. 26(7):1178-9 (2008).
Boman N, et al., "Optimization of the Retention Properties of Vincristine in Liposomal Systems," Biochim Biophys Acta. 1152(2):253-58 (1993).
Borner M, et. al., "A Randomized Phase II Trial of Capecitabine and Two Different Schedules of Irinotecan in First-Line Treatment of Metastatic Colorectal Cancer: Efficacy, Quality-of-Life and Toxicity," Ann Oncol. 16(2): 282-8 (2005).
Boulikas T, "Clinical Overview on Lipoplatin: A Successful Liposomal Formulation of Cisplatin," Expert Opin Investig Drugs. 18(8):1197-218 (2009), author manuscript version, 22 pages.
Bozzuto G and Molinari A, "Liposomes as Nanomedical Devices," Int J Nanomedicine. 10:975-99 (2015).
Brus C and Saif M, "Second Line Therapy for Advanced Pancreatic Adenocarcinoma: Where Are We and Where Are We Going?," J Pancreas (Online) 11(4):321-3 (2010).
Bulbake U, et al., "Liposomal Formulations in Clinical Use: an Updated Review," Pharmaceutics. 9(2):12 doi: 10.3390/pharmaceutics9020012 (2017), 33 pages.
Burris H and Rocha-Lima C, "New Therapeutic Directions for Advanced Pancreatic Cancer: Targeting the Epidermal Growth Factor and Vascular Endothelial Growth Factor Pathways," Oncologist. 13(3):289-98 (2008).
Butowski N, et al., "A Phase I Study of CED of Nanoliposomal-Irinotecan Using Real-Time Imaging With Gadoliniu in Patients With Recurrent High Grade Glioma." Poster presented at the American Society of Clinical Oncology (ASCO) Annual Conference, Chicago, IL, May 29-Jun. 2, 2015, 4 pages.
Butowski N, et al., Abstract TPS2081. "A Phase I Study of Convection-Enhanced Delivery of Nanoliposomal Irinotecan Using Real-Time

(56) References Cited

OTHER PUBLICATIONS

Imaging in Patients With Recurrent High Grade Glioma," J Clin Oncol. 33(15_Suppl):2081 DOI: 10.1200/jco.2015.33.15_suppl.tps2081 (2015), 2 printed pages.

Caelyx (doxorubicin), MedBroadcast, accessed Jan. 26, 2021 from medbroadcast.com/drug/getdrug/caelyx, 11 printed pages.

Cao S, et. al., "Synergistic Antitumor Activity of Capecitabine in Combination with Irinotecan," Clin Colorectal Cancer. 4(5):336-43 (2005).

Cao Y, et al., "A Gold Nanoparticle Bouquet Held on Plasma Membrane: An Ultrasensitive Dark-Field Imaging Approach for Cancer Cell Analysis," Nanotheranostics. 4(4):201-209 (2020).

Carter K, et. al., "Sphingomyelin Liposomes Containing Porphyrin—Phospholipid for Irinotecan Chemophototherapy," Theranostics. 6(13):2329-36 (2016).

Cascinu S, et al., "Pancreatic Cancer: ESMO Clinical Practice Guidelines for Diagnosis, Treatment and Follow-up," Ann Oncol. 21(Suppl 5):v55—v58 (2010).

Hann B, et. al., Abstract 5648. "Lipidic Nanoparticle CPT-11 in a Bioluminescent Orthotopic Pancreas Cancer Model," Cancer Res. 67(9 Suppl):5648 (2007), 4 printed pages.

Hare J, "Utilization of Liposomes in Combination Cancer Chemotherapy," PhD thesis, University of Alberta, Department of Pharmacology, 2011, 367 pages.

Harker-Murray P, et al., Abstract CT146. "Plasma Pharmacokinetics of Liposomal Irinotecan (nal-iri) in Pediatric Oncology Patients with Recurrent or Refractory Solid Tumors: South Plains Oncology Consortium Study 2012-001," In Proceedings of the American Association for Cancer Research Annual Meeting 2017; Apr. 1-5, 2017. Washington, DC. Cancer Res. 2017;77(13 Suppl):Abstract nr CT146, doi:10.1158/1538-7445.AM2017-CT146, 4 printed pages.

Hashimoto S, et al., "Depletion of Alveolar Macrophages Decreases Neutrophil Chemotaxis to Pseudomonas Airspace Infections," Am J Physiol. 270(5 Pt 1):L819-28 (1996).

Hattori Y, et al., "Novel Irinotecan-Loaded Liposome Using Phytic Acid with High Therapeutic Efficacy for Colon Tumors," J Control Release. 136(1):30-7 (2009).

Hay M, et. al., "Clinical Development Success Rates for Investigational Drugs," Nature Biotechnol. 32(1):40-51 (2014).

Hayes M, et al., "Genospheres: Self-Assembling Nucleic Acid-Lipid Nanoparticles Suitable for Targeted Gene Delivery," Gene Ther. 13(7):646-51 (2006).

Hayes M, et al., "Increased Target Specificity of Anti-HER2 Genospheres by Modification of Surface Charge and Degree of PEGylation," Mol Pharm. 3(6):726-36 (2006).

Heinemann V, et. al., "Randomized Phase III Trial of Gemcitabine Plus Cisplatin Compared With Gemcitabine Alone in Advanced Pancreatic Cancer," J Clin Oncol. 24(24):3946-52 (2006).

Herrera-Restrepo O, et al., "Budget Impact in the USA of Liposomal Irinotecan as a Post-Gemcitabine Treatment Option for Patients With Metastatic Pancreatic Adenocarcinoma (mPC)." Poster presented at the International Society for Pharmacoeconomics and Outcomes Research (ISPOR) Annual Meeting, New Orleans, LA, May 18-22, 2019, 12 pages.

Herrera-Restrepo O, et al., Abstract PCN80. "Budget Impact in the USA of Liposomal Irinotecan as a Post-Gemcitabine Treatment Option for Patients With Metastatic Pancreatic Adenocarcinoma (mPC)," Value in Health. 22(Suppl 2):S70 (2019).

Hidalgo M, "Pancreatic Cancer," N Engl J Med. 362(17):1605-17 (2010).

Hirsch J, et al., "Comparing Total Cost of Care for Medicare Fee-For-Service Patients With Pancreatic Cancer, By Chemotherapy Regimen." Poster presented at the American Society of Clinical Oncology Gastrointestinal Cancers Symposium (ASCO GI), San Francisco, CA, Jan. 23-25, 2020, 5 pages.

Hirsch J, et al., "Comparing Total Costs of Care for Medicare Fee-For-Service (FFS) Patients With Metastatic Pancreatic Cancer by Chemotherapy Regimen," Poster presented at the Academy of Managed Care Pharmacy, Nexus (AMCP, Nexus): virtual meeting, week of Oct. 19, 2020, 8 pages.

Hirsch J, et al., "The Cost of Adverse Events for FDA-Approved/NCCN Category 1 Treatments for Medicare Fee-For-Service (FFS) Patients With Metastatic Pancreatic Cancer." Poster presented at the Hematology Oncology Pharmacy Association (HOPA) Annual Conference, Tampa, FL, Mar. 11-14, 2020, 6 pages.

Hirsch J, et al., "The Cost of Adverse Events for FDA-Approved/NCCN Category 1 Treatments for Medicare Fee-For-Service Patients With Metastatic Pancreatic Cancer." Poster presented at the American Society of Health-System Pharmacists (ASHP) Midyear 2019 Clinical Meeting and Exhibition, Las Vegas, NV, Dec. 8-12, 2019, 6 pages.

Hirsch J, et al., Abstract 4-138. "The Cost of Adverse Events for FDA-Approved/NCCN Category 1 Treatments for Medicare Fee-For-Service Patients With Metastatic Pancreatic Cancer," American Society of Health-System Pharmacists (ASHP) Midyear Clinical Meeting Professional Poster Abstracts, (2019), 2 pages.

Hirsch J, et al., Abstract 721. "Comparing Total Cost of Care for Medicare FFS Patients With Pancreatic Cancer by Chemotherapy Regimen," J Clin Oncol. 38(4_Suppl):721 DOI: 10.1200/JCO.2020.38.4_suppl.721 (2020), 4 printed pages.

Hirsch J, et al., Abstract e19394. "Comparing Total Cost of Care for Medicare FFS Patients With Pancreatic Cancer by Chemotherapy Regimen," J Clin Oncol. 38(15_Suppl):e19394 DOI: 10.1200/JCO.2020.38.15_suppl.e19394 (2020), 2 printed pages.

Hsu M and Juliano R, "Interactions of Liposomes With the Reticuloendothelial System. II: Nonspecific and Receptor-Mediated Uptake of Liposomes by Mouse Peritoneal Macrophages," Biochim Biophys Acta. 720(4):411-419 (1982).

Huang S, et al., "Liposomes and Hyperthermia in Mice: Increased Tumor Uptake and Therapeutic Efficacy of Doxorubicin in Sterically Stabilized Liposomes," Cancer Res. 54(8):2186-91 (1994).

Huang S, et al., "Light Microscopic Localization of Silver Enhanced Liposome-Entrapped Colloidal Gold in Mouse Tissues," Biochim Biophys Acta. 1069(1):117-21 (1991).

Huang S, et al., "Microscopic Localization of Sterically Stabilized Liposomes in Colon-Carcinoma Bearing Mice," Cancer Res. 52(19):5135-43 (1992).

Huang S, et. al., "Pharmacokinetics and Therapeutics of Sterically Stabilized Liposomes in Mice Bearing C-26 Colon Carcinoma," Cancer Res. 52(24):6774-81 (1992).

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated With Gemcitabine," Presentation presented at the European Society for Medical Oncology (ESMO) World Congress on Gastrointestinal Cancer, Barcelona, Spain, Jun. 29-Jul. 2, 2016, 13 pages.

Hubner R, et al., "Prognostic Value of Baseline Neutrophil-to-Lymphocyte Ratio (NLR) for Predicting Clinical Dutcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone." Poster presented at the European Society for Medical Oncology (ESMO) Annual Congress, Madrid, Spain, Sep. 8-12, 2017, 5 pages.

Hubner R, et al., "Time Course of Selected Treatment-Emergent Adverse Events in NAPOLI-1: A Phase 3 Study of Liposomal Irinotecan (nal-IRI; MM-398) ± 5-Fluorouracil and Leucovorin (5-FU/LV) vs 5-FU/LV in Metastatic Pancreatic cancer Previously Treated With Gemcitabine-Based Therapy." Poster presented at the European Society for Medical Dncology (ESMO) Annual Congress, Copenhagen, Denmark, Oct. 7-11, 2016, 8 pages.

Hubner R, et al., Abstract 242P. "Effects of nal-IRI (MM-398) ± 5-Fluorouracil on Quality of Life (QoL) of Patients With Metastatic Pancreatic Ductal Adenocarcinoma (mPDAC) Previously Treated With Gemcitabine Based Therapy: Results From NAPOLI-1 ," Ann Oncol. 27(Supp_9):ix76 doi:10.1093/annonc/mdw582 (2016).

Hubner R, et al., Abstract 3832. "Time Course of Selected Treatment Emergent Adverse Events (TEAES) in NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.

(56) References Cited

OTHER PUBLICATIONS

Hubner R, et al., Abstract 741P. "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone," Ann Oncol. 28(Suppl_5):253 doi:10.1093/annonc/mdx369 (2017).

Hubner R, et al., Abstract. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," 2015 National Cancer Research Institute (NCRI) Cancer Conference, Nov. 1-4, 2015, (2015), 2 printed pages.

Hwang J, et al., Abstract 4618. "A Randomized Phase II Study of FOLFOX or FOLFIRI.3 as Second-Line Therapy in Patients With Advanced Pancreatic Cancer Previously Treated With Gemcitabine-Based Chemotherapy," J Clin Oncol. 27(15_Suppl):4618 (2009), 2 printed pages.

Hwang J, et. al., "Improving the Toxicity of Irinotecan/5-FU/Leucovorin: A 21-Day Schedule," Oncology. 17(9):37-43 (2003). Available at cancernetwork.com/view/improving-toxicity-irinotecan5-fu-leucovorin-21-day-schedule, 13 printed pages.

Ignatiadis M, et. al., "A Multicenter Phase II Study of Docetaxel in Combination with Gefitinib in Gemcitabine-Pretreated Patients with Advanced/Metastatic Pancreatic Cancer," Oncology. 71(3-4):159-63 (2006).

Ignatius R, et al., "Presentation of Proteins Encapsulated in Sterically Stabilized Liposomes by Dendritic Cells Initiates CD8+ T-cell Responses in Vivo," Blood. 96(10):3505-13 (2000).

Ilson D, "Nanolipoosomal Irinotecan Effective for Pancreatic Cancer," NEJM journal Watch, available at jwatch.org/na39795/2015/12/08/nanoliposomal-irinotecan-effective-pancreatic-cancer, (2015), 7 printed pages.

Immordino M, et al., "Stealth Liposomes: Review of the Basic Science, Rationale, and Clinical Applications, Existing and Potential," Int J Nanomedicine. 1(3):297-315 (2006).

Ioka T, et al., "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)." Poster presented at the European Society for Medical Oncology (ESMO) Asia 2019 Congress, Singapore, Nov. 22-24, 2019, 9 pages.

Ioka T, et al., Abstract 132P. "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)," Ann Oncol. 30 (Suppl_9):ix47-ix48 doi:10.1093/annonc/mdz422 (2019).

Ioka T, et al., Abstract 274TiP. "A Randomized Phase 2 Study of Nanoliposomal Irinotecan (nal-IRI, BAX2398)-Containing Regimen in Japanese Patients With Metastatic Pancreatic Adenocarcinoma (mPAC)," Ann Oncol. 27 (Supp_9):ix84-ix85 doi:10.1093/annonc/mdw582 (2016).

Jameson G, et al., "Adverse Events in Patients with Metastatic Pancreatic Cancer Receiving Liposomal Irinotecan: Understanding the Occurrence and How Management Affects Patient Outcomes." Poster presented at the Oncology Nursing Society (ONS) Annual Conference, Washington, DC, May 17-20, 2018, 7 pages.

Jameson G, et al., Abstract 1. "Adverse Events in Patients with Metastatic Pancreatic Cancer Receiving Liposomal Irinotecan: Understanding the Occurrence and How Management Affects Patient Outcomes," Oncology Nursing Society (ONS) 43rd Annual Congress, available at ons.confex.com/ons/2018/meetingapp.cgi/Paper/2970, (2018), 2 pages.

Jones S, et. al., Abstract 2547. "Phase I and Pharmacokinetic (PK) Study of IHL-305 (Pegylated Liposomal Irinotecan) in Patients With Advanced Solid Tumors," J Clin Oncol. 27(15_suppl):2547 and Table 1 (2009), 6 printed pages.

Kalra A, et al., Abstract 2065. "Magnetic Resonance Imaging with an Iron Oxide Nanoparticle Demonstrates the Preclinical Feasibility of Predicting Intratumoral Uptake and Activity of MM-398, a Nanoliposomal Irinotecan (nal-IRI)." In Proceedings of the 105th Annual Meeting of the American Association for Cancer Research; Apr. 5-9, 2014. Cancer Res 2014;74(19 Suppl):Abstract nr 2065, doi:10.1158/1538-7445.AM2014-2065, 1 printed page.

Kang S and Saif M, "Optimal Second Line Treatment Options for Gemcitabine Refractory Advanced Pancreatic Cancer Patients. Can We Establish Standard of Care with Available Data?," JOP. J Pancreas (Online) 9(2):83-90 (2008).

Katopodis O, et. al., "Second-Line Chemotherapy With Capecitabine (Xeloda) and Docetaxel (Taxotere) in Previously Treated, Unresectable Adenocarcinoma of Pancreas: the Final Results of a Phase II Trial," Cancer Chemother Pharmacol. 67(2):361-8 (2011). Epub 2010.

Khapzory (levoleucovrin) package insert, revised Oct. 2018, accessed from accessdata.fda.gov/drugsatfda_docs/label/2018/211226s000lbl.pdf, 9 pages.

Kim G, et al., "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens." Poster presented at the European Society for Medical Oncology (ESMO) Virtual congress 2020, Sep. 19-21, 2020, 6 pages.

Kim G, et al., "Impact of Treatment Sequence on Overall Survival in Metastatic Pancreatic Cancer Patients Treated with Liposomal Irinotecan in the Real-World Setting." Poster presented at the Hematology Oncology Pharmacy Association (HOPA) Annual Conference, Tampa, FL, Mar. 11-14, 2020, 7 pages.

Kim G, et al., Abstract 1564R "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens," Ann Oncol. 31(Suppl_4):S881-S897 10.1016/annonc/annonc285 (2020), 2 printed pages.

Drummond D, et al., "Development of a Highly Stable and Targetable Nanoliposomal Formulation of Topotecan," J Control Release. 141(1):13-21 (2010). Epub 2009.

Drummond D, et al., "Improved Pharmacokinetics and Efficacy of a Highly Stable Nanoliposomal Vinorelbine," J Pharmacol Exp Ther. 328(1):321-30 (2009). Epub 2008.

Drummond D, et al., "Liposome Targeting to Tumors using Vitamin and Growth Factor Receptors," Vitam Horm. 60:285-332 (2000).

Drummond D, et al., "Pharmacokinetics and In Vivo Drug Release Rates in Liposomal Nanocarrier Development," J Pharm Sci. 97(111:4696-740 (2008).

Drummond D, et al. Chapter 8, "Intraliposomal Trapping Agents for Improving in Vivo Liposomal Drug Formulation Stability," In Liposome Technology, Third Edition, vol. 2, Ed. G. Gregoriadis, pp. 149-168 (2006).

Drummond D, et al., Chapter 9, "Liposomal Drug Delivery Systems for Cancer Therapy," In Drug Discovery Systems in Cancer Therapy, Ed. D Brown, Humana Press, Totowa, NJ, pp. 191-213 (2004).

Duffour J, et al., "Efficacy of Prophylactic Anti-Diarrhoeal Treatment in Patients Receiving Campto for Advanced Colorectal Cancer," Anticancer Res. 22(6B): 3727-31 (2002).

Elinzano H, et al., "Nanoliposomal Irinotecan and Metronomic Temozolomide for Patients With Recurrent Glioblastoma BrUOG329, A Phase I Brown University Oncology Research Group Trial," Am J Clin Oncol. 44(2):49-52 (2021). Epub 2020 version, pp. 1-4.

Elinzano H, et al., Abstract e14548. "Nanoliposomal Irinotecan and Metronomic Temozolomide for Patients With Recurrent Glioblastoma: BrUOG329, A Phase IB/IIA Brown University Oncology Research Group (BrUOG) Trial," J Clin Oncol. 38(15_Suppl):e14548 DOI: 10.1200/JCO.2020.38.15_suppl.e14548 (2020), 2 printed pages.

Emerson D, et al., "Antitumor Efficacy, Pharmacokinetics, and Biodistribution of NX 211: A Low-Clearance Liposomal Formulation of Lurtotecan," Clin Cancer Res. 6(7):2903-12 (2000).

EP Patent Application No. 05745505.7: European Search Report dated Sep. 1, 2010, 6 pages.

Ettrich T, et al., "Liposomal Irinotecan (nal-IRI) Plus 5-Fluorouracil (5-FU) and Leucovorin (LV) or Gemcitabine Plus Cisplatin in Advanced Cholangiocarcinoma: the AIO-NIFE-Trial, an Open Label,

(56) References Cited

OTHER PUBLICATIONS

Randomized, Multicenter Phase II Trial," Poster presented at the American Society of Clinical Oncology (ASCO) Annual Meeting, Chicago, Illinois, Jun. 1-5, 2018, 5 pages.

Ettrich T, et al., Abstract TPS4145. "Liposomal Irinotecan (nal-IRI) Plus 5-Fluorouracil (5-FU) and Leucovorin (LV) or Gemcitabine Plus Cisplatin in Advanced Cholangiocarcinoma: the AIO-NIFE-Trial, an Open Label, Randomized, Multicenter Phase II Trial," J Clin Oncol. 36(15_Suppl):TPS4145 DOI: 10.1200/JCO.2018.36_15_suppl_TPS4145 (2018), 2 printed pages.

European Medicines Agency Assessment Report for Onivyde, Committee for Medicinal Products for Human Use (CHMP), Jul. 21, 2016, 107 pages.

Falcone A, et al., "Sequence Effect of Irinotecan and Fluorouracil Treatment on Pharmacokinetics and Toxicity in Chemotherapy-Naive Metastatic Colorectal Cancer Patients," J Clin Oncol. 19(15):3456-62 (2001).

Fannon M, et al., "Sucrose Octasulfate Regulates Fibroblast Growth Factor-2 Binding, Transport, and Activity: Potential for Regulation of Tumor Growth," J Cell Physiol. 215(2):434-41 (2008), NIH public access author manuscript version, 19 pages.

Farncombe M, "Management of Bleeding in a Patient with Colorectal Cancer: A Case Study," Support Care Cancer. 1(3):159-160 (1993).

FDA, "Draft Guidance on Daunorubicin Citrate," Jul. 2014, 6 pages.

FDA, "Draft Guidance on Doxorubicin Hydrochloride," Recommended Feb. 2010, Revised Nov. 2013, Dec. 2014, 6 pages.

Figer A, et. al., "A Comparison of Two Dose Regimens in Pancreatic Cancer," J Chemother. 12(5):442-5 (2000).

Fleming G, et. al., "Phase I and Pharmacokinetic Study of 24-Hour Infusion 5-Fluorouracil and Leucovorin in Patients With Organ Dysfunction," Ann Oncol. 14(7):1142-7 (2003).

Freise C, et al., "Characterization of a Cyclosporine-Containing Liposome," Transplant Proc. 23(1 Pt 1):473-4 (1991).

Freise C, et al., "Increased Efficacy of Cyclosporin Liposomes in a Rat Orthotopic Liver Transplant Model," Surgical Forum. 43:395-7 (1992).

Freise C, et al., "The Increased Efficacy and Decreased Nephrotoxicity of a Cyclosporine Liposome," Transplantation. 57(6):928-932 (1994).

Fugit K, et al., "The Role of pH and Ring-opening Hydrolysis Kinetics on Liposomal Release of Topotecan," J Control Release. 174:88-97 (2014), Epub Nov. 12, 2013, Author manuscript, pp. 1-27.

Gaber M, et al., "Thermosensitive Liposomes: Extravasation and Release of Contents in Tumor Microvascular Networks," Int J Radiat Oncol Biol Phys. 36(5):1177-87 (1996).

Gaber M, et al., "Thermosensitive Sterically Stabilized Liposomes: Formulation and in Vitro Studies on the Mechanism of Doxorubicin Release by Bovine Serum and Human Plasma," Pharm Res. 12(10):1407-16 (1995).

Gaddy D, et al., "A Systematic Literature Review to Identify and Compare Clinical Trials Evaluating Novel Therapeutic Agents in Post-Gemcitabine Advanced Pancreatic Cancer Patients." Poster presented at the International Society for Pharmacoeconomics and Outcomes Research (ISPOR) 18th Annual European Congress, Milan, Italy, Nov. 7-11, 2015, 6 pages.

Gaddy D, et al., "Preclinical Anti-tumor Activity of Nanoliposomal Irinotecan (Nal-IRI, MM-398) Supports Utilization as a Foundation of Front-Line Pancreatic Cancer Regimens." Poster presented at the American Society of Clinical Oncology Gastrointestinal Cancers Symposium (ASCO GI), San Francisco, CA, Jan. 19-21, 2017, 5 pages.

Gaddy D, et al., Abstract 336. "Preclinical Antitumor Activity of Nanoliposomal Irinotecan (Nal-IRI, MM-398) and Utilization as a Foundation of Front-Line Pancreatic Cancer Regimens," J Clin Oncol. 35(4_Suppl):336 DOI: 10.2001/JCO.2017.35.4_suppl.336 (2017), 2 printed pages.

Gaddy D, et al., Abstract PCN29. "A Systematic Literature Review to Identify and Compare Clinical Trials Evaluating Novel Therapeutic Agents in Post-Gemcitabine Advanced Pancreatic Cancer," Value in Health. 18(7):A434 (2015).

Garcia-Alfonso P, et. al., "Capecitabine in Combination with Irinotecan (XELIRI), Administered As a 2-Weekly Schedule, As First-Line Chemotherapy for Patients With Metastatic Colorectal Cancer: A Phase II Study of the Spanish GOTI Group," Br J Cancer. 101(7):1039-43 (2009).

Garcia-Carbonero R and Supko J, "Current Perspectives on the Clinical Experience, Pharmacology, and Continued Development of the Camptothecins," Clin Cancer Res. 8(3):641-61 (2002).

Gebbia V, et al., "Second-Line Chemotherapy in Advanced Pancreatic Carcinoma: A Multicenter Survey of the Gruppo Oncologico Italia Meridionale on the Activity and Safety of the FOLFOX4 Regimen in Clinical Practice," Ann Oncol. 18(Suppl 6):vi124-7 (2007).

Geddie M, et al., "Improving the Developability of an Anti-EphA2 Single-Chain Variable Fragment for Nanoparticle Targeting," MAbs. 9(1):58-67 (2017). Epub 2016.

Gelmon K, et. al., "A Phase 1 Study of OSI-211 Given As an Intravenous Infusion Days 1, 2, and 3 Every Three Neeks in Patients With Solid Cancers," Invest New Drugs. 22(3):263-75 (2004).

Gemzar (gemcitabine HCl) package insert, revision Apr. 1998, 24 pages.

Giles F, et. al., "Phase I and Pharmacokinetic Study of a Low-Clearance, Unilamellar Liposomal Formulation of Lurtotecan, a Topoisomerase 1 Inhibitor, in Patients with Advanced Leukemia," Cancer. 100(7)1149-58 (2004).

Glassman D, et al., "Nanoliposomal Irinotecan With Flurouracil for the Treatment of Advanced Pancreatic Cancer." Poster presented at the American Society of Clinical Oncology Gastrointestinal Cancers Symposium (ASCO GI), San Francisco, CA, Jan. 18-20, 2018, 7 pages.

Glassman D, et al., Abstract 471. "Nano-Liposomal Irinotecan and 5-FU/LV (N+FF) for the Treatment of Advanced PDAC: Memorial Sloan Kettering (MSK) Single Cancer Center Evaluation," J Clin Oncol. 36(4_Suppl):471 DOI: 10.1200/JCO.2018.36.4_suppl.471 (2018), 2 printed pages.

Glimelius B, et. al., "A Randomized Phase III Multicenter Trial Comparing Irinotecan in Combination With the Nordic Bolus 5-FU and Folinic Acid Schedule or the Bolus/Infused de Gramont Schedule (Lv5FU2) in Patients With Metastatic Colorectal Cancer," Ann Oncol. 19(5):909-14 (2008).

Glimelius B, et. al., "Prediction of Irinotecan and 5-Fluorouracil Toxicity and Response in Patients With Advanced Colorectal Cancer," Pharmacogenomics J. 11(1):61-71 (2011). Epub 2010.

Gounaris I, et. al., "Options for the Treatment of Gemcitabine-Resistant Advanced Pancreatic Cancer," Jop. J Pancreas (Online) 11(2):113-23 (2010).

Gourzoulidis G, et al., "The Cost-Effectiveness of Nanoliposomal Irinotecan and 5-Fluorouracil (5-FU)/Leucovorin (LV) for the Treatment of Patients With Metastatic Adenocarcinoma of Pancreas Who Have Progressed Following the Use of Gemcitabine-Related Therapies in Greece." Poster presented at the Virtual International Society for Pharmacoeconomics and Outcomes Research (ISPOR) European Congress, Milan, Italy, Nov. 16-19, 2020, 9 pages.

Gourzoulidis G, et al., Abstract PCN57. "The Cost-Effectiveness of Nanoliposomal Irinotecan and 5-Fluorouracil (5-FU)/Leucovorin (LV) for the Treatment of Patients With Metastatic Adenocarcinoma of Pancreas Who Have Progressed Following the Use of Gemcitabine-Related Therapies in Greece," Virtual International Society for Pharmacoeconomics and Outcomes Research (ISPOR) European Congress, Milan, Italy, Nov. 16-19, 2020, available at ispor.org/heor-resources/presentations-database/presentation/euro2020-3282/105175, 2 printed pages.

Greiner P, et. al., "Pharmacokinetics of (−)-Folinic Acid After Oral and Intravenous Administration of the Racemate," Br J Clin Pharmacol. 28(3)189-95 (1989).

Guichard S, et. al., "Cellular Interactions of 5-Fluorouracil and the Camptothecin Analogue CPT-11 (Irinotecan) in a Human Colorectal Carcinoma Cell Line," Biochem Pharmacol. 55(5):667-76 (1998).

Guichard S, et. al., "Sequence-Dependent Activity of the Irinotecan-5FU Combination in Human Colon-Cancer Model HT-29 In Vitro and In Vivo," Int J Cancer. 73(5)129-34 (1997).

(56) References Cited

OTHER PUBLICATIONS

Haller D, "Chemotherapy for Advanced Pancreatic Cancer," Int J Radiat Oncol Biol Phys. 56(4 Suppl):16-23 (2003).
Han S, et al., Abstract ACTR-33. "A Phase I Study of Convection-Enhanced Delivery of Liposomal-Irinotecan Using Real-Time Imaging With Gadolinium in Patients With Recurrent High Grade Glioma," Neuro-Oncology. 18(Suppl_6): vi9 doi.org/10.1093/neuonc/now212.031 (2016).
Vickers M, et. al., "Comorbidity, Age and Overall Survival in Patients With Advanced Pancreatic Cancer— Results from NCIC CTG PA.3: A Phase III Trial of Gemcitabine Plus Erlotinib or Placebo," Eur J Cancer. 48(10):1434-42 (2012). Epub 2011.
Villalona-Calero M, et. al., "Phase I Study of Low-Dose Suramin as a Chemosensitizer in Patients With Advanced Non-Small Cell Lung Cancer," Clin Cancer Res. 9(9):3303-11 (2003).
Von Hoff D, et. al., "Gemcitabine Plus nab-Paclitaxel Is an Active Regimen in Patients With Advanced Pancreatic Cancer: A PhaseI/II Trial," J Clin Oncol. 29(34):4548-54 (2011).
Von Hoff D, et. al., "Increased Survival in Pancreatic Cancer with nab-Paclitaxel plus Gemcitabine," N. Engl J Med. 369(18):1691-703 (2013).
Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021).
Walker E and Ko A, "Beyond First-Line Chemotherapy for Advanced Pancreatic Cancer: An Expanding Array of Therapeutic Options?" World J Gastroenterol. 20(9):2224-36 (2014).
Walker S, et. al., "Simulation of Y-Site Compatibility of Irinotecan and Leucovorin at Room Temperature in 5% Dextrose in Water in 3 Different Containers," Can J Hosp Pharm. 58(4):212-22 (2005).
Wang W, et. al., "Weekly 24-Hour Infusion of High-dose 5-Fluorouracil and Leucovorin in Patients with Advanced Colorectal Cancer: Taiwan Experience," Jpn J Clin Oncol. 28(1):16-19 (1998).
Wang-Gillam A, et al., "Characteristics of Long-Term Survivors in a Randomized Phase 3 Trial (NAPOLI-1) of Patients With Metastatic Pancreatic Ductal Adenocarcinoma (mDPAC) Treated With Liposomal Irinotecan (nal-IRI; MM-398) + 5-FU/LV." Poster presented at the American Society of Clinical Oncology Gastrointestinal Cancers Symposium (ASCO GI), San Francisco, CA, Jan. 19-21, 2017, 9 pages.
Wang-Gillam A, et al., "Dose Modifications of Liposomal Irinotecan (nal-IRI) + 5-Fluorouracil/Leucovorin (5-FU/LV) in NAPOLI-1: Impact on Efficacy." Poster presented at the American Society of Clinical Oncology Gastrointestinal Cancers Symposium (ASCO GI), San Francisco, CA, Jan. 18-20, 2018, 8 pages.
Wang-Gillam A, et al., "Nomogram for Predicting Overall Survival in Patients Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1." Poster presented at the American Society of Clinical Oncology Gastrointestinal Cancers Symposium (ASCO GI), San Francisco, CA, Jan. 18-20, 2018, 9 pages.
Wang-Gillam a, et al., "Updated Overall Survival Analysis of NAPOLI-1: Phase 3 Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Treated With Gemcitabine-Based Therapy" Poster presented at the American Society of Clinical Oncology Gastrointestinal Cancers Symposium (ASCO GI), San Francisco, CA, Jan. 21-23, 2016, 11 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin, vs 5-Fluorouracil and Leucovorin in Metastatic Pancreatic Ductal Adenocarcinoma Previously Treated With Gemcitabine." Poster presented at the American Society of Clinical Oncology (ASCO) Annual Meeting, Chicago, Illinois, Jun. 3-7, 2016, 8 pages.
Wang-Gillam A, et al., Abstract 293. "Characteristics of Long-Term Survivors in a Randomized Phase III Trial (NAPOLI-1) of Patients With Metastatic Pancreatic Ductal Adenocarcinoma (mPDAC) Treated With Liposomal Irinotecan (nal-IRI; MM-398) + 5-FU/LV," J Clin Oncol. 35(4_Suppl):293 DOI: 10.1200/JCO.2017.35.4_suppl.293 (2017), 2 printed pages.
Wang-Gillam A, et al., Abstract 388. "Dose Modifications of Liposomal Irinotecan (nal-IRI) + 5-Fluorouracil/Leucovorin (5-FU/LV) in NAPOLI-1: Impact on Efficacy," J Clin Oncol. 36(4_Suppl):388 DOI: 10.1200/JCO.2018.36.4_suppl.388 (2018), 2 printed pages.
Wang-Gillam A, et al., Abstract 4126. "Updated Overall Survival (OS) Analysis of NAPOLI-1: Phase 3 Study of ganoliposomal Irinotecan (nal-IRI, MM-398), With or Without 5-Fluorouracil and Leucovorin (5-FU/LV), vs 5-FU/LV in Metastatic Pancreatic Cancer (mPAC) Previously Treated With Gemcitabine (Gem)-Based Therapy," J Clin Oncol. 34(15_Suppl):4126 DOI: 10.1200/JCO.2016.34.15_suppl.4126 (2016), 5 printed pages.
Wang-Gillam A, et al., Abstract 417. "Updated Overall Survival Analysis of NAPOLI-1: Phase III Study of ganoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Rreated With Gemcitabine-Based Therapy," J Clin Oncol. 34(4_Suppl):417 DOI: 10.1200/jco.2016.34.4_suppl.417 (2016), 2 printed pages.
Wang-Gillam A, et al., Abstract 459. "Nomogram for Predicting Overall Survival (OS) in Patients (pts) Treated With Liposomal Irinotecan (nal-Iri) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1," J Clin Oncol. 36(4_Suppl):459 DOI: 10.1200/JCO.2018.36.4_suppl.459 (2018), 2 printed pages.
Wang-Gillam a, et al., Abstract e15795. "The Prognostic Value of Baseline Neutrophil-to-Lymphocyte Ratio (NLR) and Platelet-to-Lymphocyte ratio (PLR) for Predicting Clinical Outcome in Patients with Metastatic Pancreatic Ductal Adenocarcinoma (mPDAC) Treated With Liposomal Irinotecan (nalIRl; MM398) + 5-Fluorouracil and Leucovorin (5-FU/LV) vs 5-FU/LV," J Clin Oncol. 35(15_Suppl):e15795 DOI: 10.1200/JCO.2017.35.15_suppl.e15795 (2017), 3 printed pages.
Wang-Gillam A, et al., Abstract e16204. "A Survival Prediction Nomogram for Liposomal Irinotecan (nal-IRI)+5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(15_Suppl):e16204 DOI: 10.12001 JCO.2018.36.15_suppl.e16204 (2018), 2 printed pages.
Wang-Gillam A, et al., letter to editor, "Nanoliposomal Irinotecan in the Clinical Practice Guideline for Metastatic Pancreatic Cancer Applicability to Clinical Situations," J Clin Oncol. 35(6):689-90 (2017). Epub 2016.
Wei H, et al, "Active Loading Liposomal Irinotecan Hydrochloride: Preparation, In Vitro and In Vivo Evaluation," Asian J Pharm Sci. 8(5):303-11 (2013).
Weng K, et al., "Convection-Enhanced Delivery of Targeted Quantum Dot-Immunoliposome Hybrid Nanoparticles to Intracranial Brain Tumor Models," Nanomedicine (Lond). 8(12):1913-25. 2013.
Weng K, et al., "Targeted Tumor Cell Internalization and Imaging of Multifunctional Quantum Dot-Conjugated Immunoliposomes in Vitro and in Vivo," Nano Lett. 8(9):2851-7 (2008).
Willett C, et. al., "Direct Evidence That the VEGF-Specitic Antibody Bevacizumab Has Antivascular Effects in Human Rectal Cancer," Nat Med. 10(2):145-7 (2004), author manuscript version, 7 pages.
Wulaningsih W, et. al., "Irinotecan Chemotherapy Combined With Fluoropyrimidines Versus Irinotecan Alone for Overall Survival and Progression-Free Survival in Patients With Advanced and/or Metastatic Colorectal Cancer," Cochrane Database Syst Rev. 2:CD008593 doi: 10.1002/14651858.CD008593.pub3. (2016), 36 pages.
Xeloda (capecitabine) package insert, Roche, revised Nov. 2000, 19 pages.
Yamashita Y, et al., "Convection-Enhanced Delivery of a Topoisomerase I Inhibitor (Nanoliposomal Topotecan) and a Topoisomerase II Inhibitor (Pegylated Liposomal Doxorubicin) in Intracranial Brain Tumor Xenografts," Neuro Oncol. 3(1):20-8 (2007). Epub 2006.

(56) References Cited

OTHER PUBLICATIONS

Yamashita Y, et. al., "Convection-Enhanced Delivery of Liposomal Doxorubicin in Intracranial Brain Tumor Xenografts," Targ Oncol. 1:79-85 (2006).
Yang W, et. al. "Development of a Method to Quantify Total and Free Irinotecan and 7-ethyl-10-hydroxycamptothecin (ISN-38) for Pharmacokinetic and Bio-Distribution Studies After Administration of Irinotecan Liposomal Formulation," Asian J Pharm Sci. 14(6):687-97 (2019). Epub 2018.
Yang W, et. al., "The Influence of Trapping Agents on the Antitumor Efficacy of Irinotecan Liposomes: Head-to-Head comparison of Ammonium Sulfate, Sulfobutylether-β-Cyclodextrin and Sucrose Octasulfate," Biomater Sci., 7(1):419-28 (2019).
Yoo C, et al., "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial." Poster presented at the European Society for Medical Oncology (ESMO) 2019 Congress, Barcelona, Spain, Sep. 27-Oct. 1, 2019, 6 pages.
Yoo C, et al., Abstract 829TiP. "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After rogression on Gemcitabine Plus Cisplatin (GemCis): NIFTY Trial," Ann Oncol. 30(Supp_5):v318 /doi_org/10_1093/annonc/mdz247.155 (2019).
Younis I, et. al., "Enterohepatic Recirculation Model of Irinotecan (CPT-11) and Metabolite Pharmacokinetics in Patients With Glioma," Cancer Chemother Pharmacy. 63(3):517-24 (2009), author manuscript version, 16 pages.
Yu K, et al., "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," Poster presented at the Academy of Managed Care Pharmacy, Nexus (AMCP, Nexus): virtual meeting, week of Oct. 19, 2020, 9 pages.
Yu K, et al., Abstract C3. "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," J Manag Care Spec Pharm. 26(10-a):519 (2020).
Yu K, et al., "A US Multicenter Chart Review Study of Patients With Metastatic Pancreatic Ductal Adenocarcinoma Receiving Liposomal Irinotecan after Gemcitabine-Based Therapy." Poster presented at the International Conference on Pharmacoepidemiology & Therapeutic Risk Management (ICPE) All Access, Sep. 16-17, 2020, 8 pages.
Yu K, et al., "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review." Poster presented at the European Society for Medical Oncology (ESMO) Virtual Congress 2020, Sep. 19-21, 2020, 9 pages.
Yu K, et al., Abstract 1555P. "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review," Ann Oncol. 31(Suppl_4):5950-5951 doi.org/10_1016/j.annonc.2020.08.2038 (2020), 2 printed pages.
Yu K, et al., Abstract e16733. "A Multicenter Chart Review Study of Patients with Metastatic Pancreatic Ductal Adenocarcinoma Receiving Liposomal Irinotecan after Gemcitabine-Based Therapy," J Clin Oncol. 38(15_Suppl): a16733 DOI: 10.1200/JCO.2020.38.15_suppLe16733 (2020), 4 printed pages.
Yu K, et al., Abstract PO-3727. "A US Multicenter Chart Review Study of Patients With Metastatic Pancreatic Ductal Adenocarcinoma Receiving Liposomal Irinotecan after Gemcitabine-Based Therapy," International Conference on Pharmacoepidemiology & Therapeutic Risk Management (ICPE), Sep. 14, 2020, available at eventscribe.com/2020/ICPEAllAccess/PosterTitles.asp?pfp=PosterTitles, 1 page.

Yu X, et. al., "Targeted Drug Delivery in Pancreatic Cancer," Biochim Biophys Acta. 21805(1):97-104 (2010). Epub 2009, author manuscript version, 16 pages_.
Zamboni W, et. al., "Phase I and Pharmacokinetic Study of Pegylated Liposomal CKD-602 in Patients with Advanced Malignancies," Clin Cancer Res. 15(4):1466-72 (2009) and correction found at Clin Cancer Res. 15(8):2949-50 (2009).
Zhang K, et al., "Comprehensive Optimization of a Single-Chain Variable Domain Antibody Fragment as a Targeting Ligand for a Cytotoxic Nanoparticle," MAbs. 7(1):42-52 (2015).
Zhang L, et al., PEG-Coated Irinitecan Cationic Liposomes Improve the Therapeutic Efficacy of Breast Cancer in Animals, Eur Rev Med Pharmacol Sci. 17(24)3347-61 (2013).
EP3337478: EPO Notice of Sandoz AG Opposition dated May 6, 2021, 5 pages.
EP3337478: Sandoz AG Opposition dated May 6, 2021, 22 pages.
EP3337478: Sandoz AG Opposition dated May 6, 2021, D1 (History of Changes for Study NCT02551991, retrieved from ClinicalTrials.gov archive on May 3, 2021, 4 pages).
EP3337478: Sandoz Ag Opposition dated May 6, 2021, D2 (Abstract O-0003. Von Hoff D, et al., "Napoli 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or Following Gemcitabine-Based Therapy." Ann Oncol. 25(Suppl 2):ii105 (2014)).
EP3337478: Sandoz AG Opposition dated May 6, 2021, D3 (Marsh R, et al., "Pancreatic Cancer and FOLFIRINOX: A New Era and New Questions," Cancer Med. 4(6):853-63 (2015)).
EP3337478: Sandoz AG Opposition dated May 6, 2021, D4 (Onivyde [MM-398] package insert, revision Oct. 22, 2015, 18 pages).
EP3337478: Sandoz AG Opposition dated May 6, 2021, D5 (Carnevale J and Ko A, "Mm-398 (Nanoliposomal Irinotecan): Emergence of a Novel Therapy for the Treatment of Advanced Pancreatic Cancer," Future Oncol. 12(4):453-64 (2016). Epub 2015).
EP3337478: Sandoz AG Opposition dated May 6, 2021, D6 (Dean A, et al., Abstract TPS482. "A Randomized, Open-Label Phase II Study of Nanoliposomal Irinotecan (nal-IRI)-Containing Regimens Versus nab-Paclitaxel Plus Gemcitabine in Patients With Previously Untreated Metastatic Pancreatic Adenocarcinoma (mPAC)," J Clin Oncol. 34(4_Suppl.):tps482 (2016), DOI: 10.1200/jco.2016.34.4_suppl.tps482, 5 printed pages).
EP3337478: Sandoz Ag Opposition dated May 6, 2021, D7 (Zhang H, "Onivyde for the Therapy of Multiple Solid Tumors," Onco Targets Ther. 9:3001-3007 (2016)).
EP3337478: Sandoz AG Opposition dated May 6, 2021, D8 (Gaddy D, et al., "Abstract 4830: Preclinical Anti-Tumor Activity of Nanoliposomal Irinotecan (Nal-IRI, MM-398) + 5-FU + Oxaliplatin in Pancreatic Cancer." In: Proceedings of the 107th Annual Meeting of the American Association for Cancer Research; Apr. 16-20, 2016; New Orleans, LA. Cancer Res. 76(14 Suppl):Abstract nr 4830 (2016), 4 printed pages).
EP3337478: Sandoz AG Opposition dated May 6, 2021, D9 (Priyambada P, et al., "Nanotechnology-Based Combinational Drug Delivery: An Emerging Approach for Cancer Therapy," Drug Discov Today. 17(17-18):1044-52(2012)).
EP3337478: EPO Notice of Generics [UK] Limited Opposition dated May 12, 2021, 5 pages.
EP3337478: Generics [UK] Limited Opposition dated May 12, 2021, 9 pages.
EP3337478: Generics [UK] Limited Opposition dated May 12, 2021, D10 (Conroy T, et al., "Folfirinox versus Gemcitabine for Metastatic Pancreatic Cancer," N. Engl J Med. 364(19):1817-25 (2011)).
EP3337478: Generics [UK] Limited Opposition dated May 12, 2021, D11 (Gourgou-Bourgade S, et al., "Impact of Folfirinox Compared With Gemcitabine on Quality of Life With Metastatic Pancreatic Cancer: Results From the PRODIGE 4/Accord 11 Randomized Trial," J Clin Oncol. 31(1):23-9 (2013). Epub 2012.).
EP3337478: Generics [UK] Limited Opposition dated May 12, 2021, D12 (Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013)).

(56) References Cited

OTHER PUBLICATIONS

EP3337478: Generics [UK] Limited Opposition dated May 12, 2021, D13 (Hann B, et. al., Abstract 5648. "Lipidic Nanoparticle CPT-11 in a Bioluminescent Orthotopic Pancreas Cancer Model," Cancer Res. 67(9 Suppl):5648 (2007), 4 printed pages).
EP3337478: Generics [UK] Limited Opposition dated May 12, 2021, D14 (Chang T, et al., "Phase I Study of Nanoliposomal Irinotecan (PEP02) in Advanced Solid Tumor Patients," Cancer Chemother Pharmacol. 75(3):579-86 (2015)).
EP3337478: Generics [UK] Limited Opposition dated May 12, 2021, D15 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 4 printed pages).
EP3337478: Generics [UK] Limited Opposition dated May 12, 2021, D16 (Pubmed abstract retrieved on May 6, 2021 for Mahaseth H, et al., "Modified Folfirinox Regimen With Improved Safety and Maintained Efficacy in Pancreatic Adenocarcinoma," Pancreas. 42(8):1311-5 (2013), 2 printed pages).
EP3337478: Generics [UK] Limited Opposition dated May 12, 2021, D17 (Drummond D, et al., "Development of a Highly Active Nanoliposomal Irinotecan Using a Novel Intraliposomal Stabilization Strategy," Cancer Res. 66(6):3271-77 (2006)).
CAS Registry [database] Record for 23214-92-8 (doxorubicin), entered STN Nov. 16, 1984 [copyright 2010], 2 pages.
CAS Registry [database] Record for 97682-44-5 (irinotecan), entered STN Aug. 18, 1985 [copyright 2010], 1 page.
Saif M, et. al., "Pharmacokinetically Guided Dose Adjustment of 5-Fluorouracil: a Rational Approach to Improving Therapeutic Outcomes," J Natl Cancer Inst. 101(22):1543-52 (2009).
Saltz L, "Clincial Use of Irinotecan: Current Status and Future Considerations," Oncologist. 2(6):402-9 (1997).
Saltz LB, et. al., "Phase I Clinical and Pharmacokinetic Study of Irinotecan, Fluorouracil, and Leucovorin in Patients With Advanced Solid Tumors," J Clin Oncol. 14(11):2959-67 (1996).
Satoh T, et. al., "Pharmacokinetic Assessment of Irinotecan, SN-38, and SN-38-Glucuronide: A Substudy of the FIRIS Study," Anticancer Res. 33(9):3845-53 (2013).
Scheithauer W, et. al., "Fluorouracil Plus Racemic Leucovorin Versus Fluorouracil Combined With the Pure I-Isomer of Leucovorin for the Treatment of Advanced Colorectal Cancer: A Randomized Phase III Study," J Clin Oncol. 15(3):908-14 (1997).
Schroen A, et. al., "Challenges to Accrual Predictions to Phase III Cancer Clinical Trials: A Survey of Study Chairs and Lead Statisticians of 248 NCI Sponsored Trials," Clin Trials. 8(5):591-600 (2011), author manuscript version, 14 pages.
Serwer L, et al., "Investigation of Intravenous Delivery of Nanoliposomal Topotecan for Activity Against Orthotopic Glioblastoma Xenografts," Neuro Oncol. 13(12):1288-95 (2011).
Shi S, et al., "Combinational Therapy: New Hope for Pancreatic Cancer?" Cancer Lett. 317(2):127-35 (2012). Epub 2011.
Siveke J, et al., "Subgroup Analysis by Measurable Metastatic Lesion (Ml) No. And Selected Lesion Locations :Ll) at Baseline (Bl) in Napoli-1: a Phase 3 Study of Liposomal Irinotecan (nal-Iri)±5-Fluorouracil/Leucovorin (5-Fu) _V) in Patients With Metastatic Pancreatic Ductal Adenocarcinoma Previously Treated With Gemcitabine-Based Therapy." Poster presented at the American Society of Clinical Oncology Gastrointestinal Cancers Symposium (Asco 31), San Francisco, Ca, Jan. 18-20, 2018, 8 ea es.
'3I Eke J, et al., Abstract 460_ "Subgroup Analysis by Measurable Metastatic Lesion (Ml) No. And Selected _esion Locations (Ll) at Baseline (Bl) in Napoli-1: a Phase Iii Study of Liposomal Irinotecan (nal-Iri) 15-Fluorouracil/Leucovorin (5-Fu/Lv) in Patients (pts) With Metastatic Pancreatic Ductal Adenocarcinoma (mPDAC) 3reviously Treated With Gemcitabine-Based Therapy," J Clin Oncol. 36(4_Suppl):460 Doi: 10.1200/ JC0_2018_36.4_suppl.460 (2018), 2 printed pp.
3IVEKE J, et al., Abstract ID0596. "Expanded Analyses of Napoli-1: Phase 3 Study of nal-Iri (Mm-398), With or Nithout 5-Fluorouracil (5FU) and Leucovorin (Lv), Versus 5-Fluorouracil and Leucovorin (5FU/Lv), in Metastatic ancreatic Cancer (mPAC) Previously Treated With Gemcitabine-Based Therapy," Oncol Res Treat_ 39(Suppl 1)170 :2016).
Siveke J, et al., Abstract P863. "Effects of Nanoliposomal Irinotecan (nal-IRI;MM-398) ± 5-Fluorouracil and Leucavorin (5-FU/LV) on Quality of Life (QoL) in Napoli-1: A Phase 3 Study in Patients (pts) With Metastatic Pancreatic Adenocarcinoma (mPAC) Previously Treated With Gemcitabine-Based Therapy," Oncol Res Threat. 39(Suppl 3):259 (2016).
Skof E, et. al., "Capecitabine Plus Irinotecan (XELIRI Regimen) Compared to 5-FU/LV Plus Irinotecan (FOLFIRI Regimen) As Neoadjuvant Treatment for Patients With Unresectable Liver-Only Metastases of Metastatic Colorectal Cancer: A Randomised Prospective Phase II Trial," BMC Cancer 9:120 doi: 101186/1471-2407-9-120 (2009), 9 pages.
Soares H, et. al., "A Phase II Study of Capecitabine Plus Docetaxel in Gemcitabine-Pretreated Metastatic Pancreatic Cancer Patients: CapTere," Cancer Chemother Pharmacol. 73(4):839-45 (2014).
Sohal D et. al., "Metastatic Pancreatic Cancer: ASCO Clinical Practice Guideline Update," J Clin Oncol. 36(24):2545-2556 and appendix (2018).
Sohal D, et. al., "Metastatic Pancreatic Cancer: American Society of Clinical Oncology Clinical Practice Guideline," J 21in Oncol. 34(23):2784-96 and Appendix (2016).
Sohal D, et. al., "Reply to A. Wang-Gillam et al," J Clin Oncol. 35(6):690-1 (2017). Epub 2016.
Son J, et al., "Glutamine Supports Pancreatic Cancer Growth Through a Kras-Regulated Metabolic Pathway," Nature. 496(7443):101-5 (2013), author manuscript version, 16 pages.
Sousa C and Kimmelman a, "The Complex Landscape of Pancreatic Cancer Metabolism," Carcinogenesis. 35(7):1441-50 (2014).
Spigel D, et al., "Liposomal Irinotecan in Adults with Small Cell Lung Cancer Who Progressed on Platinum-Based Therapy: Subgroup Analyses by Platinum Sensitivity." Poster presented at the International Association for the Study of Lung Cancer (IASLC) 2020 North America Conference on Lung Cancer (Naclc): virtual meeting, Oct. 16-17, 2020, 9 pages.
Spigel D, et al., "Resilient Part 1, An Open-Label, Safety Run-In of Liposomal Irinotecan in Adults With Small Cell Lung Cancer (SCLC) Who Have Progressed With Platinum-Based First-Line Therapy: Subgroup Analyses by Platinum Sensitivity." Poster presented at the American Society of Clinical Oncology (ASCO) Annual Conference, virtual format, May 29-Jun. 2, 2020, 6 pages.
Spigel D, et aL, Abstract 9069. "Resilient Part I, An Open-Label, Safety Run-In of Liposomal Irinotecan in Adults With Small Cell Lung Cancer (SCLC) Who Have Progressed With Platinum-Based First-Line (1L) Therapy: Subgroup Analyses by Platinum Sensitivity," J Clin Oncol. 38(15_Suppl):9069 DOI: 10.1200/JCO.2020. 3815_supp1.9069 (2020), 2 printed pages.
Spigel D, et al., Abstract M001.39. "Liposomal Irinotecan in Adults with Small Cell Lung Cancer Who Progressed on Platinum-Based Therapy: Subgroup Analyses by Platinum Sensitivity," IASLC 2020 North America Conference on Lung Cancer Abstracts, p. 80 (2020).
Stathis A and Moore M, "Advanced Pancreatic Carcinoma: Current Treatment and Future Challenges," Nat Rev Clin Oncol. 7(3):163-72 (2010).
Stathopoulos G and Boulikas T, "Lipoplatin Formulation Review Article," J Drug Deliv. 2012:581363, Article ID 581363, doi:10.1155/2012/581363, Epub 2011, 10 pages.
Stathopoulos G, et. al., "A Multicenter Phase III Trial Comparing Irinotecan-Gemcitabine (IG) With Gemcitabine (G) Monotherapy as First-Line Treatment in Patients With Locally Advanced or Metastatic Pancreatic Cancer," Br J Cancer. 95(5):587-92 (2006).
Stathopoulos G, et. al., "Lipsomal Cisplatin Combined With Gemcitabine in Pretreated Advanced Pancreatic Cancer Patients: A phase I-II Study," Oncol Rep. 15(5):1201-4 (2006).
Stylianopoulos T and Jain R, "Combining Two Strategies to Improve Perfusion and Drug Delivery in Solid Tumors," Proc Natl Acad Sci USA. 110(46):18632-7 (2013).
Takada T et. al., "Comparison of 5-Fluorouracil, Doxorubicin and Mitomycin C with 5-Fluorouracil Alone in the Treatment of Pancreatic-Biliary Carcinomas," Oncology. 51(5):396-400 (1994).

(56) References Cited

OTHER PUBLICATIONS

Takano S, et. al., "Metronomic Treatment of Malignant Glioma Xenografts with Irinotecan (CPT-11) Inhibits Angiogenesis and Tumor Growth," J Neurooncol. 99(2):177-85 (2010).
Tardi P, et al., "Liposomal Encapsulation of Topotecan Enhances Anticancer Efficacy in Murine and Human Xenograft Models," Cancer Res_ 60(13):3389-93 (2000).
Tardi P, et. al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006.
Tempero M, et. al., "NCCN Clinical Practice Guidelines in Oncology: Pancreatic Adenocarcinoma," Version 1.2012. National Comprehensive Cancer Network, Inc. (2011), 79 pages.
Tempero M, et al., "NCCN Clinical Practice Guidelines in Oncology: Pancreatic Adenocarcinoma," Version 2.2014. National Comprehensive Cancer Network, Inc. (2014), 122 pages.
Tempero M, et al., "NCCN Clinical Practice Guidelines in Oncology: Pancreatic Adenocarcinoma," Version 2.2012. National Comprehensive Cancer Network, Inc. (2011), 94 pages.
Tempero M, et al., "Pancreatic Adenocarcinoma: Clinical Practice Guidelines in Oncology," J Natl Compr Canc Netw. 8(9):972-1017 (2010).
Thota R, et. al., "Treatment of Metastatic Pancreatic Adenocarcinoma: A Review," Oncology. 28(1):70-4 (2014). Available at cancernetwork.com/view/treatment-metastatic-pancreatic-adenocarcinoma-review, 6 printed pages.
Todaka a, et. al., "S-1 Monotherapy as Second-line Treatment for Advanced Pancreatic Cancer after Gemcitabine Failure," Jpn J Clin Oncol. 40(6):567-72 (2010).
Togawa A, et al., "Treatment With an Oral Fluoropyrimidine, S-1, Plus Cisplatin in Patients Who Failed Postoperative Gemcitabine Treatment for Pancreatic Cancer a Pilot Study," Int J Clin Oncol. 12(4):268-73 (2007).
Tomicki S, et al., "Utilization of Hospital Inpatient Services Among Patients With Metastatic Pancreatic Cancer With Commercial and Medicare Insurance Treated With FDA-Approved/NCCN Category 1 Regimens." Poster presented at the Academy of Managed Care Pharmacy, Nexus (AMCP, Nexus): virtual meeting, week of Oct. 19, 2020, 6 pages.
Toutain P and Bousquet-Melou A, "Plasma terminal half-life," J Vet Pharmacol Ther. 27(6):427-39 (2004).
U.S. Appl. No. 15/664,976: Oct. 13, 2020 Notice of Allowance including Examiner's Reasons for Allowance, 13 pages.
U.S. Appl. No. 16/586,609: Oct. 5, 2020 Non-Final Office Action, 5 pages.
Vaage J, eL aL, "Therapy of a Xenografted Human Colonic Carcinoma Using Cisplatin or Doxorubicin Encapsulated in Long-Circulating Pegylated Stealth Liposomes," Int J Cancer. 80(1):134-7 (1999).
Van Cutsem E et. al., "Phase III Trial of Bevacizumab in Combination With Gemcitabine and Erlotinib in Patients With Metastatic Pancreatic Cancer," J Clin Oncol. 27(13):2231-7 (2009).
Van Rijswijk R, et. al., "Weekly High-Dose 5-Fluorouracil and Folinic Acid in Metastatic Pancreatic Carcinoma: A Phase II Study of the EORTC Gastrointestinal Tract Cancer Cooperative Group," Eur J Cancer. 40(14):2077-81 (2004).
Veal G, et. al., "A Phase I Study in Paediatric Patients to Evaluate the Safety and Pharmacokinetics of SPI-77, A Liposome Encapsulated Formulation of Cisplatin," Br J Cancer 84(8):1029-35 (2001).
Venook A, "Critical Evaluation of Current Treatments in Metastatic Colorectal Cancer," Oncologist. 10(4):250-61 (2005).
Ventura M, et al., "Efficacy of nal-IRI and Hypoxia Modulation in Orthotopic Patient-Derived Pancreatic Tumor Models of High (OCIP51) and Low (OCIP19) Hypoxia," Presentation presented at the World Molecular Imaging Congress 2017, Philadelphia, Pennsylvania, Sep. 13-16, 2017, 15 pages.
Ventura M, et al., Abstract. "Efficacy of nal-IRI and Hypoxia Modulation in Orthotopic Patient-Derived Pancreatic Tumor Models of High (OCIP51) and Low (OCIP19) Hypoxia," The World Molecular Imaging Congress 2017, Philadelphia, Pennsylvania, Sep. 13-16, 2017, 1 page.
O'Reilly E, et al., Abstract 667. "Impact of Prior Irinotecan Exposure on Outcomes of Metastatic Pancreatic Cancer (mPC) Patients," J Clin Oncol. 38(4_Suppl):667 DOI: 10.1200/JCO.2020.38.4_suppl_667 (2020), 2 printed pages.
O'Reilly E, et. al., "A Cancer and Leukemia Group B Phase II Study of Sunitinib Malate in Patients with Previously Treated Metastatic Pancreatic Adenocarcinoma (CALGB 80603)," Oncologist 15(12):1310-9 (2010).
O'Reilly S, "Topotecan: What Dose, What Schedule, What Route?" Clin Cancer Res. 5(1):3-5 (1999).
Pal A, et.al., "Preclinical Safety, Pharmacokinetics and Antitumor Efficacy Profile of Liposome-Entrapped SN-38 Formulation," Anticancer Res. 25(1A):331-41 (2005).
Pan-Canadian Oncology Drug Review (pCODR) Expert Review Committee (pERC) Final Recommendation for Irinotecan Liposome (Onivyde) for Metastaic Pancreatic Cancer, pERC Meeting: Oct. 19, 2017, pERC Reconsideration Meeting: Dec. 17, 2017, pp. 1-14.
Papadatos-Pastos D, et.al., "Folfirinox-A New Paradigm in the Treatment of Pancreatic Cancer," Expert Rev Anticancer Ther. 14(10):1115-25 (2014).
Papahadjopoulos D, et al., "Targeting of Drugs to Solid Tumors Using Anti-HER2 Immunoliposomes," J Liposome Res. 8(4):425-42 (1998).
Papahadjopoulos D, et. al., "Sterically Stabilized Liposomes: Improvements in Pharmacokinetics and Antitumor Therapeutic Efficacy," Proc Natl Acad Sci USA. 88(24):11460-4 (1991).
Papi M, et al., "Clinically Approved PEGylated Nanoparticles Are Covered by a Protein Corona That Boosts the Uptake by Cancer Cells," Nanoscale. 9(29):10327-34 (2017).
Park J, English abstract and Table 1 and Figure 1 of "Second Line Chemotherapy for Pancreatic Cancer," Korean J Gastroenterol. 57(4):207-12 (2011).
Park J, et al., "Anti-HER2 Immunoliposomes for Targeted Therapy of Human Tumors," Cancer Lett. 118(2):153-60 (1997).
Park J, et al., "Development of Anti-p185HER2 Immunoliposomes for Cancer Therapy," Proc Natl Acad Sci U S A. 92(5):1327-31 (1995).
Park J, et al., "Immunoliposomes for Cancer Treatment," Adv Pharmacol. 40:399-435 (1997).
Park J, et al., "Sterically Stabilized Immunoliposomes: Formulations for Delivery of Drugs and Genes to Tumor Cells In Vivo," In Targeting of Drugs 6: Strategies for Stealth Therapeutic Systems, Gregoriadis G, et al., eds., Plenum Press, New York, pp. 41-47 (1998).
Park J, et al., "Tumor Targeting Using Anti-HER2 Immunoliposomes," J Control Release. 74(1-3):95-113 (2001).
Park J, et. al., "Anti-HER2 Immunoliposomes for Targeted Drug Delivery," Med Chem Res. 8(718):383-91 (1998).
Patankar N, et. al., "Topophore C: A Liposomal Nanoparticle Formulation of Topotecan for Treatment of Ovarian Cancer," Invest New Drugs. 31(1):46-58 (2013). Epub 2012.
Pavai S and Yap S, "The Clinical Significance of Elevated Levels of Serum CA19-9," Med J Malaysia. 58(5):667-72 ;2003).
Pavillard V, et al., "Determinants of the Cytotoxicity of Irinotecan in Two Human Colorectal Tumor Cell Lines," Cancer Chemother Pharmacol. 49(4):329-35 (2002).
Paz-Ares L, et al., "RESILIENT part 2: An Open-Label, Randomized, Phase 3 Study of Liposomal Irinotecan Injection in Patients With Small-Cell Lung Cancer Who Have Progressed With Platinum-Based First-Line Therapy." Poster presented at the American Society of Clinical Oncology (ASCO) Annual Conference, virtual format, May 29-Jun. 2, 2020, 7 pages.
Paz-Ares L, et aL, Abstract TPS9081. "RESILIENT part II: An Open-Label, Randomized, Phase III Study of Liposomal Irinotecan Injection in Patients With Small-Cell Lung Cancer Who Have Progressed With Platinum-Based First-Line Therapy," J Clin Oncol. 38(15_Suppl):TPS9081 DOI: 10.1200/JCO.2020.38.15_suppl.TPS9081 (2020), 2 printed pages.

(56) References Cited

OTHER PUBLICATIONS

Peikov V. et al., "pH-Dependent Association of SN-38 with Lipid Bilayers of a Novel Liposomal Formulation," Int J Pharm. 299(1-2):92-9 (2005).
Pellino A, et al., "Observational Retrospective Evaluation of Treatment With Liposomal Irinotecan Plus Fluorouracil/Leucovorin for Metastatic Pancreatic Cancer Patients: an Italian Large Real-World Analysis." Poster presented at the American Society of Clinical Oncology Gastrointestinal Cancers Symposium (ASCO GI), San Francisco, CA, Jan. 23-25, 2020, 5 pages.
Pellino A, et al., Abstract 660. "Observational Retrospective Evaluation of Treatment With Liposomal Irinotecan Plus Fluorouracil/Leucovorin for Metastatic Pancreatic Cancer Patients: An Italian Large Real-World Analysis," J Clin Oncol. 38(4_Suppl):660 DOI: 10.1200/JCO.2020.38.4_suppl.660 (2020), 2 printed pages.
Pelzer U, et al., "A Randomized Trial in Patients With Gemcitabine Refractory Pancreatic Cancer. Final Results of the CONKO-003 Study." Presentation presented at the American Society of Clinical Oncology (ASCO) Annual Meeting, Chicago, Illinois, May 30-Jun. 3, 2008, 18 pages.
Pelzer U, et al., Abstract P865. "Quality-Adjusted Time Without Symptoms or Toxicity (Q-TWIST) of Nanoliposomal Irinotecan (nal-IRI;MM-398) Plus 5-Fluorouracil and Leucovorin (5-FU/LV) vs 5-FU/LV alone in patients (pts) With Metastatic Pancreatic Adenocarcinoma (mPAC) Previously Treated With Gemcitabine-Based Therapy," Oncol Res Treat. 39(Suppl 3):260 (2016).
Petrelli F, et al., "What Else is in Gemcitabine-Pretreated Advanced Pancreatic Cancer? An Update of Second Line Therapies," Rev Recent Clin Trials. 5(1):43-56 (2010).
PharmaEngine, www.pharmaengine.com/pep02.html Webpage titled "PEP02". Aug. 4, 2011, 4 printed pages.
Philip P, et al., "Consensus Report of the National Cancer Institute Clinical Trials Planning Meeting on Pancreas Cancer Treatment," J Clin Oncol. 27(33):5660-9 (2009).
Picozzi V, et al., "An Assessment of the Total Cost of Pancreatic Cancer Using Real-World Evidence." Poster presented at the American Society of Clinical Oncology Gastrointestinal Cancers Symposium (ASCO GI), San Francisco, CA, Jan. 23-25, 2020, 6 pages.
Picozzi V, et al., Abstract 773. "An Assessment of the Total Cost of Pancreatic Cancer Using Real-World Evidence," J Clin Oncol. 38(4_Suppl):773 DOI: 10.1200/JCO.2020.38_4_suppl.773 (2020), 2 printed pages.
Pillai G, "Nanomedicines for Cancer Therapy: an Update of Fda Approved and Those under Various Stages of Development," SOJ Pharm Pharm Sci. 1(2):13 (2014), 13 pages.
Pino M, et. al., "Capecitabine and Celecoxib as Second-Line Treatment of Advanced Pancreatic and Biliary Tract Cancers," Oncology. 76(4):254-61 (2009).
Ponce S, et al., "RESILIENT Part 1: Pharmacokinetics of Second-Line (2L) Liposomal Irinotecan in Patients with Small Cell Lung Cancer (SCLC)," Poster presented at the European Society for Medical Oncology (ESMO) Virtual Congress 2020, virtual format, Sep. 19-21, 2020, 8 pages.
Ponce S, et al., Abstract 1793P. "RESILIENT Part 1: Pharmacokinetics of Second-Line (2L) Liposomal Irinotecan in Patients with Small Cell Lung Cancer (SCLC)," Ann Oncol. 31(S4):S1038-S1039 (2020).
Poplin E, et. al.,"Phase III Southwest Oncology Group 9415/Intergroup 0153 Randomized Trial of Fluorouracil, Leucovorin, and Levamisole Versus Fluorouracil Continuous Infusion and Levamisole for Adjuvant Treatment of Stage III and High-Risk Stage II Colon Cancer," J Clin Oncol. 23(9):1819-25 (2005).
Rahib L, et. al., "Evaluation of Pancreatic Cancer Clinical Trials and Benchmarks for Clinically Meaningful Future Trials: A Systematic Review," JAMA Oncol. 2(9):1209-16 (2016).
Ramnani K, et al., Abstract CT13. "Impact of Treatment Sequence on Overall Survival in Metastatic Pancreatic Cancer Patients Treated with Liposomal Irinotecan in the Real-World Setting," Hematology Oncology Pharmacy Association (HOPA) Annual Conference, Mar. 11-14, 2020, available at eventscribe.com/2020/posters/HOPAahead/SplitViewer.asp?PID=Njg0NzMyODlyNzY, (2020), 2 pages.
Ramsay E, et. al., "Irinophore C: A Liposome Formulation of Irinotecan With Substantially Improved Therapeutic Efficacy Against a Panel of Human Xenograft Tumors," Clin Cancer Res. 14(4):1208-17 (2008).
Rea D, et al., "A Phase I/II and Pharmacokinetic Study of Irinotecan in Combination with Capecitabine as First-Line Therapy for Advanced Colorectal Cancer," Ann Oncol. 16(7):1123-32 (2005).
Reni M, et. al., "Raltitrexed—Eloxatin Salvage Chemotherapy in Gemcitabine-Resistant Metastatic Pancreatic Cancer," Br J Cancer 94(6):785-91 (2006).
Renouf D, et. al., "A Phase II Study of Erlotinib in Gemcitabine Refractory Advanced Pancreatic Cancer," Eur J Cancer. 50(11):1909-15 (2014).
Reynolds J, et al., "HER2-Targeted Liposomal Doxorubicin Displays Enhanced Anti-Tumorigenic Effects Without Associated Cardiotoxicity," Toxicol Appl Pharmacol. 262(1):1-10 (2012).
Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.
Rocha Lima C, et al., "Irinotecan Plus Gemcitabine Results in No Survival Advantage Compared With Gemcitabine Monotherapy in Patients With Locally Advanced or Metastatic Pancreatic Cancer Despite Increased Tumor Response Rate," J Clin Oncol. 22(18)_3776-83 (2004).
Rosenecker J, et al., "Increased Liposome Extravasation in Selected Tissues: Effect of Substance P," Proc Natl Acad Sci U S A. 93(14):7236-41 (1996).
Roth A, et al., "Anti-CD166 Single Chain Antibody-Mediated Intracellular Delivery of Liposomal Drugs to Prostate Cancer Cells," Mol Cancer Ther. 6(10):2737-46 (2007).
Rothenberg M, et. al., "Alternative Dosing Schedules for Irinotecan," Oncology. 12(8 Suppl 6):68-71 (1998). Available at cancernetwork.com/view/alternative-dosing-schedules-irinotecan, 16 printed pages.
Rubesova E, et al., "Gd-Labeled Liposomes for Monitoring Liposome-Encapsulated Chemotherapy: Quantification of Regional Uptake in Tumor and Effect on Drug Delivery," Acad Radiol. 9(Suppl 2):S525-7 (2002).
Sadzuka Y, et al., "Effective Irinotecan (CPT-11)-containing Liposomes: Intraliposomal Conversion to the Active Metabolite SN-38." Jpn J Cancer Res. 90(2):226-32 (1999).

* cited by examiner (4 weekly doses)

Not enough mice a day 41 stats for day 31 p=.0420 t-test

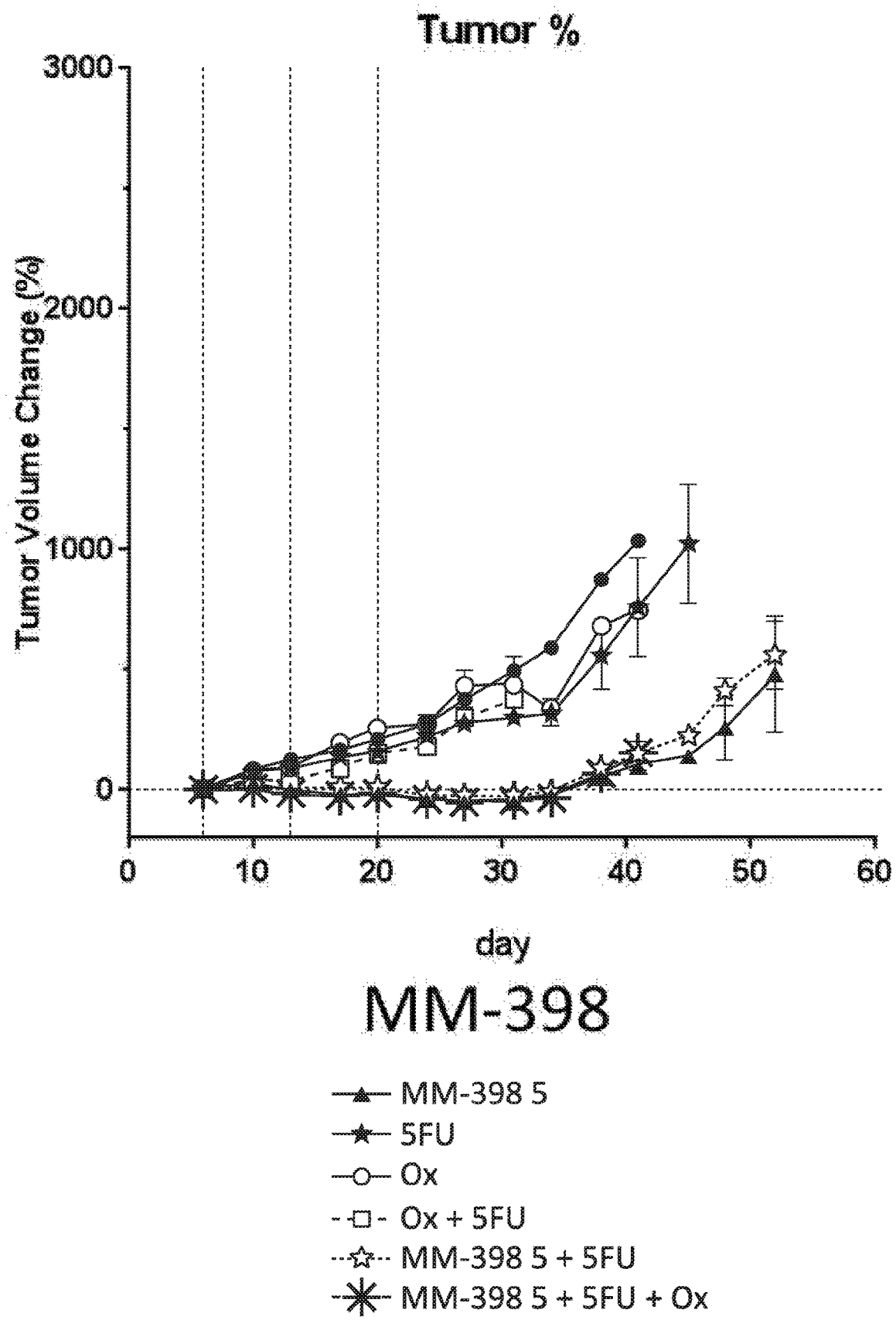

Patient Disposition
• All patients in dose level -1 are still on treatment

| Reason for treatment Termination | Dose Level 1 (N=7) | Dose Level -1 (N=6) |
|---|---|---|
| Total Discontinuations | 7 | 0 |
| Investigator Decision | 2 | 0 |
| AE | 1 | 0 |
| Symptomatic Deterioration | 1 | 0 |
| pCR | 1 | 0 |

FIG. 14

| Primary system organ class<br>Preferred term | Dose Level -1<br>(N=6) | Dose Level 1<br>(N=7) | Total<br>(N=13) |
|---|---|---|---|
| Subjects With Any TEAE(s) of CTCAE ≥ Gr 3 | 2 (33.3) | 6 (85.7) | 8 (61.5) |
| Blood and lymphatic system disorders | 1 (16.7) | 0 | 1 (7.7) |
| Febrile neutropenia | 1 (16.7) | 0 | 1 (7.7) |
| Metabolism and nutrition disorders | 1 (16.7) | 5 (71.4) | 6 (46.2) |
| Dehydration | 1 (16.7) | 4 (57.1) | 5 (38.5) |
| Decreased appetite | 0 | 2 (28.6) | 2 (15.4) |
| Hypokalaemia | 0 | 2 (28.6) | 2 (15.4) |
| Hypoalbuminaemia | 0 | 1 (14.3) | 1 (7.7) |
| Nervous system disorders | 1 (16.7) | 0 | 1 (7.7) |
| Syncope | 1 (16.7) | 0 | 1 (7.7) |
| Gastrointestinal disorders | 0 | 4 (57.1) | 4 (30.8) |
| Diarrhoea | 0 | 3 (42.9) | 3 (23.1) |
| Enteritis | 0 | 1 (14.3) | 1 (7.7) |
| Faecal incontinence | 0 | 1 (14.3) | 1 (7.7) |
| Large intestinal obstruction | 0 | 1 (14.3) | 1 (7.7) |
| Vomiting | 0 | 1 (14.3) | 1 (7.7) |
| General disorders and administration site conditions | 0 | 1 (14.3) | 1 (7.7) |
| Fatigue | 0 | 1 (14.3) | 1 (7.7) |
| Infections and infestations | 0 | 2 (28.6) | 2 (15.4) |
| Clostridium difficile colitis | 0 | 1 (14.3) | 1 (7.7) |
| Neutropenic sepsis | 0 | 1 (14.3) | 1 (7.7) |
| Pneumonia | 0 | 1 (14.3) | 1 (7.7) |
| Vascular disorders | 0 | 1 (14.3) | 1 (7.7) |
| Orthostatic hypotension | 0 | 1 (14.3) | 1 (7.7) |
| Uncoded SOC | 1 (16.7) | 2 (28.6) | 3 (23.1) |
| Uncoded: Upper GI bleed | 1 (16.7) | 0 | 1 (7.7) |
| Uncoded: Hypertension | 0 | 1 (14.3) | 1 (7.7) |
| Uncoded: Small Bowel Oedema | 0 | 1 (14.3) | 1 (7.7) |

TREATING GASTRIC CANCER USING COMBINATION THERAPIES COMPRISING LIPOSOMAL IRINOTECAN, OXALIPLATIN, 5-FLUOROURACIL (AND LEUCOVORIN)

CROSS-REFERENCE TO RELATED APPLICATIONS

This application is a national phase entry pursuant to 35 U.S.C. § 371 of International Application No. PCT/GB2017/053293, filed Nov. 1, 2017, which claims the benefit of priority of U.S. Provisional Application No. 62/416,317, filed Nov. 2, 2016, which are incorporated herein by reference.

TECHNICAL FIELD

This disclosure relates to novel therapies useful in the treatment of gastric cancer, including the use of liposomal irinotecan in combination with 5-fluorouracil and oxaliplatin for the (first line) treatment of patients diagnosed with previously untreated gastric cancer.

BACKGROUND

Gastric cancer is one of the most common causes of cancer-related mortality worldwide. Approximately 18,000 metastatic gastric cancer patients were expected to be treated with pharmaceutical regimens in the United States in 2015. Of this population, approximately 7000 patients fall into the HER2-negative frontline treatment category. HER2-negative gastric cancer is a highly heterogeneous disease and targeted therapies, such as bevacizumab, rilotumumab and cetuximab, have been unsuccessful. Complicating the prognosis, many gastric cancer patients present with advanced-stage disease at diagnosis. There is currently no globally accepted standard chemotherapeutic regimen for the treatment of advanced gastric cancer, despite the fact that several treatment regimens have been investigated with limited efficacy (5 year survival rate of ~4%). The disease is commonly treated with chemotherapy, surgery and radiation therapy. Given the poor prognosis and the low median survival rate for patients with gastric cancer, new treatment options are still needed.

Tolerability of multi-drug regimens is important in cancer treatment. The longer the duration of manageable treatment should translate into improved outcome due to longer drug exposure. One widely used first-line treatment of patients with gastric cancer is oxaliplatin plus infusional 5-fluorouracil (5-FU) and leucovorin (LV). Specifically, a modified FOLFOX6 regimen (mFOLFOX6) involves 5-FU/LV (400 mg/m$^2$ IV bolus+2400 mg/m$^2$ as 46 h infusion/400 mg/m$^2$)+oxaliplatin (85 mg/m$^2$), q2w. While the treatment is generally well-tolerated, the overall survival is not increased.

During the last 5 years, another combination chemotherapy regimen that has emerged as a first-line treatment of gastric cancer is the combination therapy of 5-fluorouricil (5-FU)/leucovorin (LV)+irinotecan+oxaliplatin (FOLFIRINOX). However, FOLFIRINOX is known to have significant toxicity, and use is limited to patients with better performance status (i.e. ECOG performance score of 0 or 1). With prolonged FOLFIRINOX treatment, oxaliplatin is often discontinued from the regimen due to toxicity. Therefore, if equally effective double regimens can be identified, patients may be able to tolerate prolonged treatment better, and even poor performance status patients may receive benefit. Although the FOLFIRINOX regimen has been recommended by the National Comprehensive Cancer Network (NCCN) as a preferred option for first-line metastatic disease since 2011, there are some concerns about the toxicity associated with FOLFIRINOX. One dose regimen of FOLFIRINOX is 85 mg/m$^2$ oxaliplatin, 180 mg/m$^2$ irinotecan, and fluorouracil at a dose of 400 mg/m$^2$ administered by IV bolus followed by a continuous infusion of 2400 mg/m$^2$. Yet due to toxicity, modified FOLFIRINOX regimens are often used (e.g. elimination of the 5-FU bolus) with unknown effects on the efficacy and safety of modified schedules.

CPT-11 is irinotecan hydrochloride trihydrate, marketed as Camptosar® in the United States, approved for use in combination with 5-fluorouracil and leucovorin as first line therapy for patients with metastatic carcinoma of the colon or rectum, or for patients with metastatic carcinoma of the colon or rectum whose disease has recurred or progressed following initial fluorouracil-based therapy.

MM-398 is a liposomal irinotecan and is marketed in the U.S. as the FDA-approved product ONIVYDE® in combination with 5-fluorouracil and leucovorin for the treatment of patients with certain forms of pancreatic cancer after disease progression following gemcitabine-based therapy.

SUMMARY

Improved antineoplastic therapies for the treatment of gastric cancer provide the administration of liposomal irinotecan in combination with oxaliplatin and 5-fluorouracil to patients with previously untreated gastric cancer. The 5-fluorouracil can be administered in combination with leucovorin. The improved antineoplastic therapies can provide improved therapeutic index (e.g., improved toxicity profiles) relative to prior FOLFIRINOX regimens.

A method of treating gastric cancer can comprise the administration of an antineoplastic therapy of liposomal irinotecan (e.g., MM-398), oxaliplatin, and 5-fluorouracil once every two weeks to the patient. Optionally, leucovorin can also be administered prior to each administration of the 5-fluorouracil. Each administration of the liposomal irinotecan can be administered in a total dose of 50 mg/m$^2$ or 55 mg/m$^2$ (may be referred to as 56 mg/m$^2$) liposomal irinotecan (dose based on free base, as defined herein) or 60 mg/m$^2$ or 65 mg/m$^2$ liposomal irinotecan (dose based on hydrochloride trihydrate as defined herein). A total of 2,400 mg/m$^2$ 5-fluorouracil can be administered over 46 hours starting on each day when the liposomal irinotecan is administered. A total of 60, 70, 75, or 85 mg/m$^2$ oxaliplatin can be administered on each day the liposomal irinotecan is administered. A total of 200 mg/m$^2$ (l) leucovorin can be administered prior to each administration of the 5-flurouracil (e.g., optionally administered as 400 mg/m$^2$ of (l+d) leucovorin). The antineoplastic therapy can be administered starting on days 1 and 15 of a 28-day treatment cycle, with the liposomal irinotecan, oxaliplatin, and optionally leucovorin administered on days 1 and 15, and initiating the 46-hour administration of the 5-fluorouracil on days 1 and 15. The total dose of each administration of liposomal irinotecan and 5-fluorouracil can be reduced by 25% for certain patients, including patients who experience a Grade 3 or 4 adverse reaction to a previous dose of the antineoplastic therapy.

The invention is based in part on several pre-clinical discoveries. First, liposomal irinotecan improved anti-tumor activity of the topoisomerase 1 inhibitor SN-38 (an active metabolite of irinotecan) relative to exposure-matched doses of non-liposomal irinotecan. Second, liposomal irinotecan combined with 5-fluorouracil and oxaliplatin consistently improved tumor growth inhibition and survival in mouse xenograft models of gastric cancer relative to non-liposomal irinotecan, without exacerbating the baseline toxicities of these agents.

In addition, the invention is based in part on the discovery that the administration of a dose of an initial antineoplastic therapy to humans consisting of 70 mg/m² liposomal irinotecan (free base) was not well tolerated in humans when administered in combination with 60 mg/m² oxaliplatin, 2400 mg/m² 5-fluorouracil and 400 mg/m² (l+d) leucovorin. In particular, the administration of this initial antineoplastic therapy resulted in unexpected gastrointestinal adverse events. However, subsequent antineoplastic therapy consisting of a novel combination of 50 mg/m² liposomal irinotecan, 60 mg/m² oxaliplatin, 2400 mg/m² 5-fluorouracil and 400 mg/m² (l+d) leucovorin did not result in any of the gastrointestinal adverse events observed with the initial antineoplastic therapy.

SN-38 is a potent active metabolite of liposomal irinotecan. The average unencapsulated SN-38 (uSN38 Cavg) is associated with increased efficacy of liposomal irinotecan, while higher levels of other PK parameters are associated with reduced tolerability of liposomal irinotecan. For example, higher total irinotecan maximum plasma concentration (tIRI Cmax) is associated with diarrhea and higher unencapsulated maximum plasma concentration of SN38 (uSN38 Cmax) is associated with neutropenia. These pharmacokinetic parameters are proportional to naI dose.

The administration of liposomal irinotecan, oxaliplatin, 5-fluorouracil and leucovorin with a dose level of 60 mg oxaliplatin and 80 mg/m² of liposomal irinotecan resulted in a greater than 100% increase in the average concentration in plasma of unencapsulated uSN38 $C_{max}$, while administering these four agents with a dose level of 60 mg oxaliplatin and 60 mg/m² of liposomal irinotecan (see dose level −1 in Table 2) resulted in an increase in of about 9%. In addition, the PK parameters associated with reduced tolerability (tIRI $C_{max}$ or uSN38 $C_{max}$) increased about 15% and 44% for the 60 mg/80 mg/m² (respectively) but decreased for dose level −1 by 3% and 27% (respectively). So unexpectedly, the administration of a lower amount of liposomal irinotecan resulted in a more tolerable dose, while at the same time retaining efficacy. In the present application the administration of oxaliplatin, liposomal irinotecan, oxaliplatin, 5-fluorouracil and leucovorin at dose level −1 or −3 (Table 2) increases the uSN38 $C_{avg}$ in plasma without significantly increasing the tIRI $C_{max}$ or uSN38 $C_{max}$, which allows for administration of these doses with greater tolerability Accordingly, preferred methods of treating (previously untreated) gastric cancer provide for the administration of a human-tolerated antineoplastic therapy once every two weeks, where each administration of the antineoplastic therapy is a combination of the antineoplastic agents liposomal irinotecan, oxaliplatin and 5-fluorouracil provided herein. Preferably, the antineoplastic therapy administered once every two weeks consists of: (a) a total dose of 50 mg/m² liposomal irinotecan (dose based on the free base, as defined herein), (b) a total dose of 60-85 mg/m² oxaliplatin (including, e.g., 60, 70, or 85 mg/m²), and (c) a total of 2,400 mg/m² 5-fluorouracil optionally administered in combination with leucovorin; or (a) a total dose of 55 mg/m² liposomal irinotecan (dose based on the free base, as defined herein), (b) a total dose of 60-85 mg/m² oxaliplatin (including, e.g., 60, 70 or 85 mg/m²), and (c) a total of 2,400 mg/m² 5-fluorouracil optionally administered in combination with leucovorin. Optionally, the combination can include administration of a total of 200 mg/m² (l)leucovorin (optionally administered as 400 mg/m² of (l+d) leucovorin), prior to initiating the administration of the 5-fluorouracil. Preferably, no other antineoplastic agent is administered during the antineoplastic therapy, other than amounts of SN-38 produced within the patient from the liposomal irinotecan, after administration of the liposomal irinotecan. For example, the antineoplastic therapy can be administered without (non-liposomal) CPT-11 irinotecan. Preferably, the liposomal irinotecan, oxaliplatin, and (optionally) leucovorin are consecutively administered as separate infusions on a single (first) day and the 5-fluorouracil is administered starting on the first day after the administration of the leucovorin (if administered) and continuing into the following day (e.g., over a total of 46 hours).

BRIEF DESCRIPTION OF THE DRAWINGS

FIG. 4A. MM-398 Tumor volume; FIG. 4B. MM-398 Body weight; FIG. 4C. Oxaliplatin tumor volume; FIG. 4D. Oxaliplatin body weight; FIG. 4E. 5-FU tumor volume; FIG. 4F. 5-FU Body weight; FIG. 4G. Free irinotecan Tumor volume and FIG. 4H. Free irinotecan Body weight. MM-398 at 5 mg/kg has better anti-tumor activity than all other treatments tested.

FIGS. 8A and 8B are graphs showing anti-tumor activity of (A) MM-398 in comparison to (B) free irinotecan at high doses.

FIG. 10A. Tumor SN-38 Concentration; FIG. 10B. Time SN-38 concentration is predicted to be above a threshold out of a 6 week cycle.

FIG. 14 is a table showing adverse events in response to treatment with Dose level −1 and dose level 1.

DETAILED DESCRIPTION

Figure 1A:
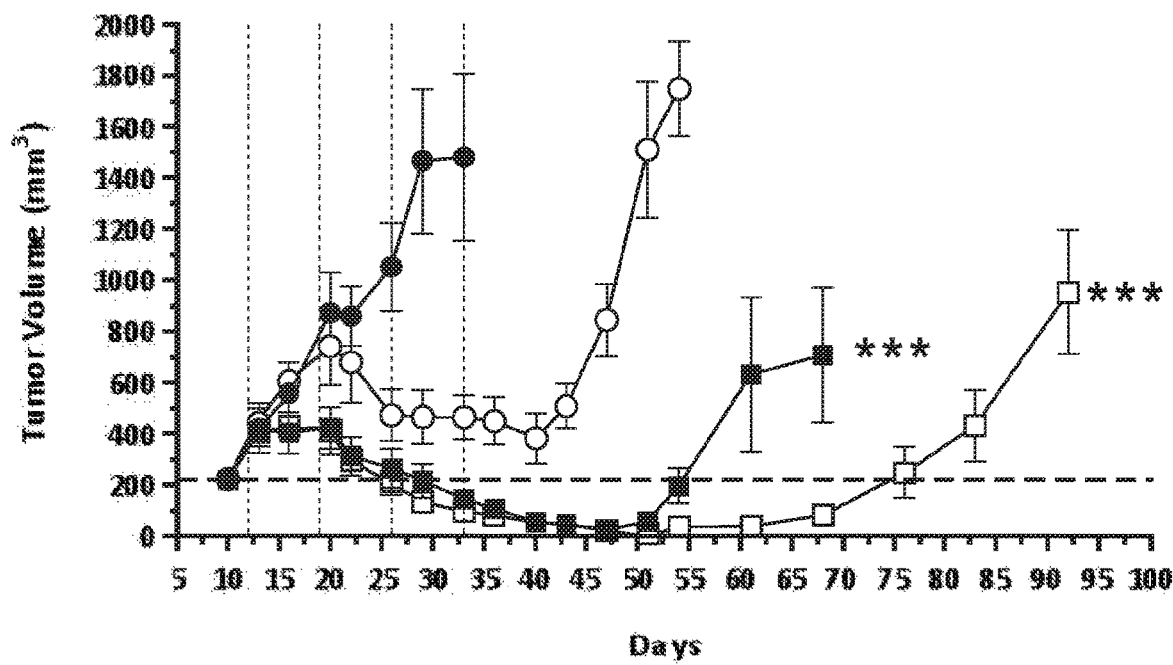
FIG. 1A is a graph showing nal-IRI activity in gastric tumor model MKN-45.

Doses of nal-IRI in some studies were calculated based on the equivalent dose of irinotecan hydrochloride trihydrate (salt); in this specification, unless specified otherwise, the doses are based on irinotecan as the free base.

There are about 866 mg of irinotecan per gram of irinotecan trihydrate hydrochloride. For example, a dose of 80 mg/m$^2$ of liposomal irinotecan based on the amount of irinotecan hydrochloride trihydrate starting material actually contains about 0.866×(80 mg/m$^2$)=69.38 mg/m$^2$ of irinotecan free base, which may be rounded to an integer to avoid dosing errors. For example 69.38 mg/m$^2$ may be rounded to 70 mg/m$^2$ as shown in Table A.

Another example is a dose of 65 mg/m$^2$ liposomal irinotecan based on the trihydrate salt, which refers to an amount of liposomal irinotecan free base providing the same amount of liposome encapsulated irinotecan that is present in 65 mg/m$^2$ of liposomal irinotecan hydrochloride trihydrate which is equivalent to a dose of 56.29 mg/m$^2$ liposomal irinotecan free base which may be rounded, in order to avoid dosing errors, to a dose from 55 mg/m$^2$ to 57 mg/m$^2$, for example, 55 mg/m$^2$, 56 mg/m$^2$ or 57 mg/m$^2$. Another example is a dose of 60 mg/m$^2$ liposomal irinotecan based on the trihydrate salt which refers to an amount of the liposomal irinotecan free base providing the same amount of liposome encapsulated irinotecan that is present in 60 mg/m$^2$ of irinotecan hydrochloride trihydrate, and is equivalent to a dose 51.96 mg/m$^2$ which can be rounded, in order to avoid dosing errors, to a dose of from about 50 mg/m$^2$ to about 52 mg/m$^2$, for example, to 50 mg/m$^2$, 51 mg/m$^2$, or 52 mg/m$^2$ of liposomal irinotecan free base. Likewise a dose of 50 mg/m$^2$ of liposomal irinotecan hydrochloride trihydrate can be converted to 43.30 mg/m$^2$ of liposomal irinotecan free base which can be rounded, in order to avoid dosing errors, to 43 mg/m$^2$ or 44 mg/m$^2$. Similarly a dose of 49 mg/m$^2$ of liposomal irinotecan hydrochloride trihydrate can be converted to 42.22 mg/m$^2$ of liposomal irinotecan free base which can be rounded, in order to avoid dosing errors, to 42 mg/m$^2$' or 43 mg/m$^2$. Another embodiment is a dose of 45 mg/m$^2$ of liposomal irinotecan hydrochloride trihydrate which can be converted to 38.97 mg/m$^2$ of liposomal irinotecan free base which can be rounded, in order to avoid dosing errors, to 38 mg/m$^2$ or 39 mg/m$^2$. In another example, a dose of 40 mg/m$^2$ of liposomal irinotecan hydrochloride trihydrate can be converted to 34.64 mg/m$^2$ of liposomal irinotecan free base which can be rounded, in order to avoid dosing errors, to 34 mg/m$^2$ or 35 mg/m$^2$. In another example, a dose of 33 mg/m$^2$ of liposomal irinotecan hydrochloride trihydrate can be converted to 28.15 mg/m$^2$ of liposomal irinotecan free base which can be rounded, in order to avoid dosing errors, to 28 mg/m$^2$ or 29 mg/m$^2$. In another example, a dose of 30 mg/m$^2$ of liposomal irinotecan hydrochloride trihydrate can be converted to 32.5 mg/m$^2$ of liposomal irinotecan free base which can be rounded, in order to avoid dosing errors, to 32 mg/m$^2$ or 33 mg/m$^2$.

Additional examples are shown in Table A.

TABLE A

| irinotecan hydrochloride trihydrate salt mg/m$^2$ | irinotecan free base mg/m$^2$ | Conversion from hydrochloride trihydrate salt to free base using 0.866 conversion factor |
| --- | --- | --- |
| 120 | 100 | 103.92 |
| 80 | 70 | 69.38 |
| 65 | 55 | 56.29 |
| 60 | 50 | 51.96 |
| 50 | 43 | 43.30 |
| 49 | 42 | 42.22 |
| 45 | 39 | 38.97 |
| 40 | 35 | 34.64 |
| 33 | 28 | 28.15 |
| 30 | 33 | 32.50 |

As used herein, unless otherwise indicated, the term "nal-IRI" (nanoliposomal irinotecan) and "MM-398" refer to a form of liposomal irinotecan. The term "CPT-11" refers to (non-liposomal) irinotecan hydrochloride trihydrate.

As used herein, "5-FU" and "5FU" and used interchangeably and refer to 5-fluorouracil.

All cited documents are incorporated herein by reference.

As used herein, the endpoints of an expressed range are included in the range. For example, a range from 30 mg to 70 mg, includes 30 and 70 (and all numbers between the endpoints).

Testing of xenograft models of gastric cancer in Example 2 demonstrated improved anti-tumor activity of liposomal irinotecan relative to exposure-matched doses of non-liposomal irinotecan. In the mouse animal studies in Example 2, a dose of "x" mg/kg liposomal irinotecan provides about the same exposure to the topoisomerase 1 inhibitor (irinotecan and/or SN-38) as a dose of "5x" non-liposomal irinotecan (CPT-11). The liposomal irinotecan consistently improved tumor growth inhibition and survival relative to non-liposomal irinotecan in preclinical models, both as a monotherapy and in combination with 5-FU and oxaliplatin. These findings illustrate the therapeutic potential of liposomal irinotecan in combination with 5-FU/LV and oxaliplatin and support a clinical trial of this triplet regimen in first-line gastric cancer (Example 4).

An animal model of the FOLFIRINOX regimen was tested against the MM-398+5-FU/LV+oxaliplatin regimen in a gastric tumor xenograft mouse model. Liposomal irinotecan (MM-398) performed better than conventional (non-liposomal) irinotecan (CPT-11) at equivalent exposure doses (5 mg/kg MM-398 vs. 25 mg/kg free IRI) in the gastric xenograft cancer models (Example 2) either alone (e.g., FIG. 2A), or in combination with oxaliplatin and/or 5-FU (e.g., FIG. 2B).

Figure 3A:
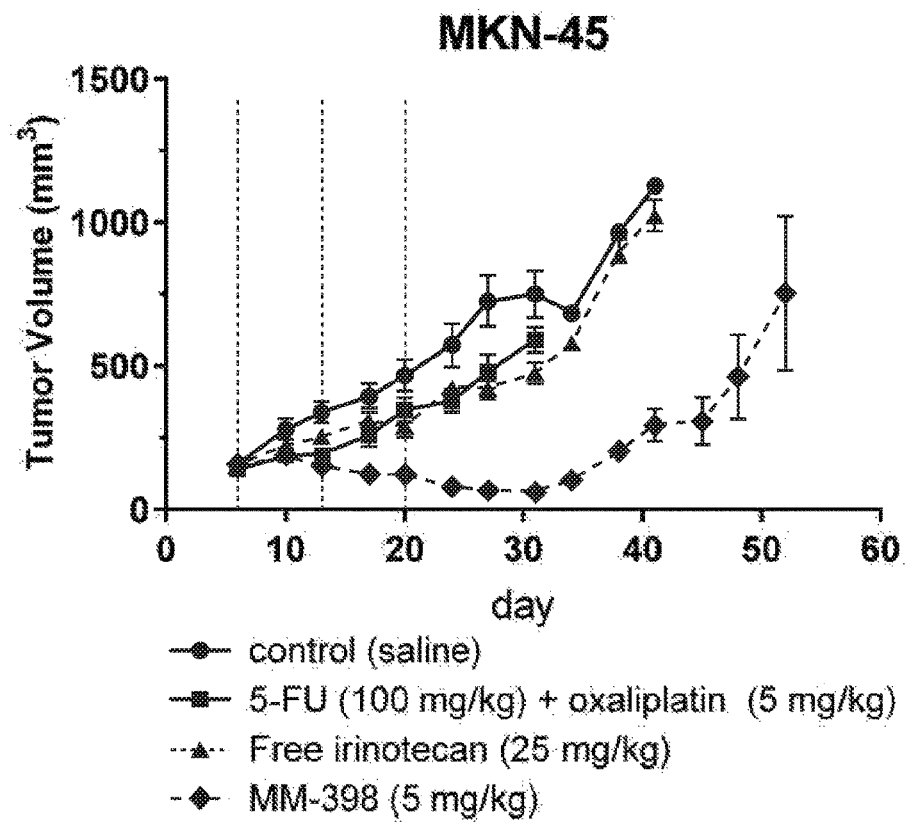
FIG. 3A is a graph showing anti-tumor activity of MM-398 in comparison to free irinotecan in the context of combination therapy with 5-FU and oxaliplatin.
Figure 3B:
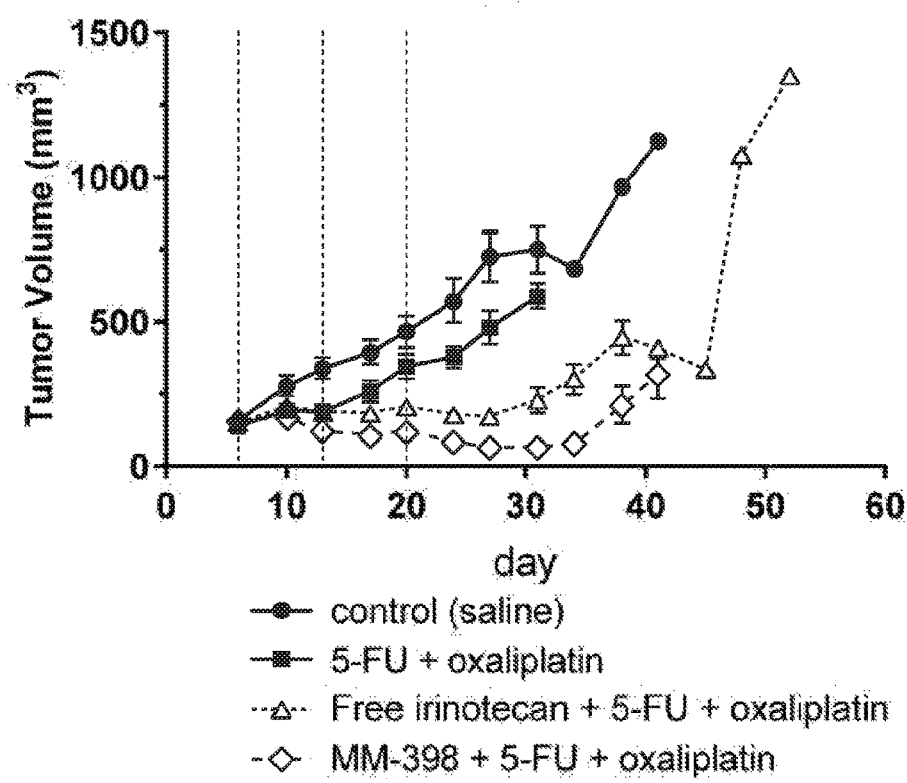
FIG. 3B is a graph showing anti-tumor activity of MM-398 in comparison to free irinotecan in the context of triplet combination therapy with 5-FU and oxaliplatin.
Figure 4A:
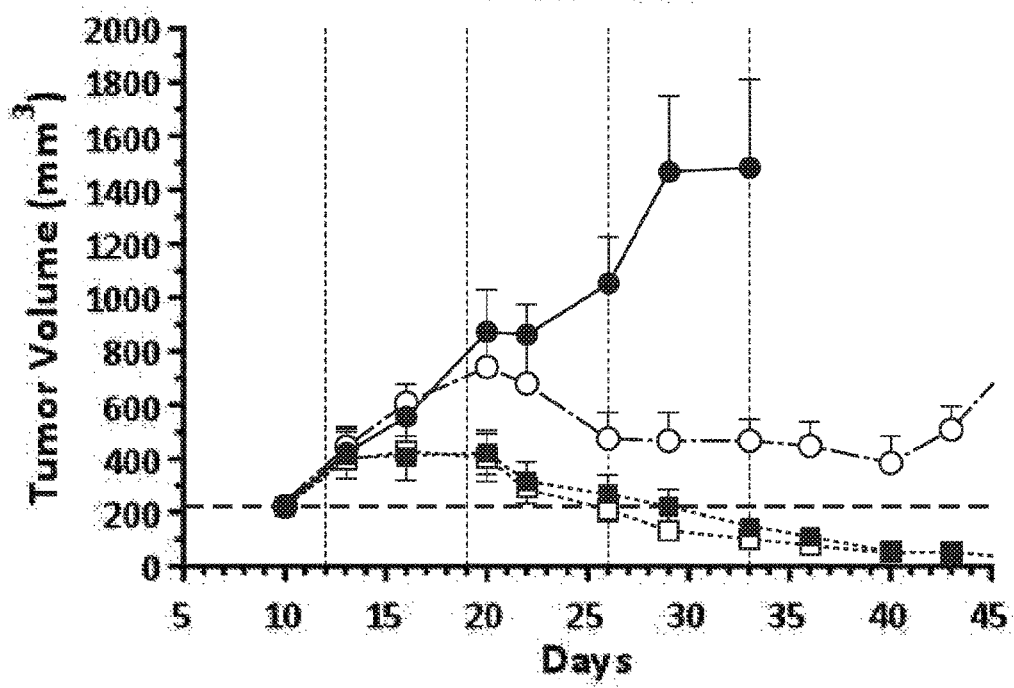
FIGS. 4A-4H, are graphs showing that MM-398 displays superior anti-tumor activity in tumor models less responsive to oxaliplatin, 5-FU and free irinotecan (equal exposure) (Efficacy Study in Gastric Model (MKN-45)—Monotherapy).
Figure 4B:
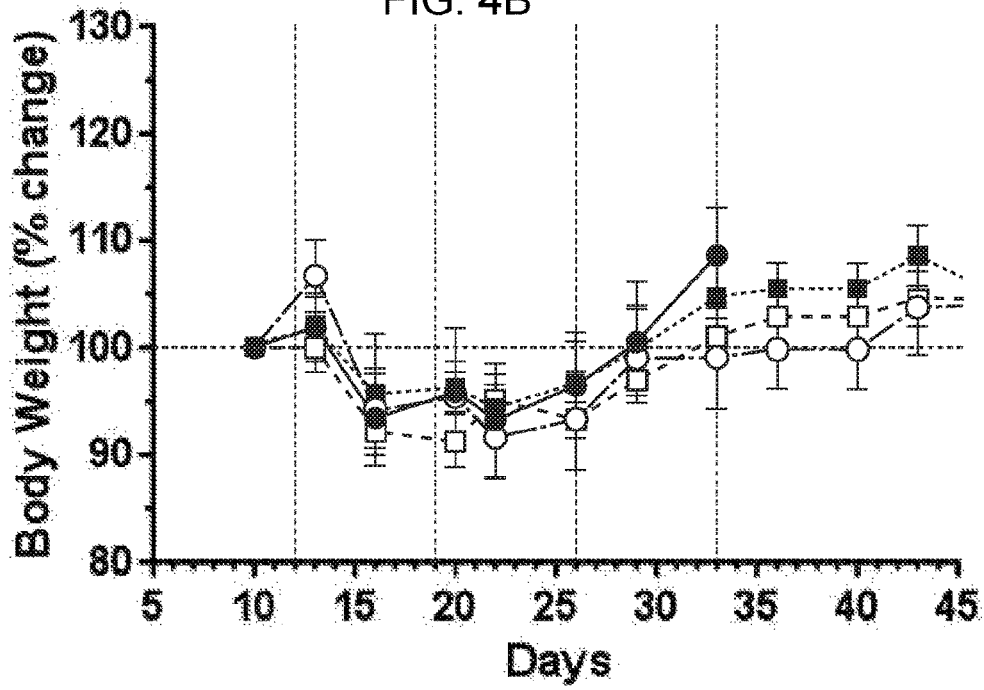
Figure 4C:
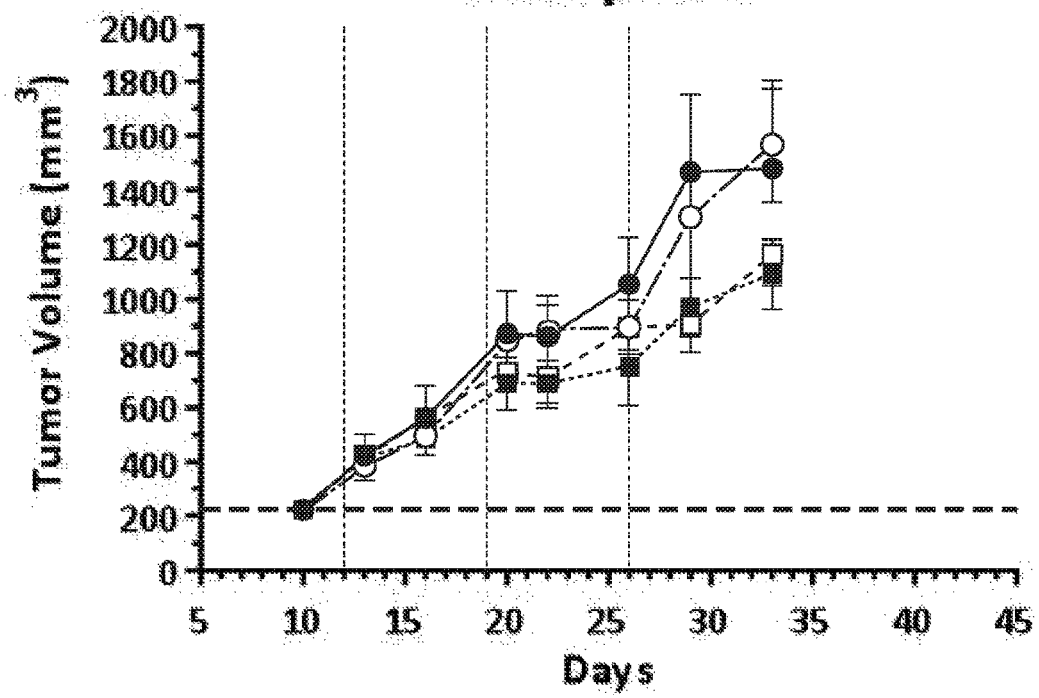
Figure 4D:
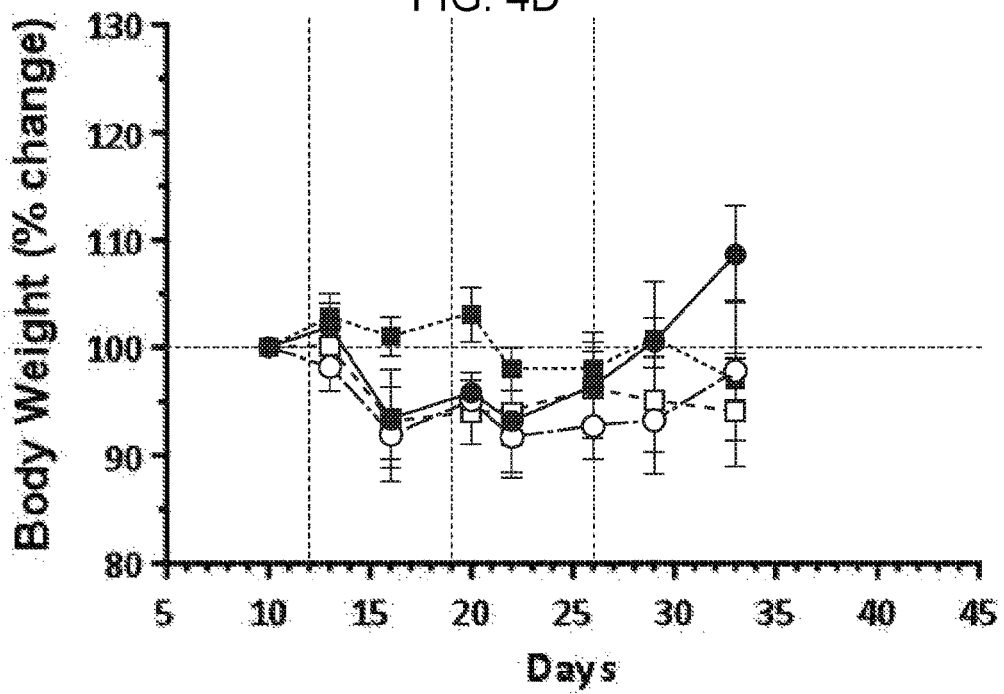
Figure 4E:
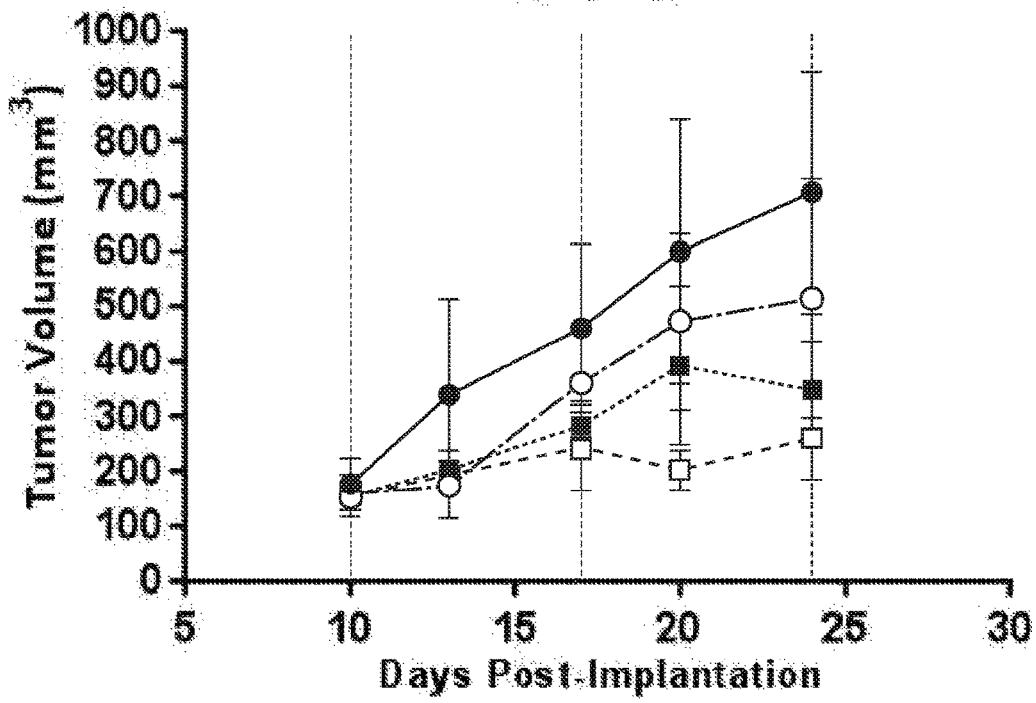
Figure 4F:
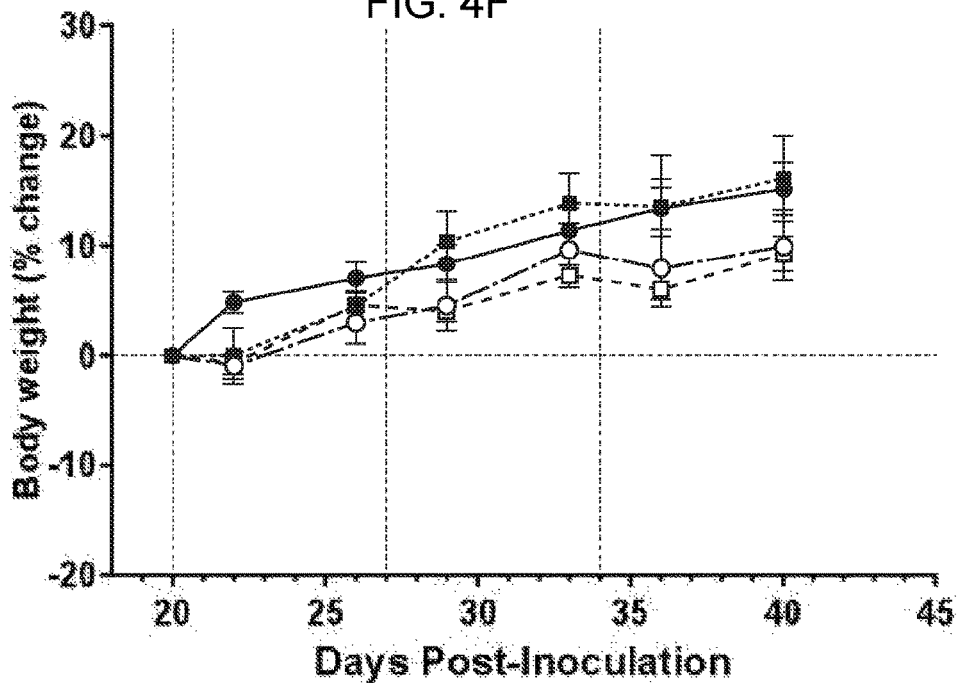
Figure 4G:
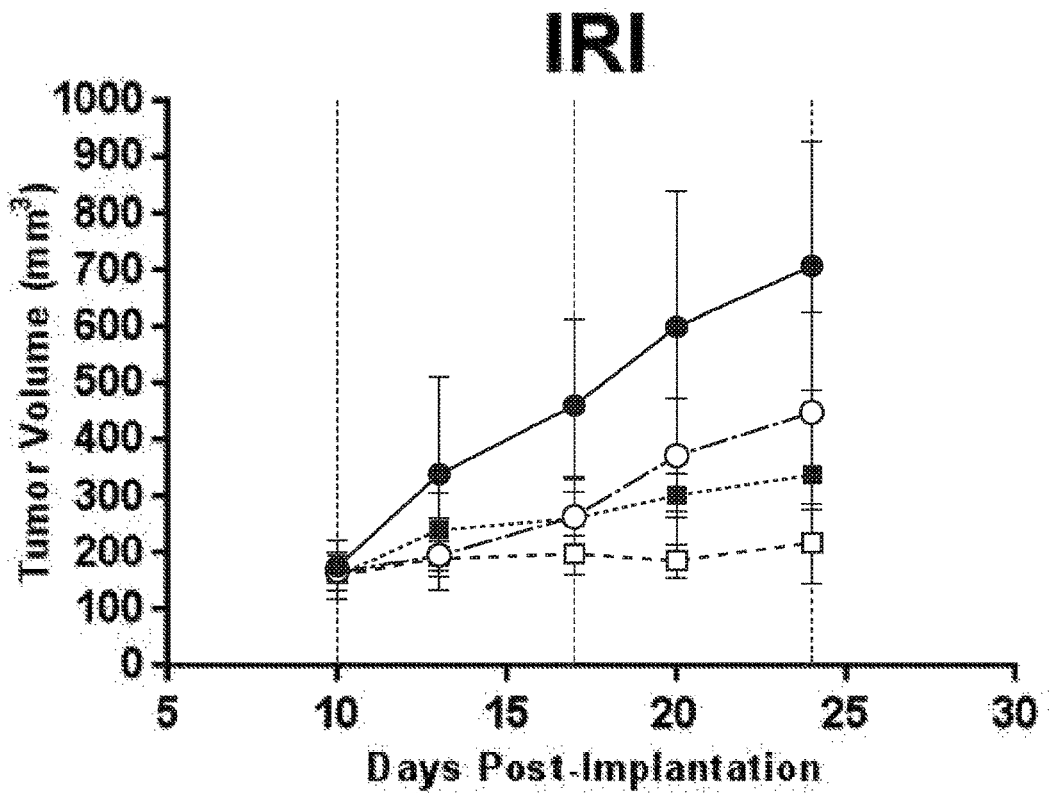
Figure 4H:
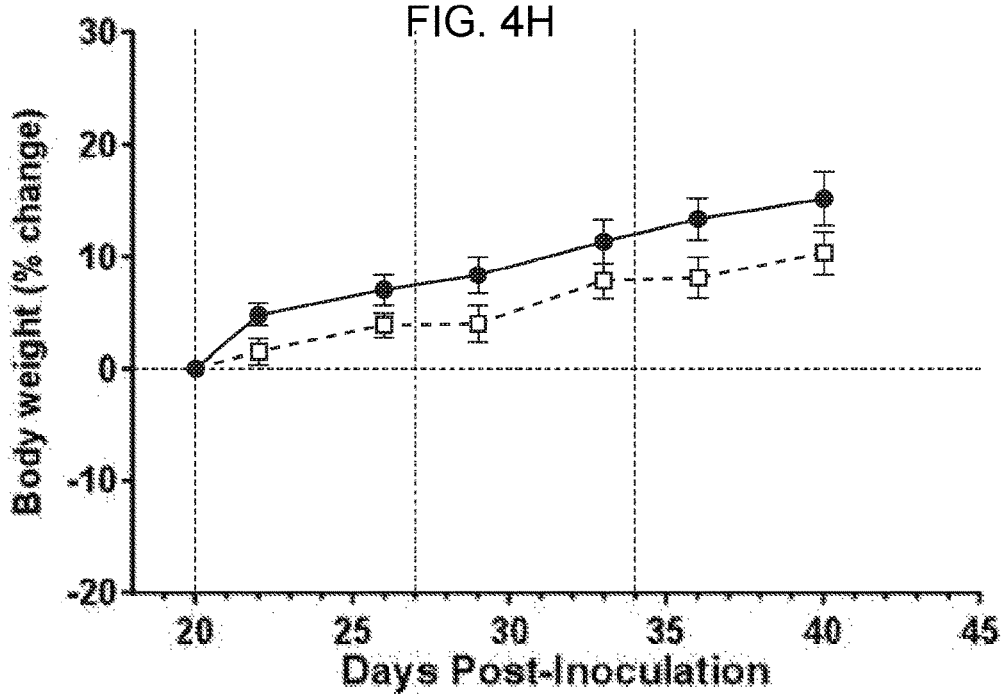
Figure 5A:
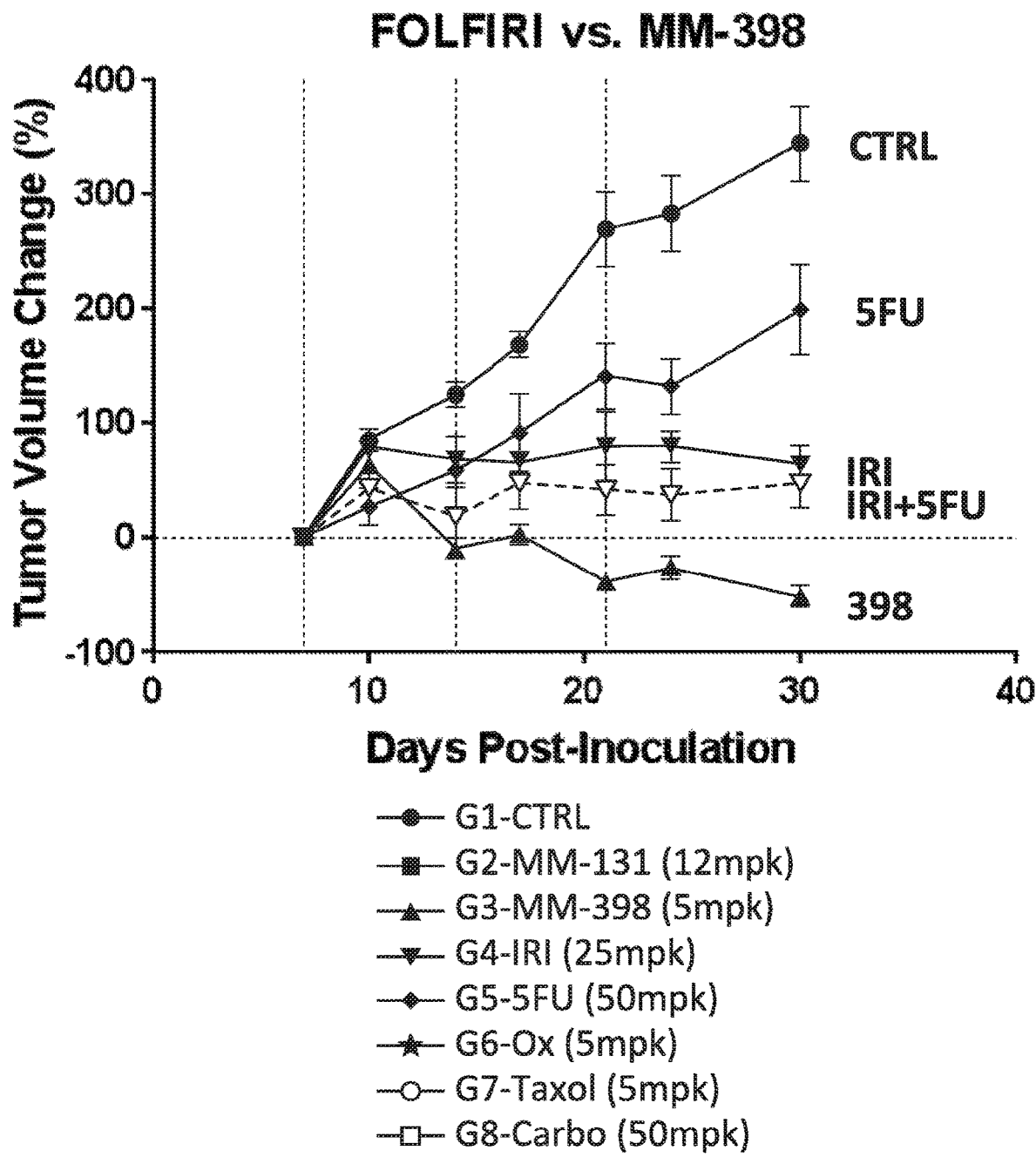
FIG. 5A depicts FOLFIRI regimen and FIG. 5B depicts FOLFOX regimen vs. MM-398 in MKN45. MM-398 monotherapy has better anti-tumor activity than FOLFIRI and FOLFOX at the doses tested.
Figure 5B:
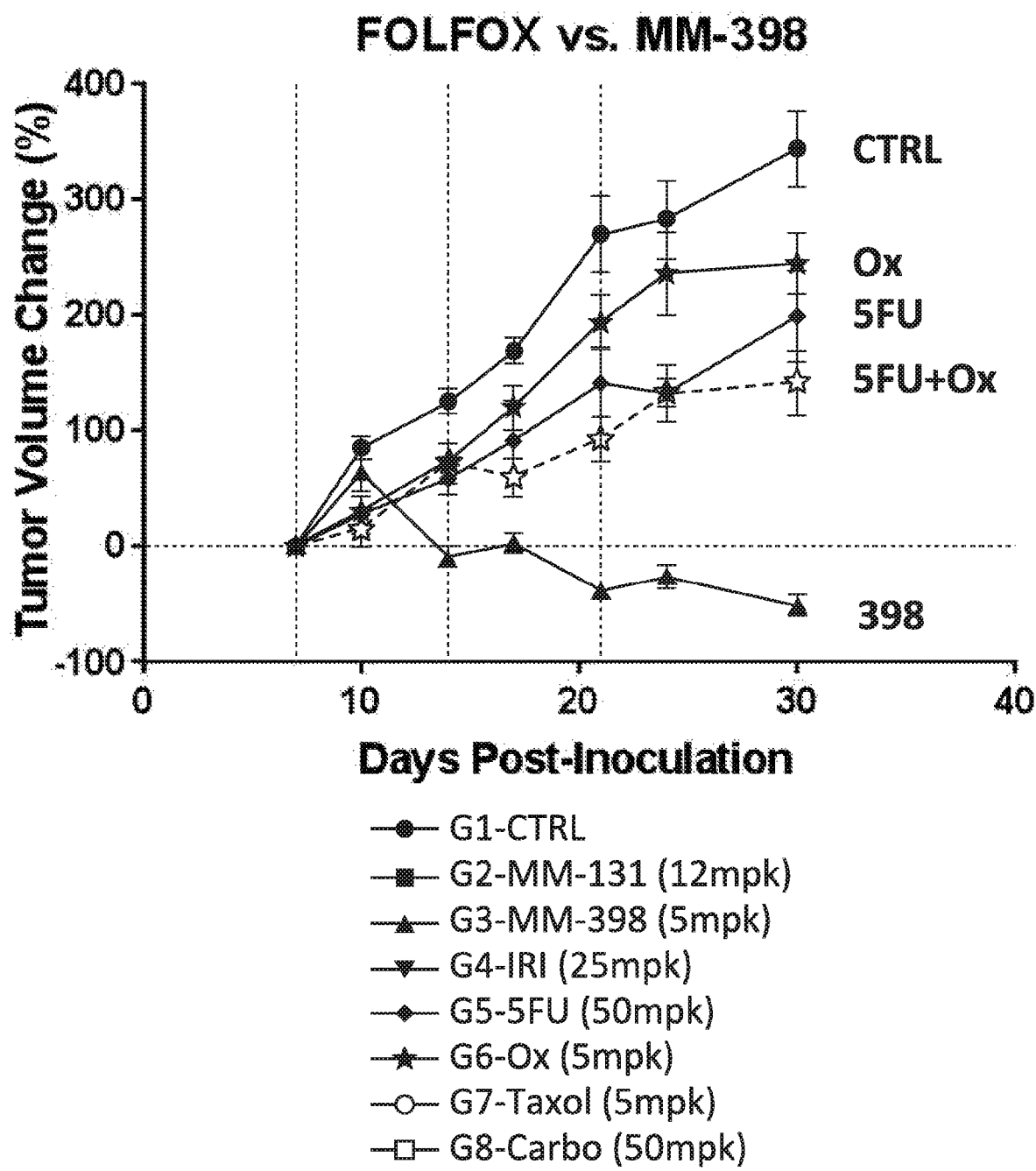
Figure 6A:
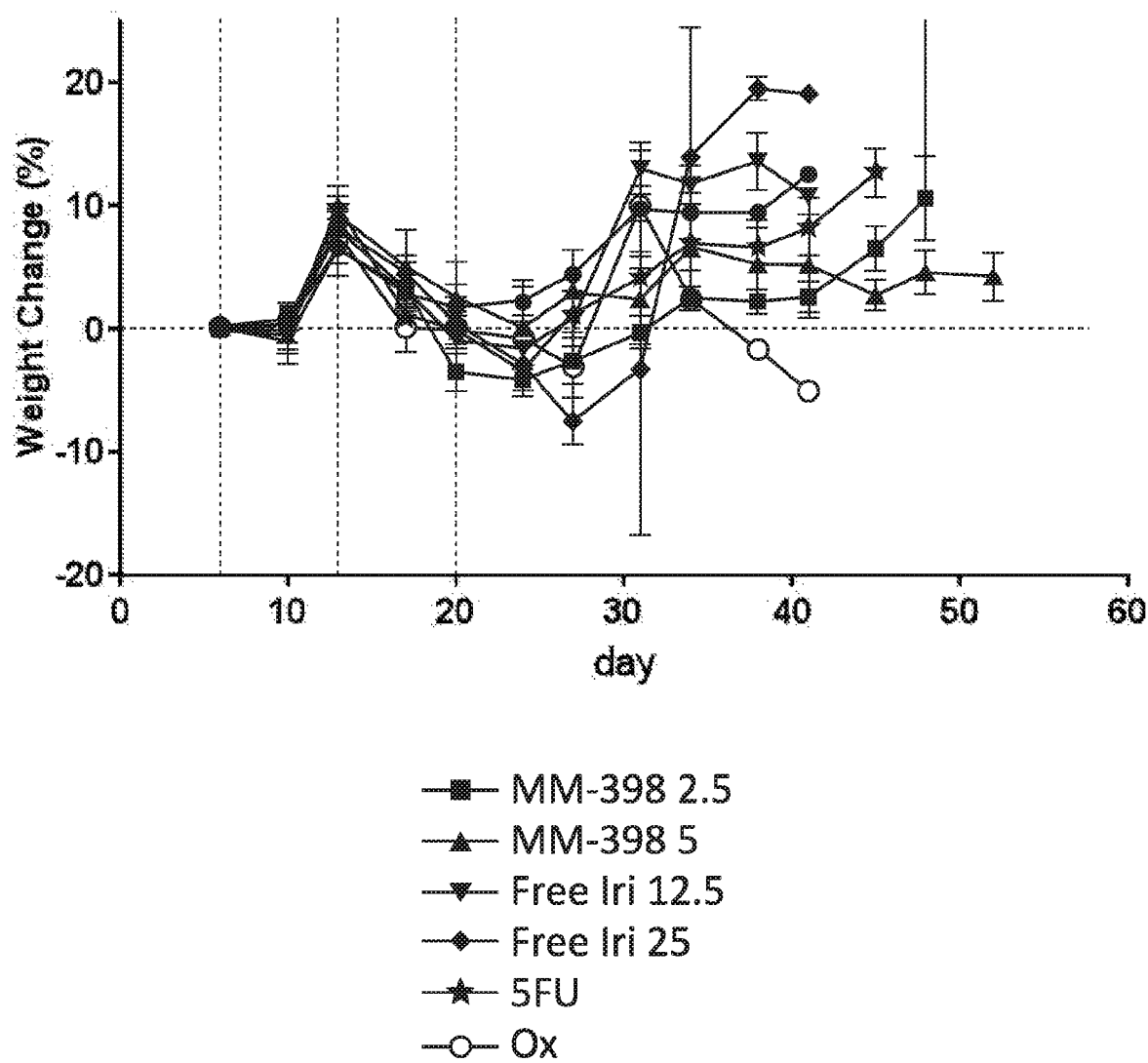
FIGS. 6A-6C depict body weight change in response to FIG. 6A. monotherapy regimens, FIG. 6B. doublet regimens and FIG. 6C. triplet regimens. There was acceptable weight loss in all groups.
Figure 6B:
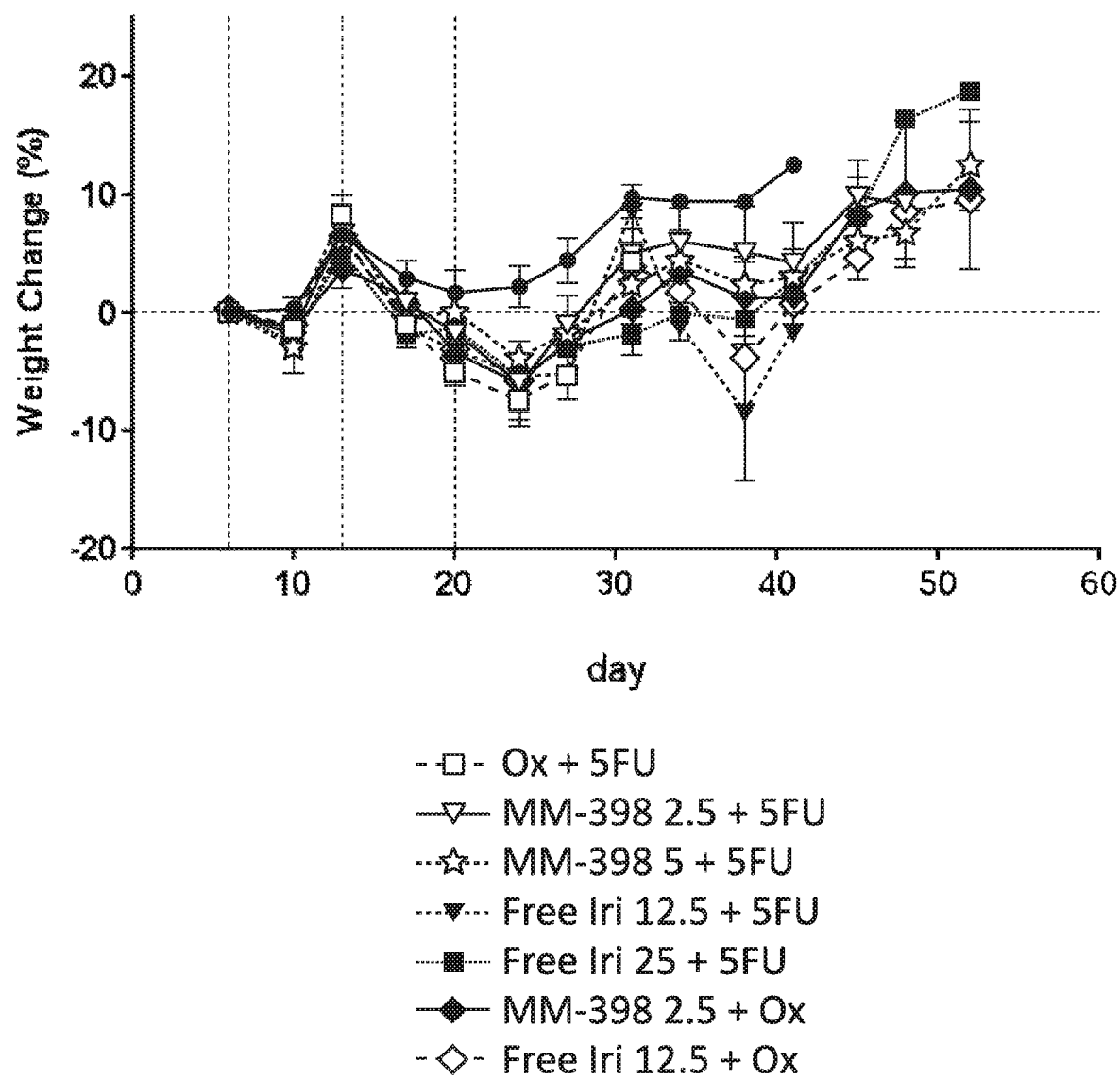
Figure 6C:
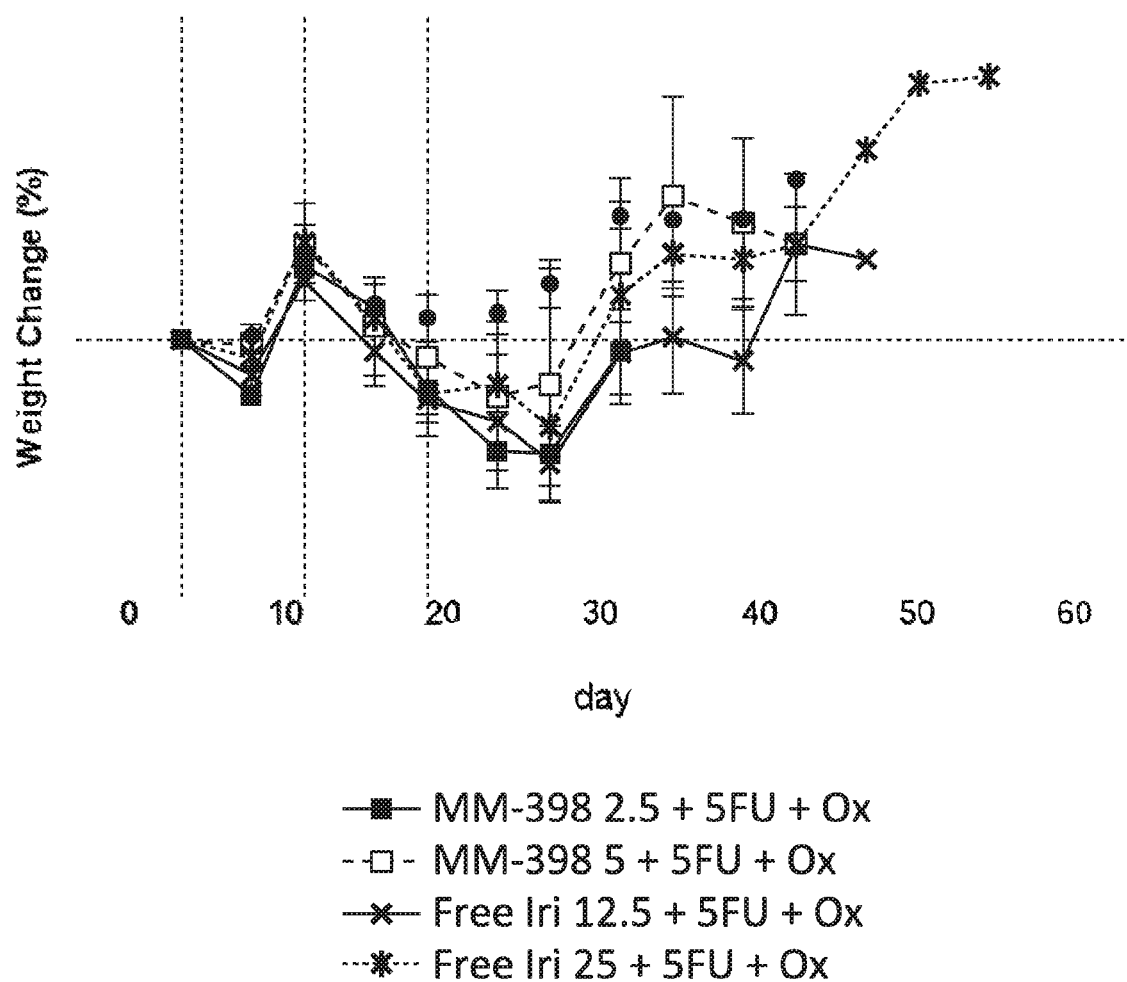
Figure 7:
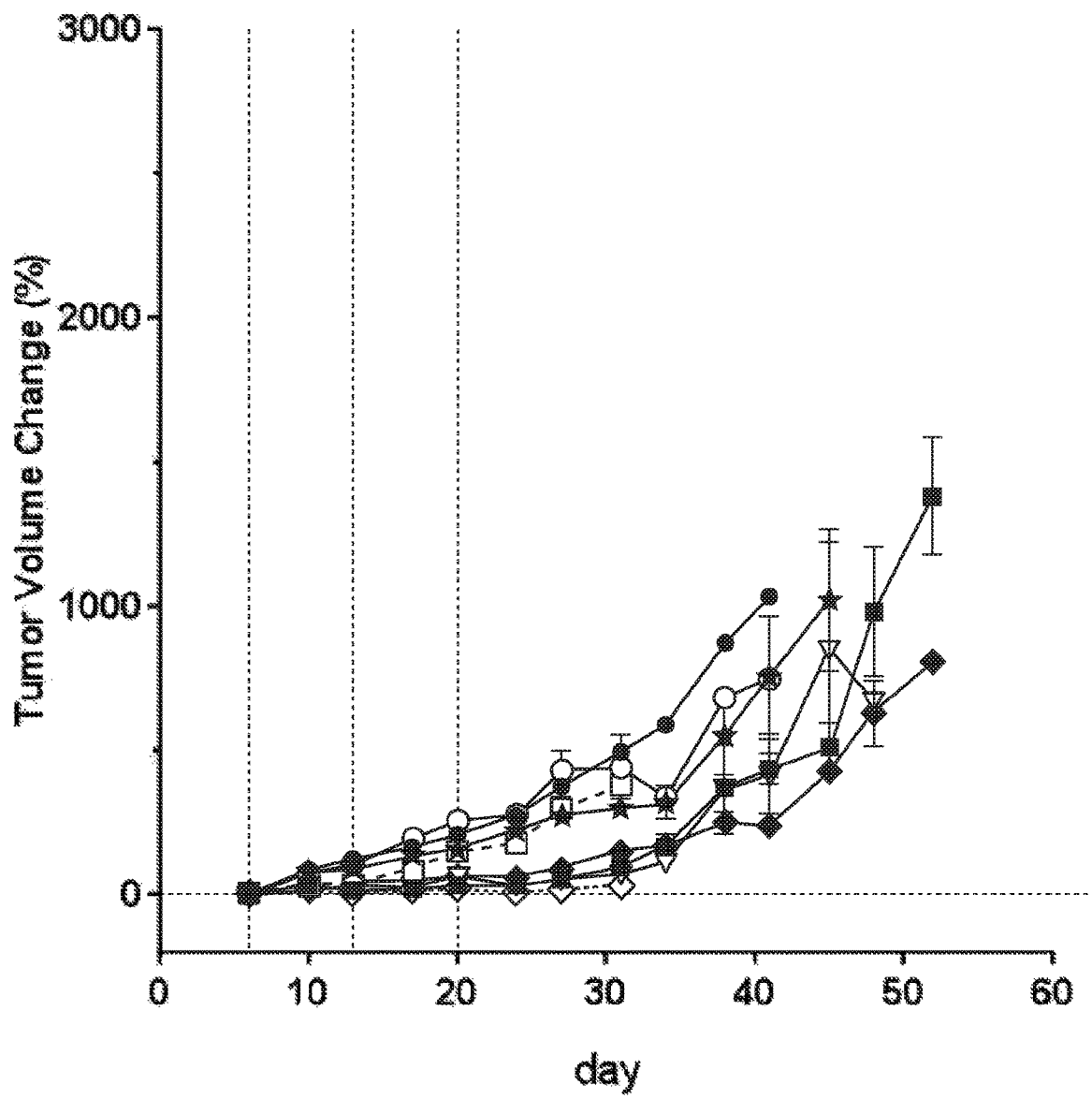
FIGS. 7A and 7B are graphs showing anti-tumor activity of (A) MM-398 in comparison to (B) free irinotecan at low doses.
Figure 7B:
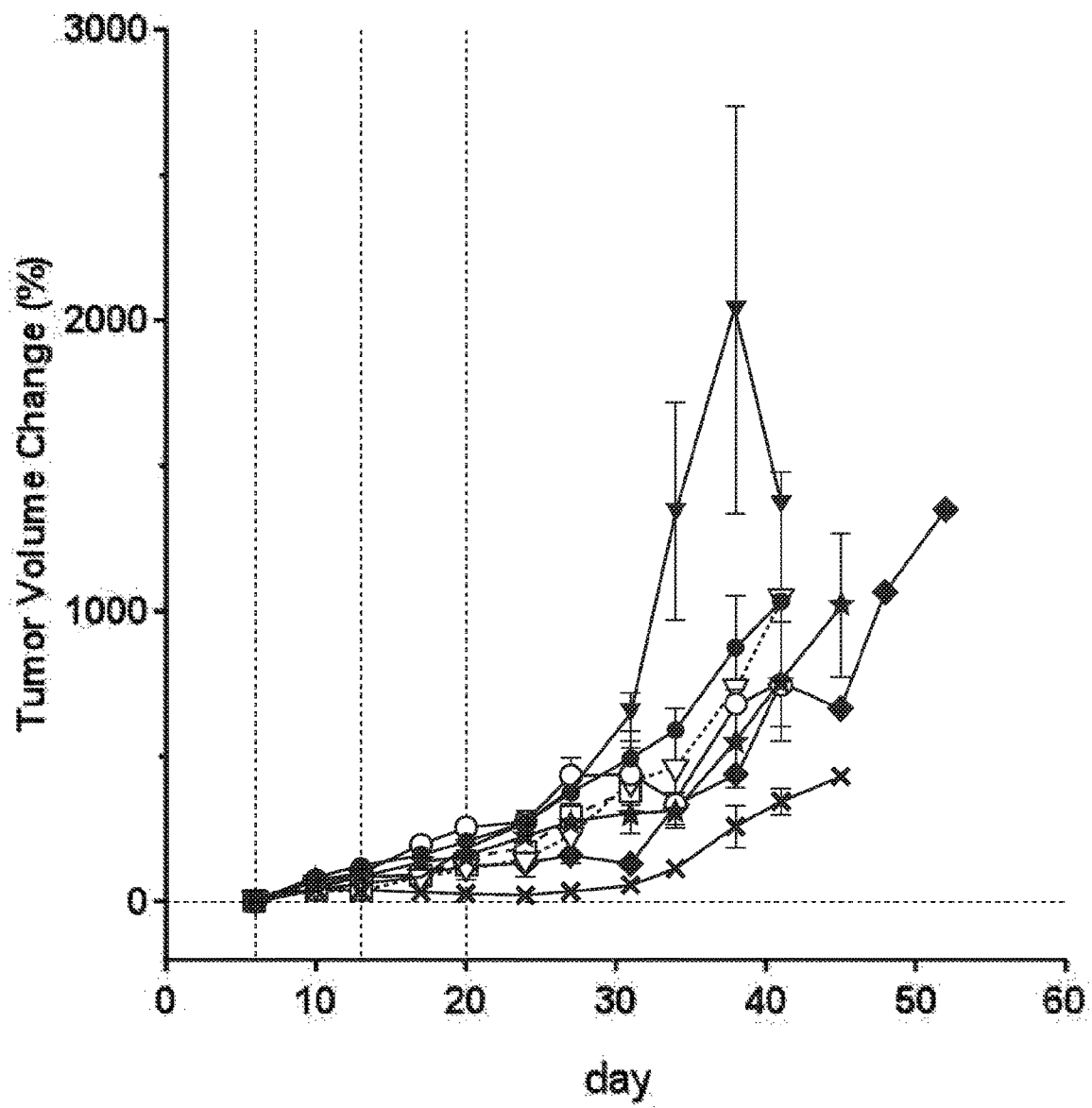
Figure 8B:
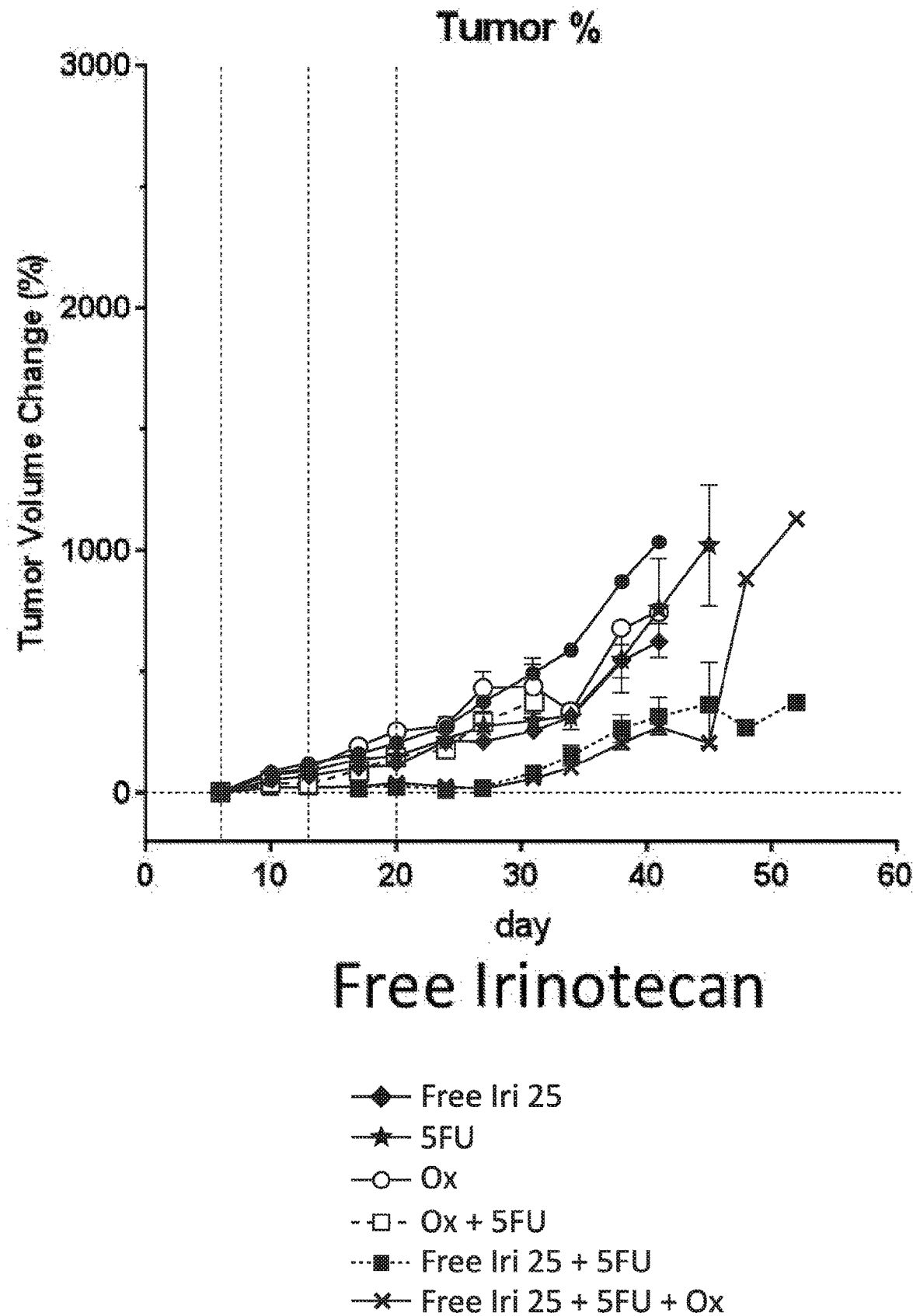

These preclinical findings support the therapeutic use of liposomal irinotecan in combination with 5-FU/LV and oxaliplatin and a clinical trial of this triplet regimen in first-line gastric cancer (Example 4). FIGS. 3A and 3B depicts a graphical representation of the study design employing the combination of MM-398+5-FU/LV+oxaliplatin as described herein.

For example, use of a combination of liposomal irinotecan, oxaliplatin, and 5-fluorouracil in treating gastric cancer in a human patient who has not previously received chemotherapy to treat the gastric cancer, the use comprising administering an antineoplastic therapy to the patient a total of once every two weeks, the antineoplastic therapy consisting of: (a) 50 mg/m$^2$ of liposomal irinotecan, 60 mg/m$^2$ oxaliplatin, 200 mg/m$^2$ of (l)-form of leucovorin or 400 mg/m² of the (l+d) racemic form of leucovorin, and 2,400 mg/m² 5-fluorouracil to treat the gastric cancer in the human patient; (b) 50 mg/m² of liposomal irinotecan, 85 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient; (c) 55 mg/m² of liposomal irinotecan, 70 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient; (d) 50 mg/m² of liposomal irinotecan, 60 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient wherein the liposomal irinotecan, oxaliplatin, 5-fluorouracil and leucovorin is administered on days 1 and 15 of a 28-day treatment cycle; (e) 50 mg/m² of liposomal irinotecan, 85 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient, wherein the liposomal irinotecan, oxaliplatin, 5-fluorouracil and leucovorin is administered on days 1 and 15 of a 28-day treatment cycle; (f) 55 mg/m² of liposomal irinotecan, 70 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient wherein the liposomal irinotecan, oxaliplatin, 5-fluorouracil and leucovorin is administered on days 1 and 15 of a 28-day treatment cycle; (g) 50 mg/m² of liposomal irinotecan, 60 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient wherein the liposomal irinotecan is administered, followed by administering the oxaliplatin, followed by administering the leucovorin, followed by administering the 5-fluorouracil; (h) 50 mg/m² of liposomal irinotecan, 85 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient wherein the liposomal irinotecan is administered, followed by administering the oxaliplatin, followed by administering the leucovorin, followed by administering the 5-fluorouracil; (i) 55 mg/m² of liposomal irinotecan, 70 mg/m² oxaliplatin, 200 mg/m² of (l)-form of leucovorin or 400 mg/m² of the (l+d) racemic form of leucovorin, and 2,400 mg/m² 5-fluorouracil to treat the gastric cancer in the human patient wherein the liposomal irinotecan is administered, followed by administering the oxaliplatin, followed by administering the leucovorin, followed by administering the 5-fluorouracil; or (j) 50 mg/m²-55 mg/m² of liposomal irinotecan, 60 mg/m²-85 mg/m² oxaliplatin, 200 mg/m² of (l)-form of leucovorin or 400 mg/m² of the (l–d) racemic form of leucovorin, and 2,400 mg/m² 5-fluorouracil to treat the gastric cancer in the human patient wherein the liposomal irinotecan, oxaliplatin, 5-fluorouracil and leucovorin is administered on days 1 and 15 of a 28-day treatment cycle, wherein the liposomal irinotecan is administered, followed by administering the oxaliplatin, followed by administering the leucovorin, followed by administering the 5-fluorouracil, wherein the administration of the oxaliplatin begins 2 hours after completing each administration of the liposomal irinotecan. Each of these exemplary uses can be modified to replace the doses of liposomal irinotecan, oxaliplatin, leucovorin and 5-flurouracil disclosed herein in the following passages relating to these specific components. Sometimes the liposomal irinotecan comprises irinotecan sucrose octasulfate encapsulated in liposomes. Sometimes, the liposomal irinotecan comprises irinotecan encapsulated in liposome vesicles consisting of 1,2-distearoyl-sn-glycero-3-phosphocholine (DSPC), cholesterol, and a N-(carbonylmethoxypolyethlyene glycol-2000)-1,2-distearoly-sn-glycero-3-phosphoethanolamine (MPEG-2000-DSPE).

As provided herein, irinotecan can be administered in an irinotecan liposome preparation. Preferably, the liposomal irinotecan is irinotecan sucrose sulfate liposome injection (otherwise termed "irinotecan sucrose octasulfate salt liposome injection" or "irinotecan sucrosofate liposome injection"), the formulation referred to herein as "MM-398" (also known as PEP02, see U.S. Pat. No. 8,147,867) is a form of "nanoliposomal irinotecan" (also called "irinotecan liposome" or "liposomal Irinotecan"). MM-398 is irinotecan as the irinotecan sucrose octasulfate salt encapsulated in a nanoliposome drug delivery system.

The liposomal irinotecan can be a pharmaceutical composition prepared for human intravenous administration. For example, the liposomal irinotecan may be provided as a sterile, injectable parenteral liquid for intravenous injection. The required amount of liposomal irinotecan may be diluted, e.g., in 500 mL of 5% dextrose injection USP, to provide a variety of concentrations, for example, 5 mg/mL, and may be infused over a 90 minute period.

The active ingredient of the MM-398 injection, irinotecan, is a member of the topoisomerase I inhibitor class of drugs and is a semi-synthetic and water soluble analog of the naturally-occurring alkaloid, camptothecin. Topoisomerase I inhibitors work to arrest uncontrolled cell growth by preventing the unwinding of DNA and therefore preventing replication. The pharmacology of irinotecan is complex, with extensive metabolic conversions involved in the activation, inactivation, and elimination of the drug. Irinotecan is a pro-drug that is converted by nonspecific carboxylesterases into a 100-1000 fold more active metabolite, SN-38. SN-38 is cleared via glucuronidation, (for which major pharmacogenetic differences have been shown), and biliary excretion. These drug properties contribute to the marked differences in efficacy and toxicity observed in clinical studies with irinotecan.

The liposomal irinotecan can be a unilamellar lipid bilayer vesicle of approximately 80-140 nm in diameter that encapsulates an aqueous space that contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for every 200 phospholipid molecules.

The amount of liposomal irinotecan administered to the human patient can range from about 30 mg/m² to about 170 mg/m², preferably 50 mg/m² or 55 mg/m² or 56 mg/m² when administered in combination with oxaliplatin and 5-fluorouracil for treatment of gastric cancer (dose expressed in terms of free base).

The plasma pharmacokinetics of total irinotecan and total SN-38 were evaluated in patients with cancer who received MM-398, as a single agent or as part of combination chemotherapy, at doses between 50 and 155 mg/m² (amount of irinotecan free base, equivalent to 60-180 mg/m² dose expressed in terms of the amount of irinotecan hydrochloride trihydrate salt) and 353 patients with cancer using population pharmacokinetic analysis. Over the dose range of 50 to 155 mg/m², the $C_{max}$ and AUC of total irinotecan increases with dose. Additionally, the $C_{max}$ of total SN-38 increases proportionally with dose; however, the AUC of total SN-38 increases less than proportionally with dose.

The pharmacokinetic parameters of total Irinotecan and total SN-38 following administration of MM-398 50 mg/m$^2$ (free base) as a single agent or part of combination chemotherapy are presented in Table B.

TABLE B

Total Irinotecan and Total SN-38 Pharmacokinetic Parameters in Patients with Solid Tumors.

| Dose (mg/m$^2$) free base | Total Irinotecan | | | Total SN-38 | |
|---|---|---|---|---|---|
| | $C_{max}$ [µg/mL] | $AUC_{0-\infty}$ [h · µg/mL] | $t_{1/2}$ [h] | $C_{max}$ [ng/mL] | $t_{1/2}$ [h] |
| Max (125%) | 32.5 | 1193.5 | 25.8 | 4.8 | 67.8 |
| 50 | 26 | 954.8 | 25.8 | 3.8 | 67.8 |
| Min (80%) | 20.8 | 763.8 | 25.8 | 3.0 | 67.8 |

The $C_{max}$ of SN-38 increases proportionally with liposomal irinotecan dose but the AUC of SN-38 increases less than proportionally with dose, enabling new methods of dosage adjustment. For example, the value of the parameter associated with adverse effects ($C_{max}$) decreases by a relatively greater extent than the value of the parameter associated with the effectiveness of treatment (AUC). Accordingly, when an adverse effect is seen, a reduction in the dosing of the liposomal irinotecan can be implemented that maximizes the difference between the reduction in $C_{max}$ and in AUC. The discovery means that in treatment regimens, a given SN-38 AUC can be achieved with a surprisingly low SN-38 Cmax. Likewise, a given SN-38 $C_{max}$ can be achieved with a surprisingly high SN-38 AUC.

Direct measurement of irinotecan liposome showed that 95% of irinotecan remains liposome encapsulated, and the ratios between total and encapsulated forms did not change with time from 0 to 169.5 hours post-dose.

In some embodiments, the liposomal irinotecan can be characterized by the parameters in Table B. In some embodiments, the liposomal irinotecan can be MM-398 or a product that is bioequivalent to MM-398. In some embodiments, the liposomal irinotecan can be characterized by the parameters in Table C, including a $C_{max}$ and/or AUC value that is 80-125% of the corresponding value in Table B. The pharmacokinetic parameters of total irinotecan for various alternative liposomal irinotecan formulations administering 50 mg/m$^2$ irinotecan free base once every two weeks is provided in Table C.

TABLE C

Total Irinotecan Pharmacokinetic Parameters in Alternative Liposomal Irinotecan Formulations

| Dose (mg/m$^2$) Free base | Total Irinotecan | |
|---|---|---|
| | $C_{max}$ [µg/mL] (n = 25) | $AUC_{0-\infty}$ [h · µg/mL] (n = 23) |
| 50 | 20.8-32.5 | 763.8-1193.5 |

$C_{max}$: Maximum plasma concentration
$AUC_{0-\infty}$: Area under the plasma concentration curve extrapolated to time infinity
$t_{1/2}$: Terminal elimination half-life The combination treatment described herein encompasses administration of MM-398 liposomal irinotecan in combination with multiple additional active agents: oxaliplatin, leucovorin and 5-fluorouracil, in doses and schedules to human patients with gastric cancer not previously treated with a prior chemotherapeutic agent in the metastatic setting as described herein.

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis. An exemplary effective amount of 5-fluorouracil administered to a human patient can range from about 2,000 mg/m$^2$ to about 3,000 mg/m$^2$. In some embodiments, the amount of 5-fluorouracil administered to the human patient is 2,400 mg/m$^2$.

Leucovorin is optionally administered prior to the 5-fluorouracil. Leucovorin acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase. Leucovorin has dextro- and levo-isomers, only the latter one being pharmacologically useful. As such, the bioactive levo-isomer ("levo-leucovorin") has also been approved by the FDA for treatment of cancer. The dosage of leucovorin is that of the racemic mixture containing both dextro (d) and levo (l) isomers, or optionally the (l) form of leucovorin at half the dosage of the (l+d) racemic form. An exemplary effective amount of leucovorin administered to the human patient can include an amount of (l)-form leucovorin ranging from about 100 mg/m$^2$ to about 300 mg/m$^2$. In some embodiments, the amount of (l)-form leucovorin administered to the human patient is 200 mg/m$^2$. In other embodiments, the leucovorin administered is the (l+d)-form of leucovorin, in an amount ranging from about 200 mg/m$^2$ to about 600 mg/m$^2$. In some embodiments, the amount of (l+d)-form of leucovorin administered is 400 mg/m$^2$.

Oxaliplatin is a platinum-based drug that acts as a DNA cross-linking agent to effectively inhibit DNA replication and transcription, resulting in cytotoxicity which is cell-cycle non-specific. Oxaliplatin is typically used in combination with infusional 5-FU/LV, and is approved for use in advanced colorectal cancer (refer to package insert for more details). The effective amount of oxaliplatin administered to the human patient can range from about 30 mg/m$^2$ to about 150 mg/m$^2$, for example, from about 40 mg/m$^2$ to about 100 mg/m$^2$, or an amount of oxaliplatin of 50 mg/m$^2$, 55 mg/m$^2$, 60 mg/m$^2$, 65 mg/m$^2$, 70 mg/m$^2$, 75 mg/m$^2$, 80 mg/m$^2$, 85 mg/m$^2$, 90 mg/m$^2$, or 95 mg/m$^2$.

Dose modifications may be made to methods of administering the combination treatment described herein as a result of adverse events, include hematological and non-hematological adverse events.

In some embodiments, methods of administering the combination treatment described herein to patients having one or more characteristics can include reducing or otherwise modifying the dose of MM-398 administered according to the embodiments herein. In some embodiments, the dose of MM-398 is modified according to Table 1A.

TABLE 1A

Examples of Dose Modifications for MM-398 (salt)

| Toxicity NCI CTCAE v4.0 | Occurrence | MM-398 adjustment in patients receiving 60 mg/m²‡ (salt) 50 mg/m² (free base) | Patients homozygous for UGT1A1*28 without previous increase to 60 mg/m² (salt) 50 mg/m² (free base) |
|---|---|---|---|
| Grade 3 or 4 adverse reactions | | Withhold MM-398. Initiate loperamide for late onset diarrhea of any severity. Administer intravenous or subcutaneous atropine 0.25 to 1 mg (unless clinically contraindicated) for early onset diarrhea of any severity. Upon recovery to ≤ Grade 1 or baseline grade resume MM-398 at: | |
| | First | 45 mg/m² (salt) | 45 mg/m² (salt) |
| | Second | 30 mg/m² (salt) | 30 mg/m² (salt) |
| | Third | Discontinue MM-398 | Discontinue MM-398 |
| Interstitial Lung Disease | First | Discontinue MM-398 | Discontinue MM-398 |
| Anaphylactic Reaction | First | Discontinue MM-398 | Discontinue MM-398 |

In some embodiments, the first, second, or any subsequent dose of MM-398 can be reduced by 20-30% (including dose reductions of 20%, 25% and/or 30%) in response to patient tolerability considerations such as an adverse reaction to a first or subsequent dose of MM-398 and/or other antineoplastic agent, and/or identifying a patient as being homozygous for the UGT1A1*28 allele. In some embodiments, the second or subsequent dose of MM-398 is reduced by another about 20%, 25% or 30% (a dose reduction of about 40%, 50% or 60% of the original dose). For example, a dose of 60 mg/m² MM-398 reduced by 25% is 45 mg/m² and a second reduction of another 25% is 30 mg/m². In some embodiments, the dose of MM-398 is reduced by 25%. In some embodiments, the dose of MM-398 is reduced by 30%. In some embodiments, the reduced dose of MM-398 is in a range starting from 30 mg/m² to (and including) 55 mg/m². In some embodiments, the dose of MM-398 is reduced to 50 mg/m². In some embodiments, the dose of MM-398 is reduced to 45 mg/m². In some embodiments, the dose of MM-398 is reduced to 35 mg/m².

Other dose reduction schedules are provided Tables 1B-1E below. When the starting (initial) dose of MM-398 is 50 mg/m², 5FU 2400 mg/m², LV (l+d) 400 mg/m² and oxaliplatin is either 85 mg/m² or 60 mg/m², then the first dose reduction in response to a grade III or IV hematotoxicity is preferably a 25% dose reduction for each of the MM-398, 5-FU and oxaliplatin doses for each administration of the antineoplastic therapy. For persistent toxicities despite the first dose reduction, an additional 25% dose reduction in each of the antineoplastic agents of MM-398, 5-fluorouracil and oxaliplatin is preferred. Further toxicity will then lead to discontinuation of treatment in some instances. For non-hematologic toxicities, the same dose reduction schema can be followed as for hematotoxicity, except for the specific toxicities associated with the drug (i.e. 5FU hand foot syndrome, and oxaliplatin neuropathy) which can be selected based on the medically appropriate dose for the patient.

TABLE 1B

Examples of Reduced Doses of MM-398 and oxaliplatin

| Dose | MM-398 (mg/m²) (salt) | Oxaliplatin (mg/m²) | 5-fluorouracil (5FU) (mg/m²) |
|---|---|---|---|
| Initial | 60 | 60 | 2400 |
| First Reduction | 45 | 45 | 1800 |
| Second Reduction | 30 | 30 | 1350 |

TABLE 1C

Examples of Reduced Doses of MM-398 and oxaliplatin

| Dose | MM-398 (mg/m²) (salt) | Oxaliplatin (mg/m²) | 5-fluorouracil (5FU) (mg/m²) |
|---|---|---|---|
| Initial | 60 | 80 | 2400 |
| First Reduction | 45 | 60 | 1800 |
| Second Reduction | 30 | 40 | 1350 |

TABLE 1D

Examples of Reduced Doses of MM-398 and oxaliplatin

| Dose | MM-398 (mg/m²) (salt) | Oxaliplatin (mg/m²) | 5-fluorouracil (5FU) (mg/m²) |
|---|---|---|---|
| Initial | 60 | 60 | 2400 |
| First Reduction | 45 | 45 | 2400 |
| Second Reduction | 30 | 30 | 1800 |

TABLE 1E

Examples of Reduced Doses of MM-398 and oxaliplatin

| Dose | MM-398 (mg/m²) (salt) | Oxaliplatin (mg/m²) | 5-fluorouracil (5FU) (mg/m²) |
|---|---|---|---|
| Initial | 60 | 80 | 2400 |
| First Reduction | 45 | 60 | 2400 |
| Second Reduction | 30 | 40 | 1800 |

In some embodiments, methods of administering the combination treatment described herein to patients having one or more characteristics can include reducing or otherwise modifying the dose of oxaliplatin administered according to the embodiments herein. In some embodiments, the dose of oxaliplatin is reduced by 20-30%. In some embodiments, the, the dose of oxaliplatin is reduced by 20%. In some embodiments, the, the dose of oxaliplatin is reduced by 25%. In some embodiments, the, the dose of oxaliplatin is reduced by 30%. In some embodiments, the reduced dose of oxaliplatin is in a range from 30 mg/m$^2$ to 75 mg/m$^2$. In some embodiments, the dose of oxaliplatin is reduced to 75 mg/m$^2$. In some embodiments, the dose of oxaliplatin is reduced to 65 mg/m$^2$. In some embodiments, the dose of oxaliplatin is reduced to 60 mg/m$^2$. In some embodiments, the dose of oxaliplatin is reduced to 45 mg/m$^2$. In some embodiments, the dose of oxaliplatin is reduced to 45 mg/m$^2$. In some embodiments, the dose of oxaliplatin is reduced to 34 mg/m$^2$.

In some embodiments, methods of administering the combination treatment described herein to patients having one or more characteristics can include reducing or otherwise modifying the dose of 5-fluorouracil administered according to the embodiments herein. In some embodiments, the dose of 5-fluorouracil is reduced by 20-30%. In some embodiments, the dose of 5-fluorouracil is reduced by 20%. In some embodiments, the dose of 5-fluorouracil is reduced by 25%. In some embodiments, the, dose of 5-fluorouracil is reduced by 30%. In some embodiments, the reduced dose of 5-fluorouracil is in a range from 1000 mg/m$^2$ to 1800 mg/m$^2$. In some embodiments, the dose of 5-fluorouracil is reduced to 1800 mg/m$^2$. In some embodiments, the dose of 5-fluorouracil is reduced to 1350 mg/m$^2$. In some embodiments, the dose of 5-fluorouracil is reduced to 1400 mg/m$^2$. In some embodiments, the dose of 5-fluorouracil is reduced to 1200 mg/m$^2$.

In some embodiments, methods of administering the combination treatment described herein to patients having one or more characteristics can include further reducing or otherwise modifying the dose of MM-398, oxaliplatin and/or 5-fluorouracil administered according to the embodiments herein.

In some embodiments, methods of administering the combination treatment described herein to patients having one or more characteristics can include reducing or otherwise modifying the dose of more than one of MM-398, oxaliplatin and 5-fluorouracil administered according to the embodiments herein.

Additional dose modifications for MM-398, oxaliplatin and/or 5-fluorouracil can be found in the respective Package Inserts, which are incorporated herein by reference.

In one embodiment, the method of administering the combination treatment comprises 30, 40, 50, or 55 mg/m$^2$ of liposomal irinotecan, 30, 36, 42, 45, 53, 60, 64, 70, or 85 mg/m$^2$ oxaliplatin, 200 mg/m$^2$ of (l)-form of leucovorin or 400 mg/m$^2$ of the (l+d) racemic form of leucovorin, and 1,200, 1,350, 1,800, or 2,400 mg/m$^2$ 5-fluorouracil to treat the gastric cancer in the human patient.

Thus, in some embodiments, the method of administering the combination treatment to treat the gastric cancer in the human patient comprises administration of the following dose of liposomal irinotecan, oxaliplatin and leucovorin as shown in Table 1F below. Leucovorin is generally administered at 200 mg/m$^2$ of (l)-form of leucovorin or 400 mg/m$^2$ of the (l+d) racemic form but the dose may be varied by the patient's doctor. Any of the embodiments in the table may be administered with 200 mg/m$^2$ of (l)-form of leucovorin or 400 mg/m$^2$ of the (l+d) racemic form or a different doctor prescribed dose.

TABLE 1F

Embodiments of the present invention

| Dose irinotecan hydrochloride trihydrate mg/m$^2$ (salt) | Dose oxaliplatin mg/m$^2$ | 5-fluorouracil mg/m$^2$ | Leucovorin |
|---|---|---|---|
| 30 | 30 | 1,200 | Yes |
| 30 | 30 | 1,350 | Yes |
| 30 | 30 | 1,400 | Yes |
| 30 | 30 | 1,800 | Yes |
| 30 | 30 | 2,400 | Yes |
| 30 | 36 | 1,200 | Yes |
| 30 | 36 | 1,350 | Yes |
| 30 | 36 | 1,400 | Yes |
| 30 | 36 | 1,800 | Yes |
| 30 | 36 | 2,400 | Yes |
| 30 | 42 | 1,200 | Yes |
| 30 | 42 | 1,350 | Yes |
| 30 | 42 | 1,400 | Yes |
| 30 | 42 | 1,800 | Yes |
| 30 | 42 | 2,400 | Yes |
| 30 | 45 | 1,200 | Yes |
| 30 | 45 | 1,350 | Yes |
| 30 | 45 | 1,400 | Yes |
| 30 | 45 | 1,800 | Yes |
| 30 | 45 | 2,400 | Yes |
| 30 | 53 | 1,200 | Yes |
| 30 | 53 | 1,350 | Yes |
| 30 | 53 | 1,400 | Yes |
| 30 | 53 | 1,800 | Yes |
| 30 | 53 | 2,400 | Yes |
| 30 | 60 | 1,200 | Yes |
| 30 | 60 | 1,350 | Yes |
| 30 | 60 | 1,400 | Yes |
| 30 | 60 | 1,800 | Yes |
| 30 | 60 | 2,400 | Yes |
| 30 | 64 | 1,200 | Yes |
| 30 | 64 | 1,350 | Yes |
| 30 | 64 | 1,400 | Yes |
| 30 | 64 | 1,800 | Yes |
| 30 | 64 | 2,400 | Yes |
| 30 | 70 | 1,200 | Yes |
| 30 | 70 | 1,350 | Yes |
| 30 | 70 | 1,400 | Yes |
| 30 | 70 | 1,800 | Yes |
| 30 | 70 | 2,400 | Yes |
| 30 | 85 | 1,200 | Yes |
| 30 | 85 | 1,350 | Yes |
| 30 | 85 | 1,400 | Yes |
| 30 | 85 | 1,800 | Yes |
| 30 | 85 | 2,400 | Yes |
| 33 | 30 | 1,200 | Yes |
| 33 | 30 | 1,350 | Yes |
| 33 | 30 | 1,400 | Yes |
| 33 | 30 | 1,800 | Yes |
| 33 | 30 | 2,400 | Yes |
| 33 | 36 | 1,200 | Yes |
| 33 | 36 | 1,350 | Yes |
| 33 | 36 | 1,400 | Yes |
| 33 | 36 | 1,800 | Yes |
| 33 | 36 | 2,400 | Yes |
| 33 | 42 | 1,200 | Yes |
| 33 | 42 | 1,350 | Yes |
| 33 | 42 | 1,400 | Yes |
| 33 | 42 | 1,800 | Yes |
| 33 | 42 | 2,400 | Yes |
| 33 | 45 | 1,200 | Yes |
| 33 | 45 | 1,350 | Yes |
| 33 | 45 | 1,400 | Yes |
| 33 | 45 | 1,800 | Yes |
| 33 | 45 | 2,400 | Yes |
| 33 | 53 | 1,200 | Yes |
| 33 | 53 | 1,350 | Yes |
| 33 | 53 | 1,400 | Yes |
| 33 | 53 | 1,800 | Yes |
| 33 | 53 | 2,400 | Yes |
| 33 | 60 | 1,200 | Yes |
| 33 | 60 | 1,350 | Yes |
| 33 | 60 | 1,400 | Yes |
| 33 | 60 | 1,800 | Yes |

TABLE 1F-continued

Embodiments of the present invention

| Dose irinotecan hydrochloride trihydrate mg/m² (salt) | Dose oxaliplatin mg/m² | 5-fluorouracil mg/m² | Leucovorin |
|---|---|---|---|
| 33 | 60 | 2,400 | Yes |
| 33 | 64 | 1,200 | Yes |
| 33 | 64 | 1,350 | Yes |
| 33 | 64 | 1,400 | Yes |
| 33 | 64 | 1,800 | Yes |
| 33 | 64 | 2,400 | Yes |
| 33 | 70 | 1,200 | Yes |
| 33 | 70 | 1,350 | Yes |
| 33 | 70 | 1,400 | Yes |
| 33 | 70 | 1,800 | Yes |
| 33 | 70 | 2,400 | Yes |
| 33 | 85 | 1,200 | Yes |
| 33 | 85 | 1,350 | Yes |
| 33 | 85 | 1,400 | Yes |
| 33 | 85 | 1,800 | Yes |
| 33 | 85 | 2,400 | Yes |
| 36 | 30 | 1,200 | Yes |
| 36 | 30 | 1,350 | Yes |
| 36 | 30 | 1,400 | Yes |
| 36 | 30 | 1,800 | Yes |
| 36 | 30 | 2,400 | Yes |
| 36 | 36 | 1,200 | Yes |
| 36 | 36 | 1,350 | Yes |
| 36 | 36 | 1,400 | Yes |
| 36 | 36 | 1,800 | Yes |
| 36 | 36 | 2,400 | Yes |
| 36 | 42 | 1,200 | Yes |
| 36 | 42 | 1,350 | Yes |
| 36 | 42 | 1,400 | Yes |
| 36 | 42 | 1,800 | Yes |
| 36 | 42 | 2,400 | Yes |
| 36 | 45 | 1,200 | Yes |
| 36 | 45 | 1,350 | Yes |
| 36 | 45 | 1,400 | Yes |
| 36 | 45 | 1,800 | Yes |
| 36 | 45 | 2,400 | Yes |
| 36 | 53 | 1,200 | Yes |
| 36 | 53 | 1,350 | Yes |
| 36 | 53 | 1,400 | Yes |
| 36 | 53 | 1,800 | Yes |
| 36 | 53 | 2,400 | Yes |
| 36 | 60 | 1,200 | Yes |
| 36 | 60 | 1,350 | Yes |
| 36 | 60 | 1,400 | Yes |
| 36 | 60 | 1,800 | Yes |
| 36 | 60 | 2,400 | Yes |
| 36 | 64 | 1,200 | Yes |
| 36 | 64 | 1,350 | Yes |
| 36 | 64 | 1,400 | Yes |
| 36 | 64 | 1,800 | Yes |
| 36 | 64 | 2,400 | Yes |
| 36 | 70 | 1,200 | Yes |
| 36 | 70 | 1,350 | Yes |
| 36 | 70 | 1,400 | Yes |
| 36 | 70 | 1,800 | Yes |
| 36 | 70 | 2,400 | Yes |
| 36 | 85 | 1,200 | Yes |
| 36 | 85 | 1,350 | Yes |
| 36 | 85 | 1,400 | Yes |
| 36 | 85 | 1,800 | Yes |
| 36 | 85 | 2,400 | Yes |
| 40 | 30 | 1,200 | Yes |
| 40 | 30 | 1,350 | Yes |
| 40 | 30 | 1,400 | Yes |
| 40 | 30 | 1,800 | Yes |
| 40 | 30 | 2,400 | Yes |
| 40 | 36 | 1,200 | Yes |
| 40 | 36 | 1,350 | Yes |
| 40 | 36 | 1,400 | Yes |
| 40 | 36 | 1,800 | Yes |
| 40 | 36 | 2,400 | Yes |
| 40 | 42 | 1,200 | Yes |
| 40 | 42 | 1,350 | Yes |
| 40 | 42 | 1,400 | Yes |
| 40 | 42 | 1,800 | Yes |
| 40 | 42 | 2,400 | Yes |
| 40 | 45 | 1,200 | Yes |
| 40 | 45 | 1,350 | Yes |
| 40 | 45 | 1,400 | Yes |
| 40 | 45 | 1,800 | Yes |
| 40 | 45 | 2,400 | Yes |
| 40 | 53 | 1,200 | Yes |
| 40 | 53 | 1,350 | Yes |
| 40 | 53 | 1,400 | Yes |
| 40 | 53 | 1,800 | Yes |
| 40 | 53 | 2,400 | Yes |
| 40 | 60 | 1,200 | Yes |
| 40 | 60 | 1,350 | Yes |
| 40 | 60 | 1,400 | Yes |
| 40 | 60 | 1,800 | Yes |
| 40 | 60 | 2,400 | Yes |
| 40 | 64 | 1,200 | Yes |
| 40 | 64 | 1,350 | Yes |
| 40 | 64 | 1,400 | Yes |
| 40 | 64 | 1,800 | Yes |
| 40 | 64 | 2,400 | Yes |
| 40 | 70 | 1,200 | Yes |
| 40 | 70 | 1,350 | Yes |
| 40 | 70 | 1,400 | Yes |
| 40 | 70 | 1,800 | Yes |
| 40 | 70 | 2,400 | Yes |
| 40 | 85 | 1,200 | Yes |
| 40 | 85 | 1,350 | Yes |
| 40 | 85 | 1,400 | Yes |
| 40 | 85 | 1,800 | Yes |
| 40 | 85 | 2,400 | Yes |
| 45 | 30 | 1,200 | Yes |
| 45 | 30 | 1,350 | Yes |
| 45 | 30 | 1,400 | Yes |
| 45 | 30 | 1,800 | Yes |
| 45 | 30 | 2,400 | Yes |
| 45 | 36 | 1,200 | Yes |
| 45 | 36 | 1,350 | Yes |
| 45 | 36 | 1,400 | Yes |
| 45 | 36 | 1,800 | Yes |
| 45 | 36 | 2,400 | Yes |
| 45 | 42 | 1,200 | Yes |
| 45 | 42 | 1,350 | Yes |
| 45 | 42 | 1,400 | Yes |
| 45 | 42 | 1,800 | Yes |
| 45 | 42 | 2,400 | Yes |
| 45 | 45 | 1,200 | Yes |
| 45 | 45 | 1,350 | Yes |
| 45 | 45 | 1,400 | Yes |
| 45 | 45 | 1,800 | Yes |
| 45 | 45 | 2,400 | Yes |
| 45 | 53 | 1,200 | Yes |
| 45 | 53 | 1,350 | Yes |
| 45 | 53 | 1,400 | Yes |
| 45 | 53 | 1,800 | Yes |
| 45 | 53 | 2,400 | Yes |
| 45 | 60 | 1,200 | Yes |
| 45 | 60 | 1,350 | Yes |
| 45 | 60 | 1,400 | Yes |
| 45 | 60 | 1,800 | Yes |
| 45 | 60 | 2,400 | Yes |
| 45 | 64 | 1,200 | Yes |
| 45 | 64 | 1,350 | Yes |
| 45 | 64 | 1,400 | Yes |
| 45 | 64 | 1,800 | Yes |
| 45 | 64 | 2,400 | Yes |
| 45 | 70 | 1,200 | Yes |
| 45 | 70 | 1,350 | Yes |
| 45 | 70 | 1,400 | Yes |
| 45 | 70 | 1,800 | Yes |
| 45 | 70 | 2,400 | Yes |
| 45 | 85 | 1,200 | Yes |
| 45 | 85 | 1,350 | Yes |

TABLE 1F-continued

Embodiments of the present invention

| Dose irinotecan hydrochloride trihydrate mg/m² (salt) | Dose oxaliplatin mg/m² | 5-fluorouracil mg/m² | Leucovorin |
|---|---|---|---|
| 45 | 85 | 1,400 | Yes |
| 45 | 85 | 1,800 | Yes |
| 45 | 85 | 2,400 | Yes |
| 49 | 30 | 1,200 | Yes |
| 49 | 30 | 1,350 | Yes |
| 49 | 30 | 1,400 | Yes |
| 49 | 30 | 1,800 | Yes |
| 49 | 30 | 2,400 | Yes |
| 49 | 36 | 1,200 | Yes |
| 49 | 36 | 1,350 | Yes |
| 49 | 36 | 1,400 | Yes |
| 49 | 36 | 1,800 | Yes |
| 49 | 36 | 2,400 | Yes |
| 49 | 42 | 1,200 | Yes |
| 49 | 42 | 1,350 | Yes |
| 49 | 42 | 1,400 | Yes |
| 49 | 42 | 1,800 | Yes |
| 49 | 42 | 2,400 | Yes |
| 49 | 45 | 1,200 | Yes |
| 49 | 45 | 1,350 | Yes |
| 49 | 45 | 1,400 | Yes |
| 49 | 45 | 1,800 | Yes |
| 49 | 45 | 2,400 | Yes |
| 49 | 53 | 1,200 | Yes |
| 49 | 53 | 1,350 | Yes |
| 49 | 53 | 1,400 | Yes |
| 49 | 53 | 1,800 | Yes |
| 49 | 53 | 2,400 | Yes |
| 49 | 60 | 1,200 | Yes |
| 49 | 60 | 1,350 | Yes |
| 49 | 60 | 1,400 | Yes |
| 49 | 60 | 1,800 | Yes |
| 49 | 60 | 2,400 | Yes |
| 49 | 64 | 1,200 | Yes |
| 49 | 64 | 1,350 | Yes |
| 49 | 64 | 1,400 | Yes |
| 49 | 64 | 1,800 | Yes |
| 49 | 64 | 2,400 | Yes |
| 49 | 70 | 1,200 | Yes |
| 49 | 70 | 1,350 | Yes |
| 49 | 70 | 1,400 | Yes |
| 49 | 70 | 1,800 | Yes |
| 49 | 70 | 2,400 | Yes |
| 49 | 85 | 1,200 | Yes |
| 49 | 85 | 1,350 | Yes |
| 49 | 85 | 1,400 | Yes |
| 49 | 85 | 1,800 | Yes |
| 49 | 85 | 2,400 | Yes |
| 50 | 30 | 1,200 | Yes |
| 50 | 30 | 1,350 | Yes |
| 50 | 30 | 1,400 | Yes |
| 50 | 30 | 1,800 | Yes |
| 50 | 30 | 2,400 | Yes |
| 50 | 36 | 1,200 | Yes |
| 50 | 36 | 1,350 | Yes |
| 50 | 36 | 1,400 | Yes |
| 50 | 36 | 1,800 | Yes |
| 50 | 36 | 2,400 | Yes |
| 50 | 42 | 1,200 | Yes |
| 50 | 42 | 1,350 | Yes |
| 50 | 42 | 1,400 | Yes |
| 50 | 42 | 1,800 | Yes |
| 50 | 42 | 2,400 | Yes |
| 50 | 45 | 1,200 | Yes |
| 50 | 45 | 1,350 | Yes |
| 50 | 45 | 1,400 | Yes |
| 50 | 45 | 1,800 | Yes |
| 50 | 45 | 2,400 | Yes |
| 50 | 53 | 1,200 | Yes |
| 50 | 53 | 1,350 | Yes |
| 50 | 53 | 1,400 | Yes |
| 50 | 53 | 1,800 | Yes |
| 50 | 53 | 2,400 | Yes |
| 50 | 60 | 1,200 | Yes |
| 50 | 60 | 1,350 | Yes |
| 50 | 60 | 1,400 | Yes |
| 50 | 60 | 1,800 | Yes |
| 50 | 60 | 2,400 | Yes |
| 50 | 64 | 1,200 | Yes |
| 50 | 64 | 1,350 | Yes |
| 50 | 64 | 1,400 | Yes |
| 50 | 64 | 1,800 | Yes |
| 50 | 64 | 2,400 | Yes |
| 50 | 70 | 1,200 | Yes |
| 50 | 70 | 1,350 | Yes |
| 50 | 70 | 1,400 | Yes |
| 50 | 70 | 1,800 | Yes |
| 50 | 70 | 2,400 | Yes |
| 50 | 85 | 1,200 | Yes |
| 50 | 85 | 1,350 | Yes |
| 50 | 85 | 1,400 | Yes |
| 50 | 85 | 1,800 | Yes |
| 50 | 85 | 2,400 | Yes |
| 60 | 30 | 1,200 | Yes |
| 60 | 30 | 1,350 | Yes |
| 60 | 30 | 1,400 | Yes |
| 60 | 30 | 1,800 | Yes |
| 60 | 30 | 2,400 | Yes |
| 60 | 36 | 1,200 | Yes |
| 60 | 36 | 1,350 | Yes |
| 60 | 36 | 1,400 | Yes |
| 60 | 36 | 1,800 | Yes |
| 60 | 36 | 2,400 | Yes |
| 60 | 42 | 1,200 | Yes |
| 60 | 42 | 1,350 | Yes |
| 60 | 42 | 1,400 | Yes |
| 60 | 42 | 1,800 | Yes |
| 60 | 42 | 2,400 | Yes |
| 60 | 45 | 1,200 | Yes |
| 60 | 45 | 1,350 | Yes |
| 60 | 45 | 1,400 | Yes |
| 60 | 45 | 1,800 | Yes |
| 60 | 45 | 2,400 | Yes |
| 60 | 53 | 1,200 | Yes |
| 60 | 53 | 1,350 | Yes |
| 60 | 53 | 1,400 | Yes |
| 60 | 53 | 1,800 | Yes |
| 60 | 53 | 2,400 | Yes |
| 60 | 60 | 1,200 | Yes |
| 60 | 60 | 1,350 | Yes |
| 60 | 60 | 1,400 | Yes |
| 60 | 60 | 1,800 | Yes |
| 60 | 60 | 2,400 | Yes |
| 60 | 64 | 1,200 | Yes |
| 60 | 64 | 1,350 | Yes |
| 60 | 64 | 1,400 | Yes |
| 60 | 64 | 1,800 | Yes |
| 60 | 64 | 2,400 | Yes |
| 60 | 70 | 1,200 | Yes |
| 60 | 70 | 1,350 | Yes |
| 60 | 70 | 1,400 | Yes |
| 60 | 70 | 1,800 | Yes |
| 60 | 70 | 2,400 | Yes |
| 60 | 85 | 1,200 | Yes |
| 60 | 85 | 1,350 | Yes |
| 60 | 85 | 1,400 | Yes |
| 60 | 85 | 1,800 | Yes |
| 60 | 85 | 2,400 | Yes |
| 65 | 30 | 1,200 | Yes |
| 65 | 30 | 1,350 | Yes |
| 65 | 30 | 1,400 | Yes |
| 65 | 30 | 1,800 | Yes |
| 65 | 30 | 2,400 | Yes |
| 65 | 36 | 1,200 | Yes |
| 65 | 36 | 1,350 | Yes |
| 65 | 36 | 1,400 | Yes |
| 65 | 36 | 1,800 | Yes |
| 65 | 36 | 2,400 | Yes |

TABLE 1F-continued

Embodiments of the present invention

| Dose irinotecan hydrochloride trihydrate mg/m² (salt) | Dose oxaliplatin mg/m² | 5-fluorouracil mg/m² | Leucovorin |
|---|---|---|---|
| 65 | 42 | 1,200 | Yes |
| 65 | 42 | 1,350 | Yes |
| 65 | 42 | 1,400 | Yes |
| 65 | 42 | 1,800 | Yes |
| 65 | 42 | 2,400 | Yes |
| 65 | 45 | 1,200 | Yes |
| 65 | 45 | 1,350 | Yes |
| 65 | 45 | 1,400 | Yes |
| 65 | 45 | 1,800 | Yes |
| 65 | 45 | 2,400 | Yes |
| 65 | 53 | 1,200 | Yes |
| 65 | 53 | 1,350 | Yes |
| 65 | 53 | 1,400 | Yes |
| 65 | 53 | 1,800 | Yes |
| 65 | 53 | 2,400 | Yes |
| 65 | 60 | 1,200 | Yes |
| 65 | 60 | 1,350 | Yes |
| 65 | 60 | 1,400 | Yes |
| 65 | 60 | 1,800 | Yes |
| 65 | 60 | 2,400 | Yes |
| 65 | 64 | 1,200 | Yes |
| 65 | 64 | 1,350 | Yes |
| 65 | 64 | 1,400 | Yes |
| 65 | 64 | 1,800 | Yes |
| 65 | 64 | 2,400 | Yes |
| 65 | 70 | 1,200 | Yes |
| 65 | 70 | 1,350 | Yes |
| 65 | 70 | 1,400 | Yes |
| 65 | 70 | 1,800 | Yes |
| 65 | 70 | 2,400 | Yes |
| 65 | 85 | 1,200 | Yes |
| 65 | 85 | 1,350 | Yes |
| 65 | 85 | 1,400 | Yes |
| 65 | 85 | 1,800 | Yes |
| 65 | 85 | 2,400 | Yes |

Liposomal irinotecan is preferably administered intravenously, in combination with oxaliplatin, 5-fluorouracil (5-FU) and leucovorin. In one embodiment, liposomal irinotecan is administered prior to oxaliplatin, 5-FU and leucovorin. In another embodiment, leucovorin is administered prior to 5-FU. In another embodiment, the MM-398 liposomal irinotecan is administered followed by administration of the oxaliplatin, followed by administration of the leucovorin, and followed by the administration of the 5-fluorouracil. In certain embodiments, the liposomal irinotecan is administered to the patient intravenously over 90 minutes. In another embodiment, the oxaliplatin is administered to the patient intravenously over 120 minutes. In another embodiment, 5-FU is administered intravenously over 46 hours. In one embodiment, the oxaliplatin is administered from about 6 to about 72 hours after administration of the liposomal irinotecan. In another embodiment, the oxaliplatin is administered for example, 6 hours, 12 hours, 24 hours, 36 hours, 48 hours, 60 hours, or 72 hours, after administration of the liposomal irinotecan. In another embodiment, leucovorin is administered intravenously over 30 minutes. In various embodiments the liposomal irinotecan is MM-398. In various embodiments, the human patient with gastric cancer is pre-medicated with dexamethasone and a 5-HT3 antagonist or other anti-emetic prior to administering the MM-398 liposomal irinotecan, and other active agents.

FURTHER EMBODIMENTS OF THE INVENTION

The following methods and embodiments can be considered alone, in combination other embodiments in this section, or in combination with the methods disclosed above. The invention provides methods for treating gastric cancer in a human patient, such as in a patient not previously treated with a chemotherapeutic agent in the metastatic setting, the method comprising administering to the patient liposomal irinotecan, also referred to as MM-398 (e.g., irinotecan sucrose octasulfate salt liposome injection) in combination with oxaliplatin, leucovorin and 5-FU.

1. A method for treating gastric cancer in a human subject who has not previously received chemotherapy to treat the gastric cancer, the method comprising: administering to the subject a therapeutically effective amount of MM-398 liposomal irinotecan in combination with oxaliplatin, leucovorin, and 5-FU to treat the gastric cancer in the human subject.

2. The method of embodiment 1, wherein the amount of MM-398 liposomal irinotecan administered is administered is 50 mg/m² (free base) or 55 mg/m² (free base).

3. A method for treating gastric cancer in a human subject who has not previously received chemotherapy to treat the gastric cancer, the method comprising: administering to the subject 60 mg/m² (salt) or 65 mg/m² (salt) of MM-398 liposomal irinotecan in combination with oxaliplatin, leucovorin, and 5-FU to treat the gastric cancer in the human subject.

4. The method of any one of embodiments 1-3, wherein the amount of oxaliplatin administered is from about 50 mg/m² to about 100 mg/m², such as about 60 mg/m² to about 85 mg/m², for example 60 mg/m², 70 mg/m², 75 mg/m², or 85 mg/m².

5. The method of any one of embodiments 1-4, wherein the leucovorin administered at a dosage of 400 mg/m² of the (l+d) racemic form, or 200 mg/m² of the (l) form.

6. The method of any one of embodiments 1-5, wherein the amount of 5-FU administered is 2,400 mg/m².

7. The method of any one of embodiments 1-6, wherein the MM-398 liposomal irinotecan, oxaliplatin, leucovorin, and 5-FU are administered at least once, such as wherein the MM-398, oxaliplatin, leucovorin, and 5-FU are administered on days 1 and 15 of a 28-day cycle.

8. The method of any one of embodiments 1-7, wherein multiple cycles are administered.

9. The method of any one of embodiments 1-8, wherein the oxaliplatin is administered to the patient prior to the leucovorin, such as wherein the leucovorin is administered to the patient prior to the 5-FU, optionally wherein the MM-398 liposomal irinotecan is administered to the patient prior to the oxaliplatin, leucovorin, and 5-FU.

10. The method of embodiment 9, wherein the MM-398 is administered over 90 minutes, followed by administration of the oxaliplatin over 120 minutes, followed by administration of the leucovorin over 30 minutes, followed by the administration of the 5-FU over 46 hours.

In a particular embodiment, a human patient with gastric cancer who has not previously been treated with any chemotherapeutic agent in the metastatic setting, is treated with a combination regimen of the present disclosure, the method comprising, intravenously administering to the patient, beginning on day 1 of a 2-week cycle, 50 mg/m² of MM-398 liposomal irinotecan over 90 minutes, followed by 60-85 mg/m² oxaliplatin, followed by 200 mg/m² of the (l) form of leucovorin, or 400 mg/m² of the (l+d) racemic form of leucovorin, followed by 2,400 mg/m² 5-FU, wherein the human patient is treated with one or multiple cycles. In another particular embodiment, a human patient with gastric cancer who has not previously been treated with any chemotherapeutic agent in the metastatic setting, is treated with a combination regimen of the present disclosure, the method comprising, intravenously administering to the patient, beginning on day 1 of a 2-week cycle, 55 mg/m² of MM-398 liposomal irinotecan over 90 minutes, followed by 60-85 mg/m² oxaliplatin, followed by 200 mg/m² of the (l) form of leucovorin, or 400 mg/m² of the (l+d) racemic form of leucovorin, followed by 2,400 mg/m² 5-FU, wherein the human patient is treated with one or multiple cycles. In the embodiments disclosed herein, the effective amount of MM-398 liposomal irinotecan administered to the human patient can range from about 30 mg/m² to about 60 mg/m², for example, from about 40 mg/m² to about 50 mg/m², or from about 50 mg/m² to about 55 mg/m². In various embodiments, the amount of MM-398 liposomal irinotecan administered to the human patient is 50 mg/m². In various embodiments, the amount of MM-398 liposomal irinotecan administered to the human patient is 55 mg/m². In the embodiments disclosed herein, the effective amount of oxaliplatin administered to the human patient can range from about 40 mg/m² to about 100 mg/m², for example, from about 60 mg/m² to about 85 mg/m², or for example, from about 60 mg/m² to about 70 mg/m². In various embodiments, the amount oxaliplatin administered to the human patient is 60 mg/m², 70 mg/m², or 85 mg/m². In one variant of this embodiment, oxaliplatin is administered over 120 minutes, leucovorin is administered over 30 minutes, and 5-FU is administered over 46 hours.

EXAMPLES

Figure 1B:
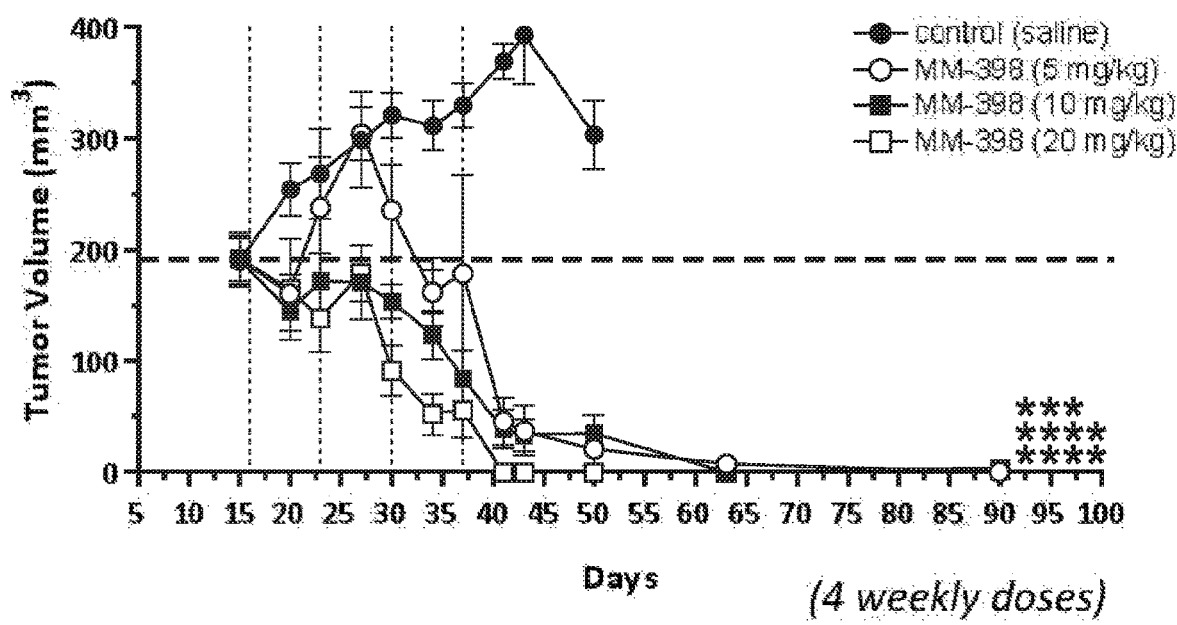
FIG. 1B is a graph showing nal-IRI activity in gastric tumor model KATO III.

Example 1: Evaluation of In Vivo Tolerability and Efficacy of nal-IRI in Gastric Tumor Models Anti-tumor activity of MM-398 was evaluated in MKN-45 and KATO III gastric tumor models. Mice bearing xenograft tumors were treated with saline, 25 mg/kg free irinotecan, 5 mg/kg MM-398, 10 mg/kg MM-398 or 20 mg/kg MM-398 given weekly for 4 weeks (FIGS. 1A and 1B). All doses were well tolerated. nal-IRI displays anti-tumor activity with tumor regression at 10 and 20 mg/kg.

Figure 2A:
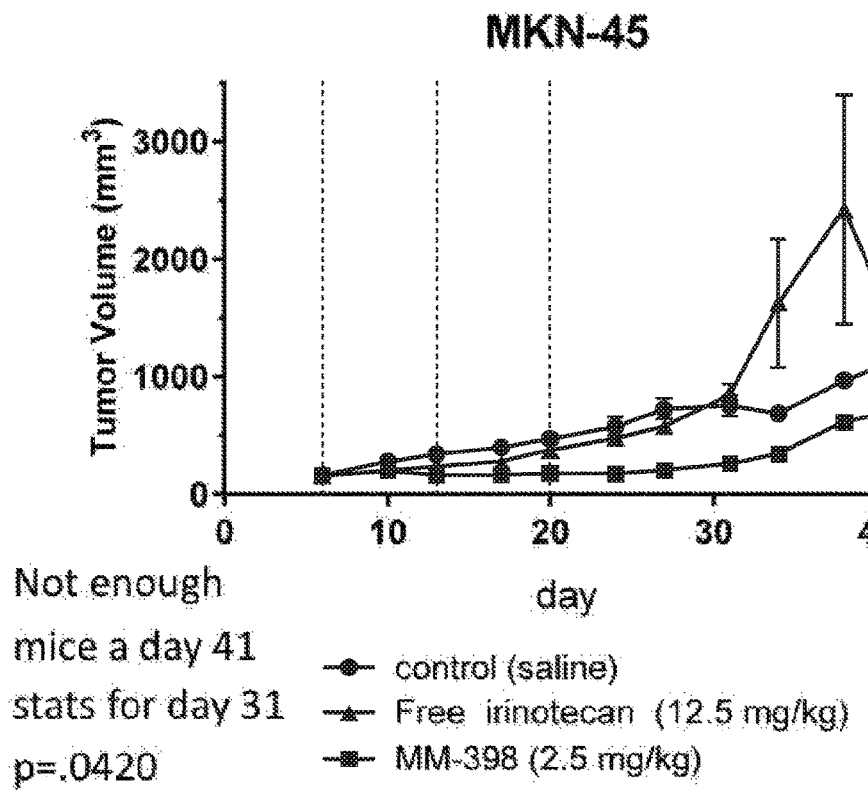
FIGS. 2A and 2B are graphs showing anti-tumor activity of MM-398 in comparison to free irinotecan monotherapy in a xenograft model of gastric cancer. Mice bearing MKN-45 tumors were treated with saline, 12.5 mg/kg free irinotecan or 2.5 mg/kg MM-398 weekly for 3 weeks (FIG. 2A) or saline, 25 mg/kg free irinotecan and 5 mg/kg MM-398 weekly for 3 weeks (FIG. 2B) (days of dosing are indicated by horizontal dashed lines; n=X per mice group).
Figure 2B:
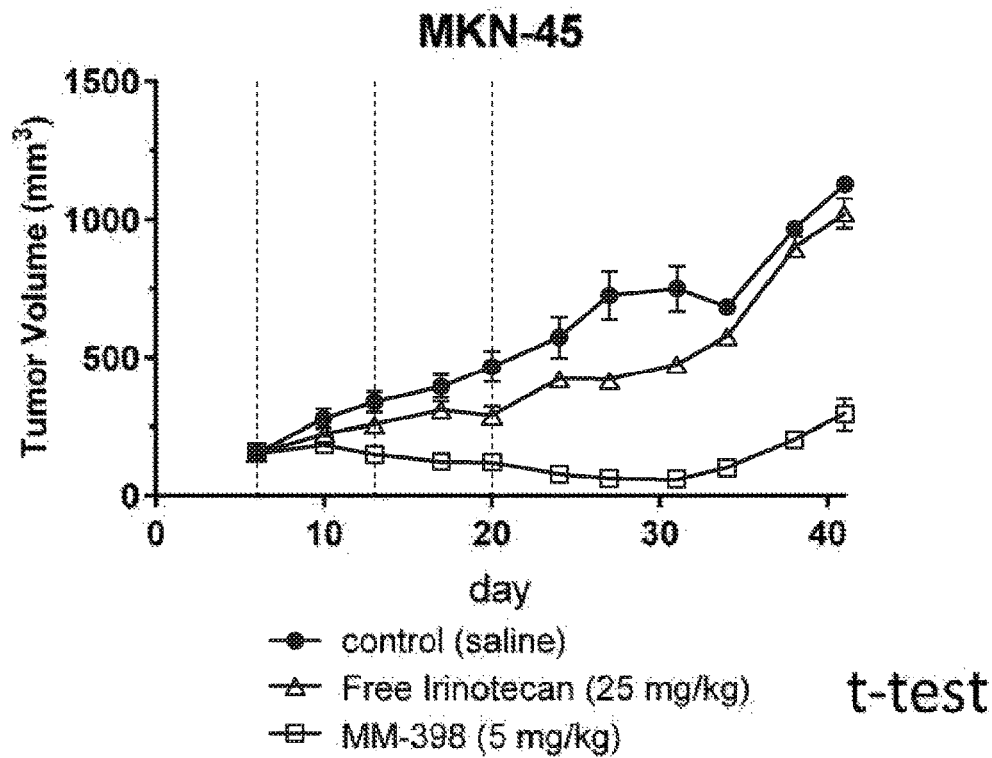

Example 2: Evaluation of In Vivo Tolerability and Efficacy of Combination Therapies in an Animal Model Anti-tumor activity of MM-398 in comparison to free irinotecan in the context of triplet combination therapy with 5-FU and oxaliplatin was evaluated. Mice bearing MKN-45 xenograft tumors were treated with saline, 100 mg/kg 5-FU+5 mg/kg oxaliplatin, 25 mg/kg free irinotecan, 5 mg/kg MM-398, the triplet of free irinotecan+5-FU+oxaliplatin or MM-398+5-FU+oxaliplatin given weekly for 3 weeks. All groups were performed in the same study and are separated into two panels for visualization purposes. 5-FU was administered intraperitoneally while all other agents were administered intravenously; days of dosing are indicated by horizontal dashed lines; n=X per mice group (FIGS. 2A and 2B).

Example 3: Tolerability of Antineoplastic Therapies in Human Clinical Trial

The tolerability of antineoplastic therapies combining liposomal irinotecan, 5-FU/leucovorin and oxaliplatin was evaluated in a human clinical trial, using two different doses: 80 mg/m² (salt) of liposomal irinotecan (MM-398) and 60 mg/m² (salt) of liposomal irinotecan (MM-398). Table 2 summarizes four dosing regimens for the treatment of previously untreated (front-line) pancreatic cancer in humans over a 28 day treatment cycle.

TABLE 2

Dose Table (MM-398 + 5-FU/LV + oxaliplatin)

| | Oxaliplatin | | 5-FU/LV | | MM-398 (nal-IRI) Dose | |
|---|---|---|---|---|---|---|
| Level | Dose (mg/m²)[a] | Dose Day[c] | Dose (mg/m²)[b] | Dose Day[c] | (mg/m²) (salt) | Dose Day[c] |
| 1 | 60 | 1, 15 | 2400/400 | 1, 15 | 80 | 1, 15 |
| 2 | 85 | 1, 15 | 2400/400 | 1, 15 | 60 | 1, 15 |
| −2A | 75 | 1, 15 | 2400/400 | 1, 15 | 60 | 1, 15 |
| 3 | 70 | 1, 15 | 2400/400 | 1, 15 | 65 | 1, 15 |

[a]First dose administration in conjunction with first dose of nal-IRI; oxaliplatin to be administered 2 hours after the completion of the nal-IRI infusion.
[b]46 hour infusion, no bolus is given; leucovorin and 5-FU will be administered last, following the completion of the oxaliplatin infusion.
[c]Day indicated is part of a 28-day cycle.
Note:
The dose of nal-IRI and 5-FU/LV in Dose Level 1 and 2 above is the same dose and schedule that was previously used in the NAPOLI-1 Phase 3 study.

Initially, a combination of oxaliplatin, MM-398 liposomal irinotecan, leucovorin and 5-fluorouracil was evaluated at dose level 1 in Table 2 above. The results are summarized in Table 3 for dose level 1 in Table 2 above (for 80 mg/m² (salt) MM-398 dose), showing that the 80 mg/m² (salt) dose of liposomal irinotecan (MM-398) in combination with oxaliplatin and 5-fluorouracil/leucovorin at dose level 1 was not tolerated in humans.

TABLE 3

Antineoplastic Therapy with 80 mg/m² liposomal irinotecan (salt) in combination with oxaliplatin/5FU/leucovorin in human clinical trials

| Patient | Cycle 1 Day 1 | Cycle 1 Day 15 | Cycle 2 Day 1 | Cycle 2 Day 15 | Cycle 3 Day 1 | Cycle 3 Day 15 | Cycle 4 Day 1 | Cycle 4 Day 15 |
|---|---|---|---|---|---|---|---|---|
| 1 | ✓ | ✓ | X | X | X | X | X | X |
| 2 | ✓ | R* | R2* | R2* | X | X | X | X |
| 3 | ✓ | X | X | X | X | X | X | X |
| 4 | ✓ | ✓ | X | X | X | X | X | X |
| 5 | ✓ | X | X | X | X | X | X | X |
| 6 | ✓ | ✓ | R1* | R1 | X | R1 | R1 | X |
| 7 | ✓ | X | X | X | X | X | X | X |

*Dosing held to allow for recovery from toxicity related to the study treatment.

Table 3 summarizes the results from treating a total of seven (7) patients diagnosed with pancreatic cancer.

A "check mark" (✓) in Table 3 indicates the patient received the antineoplastic therapy of dose level 1 in Table 2 above, starting on the indicated days of 3 consecutive 28-day treatment cycles: 80 mg/m² liposomal irinotecan (MM-398, dose based on the corresponding amount of irinotecan hydrochloride trihydrate salt), 60 mg/m² oxaliplatin, 400 mg/m² (l+d) leucovorin and 2,400 mg/m² 5-fluorouracil, as described in the protocol of Example 4.

A "R" in Table 3 indicates the patient received a reduced dose of antineoplastic therapy of dose level −1 in Table 2 on the corresponding cycle and day: 60 mg/m² liposomal irinotecan (MM-398, dose based on the corresponding amount of irinotecan hydrochloride trihydrate salt), 60 mg/m² oxaliplatin, 400 mg/m² (l+d) leucovorin and 2,400 mg/m² 5-fluorouracil, as described in the protocol of Example 4.

An "R1" in Table 3 indicates the patient received a reduced dose of antineoplastic therapy of dose level −1 in Table 2 (Example 3 above) on the corresponding cycle and day: 60 mg/m² liposomal irinotecan (MM-398, dose based on the corresponding amount of irinotecan hydrochloride trihydrate salt), 60 mg/m² oxaliplatin, 400 mg/m² (l+d) leucovorin and 2400 mg/m² 5-fluorouracil, as described in the protocol of Example 3.

An "R2" in Table 3 indicates the patient received a reduced dose of antineoplastic therapy of dose on the corresponding cycle and day: 50 mg/m² liposomal irinotecan (MM-398, dose based on the corresponding amount of irinotecan hydrochloride trihydrate salt), 60 mg/m² oxaliplatin, 400 mg/m² (l+d) leucovorin and 1,200 mg/m² 5-fluorouracil (a 50% reduction compared to dose level −1 dose), as described in the protocol of Example 3.

An "X" in Table 3 indicates the patient did not receive an antineoplastic therapy combining liposomal irinotecan, oxaliplatin, 5-fluorouracil and leucovorin, or combining liposomal irinotecan, oxaliplatin, and 5-fluorouracil. After cycle 1, day 1 and prior to cycle 1, day 15, patient 2 was determined to be homozygous for the UGT1A1*28 allele, and subsequent reduced doses of the antineoplastic therapy were administered on days indicated in Table 3, based on the protocol of Example 4. Patients 1 and 3-7 were not homozygous for UGT1A1*28 allele.

The antineoplastic therapy of dose level 1 in Table 2 (Example 3) was only administered to 3 of these 7 patients on day 15 of (28-day) cycle 1, no patients received dose level 1 for more than 2 consecutive doses, and none of the patients received this therapy after cycle 1.

Accordingly, as noted in the Table 3, antineoplastic therapies combining a dose of 80 mg/m² liposomal irinotecan (salt) with 60 mg/m² oxaliplatin and doses of 2,400 and 400 mg/m² of 5-fluorouracil and (l+d) leucovorin were not well tolerated in a human clinical trial (resulting in dose limiting toxicities). Examples of antineoplastic therapies combining a dose of 80 mg/m² liposomal irinotecan (salt) with 60 mg/m² oxaliplatin and doses of 2,400 and 400 mg/m² of 5-fluorouracil and (l+d) leucovorin include the therapies in Table 2.

Figure 12:
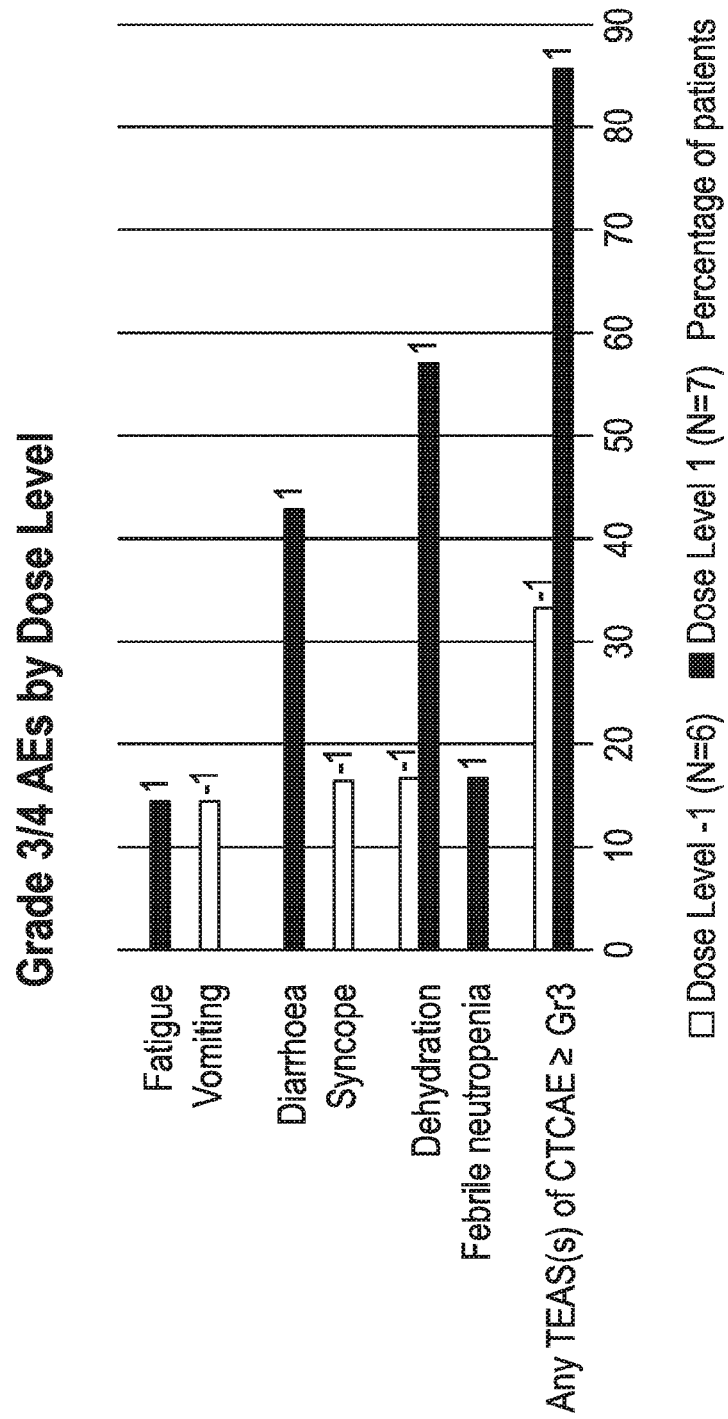
FIG. 12 is a graph showing safety of dose level 1 and dose level −1.
Figure 13:
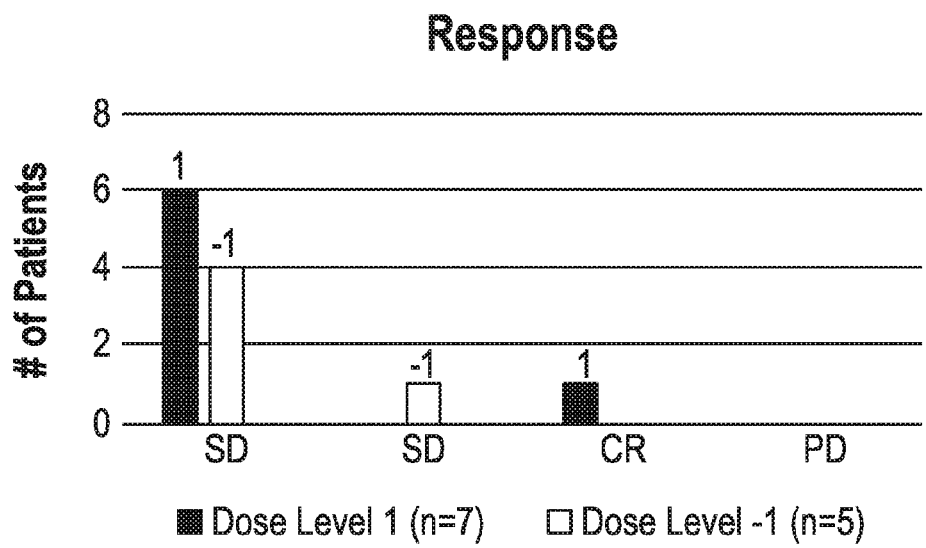
FIG. 13 is a graph showing efficacy of Dose level 1 and dose level −1.

In contrast, as noted in Table 4 below, antineoplastic therapies combining a dose of 60 mg/m² liposomal irinotecan (salt) with 60 mg/m² oxaliplatin and doses of 2,400 and 400 mg/m² of 5-fluorouracil and (l+d) leucovorin were tolerated in a human clinical trial. In particular, dose level −1 in Table 4 (a 60 mg/m² (salt) M-398 dose) was administered two or more consecutive times to multiple human patients in the clinical trial described in Example 4. These antineoplastic therapies comprising the reduced 60 mg/m² (salt) of liposomal irinotecan (MM-398) in combination with oxaliplatin and 5-fluorouracil/leucovorin were better tolerated in humans than dose level 1 (FIGS. 12-14). In other embodiments, patients are administered the therapy of dose level −2B or −3 in Table 4.

TABLE 4

Oxaliplatin Dose Table

| | Oxaliplatin | | 5-FU/LV | | MM-398 (nal-IRI) | |
|---|---|---|---|---|---|---|
| Level | Dose (mg/m²)$^a$ | Dose Day$^c$ | Dose (mg/m²)$^b$ | Dose Day$^c$ | Dose (mg/m²) | Dose Day$^c$ |
| −1 | 60 | 1, 15 | 2400/400 | 1, 15 | 60 | 1, 15 |
| 1 | 60 | 1, 15 | 2400/400 | 1, 15 | 80 | 1, 15 |
| −2B | 85 | 1, 15 | 2400/400 | 1, 15 | 60 | 1, 15 |
| −3 | 70 | 1, 15 | 2400/400 | 1, 15 | 65 | 1, 15 |

$^a$First dose administration in conjunction with first dose of MM-398; oxaliplatin to be administered 2 hours after the completion of the nal-IRI.
$^b$46 hour infusion, no bolus is given; leucovorin and 5-FU will be administered last, following the completion of the oxaliplatin infusion.
$^c$Day indicated is part of a 28-day cycle.

TABLE 5

Antineoplastic Therapy with 60 mg/m² liposomal irinotecan (salt) in combination with oxaliplatin/5FU/leucovorin in human clinical trials

| Patient | Cycle 1 Day 1 | Cycle 1 Day 15 | Cycle 2 Day 1 | Cycle 2 Day 15 | Cycle 3 Day 1 | Cycle 3 Day 15 | Cycle 4 Day 1 | Cycle 4 Day 15 | Additional Cycles |
|---|---|---|---|---|---|---|---|---|---|
| 1 | ✓ | ✓ | X | R3 | R3 | R3 | R3 | X | 4 at R3 |
| 2 | ✓˜ | X | X | X | X | X | X | X | — |
| 3 | ✓ | ✓ | ✓ | ✓ | ✓ | ✓ | ✓* | ✓ | 11 (original dose) with some dose delay |
| 4 | ✓ | ✓ | ✓ | ✓* | ✓ | ✓ | ✓ | ✓ | 1 (original dose); 11 (R4) with some dose delay |
| 5 | ✓ | ✓ | X | X | X | R5 | R6 | R6 | 2 (R6) |
| 6 | ✓ | ✓ | ✓ | ✓ | ✓ | ✓ | ✓ | ✓ | 5 (original dose) with some dose delay |
| 7 | ✓ | ✓ | ✓ | ✓ | X | X | X | X | — |

*Dosing held to allow for recovery from toxicity related to the study treatment.
˜Subject deceased (disease related).

Table 5 summarizes the results from treating a total of seven (7) patients diagnosed with pancreatic cancer. A "check mark" (✓) in Table 5 indicates the patient received the antineoplastic therapy of dose level −1 in Table 4 above, starting on the indicated days of 3 consecutive 28-day treatment cycles: 60 mg/m² liposomal irinotecan (MM-398, dose based on the corresponding amount of irinotecan hydrochloride trihydrate salt), 60 mg/m² oxaliplatin, 400 mg/m² (l+d) leucovorin and 2,400 mg/m² 5-fluorouracil, as described in the protocol of Example 4.

In contrast to the antineoplastic therapy of dose level 1 in Table 2, the antineoplastic therapy of dose level −1 in Table 2 (Example 3) was administered repeatedly to patients 3, 4, and 6 for at least 3 consecutive administrations (including 14 consecutive administrations for patient 6).

The antineoplastic therapy of dose level −1 in Table 4 (Example 3) was administered to 6 of 7 patients on days 1 and 15 of (28-day) cycle 1, and days 1 and 15 of (28 day) cycle 2, and to at least 4 of 7 patients in the study, with no dose limiting toxicities.

A "check mark" (✓) in Table 5 indicates the patient received the antineoplastic therapy of dose level −1 in Table 4 above, starting on the indicated days of 3 consecutive 28-day treatment cycles: 80 mg/m² liposomal irinotecan (MM-398, dose based on the corresponding amount of irinotecan hydrochloride trihydrate salt), 60 mg/m² oxaliplatin, 400 mg/m² (l+d) leucovorin and 2,400 mg/m² 5-fluorouracil, as described in the protocol of Example 4.

An "R3" in Table 5 indicates the patient received a reduced dose of antineoplastic therapy of dose on the corresponding cycle and day: 50 mg/m² liposomal irinotecan hydrochloride trihydrate salt), 45 mg/m² oxaliplatin, 400 mg/m² (l+d) leucovorin and 2400 mg/m² 5-fluorouracil (a 50% reduction compared to dose level −1 dose), as described in the protocol of Example 3.

An "R5" in Table 5 indicates the patient received a reduced dose of antineoplastic therapy of dose on the corresponding cycle and day: 30 mg/m² liposomal irinotecan (MM-398, dose based on the corresponding amount of irinotecan hydrochloride trihydrate salt) (a 50% reduction compared to dose level −1 dose), 30 mg/m² oxaliplatin (a 50% reduction compared to dose level −1 dose), 197 mg/m² (l+d) leucovorin and 1200 mg/m² 5-fluorouracil (a 50% reduction compared to dose level −1 dose), as described in the protocol of Example 3.

An "R6" in Table 5 indicates the patient received a reduced dose of antineoplastic therapy of dose on the corresponding cycle and day: 36 mg/m² liposomal irinotecan (MM-398, dose based on the corresponding amount of irinotecan hydrochloride trihydrate salt), 36 mg/m² oxaliplatin, 240 mg/m² (l+d) leucovorin and 1440 mg/m² 5-fluorouracil, as described in the protocol of Example 4.

Accordingly, as noted in the Table 5, antineoplastic therapies combining a dose of 60 mg/m² liposomal irinotecan (salt) with 60 mg/m² oxaliplatin and doses of 2,400 and 400 mg/m² of 5-fluorouracil and (l+d) leucovorin were well tolerated in a human clinical trial.

An example of an antineoplastic therapies combining a dose of 60 mg/m² liposomal irinotecan with 85 mg/m² oxaliplatin and doses of 2,400 and 400 mg/m² of 5-fluorouracil and (l+d) leucovorin include the therapies in Table 2.

TABLE 6

Antineoplastic Therapy with 60 mg/m² liposomal irinotecan in combination with oxaliplatin/5FU/leucovorin in human clinical trials.

| Patient | Cycle 1 Day 1 | Cycle 1 Day 15 | Cycle 2 Day 1 | Cycle 2 Day 15 | Cycle 3 Day 1 | Cycle 3 Day 15 | Cycle 4 Day 1 | Cycle 4 Day 15 | Additional Cycles (dose) |
|---|---|---|---|---|---|---|---|---|---|
| 1 | ✓^ | X | X | X | X | X | X | X | — |
| 2 | ✓ | ✓ | ✓ | ✓ | ✓ | ✓ | ✓ | ✓ | 5 (original dose) with some delay; 2 additional with reduced oxaliplatin |
| 3 | ✓ | ✓ | ✓ | ✓ | ✓ | ✓ | ✓ | X | |
| 4 | ✓^ | X | X | X | X | X | X | X | — |
| 5 | ✓ | X | X | X | X | X | X | X | — |
| 6 | ✓ | ✓ | R7* | R7 | X | R7 | R7 | R7 | 3 (original dose) with some delay |
| 7 | ✓ | X | X | X | X | X | X | X | — |
| 8 | ✓ | R7* | R7 | R7 | X | X | X | X | — |
| 9 | ✓ | ✓ | ✓ | ✓ | ✓ | ✓ | ✓ | ✓ | 2 (original dose) with some delay |
| 10 | ✓ | X | R8 | R8 | X | X | X | X | — |

*Dosing held to allow for recovery from toxicity related to the study treatment.
^Subject deceased (disease related).

can (MM-398, dose based on the corresponding amount of irinotecan hydrochloride trihydrate salt), 60 mg/m² oxaliplatin, 400 mg/m² (l+d) leucovorin and 1,800 mg/m² 5-fluorouracil (a 25% reduction compared to dose level −1 dose), as described in the protocol of Example 4. One patient in Table 5 received this reduced dose in response to Grade II symptoms (non-hematologic), but without a dose limiting toxicity.

An "R4" in Table 5 indicates the patient received a reduced dose of antineoplastic therapy of dose on the corresponding cycle and day: 60 mg/m² liposomal irinotecan (MM-398, dose based on the corresponding amount of Table 6 summarizes the preliminary clinical results from treating a total of ten (10) patients diagnosed with pancreatic cancer.

A "check mark" (✓) in Table 6 indicates the patient received the antineoplastic therapy of dose level −2B in Table 4 above, starting on the indicated days of 3 consecutive 28-day treatment cycles: 60 mg/m² liposomal irinotecan (MM-398, dose based on the corresponding amount of irinotecan hydrochloride trihydrate salt), 85 mg/m² oxaliplatin, 400 mg/m² (l+d) leucovorin and 2,400 mg/m² 5-fluorouracil, as described in the protocol of Example 3.

An "R7" in Table 6 indicates the patient received a reduced dose of antineoplastic therapy of dose on the corresponding cycle and day: 50 mg/m² liposomal irinotecan (MM-398, dose based on the corresponding amount of irinotecan hydrochloride trihydrate salt), 85 mg/m² oxaliplatin, 400 mg/m² (l+d) leucovorin and 1,800 mg/m² 5-fluorouracil (a 25% reduction compared to dose level −2B dose), as described in the protocol of Example 3.

An "R8" in Table 6 indicates the patient received a reduced dose of antineoplastic therapy of dose on the corresponding cycle and day: 50 mg/m² liposomal irinotecan (MM-398, dose based on the corresponding amount of irinotecan hydrochloride trihydrate salt), 60 mg/m² oxaliplatin, 400 mg/m² (l+d) leucovorin and 1,800 mg/m² 5-fluorouracil (a 25% reduction compared to dose level −2B dose), as described in the protocol of Example 3.

An "X" in Table 6 indicates the patient did not receive an antineoplastic therapy combining liposomal irinotecan, oxaliplatin, 5-fluorouracil and leucovorin, or combining liposomal irinotecan, oxaliplatin, and 5-fluorouracil.

Example 4: Treatment of Gastric Cancer

Figure 9:
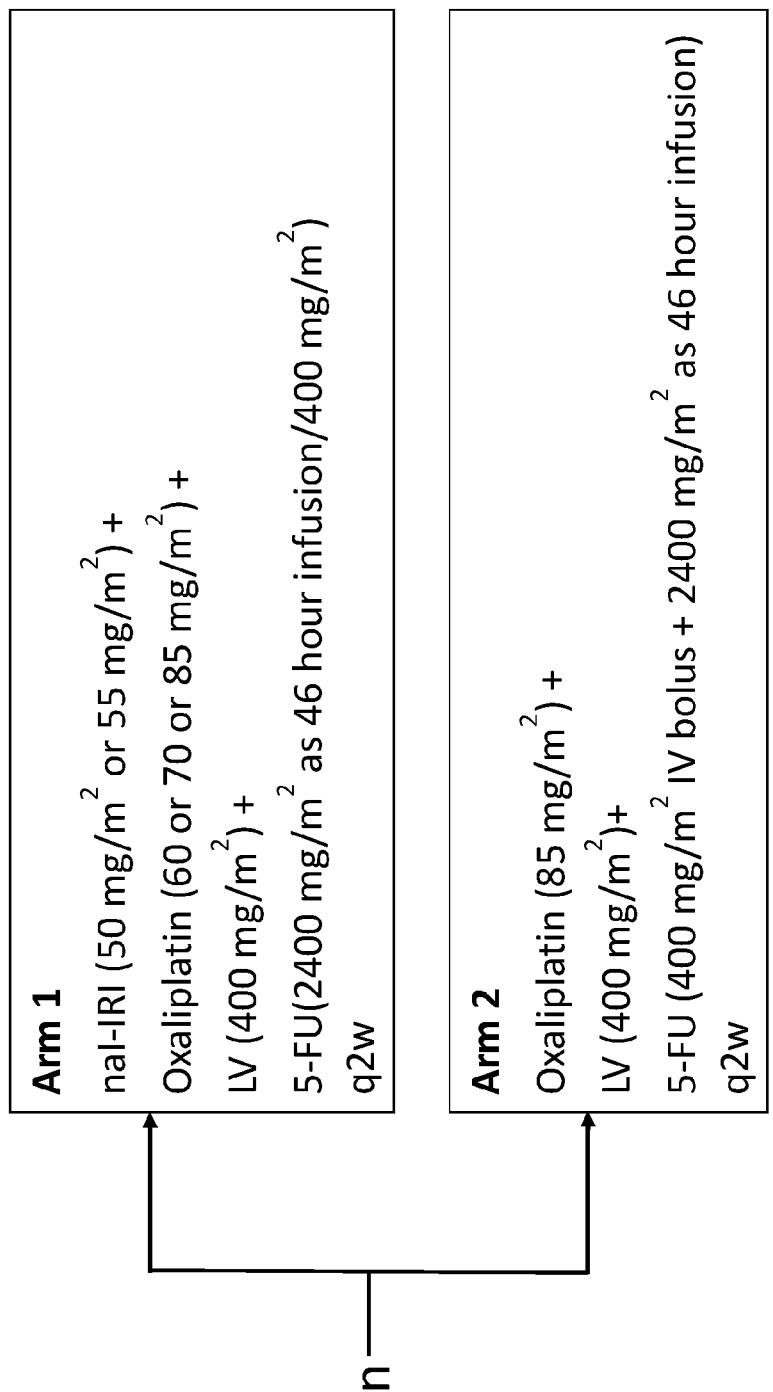
FIG. 9 is a schematic of a clinical trial in gastric cancer.
Figure 10A:
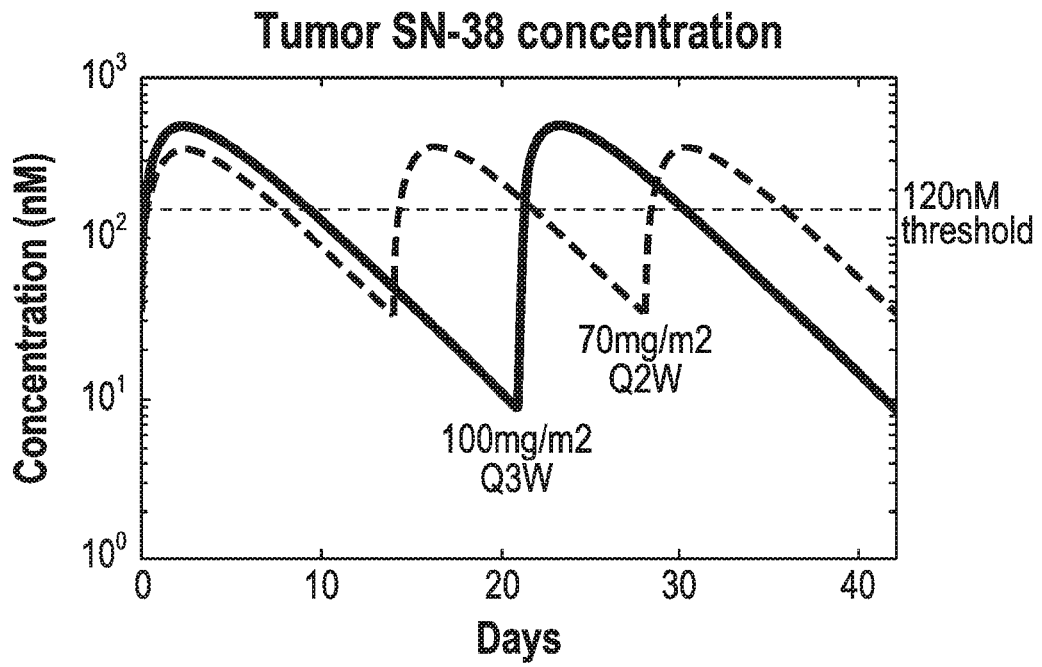
FIGS. 10A and 10B are graphs showing duration of sustained SN-38 tumor levels.
Figure 10B:
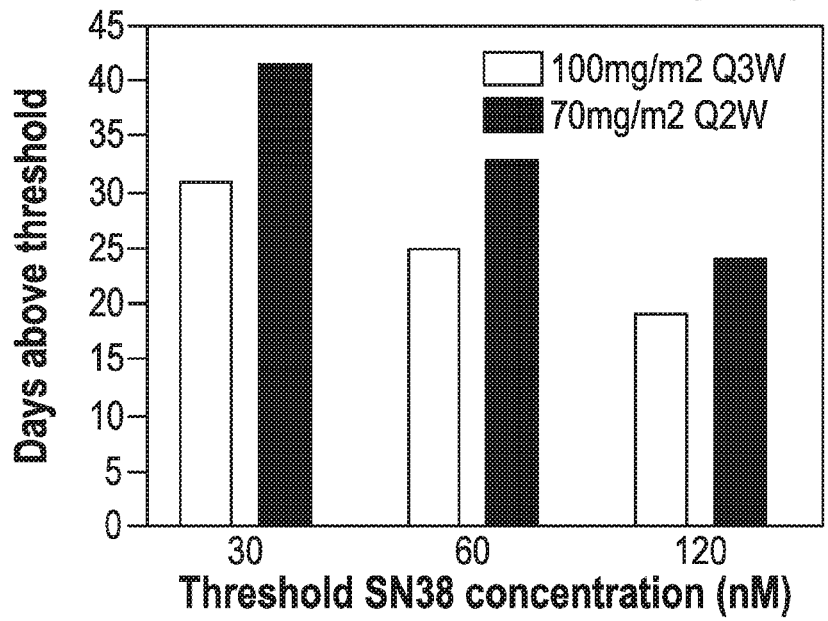
Figure 11:
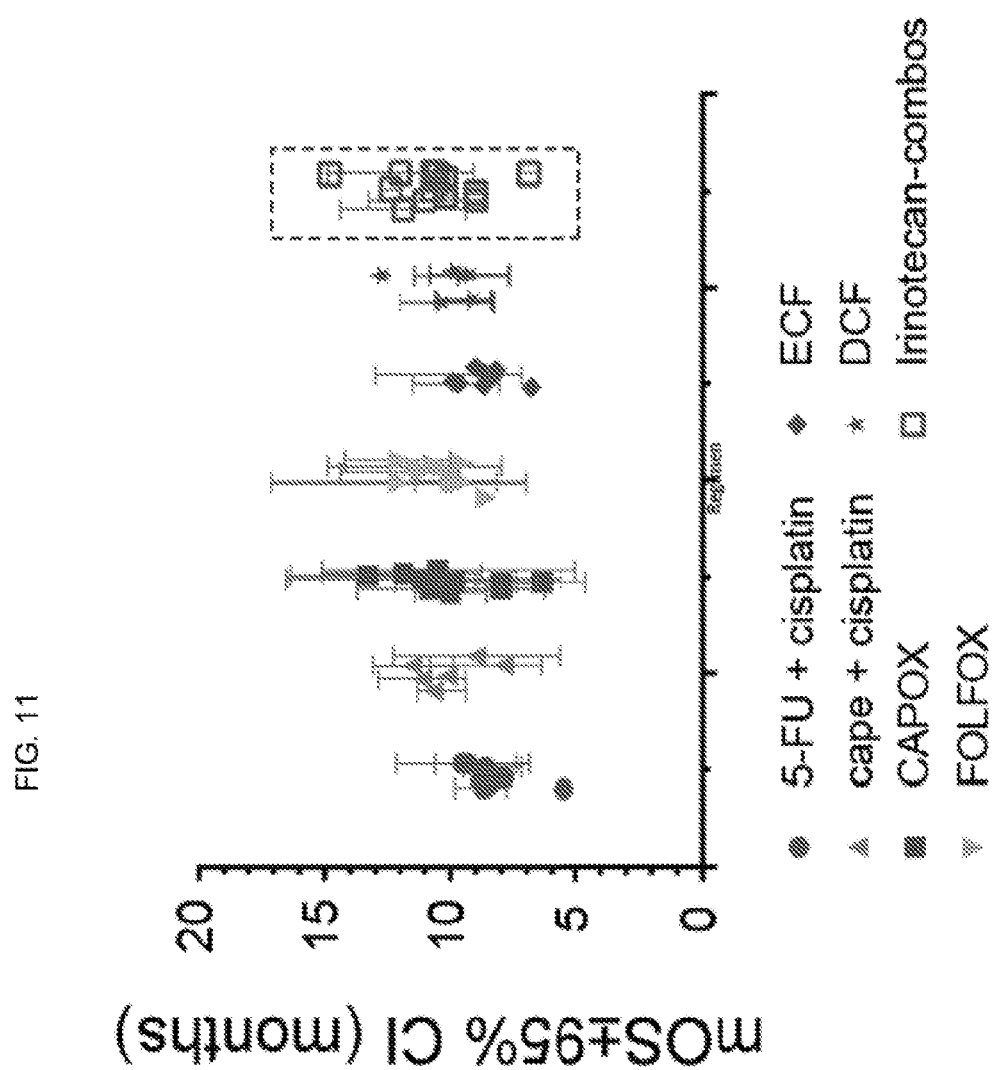
FIG. 11 is a graph showing historical median OS performance of selected first line gastric cancer regimens in various trials.

As schematically shown in FIG. 9, the present study is an open-label, phase 3 comparative study to assess the safety, tolerability, and efficacy of MM-398 in combination with other anticancer therapies, compared to mFOLFOX6, in patients with gastric cancer who have not received prior chemotherapy. This study assesses the following regimens: (1) MM-398+5-FU/LV+oxaliplatin (Arm 1) and (2) 5-FU/LV+oxaliplatin (Arm 2).

This phase 3 study evaluates the efficacy of oxaliplatin+ 5-FU/LV with or without MM-398 in patients with previously untreated gastric cancer. The study may also provide important information on the impact of MM-398 combination treatment on patient HRQL and identify potential biomarkers of response.

In the study, MM-398 is administered instead of conventional irinotecan to improve the safety, tolerability, and ultimately efficacy of a FOLFIRINOX regimen. The addition of oxaliplatin to the NAPOLI-1 regimen is included to increase DNA damage and potentiate efficacy. Further, due to the MM-398 prolonged PK properties and sustained tumor exposure, using MM-398 instead of conventional irinotecan is designed to further improve upon the efficacy of FOLFIRINOX.

A modified triplet combination regimen of liposomal irinotecan, oxaliplatin, 5-fluorouracil (5-FU)/leucovorin is provided herein, whereby no bolus of 5-FU will be administered. The target dose of oxaliplatin, 60, 70, or 85 mg/m², is evaluated in the Arm 1 combination regimen with the continuous infusion dose of 5-FU (excluding the bolus), and the every 2 week dose of MM-398 previously shown to be tolerable and efficacious in combination with 5-FU. Note that with MM-398 dosing, the $C_{max}$ of SN-38 is expected to be lower than would be expected for standard dosing with free irinotecan.

Based on previous experience with irinotecan, individuals who are homozygous for the UGT1A1*28 allele (UGT1A1 7/7 genotype) are at increased risk for neutropenia following initiation of irinotecan treatment. According to the prescribing information for irinotecan, in a study of 66 patients who received single-agent irinotecan (350 mg/m² once every-3-weeks), the incidence of grade 4 neutropenia in patients homozygous for the UGT1A1*28 allele was as high as 50%, and in patients heterozygous for this allele (UGT1A1 6/7 genotype) the incidence was 12.5%. Importantly, no grade 4 neutropenia was observed in patients homozygous for the wild-type (WT) allele (UGT1A1 6/6 genotype). In other studies, a lower prevalence of accompanying life threatening neutropenia is described (for details refer to the prescribing information for irinotecan). Population PK studies of MM-398 have not identified a relationship between UGT1A1*28 homozygosity and increased SN-38 exposure (see Investigator Brochure). In a Phase I study, no differences in toxicity were seen in cohorts of heterozygous or WT patients, and DLTs of diarrhea with or without accompanying dehydration or fatigue, were seen in both cohorts. For these reasons, and because the prevalence of UGT1A1*28 homozygosity is relatively low, testing results are not required prior to the first dose of MM-398 on this study and the starting dose for all patients will be 60 mg/m² (salt) which is equivalent to 50 mg/m² (free base). However, if patients are known to be homozygous for UGT1A1*28, the dose of MM-398 may be reduced as described herein.

Patients will be randomized to treatment (1:1:1) to either MM-398+5-FU/LV+oxaliplatin or 5-FU/LV+oxaliplatin. The randomization is stratified based on region (East Asia vs. rest of the world) and performance status (ECOG 0 vs. 1).

The following adverse events are common (≥40%) with past oxaliplatin treatment in combination with 5-FU/LV and are to be expected with the MM-398-containing combination regimen: peripheral sensory neuropathy, neutropenia, thrombocytopenia, anemia, nausea, increases in transaminases and alkaline phosphatase, diarrhea, fatigue, emesis, and stomatitis. Additional adverse events may be anticipated, as described in the package insert for oxaliplatin, including allergic and anaphylactic reactions. In a Phase 3 study of the FOLFIRINOX combination, the most common (≥5%) Grade 3-4 adverse events were: neutropenia, fatigue, vomiting, diarrhea, thrombocytopenia, sensory neuropathy, anemia, elevated alanine aminotransferase (ALT) level, thromboembolism, and febrile neutropenia. Considering these expected toxicities, Arm 1 is evaluated for safety and tolerability.

A dose of oxaliplatin of 70 mg/m² or 85 mg/m² is the target dose for this study. The study will confirm whether these doses are compatible when MM-398 is used instead of conventional irinotecan. In case there are any unexpected toxicities, patients may be treated at a lower dose of oxaliplatin (60 mg/m²).

TABLE 7

Arm 1 Dosing of (MM-398 + 5-FU/LV + oxaliplatin)

| Oxaliplatin | | 5-FU/LV | | MM-398 (nal-IRI) | |
|---|---|---|---|---|---|
| Dose (mg/m²)[a] | Dose Day[c] | Dose (mg/m²)[b] | Dose Day[c] | Dose (mg/m²) | Dose Day[c] |
| 60 | 1, 15 | 2400/400 | 1, 15 | 50 | 1, 15 |
| 85 | 1, 15 | 2400/400 | 1, 15 | 50 | 1, 15 |
| 70 | 1, 15 | 2400/400 | 1, 15 | 55 | 1, 15 |

[a]First dose administration in conjunction with first dose of MM-398; oxaliplatin to be administered 2 hours after the completion of the nal-IRI infusion.
[b]46 hour infusion, no bolus is given; leucovorin and 5-FU will be administered last, following the completion of the oxaliplatin infusion
[c]Day indicated is part of a 28-day cycle Arm 1: MM-398+5-FU/LV+Oxaliplatin The order of the infusions to be administered in the clinic is as follows: MM-398 administered first, followed by oxaliplatin, then LV, followed by 5-FU.

Patients receive the oxaliplatin infusion 2 hours after the completion of the MM-398 infusion. If no infusion reactions are seen, patients can receive oxaliplatin directly after completion of the MM-398 infusion. If any grade 3 or higher infusion reactions are seen in patients, the DSMB may elect to revert back to administration of oxaliplatin two hours after the completion of the MM-398 infusion.

Arm 2: 5-FU/LV+Oxaliplatin

Patients receive the oxaliplatin (85 mg/m²) infusion, followed by leucovorin and 5-FU (400 mg/m² IV bolus+ 2400 mg/m² as 46 h infusion/400 mg/m²).

Premedication

All patients must be premedicated prior to MM-398 infusion, 5-FU/LV infusion, and oxaliplatin infusion with standard doses of dexamethasone and a 5-HT3 antagonist, or equivalent other anti-emetics according to standard institutional practices for irinotecan, 5-FU, and oxaliplatin administration, or the Summary of Product Characteristics (SmPC) for sites located in the European Union (EU). Atropine may be prescribed prophylactically for patients who experienced acute cholinergic symptoms in the previous cycles.

Doses and Administration of MM-398 (Arm 1)

MM-398 is administered by intravenous (IV) infusion over 90 minutes (±10 minutes) every two weeks. The first cycle Day 1 is a fixed day; subsequent doses should be administered on the first day of each cycle+/−2 days.

Prior to administration, the appropriate dose of MM-398 must be diluted in 5% Dextrose Injection solution (D5W) or normal saline to a final volume of 500 mL. Care should be taken not to use in-line filters or any diluents other than D5W or normal saline. MM-398 can be administered at a rate of up to 1 mL/sec (30 mg/sec).

The actual dose of MM-398 to be administered will be determined by calculating the patient's body surface area at the beginning of each cycle. A +/−5% variance in the calculated total dose will be allowed for ease of dose administration. Since MM-398 vials are single-use vials, site staff must not store any unused portion of a vial for future use and they must discard unused portions of the product.

Doses and Administration of 5-FU and Leucovorin (Arms 1 and 2)

Leucovorin is administered at a dose of 400 mg/m$^2$ of the (l+d)-racemic form, or (l) form 200 mg/m$^2$, as an IV infusion over 30 minutes (±5 minutes), on Days 1 and 15 of each 28-day cycle 5-FU is administered at a dose of 2400 mg/m$^2$ as an IV infusion over 46-hours (±60 minutes), on Days 1 and 15 of each 28-day cycle. In Arm 2, a 400 mg/m$^2$ IV bolus of 5-FU is administered in addition to the 46 hour infusion.

Leucovorin should be reconstituted per the instructions on the package insert, SmPC or standard institutional guidelines for reconstitution of leucovorin.

Leucovorin should be administered prior to the 5-FU infusion and may be given concurrently with oxaliplatin. Actual dose of 5-FU and leucovorin to be administered is determined by calculating the patient's body surface area prior to each cycle. A +/−5% variance in the calculated total dose will be allowed for ease of dose administration.

Doses and Administration of Oxaliplatin (Arms 1 and 2)

Oxaliplatin is administered at a dose of 70 mg/m$^2$ or 85 mg/m$^2$, IV over 120 minutes (±10 minutes), on Days 1 and 15 of each 28-day cycle (if target dose is confirmed in accordance with methods described herein). If the target dose is not tolerated, the dosage of oxaliplatin can be adjusted to 60 mg/m$^2$.

Oxaliplatin should be prepared according to the instructions on the package insert, SmPC or per standard institutional guidelines for preparation and administration of oxaliplatin.

Oxaliplatin should be administered following MM-398 infusion in Arm 1. Actual dose of oxaliplatin to be administered is determined by calculating the patient's body surface area prior to each cycle. A +/−5% variance in the calculated total dose is allowed for ease of dose administration.

Dose Limiting Toxicities (DLTs)

For MM-398 administered in combination with 5-FU/LV and oxaliplatin, the following adverse events are considered as dose limiting toxicities (DLTs) if they occur during the first cycle of treatment and are deemed related to the study treatment regimen:

Grade 4 neutropenia or thrombocytopenia that does not resolve within 7 days despite optimal therapy (withholding study drug and administering concomitant medication, e.g. G-CSF administration for neutropenia);

Grade 4 neutropenia complicated by fever ≥38.5° C. (i.e. febrile neutropenia) and/or Grade 3 neutropenia with infection;

Inability to begin subsequent treatment course within 14 days of the scheduled date, due to drug-related toxicity; and Any grade 4 non-hematologic toxicity with the specific exclusion of: Fatigue/asthenia <2 weeks in duration, increases in alkaline phosphatase level, nausea and vomiting ≤3 days duration (only considered dose limiting if they last >72 hours after treatment with an optimal anti-emetic regimen), and diarrhea ≤3 days duration (only considered dose limiting if diarrhea lasts >72 hours after treatment with an optimal anti-diarrheal regimen)

Any toxicity that is related to disease progression will not be considered a DLT.

The safety assessment period for purposes of DLT evaluation and dose escalation decisions is one cycle of treatment (i.e. 28 days; or 14 days after the 2nd dose of study treatment if there is a treatment delay according as described herein). The dose can escalate to the next level only after the safety data have been evaluated at the current dose level (once the last patient enrolled in the cohort completes the first cycle of treatment) and the criteria for safety and tolerability of the optimal dose have not been exceeded. In addition, any drug-related toxicities of Grade 3 or higher that arise after Cycle 1 (if applicable) are assessed for their potential relationship to cumulative MM-398 or combination therapy doses and considered in the decision to escalate the dose. PK data may be available, but is not be required for decisions on dose escalation.

TABLE 8

| Inclusion Criteria | Exclusion Criteria |
|---|---|
| In order for inclusion into the study, patients must have/be: Pathologically confirmed gastric cancer that has not been previously treated in the metastatic setting Measurable or non-measurable disease as defined by RECIST v1.1 ECOG performance status of 0 or 1 Adequate biological parameters as evidenced by the following blood counts: ANC > 1,500 cells/μl without the use of hematopoietic growth factors, Platelet count > 100,000 cells/μl, and Hemoglobin > 9 g/dL | Patients must meet all the inclusion criteria and none of the following exclusion criteria: Prior treatment of gastric cancer in the metastatic setting with surgery, radiotherapy, chemotherapy or investigational therapy Prior treatment of gastric cancer with cytotoxic doses of chemotherapy (patients receiving prior treatment with chemotherapy as a radiation sensitizer are eligible if ≥6 months has elapsed from completion of therapy) Known metastasis to the central nervous system Clinically significant gastrointestinal disorder including hepatic disorders, bleeding, inflammation, occlusion, diarrhea > grade 1, malabsorption syndrome, ulcerative colitis, inflammatory bowel disease, or partial bowel obstruction |

TABLE 8-continued

| Inclusion Criteria | Exclusion Criteria |
| --- | --- |
| Adequate hepatic function as evidenced by:<br>Serum total bilirubin ≤ ULN (biliary drainage is allowed for biliary obstruction), and<br>AST and ALT ≤ 2.5 × ULN (≤5 × ULN is acceptable if liver metastases are present)<br>Adequate renal function as evidenced by serum creatinine ≤ 1.5 × ULN, and calculated clearance ≥ 60 mL/min/1.72 m² for patients with serum creatinine levels above or below the institutional normal value. Actual body weight should be used for calculating creatinine clearance using the Cockcroft-Gault Equation (CreatClear = Sex * ((140 − Age)/(SerumCreat)) * (Weight/72); for patients with body mass index (BMI) > 30 kg/m², lean body weight should be used instead.<br>Normal ECG or ECG without any clinically significant findings<br>Recovered from the effects of any prior surgery or radiotherapy ≥ 18 years of age<br>Agreeable to submit unstained archived tumor tissue for analysis, if available<br>Able to understand and sign an informed consent (or have a legal representative who is able to do so) | History of any second malignancy in the last 3 years; patients with prior history of in-situ cancer or basal or squamous cell skin cancer are eligible. Patients with a history of other malignancies are eligible if they have been continuously disease free for at least 3 years.<br>Known hypersensitivity to any of the components of MM-398, other liposomal products, or any components of 5-FU, leucovorin or oxaliplatin<br>Known hypersensitivity to any of the components of nab-paclitaxel or gemcitabine (Part 2 only)<br>Concurrent illnesses that would be a relative contraindication to trial participation such as active cardiac or liver disease, including:<br>Severe arterial thromboembolic events (myocardial infarction, unstable angina pectoris, stroke) less than 6 months before inclusion<br>NYHA Class III or IV congestive heart failure, ventricular arrhythmias or uncontrolled blood pressure<br>Known historical or active infection with HIV, hepatitis B, or hepatitis C<br>Active infection or an unexplained fever > 38.5° C. during screening visits or on the first scheduled day of dosing (at the discretion of the investigator, patients with tumor fever may be enrolled), which in the investigator's opinion might compromise the patient's participation in the trial or affect the study outcome<br>Use of strong CYP3A4 inhibitors or inducers, or presence of any other contraindications for irinotecan<br>Presence of any contraindications for 5-FU, leucovorin, or oxaliplatin<br>Use of strong CYP2C8 inhibitors or inducers, or presence of any other contraindications for nab-paclitaxel or gemcitabine (Part 2 only)<br>Any other medical or social condition deemed by the Investigator to be likely to interfere with a patient's ability to sign informed consent, cooperate and participate in the study, or interfere with the interpretation of the results<br>Pregnant or breast feeding; females of child-bearing potential must test negative for pregnancy at the time of enrollment based on a urine or serum pregnancy test. Both male and female patients of reproductive potential must agree to use a highly effective method of birth control, during the study and for 3 months following the last dose of study drug. |

Dose Modifications

The toxicity of each cycle must be recorded prior to the administration of a subsequent cycle and graded according to the National Cancer Institute Common Terminology Criteria for Adverse Events (NCI CTCAE) (Version 4.03). All dose reductions for all arms should be based on the worst preceding toxicity.

Dosing may be held for up to 2 weeks from when it was due to allow for recovery from toxicity related to the study treatment. If the time required for recovery from toxicity is more than 2 weeks, the patient should be discontinued from the study, unless the patient is benefiting from the study treatment, in which case the patient's continuation on study should be discussed between Investigator and Sponsor regarding risks and benefits of continuation. If oxaliplatin is not well tolerated in patients enrolled in Arm 1, oxaliplatin may be discontinued and patients may continue to receive MM-398+5-FU/LV at the discretion of the Investigator.

If a patient's dose is reduced during the study due to toxicity, it should remain reduced for the duration of the study; dose re-escalation to an earlier dose is not permitted. Any patient who has 2 dose reductions and experiences an adverse event that would require a third dose reduction must be discontinued from study treatment.

Dose Modifications

Prior to each dosing, patients must have: ANC≥1500/mm³, WBC≥3500/mm³, Platelet count≥100,000/mm³ and Diarrhea≤Grade 1.

Treatment should be delayed to allow sufficient time for recovery to levels noted above, and upon recovery, treatment should be administered according to the guidelines in the tables below. If the patient had febrile neutropenia, the ANC must have resolved to ≥1500/mm³ and the patient must have recovered from infection. For Grade 3 or 4 non-hematological toxicities, treatment should be delayed until they resolve to Grade 1 or baseline. Guidelines for dose adjustments of each individual treatment within the regimen are found in the tables below. In case a patient experiences an infusion reaction, either institutional guidelines or the guidelines provided for infusion reaction management should be followed.

For all tables below, patient should be withdrawn from study treatment if more than 2 dose reductions are required or if MM-398 reductions lower than 30 mg/m² are required. No dose adjustments for toxicity are required for leucovorin. Leucovorin must be given immediately prior to each 5-FU dose; hence, if 5-FU dose is held, leucovorin dose should be held as well.

Treatment discontinuation that is required due to MM-398 or 5-FU toxicity will result in discontinuation from the study. However, for Arm 1, toxicity that requires discontinuation from oxaliplatin only (e.g. neuropathy) will result in the option to continue on study treatment with MM-398+ 5-FU/LV only for all future dosing.

The starting dose of ONIVYDE will be either 50 mg/m$^2$ or 55 mg/m$^2$, 5FU 2400 mg/m$^2$, LV 400 mg/m$^2$ and oxaliplatin will be 85 mg/m$^2$, 70 mg/m$^2$ or 60 mg/m$^2$. Dose reduction will be 25% reduction in all agents for any grade III-IV Hematotoxicity. For persistent toxicities despite the first dose reduction, and additional 25% dose reduction in all agents will occur. Further toxicity will then lead to discontinuation from trial.

For non-hematologic toxicities, the dose reduction will be the same dose reduction schema as for hematotoxicity, except for the specific toxicities associated with the drug (i.e. 5-FU hand foot syndrome, and oxaliplatin neuropathy) which will be as shown in Table 3.

TABLE 9

Arm 1 Dose Modifications

| Worst Toxicity by CTCAE Grade | NaI-IRI (MM-398) | 5-FU | Oxaliplatin |
|---|---|---|---|
| Hematological Toxicities | | | |
| Grade 2 hematotoxicity | 100% of previous dose | | |
| Grade 3 or 4 neutropenia (ANC ≤ 1000/mm$^3$) or febrile neutropenia and/or thrombocytopenia$^a$ | $1^{st}$ occurrence: Reduce dose by 25%<br>$2^{nd}$ occurrence: Reduce dose another 25% (50% of original dose) | | |
| Other Grade 3 or 4 hematologic toxicities not specifically listed above | $1^{st}$ occurrence: Reduce dose by 25%<br>$2^{nd}$ occurrence: Reduce dose another 25% (50% of original dose) | | |
| Non-Hematological Toxicities Other than Asthenia and Grade 3 Anorexia | | | |
| Grade 1 or 2, including diarrhea | 100% of previous dose | 100% of previous dose, except for Grade 2 hand foot syndrome, Grade 2 cardiac toxicity, or any grade neurocerebellar toxicity | 100% of previous dose, except for Grade 2 sensory neuropathy |
| Grade 3 or 4, including diarrhea (except nausea and vomiting)$^d$ | $1^{st}$ occurrence: Reduce dose by 25%<br>$2^{nd}$ occurrence: Reduce dose another 25% (50% of original dose) | $1^{st}$ occurrence: Reduce dose by 25%<br>$2^{nd}$ occurrence: Reduce dose another 25% (50% of original dose)<br>*except for Grade 3 or 4 hand foot syndrome | $1^{st}$ occurrence: Reduce dose by 25%<br>$2^{nd}$ occurrence: Reduce dose another 25% (50% of original dose) |
| Grade 3 or 4 nausea and/or vomiting despite anti-emetic therapy$^d$ | Optimize anti-emetic therapy AND<br>$1^{st}$ occurrence: Reduce dose by 25%<br>$2^{nd}$ occurrence: Reduce dose another 25% (50% of original dose) | | |
| Grade 2 hand foot syndrome | 100% of previous dose | $1^{st}$ occurrence: Reduce dose by 25%<br>$2^{nd}$ occurrence: Reduce dose another 25% (50% of original dose) | 100% of previous dose |
| Grade 3 or 4 hand foot syndrome | 100% of previous dose | Discontinue therapy | 100% of previous dose |
| Any grade neurocerebellar or ≥ Grade 2 cardiac toxicity | 100% of previous dose | Discontinue therapy | 100% of previous dose |
| Sensory neuropathy | 100% of previous dose No dose modifications required | 100% of previous dose No dose modifications required | Grade 2, persistent: Reduce dose from 85 mg/m$^2$ to 60 mg/m$^2$ or from 60 mg/m$^2$ to 45 mg/m$^2$ by 25%<br>Grade 3, recovers prior to next cycle: Reduce dose from 85 mg/m$^2$ to 60 mg/m$^2$ or from 60 mg/m$^2$ to 45 mg/m$^2$ by 25% |

TABLE 9-continued

Arm 1 Dose Modifications

| Worst Toxicity by CTCAE Grade | NaI-IRI (MM-398) | 5-FU | Oxaliplatin |
|---|---|---|---|
| | | | Grade 3, persistent: Discontinue therapy<br>Grade 4: Discontinue therapy |

[a]Consider the use of G-CSF for patients who experience ≥ Grade 3 neutropenia or febrile neutropenia.
[b]Asthenia and Grade 3 Anorexia do not require dose modification
[c]Grade 1 diarrhea: 2-3 stools/day > pretreatment; Grade 2 diarrhea: 4-6 stools/day > pretreatment
[d]Grade 3 diarrhea: 7-9 stools/day > pretreatment; Grade 4 diarrhea: >10 stools/day > pretreatment Infusion reactions will be monitored. Infusion reactions will be defined according to the National Cancer Institute CTCAE (Version 4.0) definition of an allergic reaction/infusion reaction and anaphylaxis, as defined below:

TABLE 10

Grade 1: Transient flushing or rash, drug fever <38° C. (<100.4° F.); intervention not indicated
Grade 2: Intervention or infusion interruption indicated; responds promptly to symptomatic treatment (e.g., antihistamines, NSAIDS, narcotics); prophylactic medications indicated for <24 hours
Grade 3: Symptomatic bronchospasm, with or without urticaria; parenteral intervention indicated; allergy-related edema/angioedema; hypotension
Grade 4: Life-threatening consequences; urgent intervention indicated Study site policies or the following treatment guidelines shall be used for the management of infusion reactions.

TABLE 11

Grade 1

Slow infusion rate by 50%
Monitor patient every 15 minutes for worsening of condition Grade 2

Stop infusion
Administer diphenhydramine hydrochloride 50 mg IV, acetaminophen 650 mg orally, and oxygen
Resume infusion at 50% of the prior rate once infusion reaction has resolved
Monitor patient every 15 minutes for worsening of condition
For all subsequent infusions, premedicate with diphenhydramine hydrochloride 25-50 mg IV TABLE 11-continued Grade 3

Stop infusion and disconnect infusion tubing from patient
Administer diphenhydramine hydrochloride 50 mg IV, dexamethasone 10 mg IV, bronchodilators for bronchospasm, and other medications or oxygen as medically necessary
No further treatment with MM-398 will be permitted Grade 4

Stop the infusion and disconnect infusion tubing from patient
Administer epinephrine, bronchodilators or oxygen as indicated for bronchospasm
Administer diphenhydramine hydrochloride 50 mg IV, dexamethasone 10 mg IV
Consider hospital admission for observation
No further treatment with MM-398 will be permitted For patients who experience a Grade 1 or Grade 2 infusion reaction, future infusions may be administered at a reduced rate (over 120 minutes), with discretion.

For patients who experience a second grade 1 or 2 infusion reaction, administer dexamethasone 10 mg IV. All subsequent infusions should be premedicated with diphenhydramine hydrochloride 50 mg IV, dexamethasone 10 mg IV, and acetaminophen 650 mg orally.

MM-398 Dose Modifications for Hematological Toxicities

Prior to initiating a new cycle of therapy, the patients must have:
ANC≥1500/mm$^3$
Platelet count≥100,000/mm$^3$ Treatment should be delayed to allow sufficient time for recovery and upon recovery, treatment should be administered according to the guidelines in the tables below. If the patient had febrile neutropenia, the ANC must have resolved to ≥1500/mm$^3$ and the patient must have recovered from infection.

TABLE 12

MM-398 Dose Modifications for Neutrophil Count

| | MM-398 Dose for Next Cycle | | |
|---|---|---|---|
| ANC: cells/mm$^3$ (Worst CTCAE grade) | Arm A: Patients Not Homozygous for UGT1A1*28 | Arm A: Patients Homozygous for UGT1A1*28<br>Arm C: Patients Not Homozygous for UGT1A1*28 | Arm C: Patients Homozygous for UGT1A1*28 |
| ≥1000 to 1999 (Grade 1 or 2) | 100% of previous dose | 100% of previous dose | 100% of previous dose |
| <1000 (Grade 3/4) or febrile neutropenia | Reduce dose by 20 mg/m$^2$ to a minimum dose of 30 mg/m$^2$ | Reduce dose to 40 mg/m$^2$ for the first occurrence and to 30 mg/m$^2$ for the second occurrence | Reduce dose to 40 mg/m$^2$ for the first occurrence and to 30 mg/m$^2$ for the second occurrence |

TABLE 13

MM-398 Dose Modifications for Other Hematologic Toxicity

MM-398 Dose for Next Cycle

| Worst Toxicity CTCAE Grade | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
|---|---|---|---|
| ≤Grade 2 | 100% of previous dose | 100% of previous dose | 100% of previous dose |
| Grade 3/4 | Reduce dose by 20 mg/m² to a minimum dose of 30 mg/m² | Reduce dose to 40 mg/m² for the first occurrence and to 30 mg/m² for the second occurrence | Reduce dose to 40 mg/m² for the first occurrence and to 30 mg/m² for the second occurrence |

MM-398 Dose Modifications for Non-Hematological Toxicities

Treatment should be delayed until diarrhea resolves to ≤Grade 1, and for other Grade 3 or 4 non-hematological toxicities, until they resolve to Grade 1 or baseline. Guidelines for dose adjustment of MM-398 for drug related diarrhea and other Grade 3 or 4 non-hematological toxicities are provided below. Infusion reactions should be handled as described above.

TABLE 14

MM-398 Dose Modifications for Diarrhea

MM-398 Dose for Next Cycle$^a$

| Worst Toxicity CTCAE Grade | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
|---|---|---|---|
| Grade 1 or 2 (2-3 stools/day > pretreatment or 4-6 stools/day > pretreatment) | 100% of previous dose | 100% of previous dose | 100% of previous dose |
| Grade 3 (7-9 stools/day > pretreatment) or Grade 4 (>10 stools/day > pretreatment) | Reduce dose by 20 mg/m² to a minimum dose of 30 mg/m² | Reduce dose to 40 mg/m² for the first occurrence and to 30 mg/m² for the second occurrence | Reduce dose to 40 mg/m² for the first occurrence and to 30 mg/m² for the second occurrence |

TABLE 15

MM-398 Dose Modifications for Non-Hematological Toxicities Other than Diarrhea, Asthenia and Grade 3 Anorexia MM-398 Dose for Next Cycle

| Worst Toxicity CTCAE Grade | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
|---|---|---|---|
| Grade 1 or 2 | 100% of previous dose | 100% of previous dose | 100% of previous dose |
| Grade 3 or 4 (except nausea and vomiting) | Reduce dose by 20 mg/m² to a minimum dose of 30 mg/m² | Reduce dose to 40 mg/m² for the first occurrence and to 30 mg/m² for the second occurrence | Reduce dose to 40 mg/m² for the first occurrence and to 30 mg/m² for the second occurrence |
| Grade 3 or 4 nausea and or vomiting despite anti-emetic therapy | Optimize anti-emetic therapy AND reduce dose by 20 mg/m² to a minimum dose of 30 mg/m² | Optimize anti-emetic therapy AND reduce dose to 30 mg/m² | Optimize anti-emetic therapy AND reduce dose to 30 mg/m² |

5-FU and Leucovorin Dose Modifications:

Guidelines for 5-FU dose modifications are provided below. No dose adjustments for toxicity are required for leucovorin. Leucovorin must be given immediately prior to each 5-FU dose; hence, if 5-FU dose is held, leucovorin dose should be held as well. In case a patient experiences an infusion reaction, either institutional guidelines or the guidelines provided for MM-398 infusion reaction management should be used.

5-FU Dose Modifications for Hematological Toxicities

Prior to the next dose in a cycle or prior to initiating a new cycle of therapy, the patients must have:

ANC≥1500/mm$^3$

WBC≥3500/mm$^3$

Platelet count≥75,000/mm$^3$ (according to the European summary of product characteristics for 5-FU, the platelets should have recovered to ≥100,000/mm$^3$ prior to initiating therapy)

Treatment should be delayed to allow sufficient time for recovery and upon recovery, treatment should be administered according to the guidelines provided in the table below.

TABLE 16

| 5-FU Dose Modifications for Hematological Toxicities (Arm B & C) | | | | |
|---|---|---|---|---|
| ANC (cells/mm$^3$) | | Platelets (cells/mm$^3$) | 5-FU Dose for D8, D15, D22$^a$ | 5-FU Dose for Next Cycle$^a$ |
| ≥1000 | and | ≥50,000 | 100% of previous dose | 100% of previous dose |
| 500-999 | or | <50,000-25,000 | Hold; when resolved, reduce dose by 25%$^b$ | Reduce dose by 25%$^b$ |
| <500 or febrile neutropenia | or | <25,000 or thrombocytopenia with bleeding | Hold dose; when resolved, reduce dose by 25%$^b$ | Reduce dose by 25%$^b$ |

$^a$All dose modifications should be based on the worst preceding toxicity
$^b$Patients who require more than 2 dose reductions must be withdrawn from the study 5-FU Dose Modifications for Non-Hematological Toxicities Treatment should be delayed until all Grade 3 or 4 non-hematological toxicities resolve to Grade 1 or baseline. Guidelines for dose adjustment of 5-FU related toxicities are provided below.

TABLE 17

| 5-FU Dose Modifications for Non-Hematological Toxicities Other than Asthenia and Grade 3 Anorexia$^c$ | | |
|---|---|---|
| Worst Toxicity CTCAE Grade | 5-FU Dose for D8, D15, D22$^a$ | 5-FU Dose for Next Cycle$^a$ |
| Grade 1 or 2 | 100% of previous dose, except for Grade 2 hand foot syndrome, Grade 2 cardiac toxicity, or any grade neurocerebellar toxicity | 100% of previous dose, except for Grade 2 hand and foot syndrome, Grade 2 cardiac toxicity, or any grade neurocerebellar toxicity |
| Grade 2 hand foot syndrome | Reduce dose by 25%$^b$ | Reduce dose by 25%$^b$ |
| Any grade neurocerebellar or ≥ Grade 2 cardiac toxicity | Discontinue therapy | Discontinue therapy |
| Grade 3 or 4 | Hold; when resolved, reduce dose by 25%$^b$, except for Grade 3 or 4 hand foot syndrome | Reduce dose by 25%$^b$, except for Grade 3 or 4 hand foot syndrome |
| Grade 3 or 4 hand foot syndrome | Discontinue therapy | Discontinue therapy |

$^a$All dose modifications should be based on the worst preceding toxicity
$^b$Patients who require more than 2 dose reductions must be withdrawn from the study
$^c$Asthenia and Grade 3 Anorexia do not require dose modification MM-398 Dose Modifications for UGT1A1*28 Positive Patients (Arm 1)

Patients are tested for UGT1A1*28 status during screening, however the result of the test is not required prior to the initial dose of MM-398. All patients will begin dosing at 50 mg/m$^2$ (free base), however future doses may be reduced for patients who are positive (i.e. homozygous) for UGT1A1*28 7/7 genotype. Any patients who receive a reduced dose during Cycle 1 due to UGT1A1*28 homozygosity will not be evaluable for the cohort and are replaced.

TABLE 18

Part 2 Arm 2 (nal-IRI + 5-FU/LV) Dose Modifications for Hematologic Toxicities

| Worst Toxicity by CTCAE Grade | Nal-IRI | 5-FU |
|---|---|---|
| Grade 2 neutropenia (ANC < 1500-1000 cells/mm$^3$) | 100% of previous dose | |
| Grade 3 or 4 neutropenia (ANC ≤ 1000/mm$^3$) or febrile neutropenia$^a$ | 1$^{st}$ occurrence: Reduce dose to 60 mg/m$^2$<br>2$^{nd}$ occurrence: Reduce dose to 50 mg/m$^2$ | 1$^{st}$ occurrence: Reduce dose by 25%<br>2$^{nd}$ occurrence: Reduce dose another 25% (50% of original dose) |
| ≥Grade 2 thrombocytopenia (Grade 2: platelets ≤ 75,000/mm$^3$-50,000/mm$^3$ or Grade 3-4: platelets < 50,000/mm$^3$) | If Grade 2: 100% of previous dose<br>If ≥Grade 3: 1$^{st}$ occurrence: Reduce dose to 60 mg/m$^2$<br>2$^{nd}$ occurrence: : Reduce dose to 50 mg/m$^2$ | If Grade 2: 100% of previous dose<br>If ≥Grade 3: 1$^{st}$ occurrence: Reduce dose by 25%<br>2$^{nd}$ occurrence: : Reduce dose another 25% (50% of original dose) |
| Other hematologic toxicities not specifically listed above | If Grade 2: 100% of previous dose<br>If ≥Grade 3: 1$^{st}$ occurrence: Reduce dose to 60 mg/m$^2$<br>2$^{nd}$ occurrence: : Reduce dose to 50 mg/m$^2$ | If Grade 2: 100% of previous dose<br>If ≥Grade 3: 1$^{st}$ occurrence: Reduce dose by 25%<br>2$^{nd}$ occurrence: : Reduce dose another 25% (50% of original dose) |

$^a$Consider the use of G-CSF for patients who experience ≥ Grade 3 neutropenia or febrile neutropenia.

TABLE 19

Part 2 Arm 2 (nal-IRI + 5-FU/LV) Dose Modifications for non-Hematological Toxicities other than Asthenia and Grade 3 Anorexia$^{a, d, e}$

| Worst Toxicity by CTCAE Grade | Nal-IRI | 5-FU |
|---|---|---|
| Grade 1 or 2, Including diarrhea$^b$ | 100% of previous dose | 100% of previous dose, except for Grade 2 hand foot syndrome, Grade 2 cardiac toxicity, or any grade neurocerebellar toxicity |
| Grade 3 or 4, Including diarrhea$^c$ (except nausea and vomiting) | 1$^{st}$ occurrence: Reduce dose to 60 mg/m$^2$<br>2$^{nd}$ occurrence: Reduce dose to 50 mg/m$^2$ | 1$^{st}$ occurrence: Reduce dose by 25%<br>2$^{nd}$ occurrence: Reduce dose another 25% (50% of original dose)<br>Note: except for Grade 3 or 4 hand foot syndrome |
| Grade 3 or 4 nausea and/or vomiting despite anti-emetic therapy | Optimize anti-emetic therapy AND reduce dose to 60 mg/m$^2$; if the patient is already receiving 60 mg/m$^2$, reduce dose to 50 mg/m$^2$ | Optimize anti-emetic therapy AND reduce dose by 25%; if the patient is already receiving a reduced dose, reduce dose an additional 25% |
| Grade 2 hand foot syndrome | 100% of previous dose | 1$^{st}$ occurrence: Reduce dose by 25%<br>2$^{nd}$ occurrence: Reduce dose another 25% (50% of original dose) |
| Grade 3 or 4 hand foot syndrome | 100% of previous dose | Discontinue therapy |
| Any grade neurocerebellar or ≥Grade 2 cardiac toxicity | 100% of previous dose | Discontinue therapy |

$^a$Aesthenia and Grade 3 Anorexia do not require dose modification.
$^b$Grade 1 diarrhea: 2-3 stools/day > pretreatment; Grade 2 diarrhea: 4-6 stools/day > pretreatment.
$^c$Grade 3 diarrhea: 7-9 stools/day > pretreatment; Grade 4 diarrhea: >10 stools/day>
$^d$ Any toxicity ≥ Grade 2, except anemia and alopecia, can justify a dose reduction if medically indicated.
$^e$ Patients who require more than 2 dose reductions must be withdrawn from the study.

Disease Evaluation

Tumor responses are evaluated according to the Response Evaluation Criteria in Solid Tumors (RECIST) version 1.1, to establish disease progression by CT or MRI. In addition, other imaging procedures, as deemed appropriate by the Investigator, are performed to assess sites of neoplastic involvement. The same method of assessment must be used throughout the study. Investigators should select target and non-target lesions in accordance with RECIST v1.1 guidelines. Follow up measurements and overall response should also be in accordance with these guidelines.

Tumor assessments should be completed until it has been determined that the patient has progressive disease (in accordance with RECIST v1.1). For patients who do not have documented disease progression per RECIST v. 1.1 at the time of treatment termination, imaging studies should be continually performed into the follow-up period every 8 weeks until disease progression is documented. Continued imaging follow-up on schedule is recommended to reduce potential bias in the evaluations of the impacts of the experimental treatments on disease.

EORTC-QLQ-C30 and EQ-5D-5L

Health-related quality of life (HRQL) is assessed by the EORTC-QLQ-C30 and EQ-5D-5L instruments. The EORTC-QLQ-C30 is a reliable and valid measure of the quality of life of cancer patients in multicultural clinical research settings. It incorporates nine multi-item scales: five functional scales (physical, role, cognitive, emotional, and social); three symptom scales (fatigue, pain, and nausea and vomiting); and a global health and quality-of-life scale. Several single-item symptom measures are also included. EQ-5D is a generic, preference-based measurement of HRQL. The EQ-5D-5L descriptive system comprises the following 5 dimensions: mobility, self-care, usual activities, pain/discomfort and anxiety/depression. Each dimension has 5 levels: no problems, slight problems, moderate problems, severe problems, and unable to do.

Patients are required to complete both questionnaires at time points outlined in the Schedule of Assessments. On days that the patient is to receive study drug, assessments should be completed prior to study drug administration. Only those patients for whom validated translations of the questionnaires are available will be required to complete the questionnaire.

Efficacy Analysis

In the assessments of efficacy, the MM-398-containing arm is compared to the control arm. Efficacy comparisons use stratified analyses, incorporating randomization strata. Each comparison uses 0.10 level one-sided testing to evaluate whether the MM-398-containing arm improves the efficacy parameter. Confidence intervals are presented at two-sided 95% level for descriptive purposes. Hypothesis tests and confidence intervals are not adjusted for multiple comparisons. The primary efficacy comparisons are based on the ITT population, which includes all randomized patients.

Tumor evaluation is measured according to RECIST v1.1. For each patient, progression free survival time is determined as the time from randomization to the first documented radiographical Progression of Disease (PD), per investigator using RECIST 1.1, or death from any cause, whichever comes first. If the progression or death occurs at a time point that is greater than 12 weeks after the non-PD last tumor assessment, then progression-free survival time is censored at the time of the last non-PD tumor assessment.

A primary analysis is conducted when the Week 24 progression-free status for all randomized patients can be determined, anticipated at approximately 24 weeks after the last patient is randomized. A subsequent analysis for PFS and other endpoints is performed when PFS events have occurred in at least 120 (i.e. 80% of randomized patients) patients.

Primary Efficacy Analysis

In the intention-to-treat (ITT) analysis, a patient is considered to have achieved progression-free survival at 24 weeks if the patient has data to indicate the patient has not progressed at 24 weeks. That is, a patient is considered a responder if there is at least one non-PD assessment, prior to progression or new anticancer therapy, at Week 24 or later.

Patients who do not meet the 24-week progression-free achievement criteria (e.g. patients progressed/died up to Week 24, patients censored prior to Week 24), if progression or death occurs at a time point that is greater than 12 weeks after the non-PD last tumor assessment.

For each arm, the progression-free survival achievement rate at 24 weeks is estimated by the number of patients meeting the 24 week achievement criteria divided by the number of ITT patients in the arm. The rate estimates are presented with corresponding 95% confidence intervals. The MM-398 containing arm is assessed for increase in rate relative to the control arm using a one-sided Cochran-Mantel-Haenszel test, incorporating randomization stratification factors, at 0.10 level of significance.

Secondary Efficacy Analyses

Progression-Free Survival (PFS) is descriptively summarized for each arm using Kaplan-Meier methodology. Median PFS time and corresponding 95% confidence limits are presented. For the MM-398-containing arm, PFS is compared to the control arm. Hypothesis tests are conducted for differences in PFS using a one-sided stratified log-rank test. Hazard ratios (with 95% confidence interval) for PFS are estimated using stratified Cox models.

Best Overall Response (BOR) is defined as the best response as recorded from the start of study drug until disease progression. Patients without a post-baseline tumor assessment are considered to be non-evaluable for BOR. To classify BOR as stable disease (SD), there should be a qualifying SD assessment at least 6 weeks from randomization. Objective Response Rate (ORR) is defined as the proportion of patients with a BOR characterized as either a Complete Response (CR) or Partial Response (PR) relative to the total number of evaluable patients. Only patients with measurable disease at baseline will be included in the analysis of the objective response. Estimates of objective response rate and its corresponding 95% CI are calculated for each treatment arm. For each MM-398-containing arm, ORR is compared to the control arm. Differences in objective response rate between the MM-398-containing arm and control arm are provided with 95% CIs. Cochran-Mantel-Haenszel tests, adjusting by randomization strata, are used to compare objective response rates.

Overall Survival (OS) is the time from randomization to the date of death from any cause. Patients who are alive or lost to follow-up at the time of the analysis will be censored at the last known alive date. OS is descriptively summarized for each arm using Kaplan-Meier methodology. For the MM-398-containing arm, OS is compared to the control arm. Hypothesis tests are conducted for differences in OS using a one-sided stratified log-rank test. Hazard ratios (with 95% confidence interval) for PFS are estimated using stratified Cox models.

Quality of Life Analyses

Quality of life analyses are performed using patients in the analysis populations for each quality of life instrument (EORTC-QLC-C30, EQ-5D-5L). EORTC-QLQ-30 and EQ-5D-5L results will be summarized at each visit by treatment group.

For each EORTC QLQ-C30 administered, scores are computed for the following scales: Global Health Status, Physical Functioning, Role Functioning, Emotional Functioning, Cognitive Functioning, Social Functioning, Fatigue, Nausea and vomiting, Pain, Dyspnea, Insomnia, Appetite Loss, Constipation, Diarrhea, Financial difficulties.

Scoring is carried out as described in the EORTC QLQ-C30 Scoring Manual (Fayers, Aaronson, Bjordal, Curran, & Groenvald, 2001). Linear transformations are applied to the raw scores so that the reported score will have range 0-100 for all scales. Summary statistics are presented for each subscale. A summary health state index value is computed for each EQ-5D-5L assessment. Summary statistics are presented for summary health state index. For each EQ-5D-5L attribute (mobility, self-care, usual activities, pain/discomfort, and anxiety/depression), responses are tabulated.

Safety Analysis

Safety analyses (adverse events and laboratory analyses) will be performed using the safety population. Adverse events are reported by the MedDRA version 17.1 or higher. Toxicity is graded according to the NCI CTCAE version 4.03.

The period for treatment-emergent adverse events and safety findings is from the time of first study drug administration to 30 days after the date of last study drug administration. If an adverse event begins on the date of first study drug administration with no time recorded, the event is then considered as treatment-emergent.

Tabular summaries are to be presented for all adverse events, pre-treatment adverse events, treatment-emergent adverse events (TEAE), serious adverse events, adverse events leading to study drug discontinuation, TEAE-related to study drug and TEAE Grade 3/4. Adverse events are to be summarized by System Organ Class and preferred term. All adverse event data is to be listed by patient.

Laboratory data is presented by cycle. Abnormal laboratory values are assessed using all available data and toxicity grading will be assigned according to NCI CTCAE toxicity scale, where criteria are available to do so. Maximum and minimum decrease/increase in continuous laboratory data are reported. Frequency and percent of abnormal laboratory values (L/ULN, 2*L/ULN) are assessed. Shift to most severe toxicity grade are summarized.

Vital signs and ECG are tabulated for the change from baseline by time point. Additional analyses may be performed as described in detail within the SAP.

Vital signs are tabulated for the change from baseline by time point. Additional analyses may be performed as described in detail within the SAP.

Biomarker Subgroup Analysis

Analyses are performed to assess the associations between potential biomarkers (from plasma and archived tissue) and efficacy parameters (ORR, percent change in target lesion size, and PFS or as appropriate). Graphical displays are performed when appropriate.

Pharmacokinetics Analysis

Plasma concentrations of MM-398 and oxaliplatin can be used to characterize PK parameters. Due to the sparse PK sampling schedule, PK parameters for individual patients can be estimated based on the Empirical Bayesian Estimation method with priors from the previously estimated (MM-398) or published (oxaliplatin) population PK model parameters. The model simulated exposures, e.g., $C_{max}$, AUC (area under the curve), are used to examine any possible interactions between MM-398 and oxaliplatin by comparing the least squares geometric mean ratios (LS-GMR) of drug exposures. NONMEM®, Version 7.3, is used to estimate individual PK parameters and simulate plasma exposures.

Example 5: ONIVYDE® (Irinotecan Liposome Injection) Liposomal Irinotecan

One preferred example of an irinotecan liposome described herein is the product marketed as ONIVYDE® (irinotecan liposome injection). ONIVYDE® is a topoisomerase inhibitor, formulated with irinotecan in a liposomal dispersion, for intravenous use.

The finished ONIVYDE® product is a white to slightly yellow opaque sterile concentrate for infusion. It consists of an isotonic dispersion of liposomes containing irinotecan hydrochloride trihydrate. The liposomes are small unilamellar lipid bilayer vesicles, approximately 110 nm in diameter, enclosing an aqueous compartment that contains irinotecan in a gelated or precipitated state, as sucrosofate salt. The vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. Each mL also contains 2-[4-(2-hydroxyethyl)piperazin-1-yl]ethanesulfonic acid (HEPES) as a buffer 4.05 mg/mL and sodium chloride as an isotonicity reagent 8.42 mg/mL. The liposomes are dispersed in an aqueous buffered solution.

The ONIVYDE® product contains irinotecan sucrosofate encapsulated in a liposome, obtained from an irinotecan hydrochloride trihydrate starting material. The chemical name of irinotecan is (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. The dosage of ONIVYDE® can be calculated based on the equivalent amount of irinotecan trihydrate hydrochloride starting material used to prepare the irinotecan liposomes, or based on the amount of irinotecan in the liposome. There are about 866 mg of irinotecan per gram of irinotecan trihydrate hydrochloride. For example, an ONIVYDE® dose of 80 mg based on the amount of irinotecan hydrochloride trihydrate starting material actually contains about 0.866x (80 mg) of irinotecan in the final product (i.e., a dose of 80 mg/m$^2$ of ONIVYDE® based on the weight of irinotecan hydrochloride starting material is clinically equivalent to about 70 mg/m$^2$ of irinotecan in the final product). Each 10 mL single-dose vial contains 43 mg irinotecan free base at a concentration of 4.3 mg/mL.

The invention claimed is:

1. A method of treating gastric cancer in a human patient who has not previously received an antineoplastic agent to treat the gastric cancer, the method comprising administering an antineoplastic therapy to the patient once every two weeks, the antineoplastic therapy consisting of:
   a) 50 or 55 mg/m$^2$±5% of liposomal irinotecan,
   b) 60, 70, or 85 mg/m$^2$±5% oxaliplatin,
   c) 200 mg/m$^2$ of the (l)-form of leucovorin or 400 mg/m$^2$ of the (l+d) racemic form of leucovorin, and
   d) 2,400 mg/m$^2$ 5-fluorouracil;
to treat the gastric cancer in the human patient.

2. The method of claim 1, wherein 50 mg/m$^2$±5% of liposomal irinotecan is administered to the patient during the antineoplastic therapy once every two weeks.

3. The method of claim 1, wherein 55 mg/m²±5% liposomal irinotecan is administered to the patient during the antineoplastic therapy once every two weeks.

4. The method of claim 1, wherein 60 mg/m²±5% oxaliplatin is administered to the patient during the antineoplastic therapy once every two weeks.

5. The method of claim 1, wherein 70 mg/m²±5% oxaliplatin is administered to the patient during the antineoplastic therapy once every two weeks.

6. The method of claim 1, wherein 85 mg/m²±5% oxaliplatin is administered to the patient during the antineoplastic therapy once every two weeks.

7. The method of claim 1, wherein 50 mg/m²±5% of liposomal irinotecan and 60 mg/m²±5% oxaliplatin is administered to the patient during the antineoplastic therapy once every two weeks.

8. The method of claim 1, wherein 55 mg/m²±5% of liposomal irinotecan and 70 mg/m²±5% oxaliplatin is administered to the patient during the antineoplastic therapy once every two weeks.

9. The method of claim 1, wherein 50 mg/m²±5% of liposomal irinotecan and 85 mg/m²±5% oxaliplatin is administered to the patient during the antineoplastic therapy once every two weeks.

10. The method of claim 1, wherein each administration of the oxaliplatin begins 2 hours after completing each administration of the liposomal irinotecan.

11. The method of claim 1, wherein the leucovorin is administered immediately prior to the 5-fluorouracil and wherein the 5-fluorouracil is administered as an infusion over 46 hours.

12. The method of claim 1, wherein the liposomal irinotecan, oxaliplatin, 5-fluorouracil and leucovorin are administered on days 1 and 15 of a 28-day treatment cycle.

13. The method of claim 1, wherein the liposomal irinotecan is administered as an infusion over a total of about 90 minutes, followed by administering the oxaliplatin, followed by administering the leucovorin, followed by administering the 5-fluorouracil.

14. The method of claim 1, wherein the liposomal irinotecan comprises irinotecan sucrose octasulfate encapsulated in liposomes.

15. The method of claim 1, wherein the liposomal irinotecan comprises phosphatidylcholine, cholesterol, and a polyethleneglycol-derivatized phosphatidyl-ethanolamine in the amount of approximately one polyethyleneglycol (PEG) molecule for 200 phospholipid molecules.

16. The method of claim 15, wherein the liposomal irinotecan, oxaliplatin, 5-fluorouracil, and leucovorin are administered on days 1 and 15 of a 28-day treatment cycle; each administration of the liposomal irinotecan is administered prior to the leucovorin; the leucovorin is administered immediately prior to each administration of the 5-fluorouracil, and each administration of 5-fluorouracil is administered as an infusion over 46 hours.

17. The method of claim 15, wherein the liposomal irinotecan comprises irinotecan sucrose octasulfate 1,2-distearoyl-sn-glycero-3-phosphocholine (DSPC), cholesterol, and a N-(carbonylmethoxypolyethlyene glycol-2000)-1,2-distearoly-sn-glycero-3-phosphoethanolamine (MPEG-2000-DSPE).

18. A method of treating gastric cancer in a human patient who has not previously received gemcitabine to treat the gastric cancer, the method comprising administering an antineoplastic therapy to the patient once every two weeks, the antineoplastic therapy consisting of:
  a) 50 mg/m²±5% of liposomal irinotecan,
  b) 85 mg/m²±5% oxaliplatin,
  c) 200 mg/m² of the (l)-form of leucovorin or 400 mg/m² of the (l+d) racemic form of leucovorin, and
  d) 2,400 mg/m² 5-fluorouracil;
  to treat the gastric cancer in the human patient.

19. A method of treating gastric cancer in a human patient who has not previously received gemcitabine to treat the gastric cancer, the method comprising administering an antineoplastic therapy to the patient once every two weeks, the antineoplastic therapy consisting of:
  a) 55 mg/m²±5% of liposomal irinotecan,
  b) 60 mg/m²±5% oxaliplatin,
  c) 200 mg/m² of the (l)-form of leucovorin or 400 mg/m² of the (l+d) racemic form of leucovorin, and
  d) 2,400 mg/m² 5-fluorouracil;
  to treat the gastric cancer in the human patient.

20. The method of claim 18, wherein
  a) the liposomal irinotecan comprises irinotecan sucrose octasulfate, phosphatidylcholine, cholesterol, and a polyethleneglycol-derivatized phosphatidyl-ethanolamine in the amount of approximately one polyethyleneglycol (PEG) molecule for 200 phospholipid molecules;
  b) the liposomal irinotecan, oxaliplatin, 5-fluorouracil and leucovorin are administered on days 1 and 15 of a 28-day treatment cycle;
  c) each administration of the liposomal irinotecan is administered prior to the leucovorin;
  d) the leucovorin is administered immediately prior to each administration of the 5-fluorouracil;
  e) each administration of 5-fluorouracil is administered as an infusion over 46 hours;
  f) each administration of the oxaliplatin begins after completing each administration of the liposomal irinotecan; and
  g) optionally administering a corticosteroid and anti-emetic to the patient prior to the antineoplastic therapy.

21. The method of claim 19, wherein
  a) the liposomal irinotecan comprises irinotecan sucrose octasulfate, phosphatidylcholine, cholesterol, and a polyethleneglycol-derivatized phosphatidyl-ethanolamine in the amount of approximately one polyethyleneglycol (PEG) molecule for 200 phospholipid molecules;
  b) the liposomal irinotecan, oxaliplatin, 5-fluorouracil and leucovorin are administered on days 1 and 15 of a 28-day treatment cycle;
  c) each administration of the liposomal irinotecan is administered prior to the leucovorin;
  d) the leucovorin is administered immediately prior to each administration of the 5-fluorouracil;
  e) each administration of 5-fluorouracil is administered as an infusion over 46 hours;
  f) each administration of the oxaliplatin begins after completing each administration of the liposomal irinotecan; and
  g) optionally administering a corticosteroid and anti-emetic to the patient prior to the antineoplastic therapy.

* * * * *